(12) United States Patent
Chen et al.

(10) Patent No.: US 9,359,355 B2
(45) Date of Patent: Jun. 7, 2016

(54) FUSED TRICYCLIC DUAL INHIBITORS OF CDK 4/6 AND FLT3

(71) Applicant: AMGEN INC., Thousand Oaks, CA (US)

(72) Inventors: Xiaoqi Chen, Palo Alto, CA (US); Kang Dai, Albany, CA (US); Jason Duquette, South San Francisco, CA (US); Michael W. Gribble, Jr., San Francisco, CA (US); Justin N. Huard, Seattle, WA (US); Kathleen S. Keegan, Bainbridge Island, WA (US); Zhihong Li, Millbrae, CA (US); Sarah E. Lively, San Carlos, CA (US); Lawrence R. McGee, Pacifica, CA (US); Mark L. Ragains, Fort Worth, TX (US); Xianghong Wang, Dublin, CA (US); Margaret F. Weidner, Woodinville, WA (US); Jian Zhang, Foster City, CA (US)

(73) Assignee: AMGEN INC., Thousand Oaks, CA (US)

( * ) Notice: Subject to any disclaimer, the term of this patent is extended or adjusted under 35 U.S.C. 154(b) by 72 days.

(21) Appl. No.: 14/088,796

(22) Filed: Nov. 25, 2013

(65) Prior Publication Data

US 2014/0163052 A1 Jun. 12, 2014

Related U.S. Application Data

(62) Division of application No. 13/425,817, filed on Mar. 21, 2012, now Pat. No. 8,623,885.

(60) Provisional application No. 61/466,841, filed on Mar. 23, 2011.

(51) Int. Cl.
*C07D 471/14* (2006.01)
*C07D 519/00* (2006.01)

(52) U.S. Cl.
CPC ............ *C07D 471/14* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 3,452,013 A | 6/1969 | Gladych et al. |
| 6,498,163 B1 | 12/2002 | Boschelli et al. |
| 6,599,908 B1 | 7/2003 | Davis et al. |
| 6,627,637 B2 | 9/2003 | Ritzeler et al. |
| 7,026,313 B2 | 4/2006 | Repine |
| 7,208,489 B2 | 4/2007 | Barvian et al. |
| 7,452,887 B2 | 11/2008 | Dickson et al. |
| 7,763,629 B2 | 7/2010 | Charrier et al. |
| 2003/0203907 A1 | 10/2003 | Hayama et al. |
| 2004/0236084 A1 | 11/2004 | Biwersi et al. |
| 2005/0059670 A1 | 3/2005 | Beylin et al. |
| 2005/0137214 A1 | 6/2005 | Barvian et al. |
| 2005/0182078 A1 | 8/2005 | Barvian et al. |
| 2005/0222163 A1 | 10/2005 | Eck et al. |
| 2005/0272755 A1 | 12/2005 | Denis et al. |
| 2006/0047118 A1 | 3/2006 | Stadtmueller et al. |
| 2006/0074102 A1 | 4/2006 | Cusuck et al. |
| 2006/0142312 A1 | 6/2006 | Flamme et al. |
| 2006/0194805 A1 | 8/2006 | Bakthavatchalam et al. |
| 2007/0004684 A1 | 1/2007 | Sennhenn et al. |
| 2007/0060566 A1 | 3/2007 | Bailey et al. |
| 2007/0072863 A1 | 3/2007 | Bennett et al. |
| 2007/0072882 A1 | 3/2007 | Guzi et al. |
| 2007/0082900 A1 | 4/2007 | Guzi et al. |
| 2007/0185143 A1 | 8/2007 | Traquandi et al. |
| 2007/0270362 A1 | 11/2007 | Harlan et al. |
| 2007/0281943 A1 | 12/2007 | Andrews et al. |
| 2007/0293558 A1 | 12/2007 | Gao et al. |
| 2008/0070914 A1 | 3/2008 | Freyne et al. |
| 2008/0125588 A1 | 5/2008 | Erdman et al. |
| 2008/0182853 A1 | 7/2008 | Kruman et al. |
| 2009/0030005 A1 | 1/2009 | Kamb et al. |
| 2009/0062318 A1 | 3/2009 | Gangjee |
| 2009/0082374 A1 | 3/2009 | Gangjee |
| 2009/0142337 A1 | 6/2009 | Squires |
| 2010/0056506 A1 | 3/2010 | Huang et al. |
| 2011/0142796 A1 | 6/2011 | Connors et al. |
| 2012/0244110 A1 | 9/2012 | Chen et al. |

FOREIGN PATENT DOCUMENTS

| | | |
|---|---|---|
| WO | WO 83/01446 | 4/1983 |
| WO | WO 01/70741 A1 | 9/2001 |
| WO | WO 01/72717 A1 | 10/2001 |
| WO | WO 02/02550 A1 | 1/2002 |
| WO | WO 03/062236 A1 | 7/2003 |
| WO | WO 03/080064 A1 | 10/2003 |
| WO | WO 2004/065378 A1 | 8/2004 |
| WO | WO 2005/077951 A2 | 8/2005 |
| WO | WO 2006/021547 A1 | 3/2006 |
| WO | WO 2006/042102 A2 | 4/2006 |
| WO | WO 2006/074985 A1 | 7/2006 |
| WO | WO 2006/077428 A1 | 7/2006 |
| WO | WO 2006/131552 A1 | 12/2006 |
| WO | WO 2007/024680 A1 | 3/2007 |
| WO | WO 2007/120752 A2 | 10/2007 |
| WO | WO 2007/125405 A2 | 11/2007 |
| WO | WO 2007/140222 A2 | 12/2007 |
| WO | WO 2008/001076 A1 | 1/2008 |
| WO | WO 2008/082490 A2 | 7/2008 |
| WO | WO 2008/115974 A2 | 9/2008 |
| WO | WO 2009/061345 A2 | 5/2009 |
| WO | WO 2009/061781 A1 | 5/2009 |
| WO | WO 2009/083780 A1 | 7/2009 |
| WO | WO 2009/085185 A1 | 7/2009 |
| WO | WO 2009/087225 A2 | 7/2009 |
| WO | WO 2009/126584 A1 | 10/2009 |

OTHER PUBLICATIONS

International Search Report and Written Opinion for analogous PCT Application No. PCT/US2012/030007.
Barbara, J-G et al., "Quantal release at a neuronal nicotinic synapse from rat adrenal gland," Proc. Natl. Acad. Science 93(18), 9905-9909 (1996).
Baughn, L. B. et al., "A Novel Orally Active Small Molecule Potently Induces $G_1$ Arrest in Primary Myeloma Cells and Prevents Tumor Growth by Specific Inhibition of Cyclin-Dependent Kinase," Cancer Research 66(15), 7661-7667 (2006).
Brooks, E.E. et al., "CVT-313, a specific and Potent Inhibitor of CDK2 That Prevents Neointimal Proliferation", The Journal of Biological Chemistry 272(46), 29207-29211 (1997).
Bukanov, N.O. et al., "Long-lasting arrest of murine polycystic kidney disease with CDK inhibitor roscovitine", Nature 444(7121), 949-952 (2006).

Chang, M.W. et al., "Adenovirus-mediated Over-expression of the Cyclin/Cyclin-dependent Kinase Inhibitor, p21 Inhibits Vascular Smooth Muscle Cell Proliferation and Neointima Formation in the Rat Carotid Artery Model of Balloon Angioplasty", Journal of Clinical Investigation 96(5), 2260-2268 (1995).
Chen, X. et al., "Protection of Normal Proliferating Cells Against Chemotherapy by Staurosporine-Mediated, Selective, and Reversible $G_1$ Arrest", Journal of the National Cancer Institute 92(24), 1999-2008 (2000).
de Carcer, G. et al., "Targeting Cell Cycle Kinases for Cancer Therapy", Current Medicinal Chemistry 14(9), 969-985 (2007).
Fry, D. W. et al., "Specific inhibition of cyclin-dependent kinase 4/6 by PD 0332991 and associated antitumor activity in human tumor xenografts," Molecular Cancer Therapeutics 3(11), 1427-1438 (2004).
Gladych, J.M. Z et al. "Antiviral agents. 5H-as-Triazino[5,6-b]Indoles", Journal Medicinal Chemistry vol. 15(3), pp. 277-281 (1972).
Hassan, A.A. et al., "Novel Heterocyclics from 3-Substituted-5H-1,2,4-Triazino[5,6-b]indoles and Pi-Acceptors", Tetrahedron, vol. 50(33), pp. 9997-10010 (1994).
Kamb, A., "Cyclin-Dependent Kinase Inhibitors and Human Cancer", Current Topics in Microbiology and Immunology 227, 139-148 (1998).
Leach, A.G. et al., "Matched Molecular Pairs as a Guide in the Optimization of Pharmaceutical Properties; a Study of Aqueous Solubility, Plasma Protein Binding and Oral Exposure," Journal of Medicinal Chemistry 49(23), 6672-6682 (2006).
Lu, H. et al., "Toward Understanding the Structural Basis of Cyclin-Dependent Kinase 6 Specific Inhibition," Journal of Medicinal Chemistry 49(13), 3826-3831 (2006).
Malumbres, M. et al, "To Cycle or Not to Cycle: A Critical Decision in Cancer", Nature Rev Cancer 1, 222-231 (2001).
Mascarenhas, N.M. et al., "Combined Ligand and Structure Based Approaches for Narrowing on the Essential Physicochemical Characteristics for CDK4 Inhibition," Journal of Chemical Information and Modeling 48(7), 1325-1336 (2008).
Menu, E. et al., "A Novel Therapeutic Combination Using PD 0332991 and Bortezomib: Study in the 5T33MM Myeloma Model," Cancer Research 68(14), 5519-5523 (2008).
Menu, E. et al., "Correction on Combination Therapy Using PD 0332991 and Bortezomib," Cancer Research 69(5), 2149 (2009).
Mohammed, M.I., "Synthesis and antibacterial activity of some novel heterocycles," Bulgarian Chemical Communications 36(4), 241-248 (2004).
Morgan D.O., "Cyclin-Dependent Kinases: Engines, Clocks and Microprocessors," Annu. Rev. Cell. Dev. Biol. 13, 261-291 (1997).
Novak, M. et al., "Kinetics of Hydrolysis of 8-(Arylamino)-2'-deoxyguanosines," Journal of Organic Chemistry 67(7), 2303-2308 (2002).
Perry, B. et al., "Optimization of a series of multi-isoform PI3 kinase inhibitors," Bioorganic & Medicinal Chemistry Letters 18(19), 5299-5302 (2008).
Saab, R. et al., "Pharmacologic inhibition of cyclin-dependent kinase 4/6 activity arrests proliferation in myoblasts and rhabdomyosarcoma-derived cells," Molecular Cancer Therapeutics 5(5), 1299-1308 (2006).
Saris, C.P. et al., "Chemical properties of the ultimate metabolites of 2-amino-5-phenylpyridine (PHE-P-1) and its ortho-methyl derivative," Chemico-Biological Interactions 95(1,2), 29-40 (1995).
Schang, L.M. et al., "Requirement for cellular cyclin-dependent kinases in herpes simplex virus replication and transcription", Journal of Virology 72(7), 5626-5637 (1998).
Schmidt, M. et al., "Protection against chemotherapy-induced cytotoxicity by cyclin-dependent kinase inhibitors (CKI) in CKI-responsive cells compared with CKI-unresponsive cells," Oncogene 20(43), 6164-6171 (2001).
Taniguchi, K. et al., "Induction of the p16INK4a senescence gene as a new therapeutic strategy for the treatment of rheumatoid arthritis", Nature Medicine 5(7) 760-767 (1999).
Toogood, P.L. et al., "Discovery of a Potent and Selective Inhibitor of Cyclin-Dependent Kinase 4/6," Journal of Medicinal Chemistry 48(7), 2388-2406 (2005).

Wang, L. et al., "Pharmacologic inhibition of CDK4/6: mechanistic evidence for selective activity or acquired resistance in acute myeloid leukemia," Blood 110(6), 2075-2083 (2007).
Wyatt, P. G. et al., "Identification of N-(4-Piperidinyl)-4-(2,6-dichlorobenzoylamino)-1H-pyrazole-3-carboxamide (AT7519), a Novel Cyclin Dependent Kinase Inhibitor Using Fragment-Based X-Ray Crystallography and Structure Based Drug Design," Journal of Medicinal Chemistry 51(16), 4986-4999 (2008).
Youssef, A. S. A. et al., "Synthesis of some heterocyclic systems of anticipated biological activities via 6-aryl-4-pyrazol-1-ylpyridazin-3-one," Canadian Journal of Chemistry 83(3), 251-259 (2005).
Youssef, A. S. A. et al., "Synthesis of some heterocyclic systems of anticipated biological activities via 6-aryl-4-pyrazol-1-ylpyridazin-3-one," Afinidad 61(514), 500-509 (2004).
Zhang, C. et al, "Advancing Bioluminescence Imaging Technology for the Evaluation of Anticancer Agents in the MDA-MB-435-HAL-Luc Mammary Fat Pad and Subrenal Capsule Tumor Models," Clinical Cancer Research 15(1), 238-246 (2009).
Prosecution History of U.S. Appl. No. 13/425,817.

*Primary Examiner* — Savitha Rao
*Assistant Examiner* — Gregg Polansky
(74) *Attorney, Agent, or Firm* — Mintz, Levin, Cohn, Ferris, Glovsky and Popeo, P.C.

(57) ABSTRACT

Compounds of Formula I are useful inhibitors of CDK 4, CDK6, and FLT3. Such compounds are useful in treating cancer and various other disease conditions. Compounds of Formula I have the following structure:

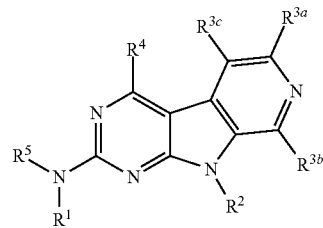

where $R^1$ is a group of Formula IA, Formula IB, Formula IC, or Formula ID

-continued
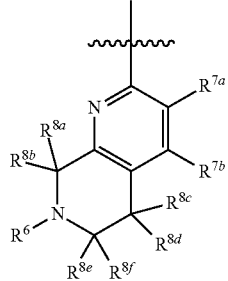
IC
-continued
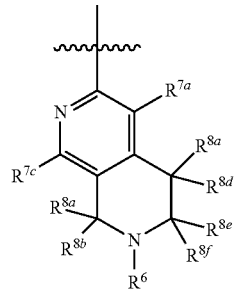
ID
and the definitions of the other variables are provided herein.
14 Claims, 3 Drawing Sheets

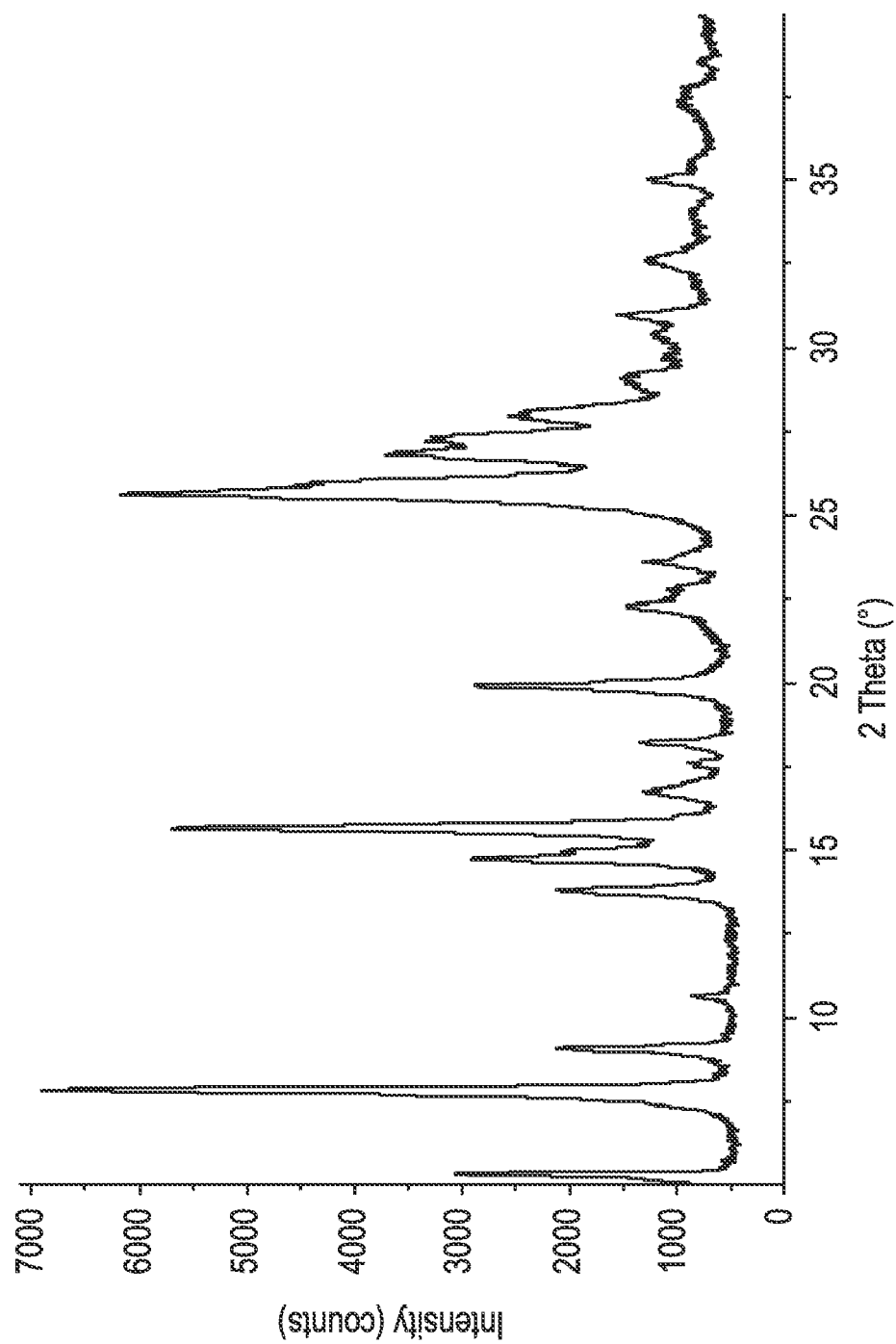

FUSED TRICYCLIC DUAL INHIBITORS OF CDK 4/6 AND FLT3

CROSS REFERENCES TO RELATED APPLICATIONS

This application is a divisional of, and claims priority to, U.S. patent application Ser. No. 13/425,817, filed on Mar. 21, 2012, which claims the benefit of, and priority to, U.S. Provisional Application No. 61/466,841, filed on Mar. 23, 2011, both of which are hereby incorporated by reference in their entireties and for all purposes as if fully set forth herein.

FIELD OF THE INVENTION

The present invention relates to compounds capable of inhibiting the kinase activity of cyclin dependent kinases such as CDK4 and CDK6, and compositions that include compounds that inhibit cyclin dependent kinases. The present invention also relates to compounds capable of inhibiting the kinase activity of FLT3, and compositions that include compounds that inhibit FLT3. The compounds and compositions may be used to treat various diseases or conditions modulated by these kinases such as cancer and are especially useful in treating patients with cancers.

BACKGROUND OF THE INVENTION

Acute myeloid leukemia (AML) represents a significant unmet medical need. It is a hematological malignancy characterized by a block in differentiation and aberrant proliferation of the myeloid lineage of hematopoietic progenitor cells. There are approximately 13,000 new cases and 9,000 deaths per year in the United States. The survival rate is 25-70% in patients younger than 60 years and 5-15% in older patients, with worse outcomes in patients with poor risk cytogenetics. Current standard of care treatment is daunorubicin and cytarabine chemotherapy with induction and consolidation phases. Bone marrow stem cell transplant is also used for treating AML in younger patients.

Cyclin-dependent kinases (CDKs) are a family of serine/threonine protein kinases playing important cellular functions. The cyclins are the regulatory subunits that activate the catalytic CDKs. CDK1/Cyclin B1, CDK2/Cyclin A, CDK2/Cyclin E, CDK4/Cyclin D, CDK6/Cyclin D are critical regulators of cell cycle progression. CDKs also regulate transcription, DNA repair, differentiation, senescence and apoptosis (Morgan, D. O., Annu. Rev. Cell. Dev. Biol., 13:261-291 (1997)).

Small molecule inhibitors of CDKs have been developed to treat cancer (de Carcer, G. et al., Curr. Med. Chem., 14:969-85 (2007)). A large amount of genetic evidence supports that CDKs, their substrates or regulators have been shown to be associated with many human cancers (Malumbres, M. et al, Nature Rev. Cancer, 1:222-231 (2001)). Endogenous protein inhibitors of CDKs including p16, p21 and p27 inhibit CDK activity and their overexpression results in cell cycle arrest and inhibition of tumor growth in preclinical models (Kamb, A., Curr. Top. Microbiolo. Immunol., 227:139-148 (1998)).

Small molecule inhibitors of CDKs may also be used to treat variety of other diseases that result from aberrant cell proliferation, including cardiovascular disorders, renal diseases, certain infectious diseases and autoimmune diseases. Cell proliferation pathways including genes involved in the cell cycle G1 and S phase checkpoint (p53, pRb, p15, p16, and Cyclins A, D, E, CDK 2 and CDK4) have been associated with plaque progression, stenosis and restenosis after angioplasty. Over-expression of the CDK inhibitor protein p21 has been shown to inhibit vascular smooth muscle proliferation and intimal hyperplasia following angioplasty (Chang, M. W. et al., J. Clin. Invest., 96:2260 (1995); Yang, Z-Y. et al., Proc. Natl. Acad. Sci. (USA) 93:9905 (1996)). A small molecule CDK2 inhibitor CVT-313 (Ki=95 nM) was shown to cause significant inhibition of neointima formation in animal models (Brooks, E. E. et al., J. Biol. Chem., 272:29207-29211 (1997)). Disregulation of cell cycle has been associated with polycystic kidney diseases, which are characterized by the growth of fluid-filled cysts in renal tubules. Treatment with small molecule inhibitors of CDKs yielded effective arrest of cystic disease in mouse models (Bukanov, N. O., et al., Nature, 4444:949-952 (2006)). Infection by a variety of infectious agents, including fungi, protozoan parasites such as *Plasmodium falciparum*, and DNA and RNA viruses may be treated with CDK inhibitors. CDKs have been shown to be required for replication of herpes simplex virus (HSV) (Schang, L. M. et al., J. Virol., 72:5626 (1998)). Synovial tissue hyperplasia plays important roles in the development of rheumatoid arthritis; inhibition of synovial tissue proliferation may suppress inflammation and prevent joint destruction. It has been shown that over-expression of CDK inhibitor protein p16 inhibited synovial fibroblast growth (Taniguchi, K. et al., Nat. Med., 5:760-767 (1999)) and joint swelling was substantially inhibited in animal arthritis models.

Selective inhibitors of some CDKs may also be used to protect normal untransformed cells by inhibiting specific phases of cell cycle progression (Chen, et al., J. Natl. Cancer Institute, 92:1999-2008 (2000)). Pre-treatment with a selective CDK inhibitor prior to the use of a cytotoxic agent that inhibits a different phase of the cell cycle may reduce the side effects associated with the cytotoxic chemotherapy and possibly increase the therapeutic window. It has been shown that induction of cellular protein inhibitors of CDKs (p16, p27 and p21) conferred strong resistance to paclitaxel- or cisplatin-mediated cytotoxicity on the inhibitor-responsive cells but not on the inhibitor-unresponsive cells (Schmidt, M, Oncogene, 2001 20:6164-71).

CDK4 and CDK6 are two functionally indistinguishable cyclin D dependent kinases. They are widely expressed with high levels of expression observed in cells of hematopoeitic lineage (CDK4/6 will be used throughout this document to reference both CDK4 and CDK6). CDK4/6 promotes G1-S transition of the cell cycle by phosphorylating the retinoblastoma protein (Rb). CDK4 and CDK6 single knockout mice are viable and double knockout mice die around birth with defective hematopoiesis (Satyanarayana, A. et al., Oncogene, 28:2925-39 (2009); Malumbres, M. et al., Cell, 118:493-504 (2004)). Strong evidence supports a significant involvement of the cyclin D-CDK4-p16$^{INK4A}$-Rb pathway in cancer development (Malumbres, M. et al., Nature Rev. Cancer, 1:222-31 (2001)). Rb negatively regulates the cell cycle at G1 by sequestering E2F proteins that are required for initiation of S phase. p16$^{INK4A}$ is a key member of the INK4 family of CDK4/6 cellular inhibitors. The genes for Rb and p16$^{INK4A}$ are tumor suppressors that are often deleted or silenced in cancer cells. Additionally CDK4, CDK6 and cyclin D are reported to be amplified in hematologic malignancies and solid tumors. The importance of this pathway in oncogenesis is further supported by the finding that depletion or inactivation of CDK4 inhibits tumor growth in mouse tumor models (Yu, Q. et al., Cancer Cell, 9:23-32 (2006); Puyol, M. Cancer Cell, 18:63-73 (2010)). Rb and p16$^{INK4A}$ are rarely deleted in AML. However, the p15$^{INK4B}$ gene, another member of the INK4 family, has been reported to be down regulated by hypermethylation in up to 60% of AML (Naofumi, M. et al., Leukemia Res., 29:557-64 (2005); Drexler, H. G. Leukemia, 12:845-59 (1998); Herman, J. G. et al., Cancer Res., 57:837-41 (1997)), suggesting a possible critical role for CDK4/6 in AML cells.

FLT3 (Fms-like tyrosine kinase 3, FLK2) is a class III receptor tyrosine kinase. It is activated by the FLT3 ligand (FL) and signals through the PI3K, RAS, and JAK/STAT pathways (Scholl C. et al., Semin. Oncol., 35:336-45 (2008); Meshinchi S. et al., Clin. Cancer Res., 15:4263-9 (2009)). FLT3 plays a role in early hematopoiesis and FLT3 deficient mice have reduced numbers of progenitors of multiple lymphoid lineages (Mackarehtschian K, et al., Immunity, 3:147-61 (1995). Activating mutations in FLT3 are found in approximately 30% of AML patients, representing the most frequent genetic alteration in the disease. About 75% of the activating mutations are internal tandem duplications (ITD) and 25% are point mutations in the activation loop of the kinase domain. The most frequently identified activating point mutation is D835Y (Yamamoto et al., Blood, 97(8): 2434-2439 (2001)). However, mutations have also been found at N841I (Jiang, J. et al., Blood, 104(6): 1855-1858 (2004)) and Y842C (Kindler et al., Blood, 105(1): 335-340 (2005)). Additional point mutations have been identified in the juxtamembrane domain and kinase domain, although these have been shown to result in lower transforming potential (Reindel et al., Blood 107(9): 3700-3707 (2006)).

Murine bone marrow transplanted with a retrovirus expressing the FLT3-ITD has been shown to result in the production of a lethal myeloproliferative disease in mice (Kelly et al., Blood 99: 310-318 (2002)) characterized by leukocytosis consisting of mature neutrophils. This disease did not show a block in differentiation as seen in human AML suggesting that FLT3 mutations confer a proliferative or survival advantage to the cells. Additional oncogene mutation producing a block in differentiation such as AML1/ETO is hypothesized to be required to produce disease that is more similar to human AML.

A number of FLT3 inhibitors have been tested in clinical trials. Although they have shown initial clinical responses in AML, the responses observed were transient and resistance can develop rapidly (Weisberg, E. et al., Oncogene, 29:5120-34 (2010)). The major resistance mechanism appears to be through the acquisition of secondary mutations in FLT3, which may interfere with the binding of FLT3 inhibitors to the FLT3 receptor (Weisberg, E. et al., Oncogene, 29:5120-34 (2010); Chu, S. H. et al., Drug Resist. Update, 12:8-16 (2009)). One such resistance mutation (N676K) was identified in a patient at the time of clinical relapse while on multikinase FLT3 inhibitor midostaurin (PKC412) monotherapy (Heidel, F. et al., Blood, 107:293-300 (2006)). Combinations of FLT3 inhibitors with chemotherapy are being tested in clinical trials despite the recognition that chemotherapy is poorly tolerated. Additional possible mechanisms for lack of durable responses include inadequate target coverage (Pratz, K. W., et al., Blood, 139:3938-46 (2009)) and protection of AML cells in the bone marrow where stromal growth factors may provide proliferative signals in addition to FLT3 activation (Tam, W. F. et al., Best Pract. Res. Clin. Haematol., 21:13-20 (2008)). Inhibitors with combined FLT3 and CDK4/6 inhibitory activities are novel and may prove beneficial in treating various cancers including, but not limited to, AML.

Fused tricyclic pyridine, pyrimidine, and triazine compounds useful for treating diseases mediated by CDK4 are disclosed in WO 2009/085185, published on Jul. 9, 2009, which is hereby incorporated by reference in its entirety and for all purposes as if fully set forth herein. Various gem-disubstituted and spirocyclic compounds useful for treating diseases mediated by CDK4 are disclosed in WO 2009/0126584, published on Oct. 15, 2009, which is hereby incorporated by reference in its entirety and for all purposes as if fully set forth herein.

A continued need exists for new compounds that can be used to modulate CDK4, CDK6, and/or FLT3 and can be used to treat various disease conditions associated with these kinases. The compounds of the present invention provide significant improvements in inhibition in one or more of these kinases and have properties making them excellent therapeutic candidates.

SUMMARY OF THE INVENTION

In one aspect, the invention provides a compound of Formula I:

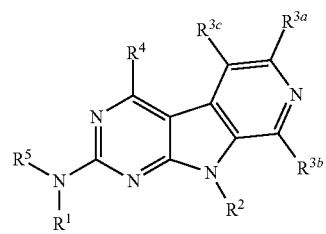

or a pharmaceutically acceptable salt thereof, a hydrate thereof, or a mixture thereof, wherein:

$R^1$ is a group of Formula IA, Formula IB, Formula IC, or Formula ID

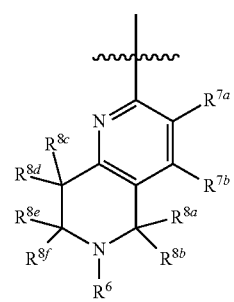

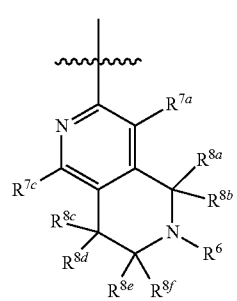

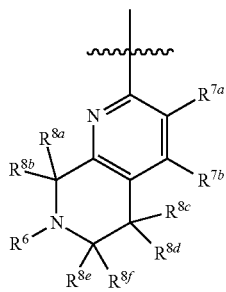

IC

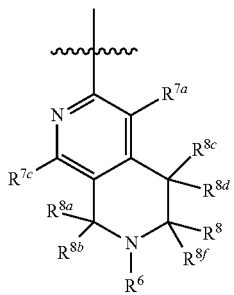

ID wherein the ⌇ symbol indicates the point of attachment of the group of Formula IA, IB, IC, or ID to the rest of the molecule;

$R^2$ is a $C_5$-$C_7$ cycloalkyl group, is a 5 to 7-membered heterocyclyl group that includes 1, 2, or 3 heteroatoms selected from N, O, and S, or is a $C_7$-$C_{10}$ bicyclic group; wherein the $C_5$-$C_7$ cycloalkyl group, the 5 to 7 membered heterocyclyl group, or the $C_7$-$C_{10}$ bicyclic group is unsubstituted or is substituted with 1-3 substituents independently selected from unsubstituted —($C_1$-$C_6$ alkyl), —OH, halo, —O—($C_1$-$C_6$ alkyl), —CO$_2$H, —C(=O)—O—($C_1$-$C_6$ alkyl), —C(=O)—NR'R", —NR'R", or a substituted —($C_1$-$C_4$ alkyl), wherein the substituted —($C_1$-$C_4$ alkyl) is substituted with 1-3 substituents independently selected from halo, —OH, —OCH$_3$, —S(=O)$_2$—CH$_3$, or —C(=O)—CH$_3$;

$R^{3a}$ is selected from —H, —F, or —Cl, —($C_1$-$C_3$ alkyl), or —O—($C_1$-$C_3$ alkyl);

$R^{3b}$ is —H, halo, —OH, —O—($C_1$-$C_6$ alkyl), unsubstituted —($C_1$-$C_6$ alkyl), —NR'R", —C(=O)—($C_1$-$C_6$ alkyl), —C(=O)—O—($C_1$-$C_6$ alkyl), —C(=O)—NR'R", or a substituted —($C_1$-$C_6$ alkyl), wherein the substituted —($C_1$-$C_6$ alkyl) is substituted with 1-3 substituents independently selected from halo, —OH, —OCH$_3$, —CN, or —NO$_2$;

$R^{3c}$ is —H, —($C_1$-$C_3$ alkyl), or halo;

$R^4$ is —H;

$R^5$ is —H;

$R^6$ is selected from —H, —($C_1$-$C_6$ alkyl), —C(=O)—($C_1$-$C_6$ alkyl), —C(=O)—O—($C_1$-$C_6$ alkyl), —C(=O)—C(=O)—OH, —C(=O)—NR'R", or —S(=O)—NR'R", wherein the alkyl group of the —($C_1$-$C_6$ alkyl), —C(=O)—($C_1$-$C_6$ alkyl), and —C(=O)—O—($C_1$-$C_6$ alkyl) groups is unsubstituted or is substituted with 1-3 substituents independently selected from —OH, F, —S(=O)$_2$—($C_1$-$C_6$ alkyl), —O—($C_1$-$C_6$ alkyl), —NR'R", or —CN;

$R^{7a}$ is —H, —CH$_3$, or halo;

$R^{7b}$ is —H, —($C_1$-$C_6$ alkyl), or halo; or $R^{7b}$ is absent if $R^1$ is a group of Formula IB or Formula ID;

$R^{7c}$ is —H, unsubstituted —($C_1$-$C_6$ alkyl), halo, —O—($C_1$-$C_6$ alkyl), —NO$_2$, —CN, —NR'R", —CO$_2$H, —C(=O)—O—($C_1$-$C_6$ alkyl), —C(=O)—NR'R", or a substituted —($C_1$-$C_6$ alkyl), wherein the substituted —($C_1$-$C_6$ alkyl) is substituted with 1-3 substituents independently selected from —OH, halo, —O—($C_1$-$C_6$ alkyl), —CN, —NR'R", or —S(=O)$_2$—CH$_3$; or $R^{7e}$ is absent if $R^1$ is a group of Formula IA or Formula IC;

$R^{8a}$ is —H, unsubstituted —($C_1$-$C_6$ alkyl), or a substituted —($C_1$-$C_6$ alkyl), wherein the substituted —($C_1$-$C_6$ alkyl) is substituted with 1-3 substituents independently selected from —OH, halo, or —O—($C_1$-$C_6$ alkyl);

$R^{8b}$ is —H, unsubstituted —($C_1$-$C_6$ alkyl), or a substituted —($C_1$-$C_6$ alkyl), wherein the substituted —($C_1$-$C_6$ alkyl) is substituted with 1-3 substituents independently selected from —OH, halo, or —O—($C_1$-$C_6$ alkyl); or $R^{8a}$ and $R^{8b}$, when taken together, can represent =O;

$R^{8c}$ is selected from —H, —OH, unsubstituted —($C_1$-$C_6$ alkyl), or a substituted —($C_1$-$C_6$ alkyl), wherein the substituted —($C_1$-$C_6$ alkyl) is substituted with 1-3 substituents independently selected from —OH, halo, or —O—($C_1$-$C_6$ alkyl);

$R^{8d}$ is —H, unsubstituted —($C_1$-$C_6$ alkyl), or a substituted —($C_1$-$C_6$ alkyl), wherein the substituted —($C_1$-$C_6$ alkyl) is substituted with 1-3 substituents independently selected from —OH, halo, or —O—($C_1$-$C_6$ alkyl);

$R^{8e}$ is —H, unsubstituted —($C_1$-$C_6$ alkyl), or a substituted —($C_1$-$C_6$ alkyl), wherein the substituted —($C_1$-$C_6$ alkyl) is substituted with 1-3 substituents independently selected from —OH, halo, or —O—($C_1$-$C_6$ alkyl);

$R^{8f}$ is —H, unsubstituted —($C_1$-$C_6$ alkyl), or a substituted —($C_1$-$C_6$ alkyl), wherein the substituted —($C_1$-$C_6$ alkyl) is substituted with 1-3 substituents independently selected from —OH, halo, or —O—($C_1$-$C_6$ alkyl); or $R^{8e}$ and $R^{8f}$, when taken together, can represent =O; and R' and R" are independently selected from —H, unsubstituted —($C_1$-$C_4$ alkyl), or —($C_1$-$C_4$ alkyl) substituted with 1 to 3 substituents independently selected from —OH or —F.

In some embodiments of the compound of Formula I or the pharmaceutically acceptable salt thereof, the hydrate thereof, or the mixture thereof, $R^2$ is a $C_5$-$C_7$ cycloalkyl group that is unsubstituted or is substituted with 1-3 substituents independently selected from unsubstituted —($C_1$-$C_6$ alkyl), —OH, halo, —O—($C_1$-$C_6$ alkyl), —CO$_2$H, —C(=O)—O—($C_1$-$C_6$ alkyl), —C(=O)—NR'R", —NR'R", or a substituted —($C_1$-$C_4$ alkyl), wherein the substituted —($C_1$-$C_4$ alkyl) is substituted with 1-3 substituents independently selected from halo, —OH, —OCH$_3$, —S(=O)$_2$—CH$_3$, or —C(=O)—CH$_3$.

In some embodiments of the compound of Formula I or the pharmaceutically acceptable salt thereof, the hydrate thereof, or the mixture thereof, $R^2$ is an unsubstituted or substituted cyclohexyl ring. In some such embodiments, $R^2$ is a cyclohexyl group substituted with a —($C_1$-$C_2$ alkyl) group. In still further such embodiments, $R^2$ is a cyclohexyl group substituted with a methyl group. In some such embodiments, $R^2$ is a group of formula

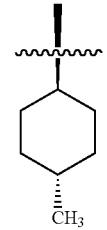

where the ⌇⌇⌇ symbol indicates the point of attachment to the rest of the molecule. In some embodiments, $R^2$ is an unsubstituted cyclohexyl group.

In some embodiments of the compound of Formula I or the pharmaceutically acceptable salt thereof, the hydrate thereof, or the mixture thereof, R' and R" are independently selected from —H or unsubstituted —($C_1$-$C_4$ alkyl).

In some embodiments of the compound of Formula I or the pharmaceutically acceptable salt thereof, the hydrate thereof, or the mixture thereof, $R^2$ is an unsubstituted or substituted cyclopentyl ring. In some such embodiments, $R^2$ is a cyclopentyl group substituted with a —($C_1$-$C_2$ alkyl) group. In still further such embodiments, $R^2$ is a cyclopentyl group substituted with a methyl group. In some such embodiments, $R^2$ is an unsubstituted cyclopentyl group.

In some embodiments of the compound of Formula I or the pharmaceutically acceptable salt thereof, the hydrate thereof, or the mixture thereof, $R^1$ is a group of Formula IA or IB. In some such embodiments, $R^1$ is a group of Formula IA. In other such embodiments, $R^1$ is a group of Formula IB.

In some embodiments of the compound of Formula I or the pharmaceutically acceptable salt thereof, the hydrate thereof, or the mixture thereof, $R^1$ is a group of Formula IC or ID. In some such embodiments, $R^1$ is a group of Formula IC. In other such embodiments, $R^1$ is a group of Formula ID.

In some embodiments of the compound of Formula I or the pharmaceutically acceptable salt thereof, the hydrate thereof, or the mixture thereof, $R^2$ is a $C_5$-$C_7$ cycloalkyl group that is unsubstituted or is substituted with 1-3-($C_1$-$C_6$ alkyl) groups;

$R^{3a}$ is selected from —H, —($C_1$-$C_3$ alkyl), or —O—($C_1$-$C_3$ alkyl);

$R^{3b}$ is —H;

$R^{3c}$ is —H;

$R^4$ is —H;

$R^5$ is —H;

$R^6$ is selected from —H, —($C_1$-$C_6$ alkyl), —C(=O)—($C_1$-$C_6$ alkyl), or —C(=O)—C(=O)—OH, wherein the alkyl group of the —($C_1$-$C_6$ alkyl) and —C(=O)—($C_1$-$C_6$ alkyl) groups is unsubstituted or is substituted with 1-3 substituents independently selected from —OH, F, —S(=O)$_2$—($C_1$-$C_6$ alkyl), or —O—($C_1$-$C_6$ alkyl);

$R^{7a}$ is —H;

$R^{7b}$ is —H; or is absent if $R^1$ is a group of Formula IB or Formula ID;

$R^{7c}$ is —H; or is absent if $R^1$ is a group of Formula IA or Formula IC;

$R^{8a}$ is —H;

$R^{8b}$ is —H;

$R^{8c}$ is selected from —H, —OH, or unsubstituted —($C_1$-$C_6$ alkyl);

$R^{8d}$ is —H;

$R^{8e}$ is —H; and $R^{8f}$ is —H.

In some such embodiments, $R^1$ is a group of Formula IA. In other embodiments, $R^1$ is a group of Formula IB. In other embodiments, $R^1$ is a group of Formula IC. In other embodiments, $R^1$ is a group of Formula ID.

In some embodiments of the compound of Formula I or the pharmaceutically acceptable salt thereof, the hydrate thereof, or the mixture thereof, $R^6$ is selected from —H, —($C_1$-$C_6$ alkyl), —C(=O)—($C_1$-$C_6$ alkyl), —C(=O)—C(=O)—OH, —C(=O)—NR'R", or —S(=O)—NR'R", wherein the alkyl group of the —($C_1$-$C_6$ alkyl) and —C(=O)—($C_1$-$C_6$ alkyl) groups is unsubstituted or is substituted with 1-3 substituents independently selected from —OH, F, —S(=O)$_2$—($C_1$-$C_6$ alkyl), —O—($C_1$-$C_6$ alkyl), —NR'R", or —CN.

In some embodiments of the compound of Formula I or the pharmaceutically acceptable salt thereof, the hydrate thereof, or the mixture thereof, the compound is the glucuronide adduct.

In some embodiments of the compound of Formula I or the pharmaceutically acceptable salt thereof, the hydrate thereof, or the mixture thereof, the compound has the Formula IIA

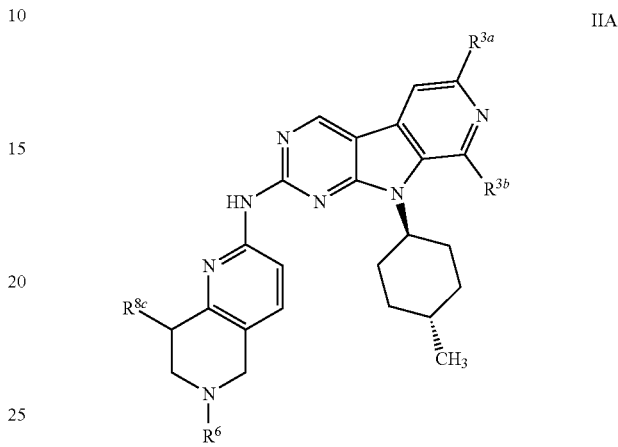

$R^{3a}$ is selected from —H, —F, or —Cl, —($C_1$-$C_3$ alkyl), or —O—($C_1$-$C_3$ alkyl);

$R^{3b}$ is —H, halo, —OH, —O—($C_1$-$C_6$ alkyl), unsubstituted —($C_1$-$C_6$ alkyl), —NR'R", —C(=O)—($C_1$-$C_6$ alkyl), —C(=O)—O—($C_1$-$C_6$ alkyl), —C(=O)—NR'R", or a substituted —($C_1$-$C_6$ alkyl), wherein the substituted —($C_1$-$C_6$ alkyl) is substituted with 1-3 substituents independently selected from halo, —OH, —OCH$_3$, —CN, or —NO$_2$;

$R^6$ is selected from —H, —($C_1$-$C_6$ alkyl), —C(=O)—($C_1$-$C_6$ alkyl), —C(=O)—C(=O)—OH, —C(=O)—NR'R", or —S(=O)—NR'R", wherein the alkyl group of the —($C_1$-$C_6$ alkyl) and —C(=O)—($C_1$-$C_6$ alkyl) groups is unsubstituted or is substituted with 1-3 substituents independently selected from —OH, F, —S(=O)$_2$—($C_1$-$C_6$ alkyl), —O—($C_1$-$C_6$ alkyl), —NR'R", or —CN; and $R^{8c}$ is selected from —H, —OH, unsubstituted —($C_1$-$C_6$ alkyl), or a substituted —($C_1$-$C_6$ alkyl), wherein the substituted —($C_1$-$C_6$ alkyl) is substituted with 1-3 substituents independently selected from —OH, halo, or —O—($C_1$-$C_6$ alkyl).

In some embodiments of the compound of Formula IIA or the pharmaceutically acceptable salt thereof, stereoisomer thereof, pharmaceutically acceptable salt of the stereoisomer, or the mixture thereof, $R^{3a}$ is selected from —H, —($C_1$-$C_3$ alkyl), or —O—($C_1$-$C_3$ alkyl);

$R^{3b}$ is —H;

$R^6$ is selected from —H, —($C_1$-$C_6$ alkyl), —C(=O)—($C_1$-$C_6$ alkyl), or —C(=O)—C(=O)—OH, wherein the alkyl group of the —($C_1$-$C_6$ alkyl) and —C(=O)—($C_1$-$C_6$ alkyl) groups is unsubstituted or is substituted with 1-3 substituents independently selected from —OH, F, —S(=O)$_2$—($C_1$-$C_6$ alkyl), or —O—($C_1$-$C_6$ alkyl); and $R^{8c}$ is selected from —H, unsubstituted —($C_1$-$C_6$ alkyl), or —OH.

In some embodiments of the compound of Formula IIA or the pharmaceutically acceptable salt thereof, the hydrate thereof, or the mixture thereof, $R^{8c}$ is selected from —H, —CH$_3$, or —OH. In some such embodiments, $R^{8c}$ is —H.

In some embodiments of the compound of Formula IIA or the pharmaceutically acceptable salt thereof, the hydrate thereof, or the mixture thereof, $R^{3b}$ is —H.

In some embodiments of the compound of Formula IIA or the pharmaceutically acceptable salt thereof, the hydrate thereof, or the mixture thereof, $R^{3c}$ is —H or —OCH$_3$. In some such embodiments, $R^{3a}$ is —H.

In some embodiments of the compound of Formula IIA or the pharmaceutically acceptable salt thereof, the hydrate thereof, or the mixture thereof, $R^6$ is selected from —H, —C(=O)—CH$_3$, —CH$_2$CH$_2$OH, —CH$_2$CH$_2$CH$_2$OH, —C(=O)—CH$_2$OH, —C(=O)—C(=O)—OH, —CH$_2$CH$_2$CF$_3$, —CH$_2$CH$_2$F, —CH$_2$CH$_2$S(=O)$_2$—CH$_3$, or —CH$_2$CH$_2$OCH$_3$. In some embodiments, $R^6$ is —H. In other embodiments, $R^6$ is selected from —C(=O)—CH$_3$ or —C(=O)—CH$_2$OH. In still other embodiments, $R^6$ is selected from —CH$_2$CH$_2$OH, —CH$_2$CH$_2$CH$_2$OH, or —CH$_2$CH$_2$OCH$_3$. In still other embodiments, $R^6$ is selected from —CH$_2$CH$_2$CF$_3$, —CH$_2$CH$_2$F, or —CH$_2$CH$_2$S(=O)$_2$—CH$_3$. In some embodiments of any of these embodiments, $R^{3a}$ is —H and $R^{3b}$ is —H. In still other such embodiments, $R^{8c}$ is —H.

In some embodiments of the compound of Formula I or the pharmaceutically acceptable salt thereof, the hydrate thereof, or the mixture thereof, the compound has the Formula IIIA

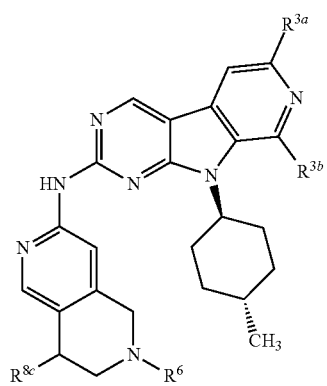

IIIA $R^{3a}$ is selected from —H, —F, or —Cl, —(C$_1$-C$_3$ alkyl), or —O—(C$_1$-C$_3$ alkyl);

$R^{3b}$ is —H, halo, —OH, —O—(C$_1$-C$_6$ alkyl), unsubstituted —(C$_1$-C$_6$ alkyl), —NR'R", —C(=O)—(C$_1$-C$_6$ alkyl), —C(=O)—O—(C$_1$-C$_6$ alkyl), —C(=O)—NR'R", or a substituted —(C$_1$-C$_6$ alkyl), wherein the substituted —(C$_1$-C$_6$ alkyl) is substituted with 1-3 substituents independently selected from halo, —OH, —OCH$_3$, —CN, or —NO$_2$;

$R^6$ is selected from —H, —(C$_1$-C$_6$ alkyl), —C(=O)—(C$_1$-C$_6$ alkyl), —C(=O)—C(=O)—OH, —C(=O)—NR'R", or —S(=O)—NR'R", wherein the alkyl group of the —(C$_1$-C$_6$ alkyl) and —C(=O)—(C$_1$-C$_6$ alkyl) groups is unsubstituted or is substituted with 1-3 substituents independently selected from —OH, F, —S(=O)$_2$—(C$_1$-C$_6$ alkyl), —O—(C$_1$-C$_6$ alkyl), —NR'R", or —CN; and $R^{8c}$ is selected from —H, —OH, unsubstituted —(C$_1$-C$_6$ alkyl), or a substituted —(C$_1$-C$_6$ alkyl), wherein the substituted —(C$_1$-C$_6$ alkyl) is substituted with 1-3 substituents independently selected from —OH, halo, or —O—(C$_1$-C$_6$ alkyl).

In some embodiments of the compound of Formula IIIA or the pharmaceutically acceptable salt thereof, the hydrate thereof, or the mixture thereof, $R^{3a}$ is selected from —H, —(C$_1$-C$_3$ alkyl), or —O—(C$_1$-C$_3$ alkyl);

$R^{3b}$ is —H;

$R^6$ is selected from —H, —(C$_1$-C$_6$ alkyl), —C(=O)—(C$_1$-C$_6$ alkyl), or —C(=O)—C(=O)—OH, wherein the alkyl group of the —(C$_1$-C$_6$ alkyl) and —C(=O)—(C$_1$-C$_6$ alkyl) groups is unsubstituted or is substituted with 1-3 substituents independently selected from —OH, F, —S(=O)$_2$—(C$_1$-C$_6$ alkyl), or —O—(C$_1$-C$_6$ alkyl); and $R^{8c}$ is selected from —H, unsubstituted —(C$_1$-C$_6$ alkyl), or —OH.

In some embodiments of the compound of Formula IIIA or the pharmaceutically acceptable salt thereof, the hydrate thereof, or the mixture thereof, $R^{8c}$ is —H.

In some embodiments of the compound of Formula IIIA or the pharmaceutically acceptable salt thereof, the hydrate thereof, or the mixture thereof, $R^{3b}$ is —H.

In some embodiments of the compound of Formula IIIA or the pharmaceutically acceptable salt thereof, the hydrate thereof, or the mixture thereof, $R^{3a}$ is —H or —OCH$_3$. In some such embodiments, $R^{3a}$ is —H In some embodiments of the compound of Formula IIIA or the pharmaceutically acceptable salt thereof, the hydrate thereof, or the mixture thereof, $R^6$ is selected from —H, —C(=O)—CH$_3$, —CH$_2$CH$_2$OH, —CH$_2$CH$_2$CH$_2$OH, —C(=O)—CH$_2$OH, —C(=O)—C(=O)—OH, —CH$_2$CH$_2$CF$_3$, —CH$_2$CH$_2$F, —CH$_2$CH$_2$S(=O)$_2$—CH$_3$, or —CH$_2$CH$_2$OCH$_3$. In other embodiments, $R^6$ is —H. In still other embodiments, $R^6$ is selected from —C(=O)—CH$_3$ or —C(=O)—CH$_2$OH. In still other embodiments, $R^6$ is selected from —CH$_2$CH$_2$OH, —CH$_2$CH$_2$CH$_2$OH, or —CH$_2$CH$_2$OCH$_3$. In still further embodiments, $R^6$ is selected from —CH$_2$CH$_2$CF$_3$, —CH$_2$CH$_2$F, or —CH$_2$CH$_2$S(=O)$_2$—CH$_3$. In some embodiments of any of these embodiments, $R^{3a}$ is —H and $R^{3b}$ is —H. In still other such embodiments, $R^{8c}$ is —H.

In some embodiments of the compound of Formula, the compound is selected from

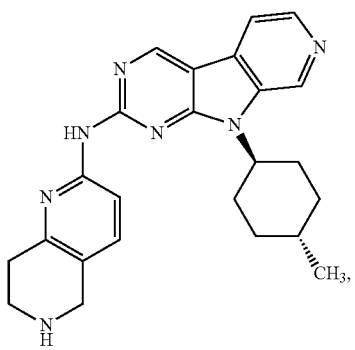

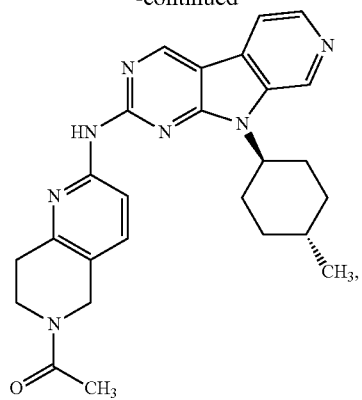
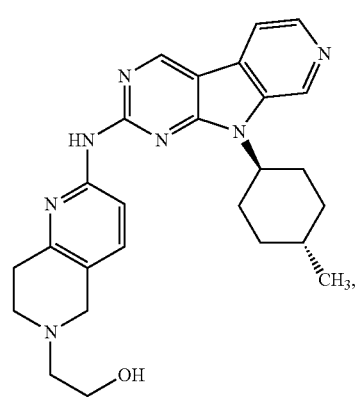
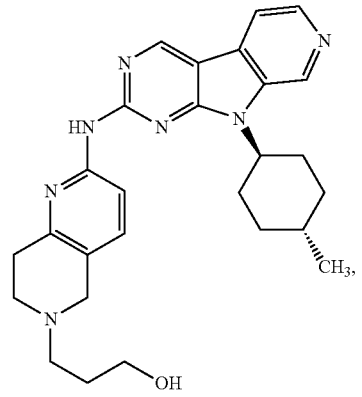
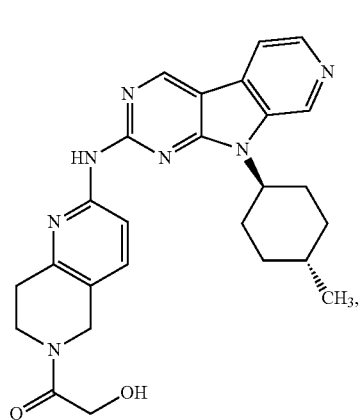
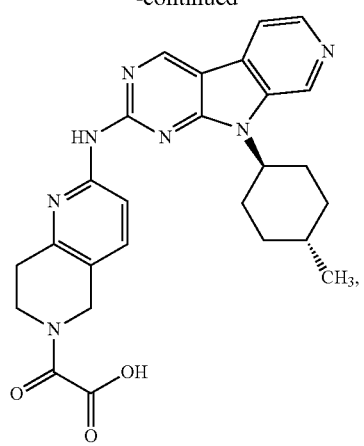
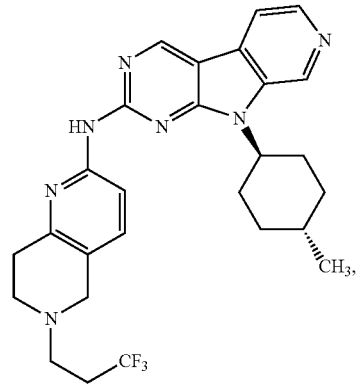
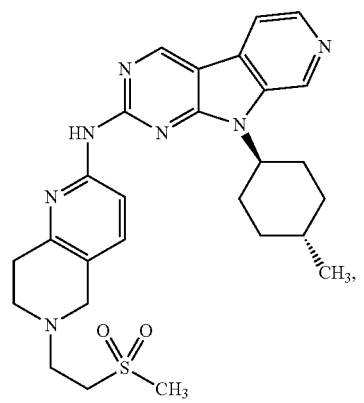
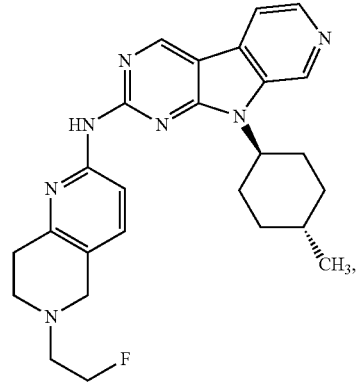

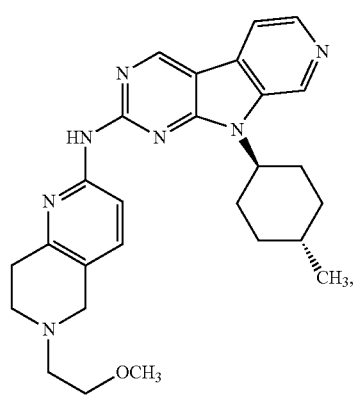
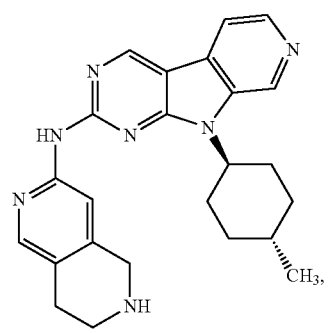
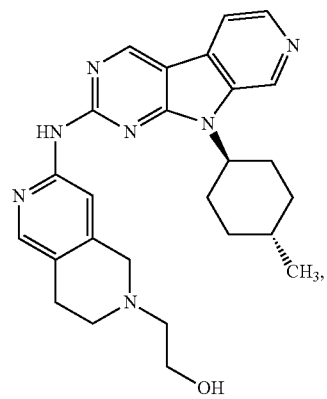
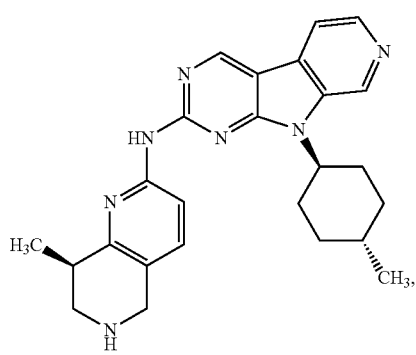
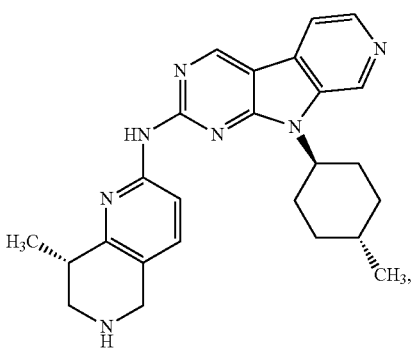
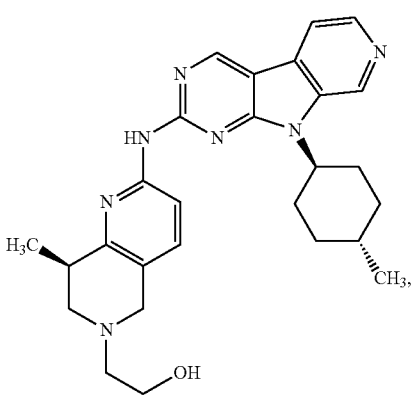
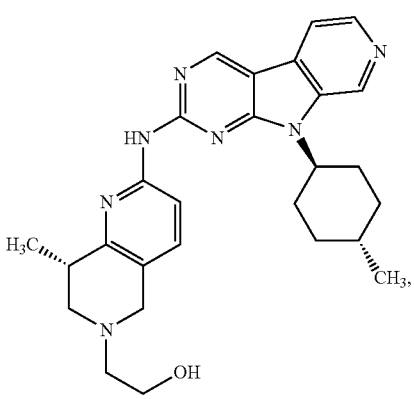
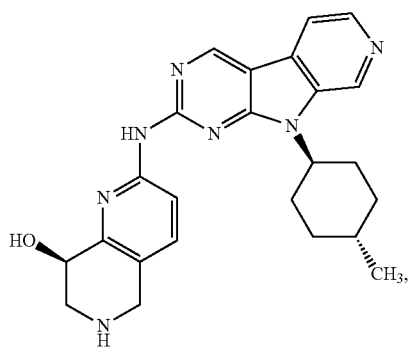

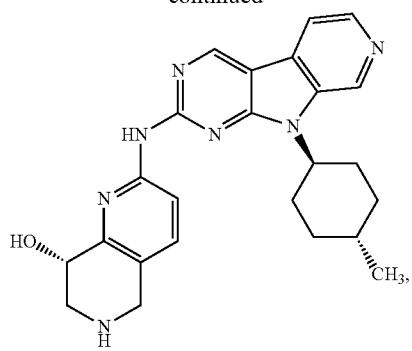
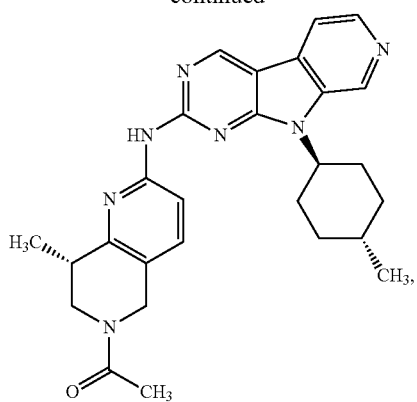
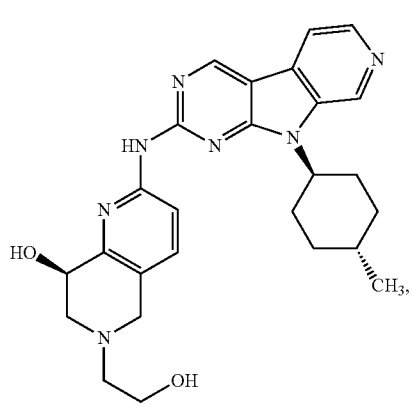
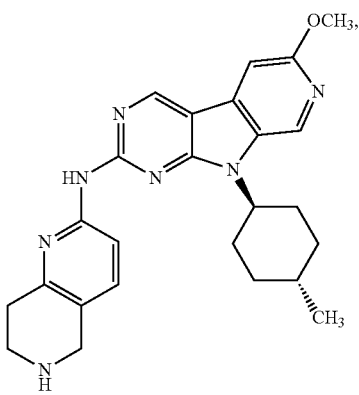
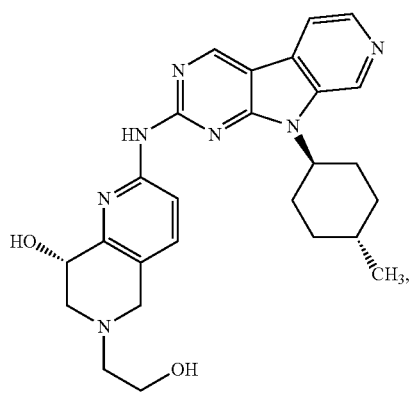
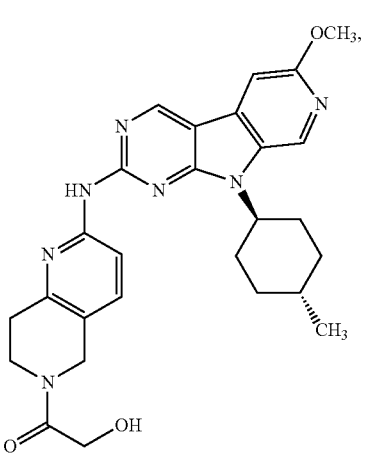
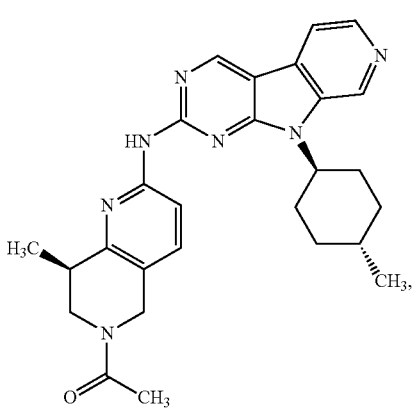
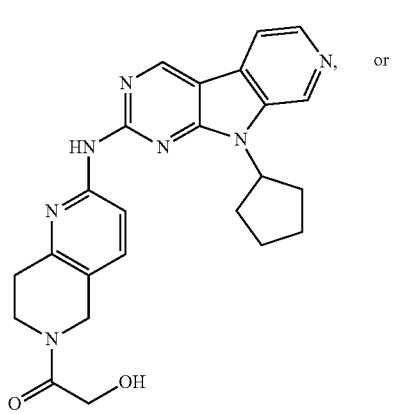

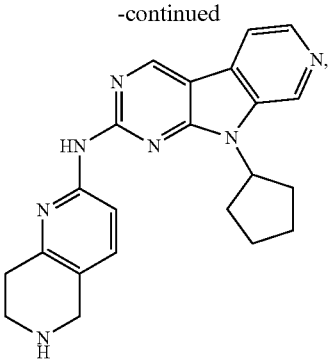

or is a pharmaceutical salt or hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt. For example, in some embodiments, the compound may be a chloride salt that is a monohydrate, a dihydrate, or a trihydrate.

In some embodiments of the compound of Formula I or the pharmaceutically acceptable salt thereof, the hydrate thereof, or the mixture thereof, the compound is in a neutral form.

In some embodiments of the compound of Formula I or the pharmaceutically acceptable salt thereof, the hydrate thereof, or the mixture thereof, the compound is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt.

Also provided are pharmaceutical compositions that include at least one pharmaceutically acceptable carrier, excipient or diluent and a therapeutically effective amount of the compound, the pharmaceutically acceptable salt, the hydrate, or the mixture thereof according to any of the embodiments described herein. In some such embodiments, the compound is present in an amount effective for the treatment of cancer. In some embodiments, the pharmaceutical composition includes at least one pharmaceutically acceptable carrier, excipient or diluent and a therapeutically effective amount of the compound in a neutral form. In other embodiments, the pharmaceutical composition includes at least one pharmaceutically acceptable carrier, excipient or diluent and a therapeutically effective amount of the pharmaceutically acceptable salt. In some such embodiments, the salt is a chloride salt. In other embodiments the salt is a methanesulfonate salt. In still other embodiments the salt is a benzenesulfonate salt. In some of any of these embodiments, the pharmaceutical composition further includes at least one second therapeutic agent. In some such embodiments, the second therapeutic agent is one that is used in treating cancer. In some such embodiments, the second therapeutic agent is used in treating acute myeloid leukemia or any of the other cancers described below. In some embodiments, the second therapeutic agent is selected from cytosine arabinoside, daunorubicin, idarubicin, doxorubicin, cyclophosphamide, etoposide, carboplatin, fludarabine, mitoxantrone, dexamethasone, rituximab, midostaurin, a granulocyte colony-stimulating factor, filgrastim, PEG-filgrastim, lenograstim, decitabine, azacitidine, paclitaxel, gemcitibine, motesanib disphosphate, panitumumab, an antibody directed against CD33, or a CD33 bispecific T-cell engager antibody. In other embodiments, the second therapeutic agent is selected from cytosine arabinoside, daunorubicin, idarubicin, doxorubicin, cyclophosphamide, etoposide, carboplatin, fludarabine, mitoxantrone, dexamethasone, rituximab, midostaurin, a granulocyte colony-stimulating factor, filgrastim, PEG-filgrastim, lenograstim, decitabine, azacitidine, paclitaxel, gemcitibine, motesanib disphosphate, panitumumab. In still other such embodiments, the second therapeutic agent is selected from cytosine arabinoside, daunorubicin, idarubicin, doxorubicin, cyclophosphamide, etoposide, carboplatin, fludarabine, mitoxantrone, dexamethasone, rituximab, midostaurin, decitabine, azacitidine, paclitaxel, gemcitibine, or motesanib disphosphate. In some such embodiments, the second therapeutic agent is cytosine arabinoside. In other embodiments, the second therapeutic agent is daunorubicin, idarubicin, or doxorubicin. In still other embodiments, the second therapeutic agent is azacitidine or decitabine. In some embodiments, the second therapeutic agent is an anthracycline. In some embodiments, the second therapeutic agent is an aurora kinase inhibitor such as N-(4-((3-(2-amino-4-pyrimidinyl)-2-pyridinyl)oxy)phenyl)-4-(4-methyl-2-thienyl)-1-phthalazinamine or another compound disclosed in WO 2007/087276.

Further provided are pharmaceutical compositions that include at least one pharmaceutically acceptable carrier, and a therapeutically effective amount of the composition of matter of any of the embodiments described herein in combination with at least one additional compound such as a cytotoxic agent or a compound that inhibits another kinase.

In other embodiments, the invention provides a method of treating cancer. In some such embodiments, the cancer is resistant to other agents such as to an anthracycline therapeutic agent. Such methods typically include administering to a subject an effective amount of the compound, the pharmaceutically acceptable salt thereof, the hydrate thereof, or the mixture thereof of any of the embodiments or a pharmaceutical composition of any of the embodiments. In some such embodiments, the cancer is selected from acute myeloid leukemia, acute lymphoblastic leukemia myelodysplastic syndrome, multiple myeloma, chronic myeloid leukemia, acute lymphocytic leukemia, chronic lymphocytic leukemia, non-Hodgkin lymphoma, another lymphoma, another myeloma, or another leukemia. Examples of other cancers that may be treated with the compounds of the present invention include Burkitt's lymphoma and mantle cell lymphoma. In some such embodiments, the cancer is acute myeloid leukemia. In some such embodiments, the subject is a human patient with mutant FLT3 such as a patient with FLT3-ITD positive acute myeloid leukemia. In some such embodiments, the method may also include determining whether the patient has FLT3-ITD positive acute myeloid leukemia. For example, such a method might include obtaining a sample from a patient and analyzing whether the sample is FLT3-ITD positive. In other such embodiments, the subject is a human patient with wild type FLT3 acute myeloid leukemia. In another embodiment, the cancer is acute lymphoblastic leukemia. In other embodiments, the cancer is selected from breast cancer, colorectal cancer, small cell lung carcinoma, head and neck, glioblastoma, pancreatic, gastrointestinal, liver, prostate, ovarian, testicular, endometrial, bladder, melanoma, osteosarcoma, or another sarcoma. In some embodiments, the cancer is Rb-positive whereas in other embodiments, the cancer is not Rb-positive. In some embodiments, the subject is a mammal, and in some embodiments, is a human cancer patient. In some such embodiments, the cancer is a hematological cancer. In other embodiments, the cancer is a solid tumor. In some embodiments, the method includes administering to a subject an effective amount of the compound, the pharmaceutically acceptable salt thereof, the hydrate thereof, or the mixture thereof of any of the embodiments or a pharmaceutical composition of any of the embodiments where the patient is a human cancer patient with mutant FLT3 and in some such embodiments is a human cancer patient with FLT3-ITD.

As noted above, the compounds of the invention have been found to be active in cancer cells, for example acute myeloid leukemia cells, that are both wild type and mutant with respect to FLT3. Therefore, in some embodiments, the invention provides methods for treating cancer in patients with wild type FLT3 whereas in other embodiments, the invention provides methods for treating cancer in patients with mutant FLT3. Such methods typically include administering to a subject such as a human cancer patient an effective amount of the compound, the pharmaceutically acceptable salt thereof, the hydrate thereof, or the mixture thereof of any of the embodiments or a pharmaceutical composition of any of the embodiments. In some such embodiments, the cancer is acute myeloid leukemia. In some such embodiments, the subject is a human patient with mutant FLT3 such as a patient that tests positive for a mutant FLT3 acute myeloid leukemia. Examples of FLT3 mutants include, but are not limited to, FLT3-ITD, FLT3 with activation loop point mutations such as FLT3-D835Y, FLT3-D835H, and FLT3-D835V, FLT3-K663Q, and FLT3-N841I. Therefore, in some embodiments, the FLT3 mutant is FLT3-ITD. In other embodiments, the FLT3 mutant is FLT3-D835Y. In still other embodiments, the FLT3 mutant is FLT3-D835H. In other embodiments, the FLT3 mutant is FLT3-D835V. In still other embodiments, the FLT3 mutant is FLT3-K663Q. In still further such embodiments, the FLT3 mutant is FLT3-N841I. In some such embodiments, the method may include determining whether the patient has mutant FLT3 acute myeloid leukemia. For example, such a method might include obtaining a sample from a patient and analyzing whether the sample tests positive for one or more FLT3 mutant. In some embodiments, the method includes administering to a subject an effective amount of the compound, the pharmaceutically acceptable salt thereof, the hydrate thereof, or the mixture thereof of any of the embodiments or a pharmaceutical composition of any of the embodiments where the patient is a human cancer patient with mutant FLT3 and in some such embodiments is a human cancer patient with acute myeloid leukemia.

In some methods of treating cancer, the patient is a human cancer patient with a solid or hematological tumor in which the tumor exhibits low $p15^{INK4B}$ and/or low $p16^{INK4A}$ expression and in some such embodiments is a human patient with acute myeloid leukemia where the tumor exhibits low $p15^{INK4A}$ and/or low $p16^{INK4A}$ expression. In some embodiments, a tumor that exhibits low $p15^{INK4B}$ and/or low $p16^{INK4A}$ expression is determined using an assay that measures the levels of these proteins or mRNA or both and compares them to the levels in a normal myeloid tumor. This method could also be used for other tumor types. A tumor that contains less of the $p15^{INK4B}$ and/or $p16^{INK4A}$ proteins or mRNA or both than is found in a normal cell would be one that exhibits low $p15^{INK4B}$ and/or $p16^{INK4A}$ expression. In some embodiments, the tumor includes less than 90%, less than 80%, less than 70%, less than 60%, or less than 50% of $p15^{INK4B}$ and/or $p16^{INK4A}$ than occurs in a normal cell.

Any of the methods described herein may include the use of a second therapeutic agent such as those described above.

For example, in one embodiment, the invention provides a method of treating cancer which includes administering to a subject (a) an effective amount of the compound, the pharmaceutically acceptable salt thereof, the hydrate thereof or the mixture thereof of any of the embodiments or the pharmaceutical composition of any of the embodiments; and (b) at least one second therapeutic agent used in the treatment of cancer. In some such embodiments, the second therapeutic agent is used in treating acute myeloid leukemia or any of the other cancers described herein. In some embodiments, the second therapeutic agent is selected from cytosine arabinoside, daunorubicin, idarubicin, doxorubicin, cyclophosphamide, etoposide, carboplatin, fludarabine, mitoxantrone, dexamethasone, rituximab, midostaurin, a granulocyte colony-stimulating factor, filgrastim, PEG-filgrastim, lenograstim, decitabine, azacitidine, paclitaxel, gemcitibine, motesanib disphosphate, panitumumab, an antibody directed against CD33, or a CD33 bispecific T-cell engager antibody. In other embodiments, the second therapeutic agent is selected from cytosine arabinoside, daunorubicin, idarubicin, doxorubicin, cyclophosphamide, etoposide, carboplatin, fludarabine, mitoxantrone, dexamethasone, rituximab, midostaurin, a granulocyte colony-stimulating factor, filgrastim, PEG-filgrastim, lenograstim, decitabine, azacitidine, paclitaxel, gemcitibine, motesanib disphosphate, panitumumab. In still other such embodiments, the second therapeutic agent is selected from cytosine arabinoside, daunorubicin, idarubicin, doxorubicin, cyclophosphamide, etoposide, carboplatin, fludarabine, mitoxantrone, dexamethasone, rituximab, midostaurin, decitabine, azacitidine, paclitaxel, gemcitibine, or motesanib disphosphate. In some such embodiments, the second therapeutic agent is cytosine arabinoside. In other embodiments, the second therapeutic agent is daunorubicin, idarubicin, or doxorubicin. In still other embodiments, the second therapeutic agent is azacitidine or decitabine. In some embodiments, the second therapeutic agent is an anthracycline. In some embodiments, the second therapeutic agent is an aurora kinase inhibitor such as N-(4-((3-(2-amino-4-pyrimidinyl)-2-pyridinyl)oxy)phenyl)-4-(4-methyl-2-thienyl)-1-phthalazinamine or another compound disclosed in WO 2007/087276. In some embodiments, the compound, the pharmaceutically acceptable salt thereof, or the mixture thereof of any of the embodiments or the pharmaceutical composition of any of the embodiments is administered to the subject after the at least one second therapeutic agent is administered to the subject. In other embodiments, the compound, the pharmaceutically acceptable salt thereof, or the hydrate thereof, or the mixture thereof of any of the embodiments or the pharmaceutical composition of any of the embodiments is administered to the subject before the at least one second therapeutic agent is administered to the subject. In still other embodiments, the compound, the pharmaceutically acceptable salt thereof, the hydrate thereof, or the mixture thereof of any of the embodiments or the pharmaceutical composition of any of the embodiments is administered to the subject at the same time that the at least one second therapeutic agent is administered to the subject.

The invention further provides a compound for use in the preparation of a medicament. Any of the compounds, salts, hydrates or mixtures of any of the embodiments described herein can be used to prepare the medicament. In some embodiments, the cancer is selected from acute myeloid leukemia, myelodysplastic syndrome, multiple myeloma, chronic myeloid leukemia, acute lymphocytic leukemia, chronic lymphocytic leukemia, non-Hodgkin lymphoma, another lymphoma, another myeloma, or another leukemia. In some such embodiments, the cancer is acute myeloid leukemia. In other embodiments, the cancer is selected from breast cancer, colorectal cancer, small cell lung carcinoma, head and neck, glioblastoma, pancreatic, gastrointestinal, liver, prostate, ovarian, testicular, endometrial, bladder, melanoma, osteosarcoma, or another sarcoma. In some embodiments, the cancer is Rb-positive whereas in other embodiments, the cancer is not Rb-positive. In some embodiments, the subject is a human cancer patient and, in some such embodiments, the cancer is a hematological cancer.

Other objects, features and advantages of the invention will become apparent to those skilled in the art from the following description and claims.

BRIEF DESCRIPTION OF THE DRAWINGS

FIG. 3 is an X-ray Powder Diffraction (XRPD) Spectrum of the hydrochloride salt of Example 5 showing 2Theta (°) on the x-axis and Intensity (counts) on the y axis.

DETAILED DESCRIPTION OF THE INVENTION

Figure 1:
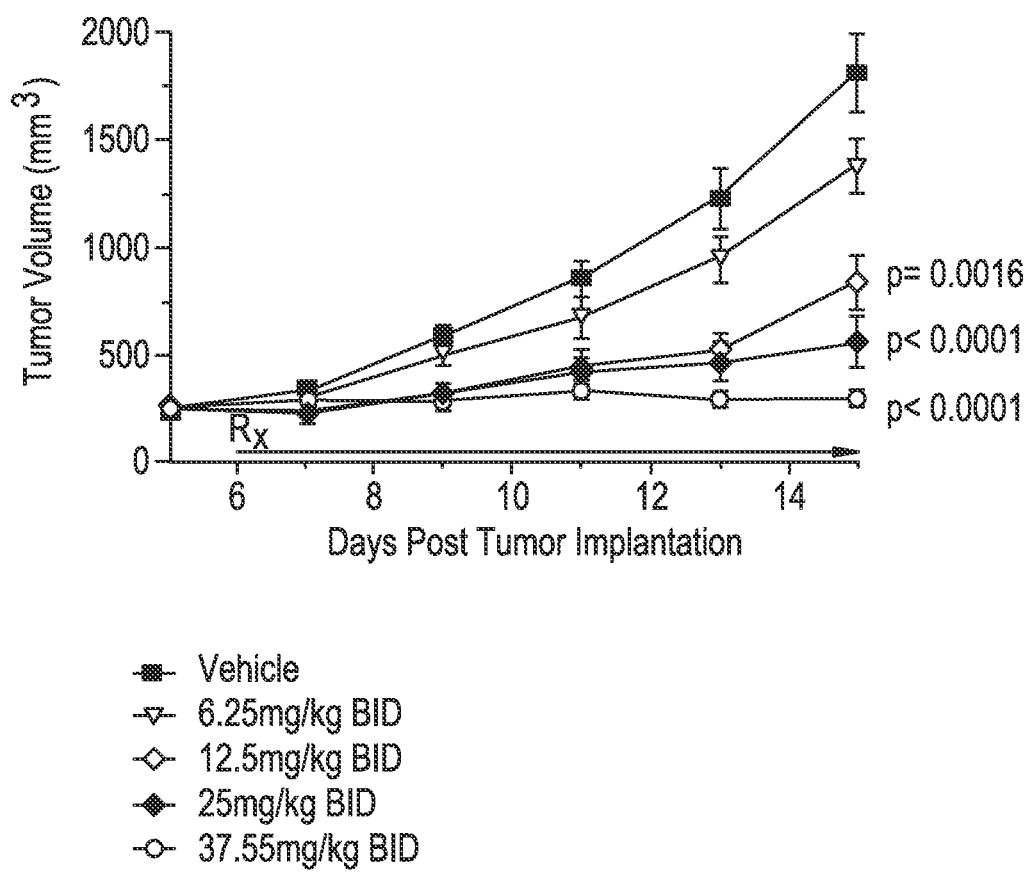
FIG. 1 is a graph showing the dose dependent anti-tumor activity observed after twice daily dosing (BID) with Example 5 in CrTac:NCR-Foxn1$^{nu}$ nude mice with MOLM13 subcutaneous xenograft tumors.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound. The compounds of the present disclosure may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan.

Certain compounds of the invention may possess asymmetric carbon atoms (optical centers) or double bonds; the racemates, enantiomers, diastereomers, geometric isomers and individual isomers are all intended to be encompassed within the scope of the invention. Furthermore, atropisomers and mixtures thereof such as those resulting from restricted rotation about two aromatic or heteroaromatic rings bonded to one another are intended to be encompassed within the scope of the invention. As noted above, various compounds of the invention may contain one or more chiral centers, and can exist as racemic mixtures of enantiomers, mixtures of diastereomers or enantiomerically or optically pure compounds. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al. (1997) Tetrahedron 33:2725; Eliel, E. L., Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, 1N, 1972).

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed.

As known by those skilled in the art, certain compounds of the invention may exist in one or more tautomeric forms. Because one chemical structure may only be used to represent one tautomeric form, it will be understood that for convenience, referral to a compound of a given structural formula includes tautomers of the structure represented by the structural formula. The same is true with respect to stereoisomers unless a specific stereochemistry is shown or noted. For example, a compound of a specific formula includes all stereoisomers or mixtures thereof. Similarly, a pharmaceutically acceptable salt of the compound includes pharmaceutically acceptable salts of all individual stereoisomers or mixtures thereof.

As noted above, prodrugs also fall within the scope of chemical entities, for example, ester or amide derivatives of the compounds of Formula I. The term "prodrugs" includes any compounds that become compounds of Formula I when administered to a patient, e.g., upon metabolic processing of the prodrug. Examples of prodrugs include, but are not limited to, acetate, formate, benzoate, carbomethoxy, carboethoxy and like derivatives of functional groups (such as alcohol, carboxylic acid, ether, ester, or amine groups) in the compounds of Formula I.

The term "solvate" refers to the compound formed by the interaction of a solvent and a compound. Suitable solvates are pharmaceutically acceptable solvates, such as hydrates, including monohydrates and hemi-hydrates. The term hydrate refers to monohydrates, dihydrates, and trihydrates.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic or prophylactic agents, research reagents, e.g., assay reagents such as the $^{14}$C thymidine incorporation assay, and diagnostic agents, e.g., in vivo imaging agents. All isotopic variations of the compounds of the invention, whether radioactive or not, are intended to be encompassed within the scope of the invention. For example, if a variable is said to be H or —H, this means that the variable may also be deuterium (D) or tritium (T).

As used herein, the terms "comprising" and "including" and other forms of these words are used herein in their open, non-limiting sense. For example, if a composition is said to comprise A, B, and C, then A, B, and C are in the composition, but D, E, and/or F may be in the composition as well.

"CDK4" refers to cyclin dependent kinase 4. Cyclin dependent kinases are a family of serine/threonine kinases that play important roles in cellular function and cell cycle progression. CDK4 is a catalytic subunit of the protein kinase complex that is important for cell cycle G1 phase progression. The activity of CDK4 is restricted to the G1-S phase, which is controlled by the regulatory subunits D-type cyclins and CDK inhibitor p16$^{INK4A}$. CDK4 has been demonstrated to be responsible for the phosphorylation of retinoblastoma gene product (Rb). Mutations in this gene as well as in its related proteins including D-type cyclins, p16$^{INK4A}$ and Rb have all been found to be associated with tumorigenesis in a variety of cancers.

"CDK6" refers to cyclin dependent kinase 6. Cyclin dependent kinases are a family of serine/threonine kinases that play important roles in cellular function and cell cycle progression. CDK6 is a catalytic subunit of a protein kinase complex important for cell cycle G1 phase progression and G1/S transition. The activity of CDK6 first appears mid-G1 phase, which is controlled by the regulatory subunits including D-type cyclins and members of INK4 family of CDK inhibitors. CDK6 kinase has also been shown to phosphorylate, and thus regulate the activity of, tumor suppressor protein Rb.

"FLT3" refers to FMS-like receptor tyrosine kinase. FLT3 is a member of the class III tyrosine kinase receptor family. Structural features of this family include an extracellular domain containing five immunoglobulin-like domains, a transmembrane domain a juxtamembrane domain and an intracellular region containing tyrosine kinase activity. Several mutations in FLT3 have been identified and shown to result in constitutive activation of the receptor. In acute myeloid leukemia, these mutations are the most common genetic alteration associated with the disease, making up approximately 25% of patients with AML. FLT3 has been shown to phosphorylate and regulate the activity of STAT5.

"FLT3-ITD" refers to FLT3 internal tandem duplication. FLT3-ITD is a somatic mutation in acute myeloid leukemia with variation in the position, length, and number of duplications of the FLT3 gene. A patient with FLT3-ITD positive acute myeloid leukemia is a patient with acute myeloid leukemia in which the FLT3 gene exhibits this duplication.

The phrase "Rb-positive" refers to cells that express a functional retinoblastoma (Rb) protein. Rb is a tumor suppressor that regulates progression of cells through the cell cycle at the G1-S transition. Phosphorylation of Rb regulates its activity. When Rb is in a hypophosphorylated state, it prevents cell cycle progression and allows it to carry out its tumor suppressor function. Many cancer cells have been shown to contain mutated or deleted Rb.

The term "alkyl" refers to a saturated, branched or straight-chain monovalent hydrocarbon group derived by the removal of one hydrogen atom from a single carbon atom of a parent alkane. Typical alkyl groups include, but are not limited to, methyl (—CH$_3$); ethyl (—CH$_2$CH$_3$); propyls such as propan-1-yl (—CH$_2$CH$_2$CH$_3$), and propan-2-yl (—CH(CH$_3$)$_2$); and butyls such as butan-1-yl (—CH$_2$CH$_2$CH$_2$CH$_3$), butan-2-yl, —CH(CH$_3$)CH$_2$CH$_3$ 2-methyl-propan-1-yl (—CH$_2$CH(CH$_3$)$_2$, 2-methyl-propan-2-yl (—C(CH$_3$)$_3$), and tert-butyl (—C(CH$_3$)$_3$); and the like. In certain embodiments, an alkyl group comprises 1 to 20 carbon atoms. In some embodiments, alkyl groups include 1 to 6 carbon atoms whereas in other embodiments, alkyl groups include 1 to 4 or 1 to 3 carbon atoms. In still other embodiments, an alkyl group includes 1 or 2 carbon atoms. Branched chain alkyl groups include at least 3 carbon atoms and typically include 3 to 7, or in some embodiments, 3 to 6 carbon atoms. An alkyl group having 1 to 6 carbon atoms may be referred to as a —(C$_1$-C$_6$)alkyl or —(C$_1$-C$_6$)alkyl group, an alkyl group having 1 to 4 carbon atoms may be referred to as a —(C$_1$-C$_4$)alkyl or —(C$_1$-C$_4$) alkyl, and an alkyl group having 1 to 3 carbon atoms may be referred to as a —(C$_1$-C$_3$)alkyl or —(C$_1$-C$_3$)alkyl. The same designation system applies to alkyl groups with different numbers of carbon atoms. Alkyl groups may be substituted or may be unsubstituted. In some embodiments, alkyl groups are unsubstituted. In other embodiments, an alkyl group may be substituted with one or more substituents. For example, in some embodiments, an alkyl group may be substituted with 1, 2 or 3 substituents whereas in another embodiment, an alkyl group may, where permitted by valence, be substituted with 1 to 5 substituents.

The term "alkoxy" refers to a radical —OR where R represents a straight or branched chain alkyl group as defined above. Representative examples include, but are not limited to, methoxy (—OCH$_3$), ethoxy (—OCH$_2$CH$_3$), propoxy (—OCH$_2$CH$_2$CH$_3$), isopropoxy (—OCH(CH$_3$)$_2$), butoxy (—OCH$_2$CH$_2$CH$_2$CH$_3$), pentoxy(—OCH$_2$CH$_2$CH$_2$CH$_2$CH$_3$), t-butoxy (—OC(CH$_3$)$_3$) and the like. Typical alkoxy groups include 1 to 10 carbon atoms, 1 to 6 carbon atoms, 1 to 4 carbon atoms, 1 to 3 carbon atoms, or 1 to 2 carbon atoms in the R group. Alkoxy groups that include 1 to 6 carbon atoms may be designated as —O—(C$_1$-C$_6$ alkyl) groups. Similarly, alkoxy groups that include 1 to 3 carbon atoms may be designated as —O—(C$_1$-C$_3$ alkyl) groups. Other alkoxy groups may be represented using the same methodology.

The term "carboxy" refers to the radical —C(O)OH which may alternatively be written as —C(=O)OH, —C(=O)—OH, —COOH or —CO$_2$H. When the H atom of a carboxy group is removed and replaced with a bond to an alkyl group, the group may be written as —C(=O)—O-alkyl. Typical such groups include alkyl groups with 1 to 10 carbon atoms, 1 to 6 carbon atoms, 1 to 4 carbon atoms, 1 to 3 carbon atoms, or 1 to 2 carbon atoms. —C(=O)—O-alkyl groups that include alkyl groups with 1 to 6 carbon atoms may be designated as —C(=O)—O—(C$_1$-C$_6$ alkyl) groups. Similarly, such groups that include alkyl groups with 1 to 4 or 1 to 3 carbon atoms may be respectively designated as —C(=O)—O—(C$_1$-C$_4$ alkyl) and —C(=O)—O—(C$_1$-C$_3$ alkyl) groups. Other such groups may be represented using the same methodology.

The term "carbonyl" refers to a radical —C(=O)—. Carbonyl groups may be bonded to alkyl groups and written as —C(=O)-alkyl groups where alkyl has the meaning set forth above. Typical alkyl groups in such —C(=O)-alkyl groups have 1 to 10 carbon atoms, 1 to 6 carbon atoms, 1 to 4 carbon atoms, 1 to 3 carbon atoms, or 1 to 2 carbon atoms. The —C(=O)-alkyl groups with alkyl groups of 1 to 6 carbon atoms may be designated as —C(=O)—($C_1$-$C_6$ alkyl) groups. Similarly, such groups where the alkyl groups have 1 to 4 or 1 to 3 carbon atoms may be respectively designated as —C(=O)—($C_1$-$C_4$ alkyl) and —C(=O)—($C_1$-$C_3$ alkyl) groups. Other such groups may be represented using the same methodology.

The term "cyano" refers to the radical —CN which may also be written as —CN.

The term "cycloalkyl" refers to a saturated cyclic alkyl group derived by the removal of one hydrogen atom from a single carbon atom of a parent cycloalkane. Typical cycloalkyl groups include, but are not limited to, cyclopropane, cyclobutane, cyclopentane, cyclohexane, cycloheptane and the like. In certain embodiments, the cycloalkyl group can be $C_3$-$C_{10}$ cycloalkyl, such as, for example, $C_3$-$C_6$ cycloalkyl. In some embodiments, a cycloalkyl group is a $C_5$-$C_7$ group such as a cyclopentyl, cyclohexyl, or cycloheptyl group. Cycloalkyl groups may be substituted or unsubstituted.

The term "bicyclic group" refers to a cyclic alkyl group that includes two, three, or more rings derived by the removal of one hydrogen atom from a single carbon atom of a parent bicyclic cycloalkane. Typical bicyclic groups include, but are not limited to, adamantyl, norbornyl, decalinyl, octahydro-1H-indenyl, bicyclo[2.2.2]octanyl, octahydropentalenyl, and the like. In certain embodiments, the bicyclic group is $C_6$-$C_{14}$ bicyclic group, a $C_6$-$C_{10}$ bicyclic group, a $C_7$-$C_{14}$ bicyclic group, a $C_7$-$C_{10}$ bicyclic group, or a similar type bicyclic group. In some embodiments, a bicyclic group is a $C_7$-$C_{10}$ group. Cycloalkyl groups may be substituted or unsubstituted.

The term "heterocyclyl group" refers to a cycloalkyl group, except that in a heterocyclyl group at least one ring atom is replaced by a heteroatom. Typically, heterocyclyl groups are characterized by the number of ring members and include 1, 2, or 3 heteroatoms independently selected from N, O, or S. In some embodiments, the heterocyclyl group can have 3 to 10 ring members, from 3 to 7 ring members, or from 5 to 7 ring members. In some embodiments, a heterocyclyl group is a 5 to 7 membered ring that includes 1, 2, or 3 heteroatoms independently selected from N, O, or S. Examples of heterocyclyl groups include, but are not limited to, aziridinyl, azetidinyl, oxetanyl, thiatanyl, tetrahydrofuranyl, tetrahydrothiophenyl, pyrrolidinyl, piperazinyl, piperidinyl, tetrahydro-2H-pyranyl, tetrahydro-2H-thiopyranyl, morpholinyl, thiomorpholinyl, azepanyl, oxepanyl, thiepanyl, and the like. Heterocyclyl groups may be substituted or unsubstituted. Some examples of alkyl substituted heterocycles include N-methylmorpholinyl, N-methylpiperidinyl, N-ethylpiperidinyl, N-methylpiperazinyl, N-propylpiperazinyl, 3-methylpiperidinyl, 2-methylpiperidinyl, and the like.

The term "halo" or "halogen" refers to a fluoro (—F), chloro (—Cl), bromo (—Br), or iodo (—I) group.

The term "haloalkyl" refers to an alkyl group as defined above in which at least one hydrogen atom is replaced with a halogen. Thus, the term "haloalkyl" includes "monohaloalkyl" (an alkyl substituted with one halogen atom), "dihaloalkyl" (an alkyl substituted with two halogen atoms which may be the same or different), and "trihaloalkyl" (an alkyl substituted with three halogen atoms which may be the same or different). The term "polyhaloalkyl" refers to an alkyl group that is substituted with two or more halogen atoms. The term "perhaloalkyl" means, unless otherwise stated, an alkyl group in which each of the hydrogen atoms is replaced with a halogen atom. For example, the term "perhaloalkyl", includes, but is not limited to, trifluoromethyl (—$CF_3$), pentachloroethyl, 1,1,1-trifluoro-2-bromo-2-chloroethyl, and the like.

The term "hydroxy" refers to the hydroxyl group (—OH).

The term "nitro" refers to a radical of formula —$NO_2$.

The term "sulfonyl" refers to a radical —S(=O)$_2$—, or alternatively —$SO_2$—. Sulfonyl groups are typically bonded to R groups and may be written as —S(=O)$_2$—R or as —$SO_2$—R where R is a substituted or unsubstituted alkyl, cycloalkyl, or other specified group as defined herein. Representative examples where R is a straight chain alkyl, an alkylsulfonyl, include, but are not limited to, methylsulfonyl (—S(=O)$_2$—$CH_3$), ethylsulfonyl (—S(=O)$_2$—$CH_2CH_3$), propylsulfonyl (—S(=O)$_2$—$CH_2CH_2CH_3$), butylsulfonyl (—S(=O)$_2$—$CH_2CH_2CH_2CH_3$), and the like. Typical alkylsulfonyl groups include 1 to 10 carbon atoms, 1 to 6 carbon atoms, 1 to 4 carbon atoms, 1 to 3 carbon atoms, or 1 to 2 carbon atoms in the alkyl R group. Alkylsulfonyl groups that include 1 to 6 carbon atoms may be designated as —S(=O)$_2$—($C_1$-$C_6$ alkyl) groups. Similarly, alkylsulfonyl groups that include 1 to 3 carbon atoms may be designated as —S(=O)$_2$—($C_1$-$C_3$ alkyl) groups. Other alkylsulfonyl groups may be described using the same methodology.

The term "amino" refers to a radical —NR'R" where R' and R" are independently chosen from —H, or substituted or unsubstituted straight or branched chain alkyl, cycloalkyl, or other specified group as defined herein. When R' and R" are both —H, the —NR'R" group is a —$NH_2$ group. When one of R' and R" is —H and the other is an alkyl group, the —NR'R" is a —NH-alkyl which may also be designated as a —NH(alkyl) or —N(H)(alkyl) group. When R' and R" are both alkyl groups, the alkyl groups may be different, and the group may be designated as a —N(alkyl)(alkyl) group. If R' and R" are both alkyl groups and the alkyl groups are the same, the group may be referred to as a —N(alkyl)$_2$. The alkyl groups of the R' and R" may be designated based on the number of carbon atoms in the alkyl group. For example, an R' or R" alkyl group with 1 to 6 carbon atoms may be designated as a —($C_1$-$C_6$ alkyl). Similarly, an R' or R" alkyl group with 1 to 4 carbon atoms may be designated as a —($C_1$-$C_4$ alkyl). By way of nonlimiting example, a —NR'R" group in which one of R' and R" is a —H and the other is an alkyl groups with 1-4 carbon atoms, may be referred to as a —NH($C_1$-$C_4$ alkyl) group or as a —N(H)($C_1$-$C_4$ alkyl) group. Similar methodology may be used to describe different —NR'R" groups. Typical R' and R" alkyl groups of —NR'R" groups include 1 to 10 carbon atoms, 1 to 6 carbon atoms, 1 to 4 carbon atoms, 1 to 3 carbon atoms, or 1 to 2 carbon atoms.

The term "carboxamide" as used herein, refers to a group of formula —C(=O)—NR'R" which may also be referred to a —C(=O)NR'R" where R' and R" are independently chosen from —H, or substituted or unsubstituted straight or branched chain alkyl, cycloalkyl, or other specified group as defined herein. When R' and R" are both —H, the carboxamide may be written as a —C(=O)$NH_2$ or —C(=O)—$NH_2$ group. When one of R' and R" is —H and the other is an alkyl group, the carboxamide is a —C(=O)—NH-alkyl which may also be designated as a —C(=O)—N(H)-alkyl, —C(=O)—N(H)(alkyl), —C(=O)N(H)-alkyl, or —C(=O)N(H)(alkyl) group. When R' and R" are both alkyl groups, the alkyl groups may be different, and the group may be designated as a —C(=O)—N(alkyl)(alkyl) group or as a —C(=O)N(alkyl)(alkyl) group. If R' and R" are both alkyl groups and the alkyl groups are the same, the group may be referred to as a —C(=O)—N(alkyl)$_2$, or as a —C(=O)N(alkyl)$_2$ group. The alkyl groups of the R' and R" groups may be designated based on the number of carbon atoms in the alkyl group. For example, an R' or R" alkyl group with 1 to 6 carbon atoms may be designated as a —($C_1$-$C_6$ alkyl). Similarly, an R' or R" alkyl group with 1 to 4 carbon atoms may be designated as a —($C_1$-$C_4$ alkyl). By way of nonlimiting example, a —C(=O)—NR'R" group in which one of R' and R" is a —H and the other is an alkyl groups with 1-4 carbon atoms, may be referred to as a —C(=O)—NH($C_1$-$C_4$ alkyl) group or as a —C(=O)—N(H)($C_1$-$C_4$ alkyl) group. Similar methodology may be used to describe different —C(=O)—NR'R" groups. Typical R' and R" alkyl groups include 1 to 10 carbon atoms, 1 to 6 carbon atoms, 1 to 4 carbon atoms, 1 to 3 carbon atoms, or 1 to 2 carbon atoms.

The term "sulfonamide" as used herein, refers to a group of formula —S(=O)$_2$—NR'R" which may also be referred to a —S(=O)$_2$NR'R" where R' and R" are independently chosen from —H, or substituted or unsubstituted straight or branched chain alkyl, cycloalkyl, or other specified group as defined herein. When R' and R" are both —H, the sulfonamide may be written as a —S(=O)$_2$NH$_2$ or —S(=O)$_2$—NH$_2$ group. When one of R' and R" is —H and the other is an alkyl group, the sulfonamide is a —S(=O)$_2$—NH-alkyl which may also be designated as a —S(=O)$_2$—N(H)-alkyl, —S(=O)$_2$—N(H)(alkyl), —S(=O)$_2$N(H)-alkyl, or —S(=O)$_2$N(H)(alkyl) group. When R' and R" are both alkyl groups, the alkyl groups may be different, and the group may be designated as a —S(=O)$_2$—N(alkyl)(alkyl) group or as a —S(=O)$_2$N(alkyl)(alkyl) group. If R' and R" are both alkyl groups and the alkyl groups are the same, the group may be referred to as a —S(=O)$_2$—N(alkyl)$_2$, or as a —S(=O)$_2$N(alkyl)$_2$ group. The alkyl groups of the R' and R" may be designated based on the number of carbon atoms in the alkyl group. For example, an R' or R" alkyl group with 1 to 6 carbon atoms may be designated as a —($C_1$-$C_6$ alkyl). Similarly, an R' or R" alkyl group with 1 to 4 carbon atoms may be designated as a —($C_1$-$C_4$ alkyl). By way of nonlimiting example, a —S(=O)$_2$—NR'R" group in which one of R' and R" is a —H and the other is an alkyl groups with 1-4 carbon atoms, may be referred to as a —S(=O)$_2$—NH($C_1$-$C_4$ alkyl) group or as a —S(=O)$_2$—N(H)($C_1$-$C_4$ alkyl) group. Similar methodology may be used to describe different —S(=O)$_2$—NR'R" groups. Typical R' and R" alkyl groups include 1 to 10 carbon atoms, 1 to 6 carbon atoms, 1 to 4 carbon atoms, 1 to 3 carbon atoms, or 1 to 2 carbon atoms.

"Disease" refers to any disease, disorder, condition, symptom, or indication.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, salicylic acid, benzoic acid, 3-(4-hydroxybenzoyl)benzoic acid, cinnamic acid, mandelic acid, methanesulfonic acid, ethanesulfonic acid, benzenesulfonic acid, p-toluenesulfonic acid, ethane disulfonic acid and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like. Several salt forms may exist as hydrates such that the use of the term salt is generally defined to include hydrated and non-hydrated forms of the salt.

"Pharmaceutically acceptable excipient," "pharmaceutically acceptable carrier," or "pharmaceutically acceptable adjuvant" refer, respectively, to an excipient, carrier or adjuvant with which at least one compound of the present disclosure is administered. "Pharmaceutically acceptable vehicle" refers to any of a diluent, adjuvant, excipient or carrier with which at least one compound of the present disclosure is administered.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereomers."

"Subject" includes mammals and humans. The terms "human" and "subject" are used interchangeably herein.

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

In one aspect, the invention provides a compound of Formula I:

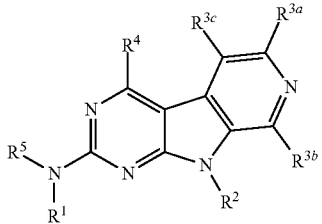

or a pharmaceutically acceptable salt thereof, a hydrate thereof, or a mixture thereof, wherein:

$R^1$ is a group of Formula IA, Formula IB, Formula IC, or Formula ID

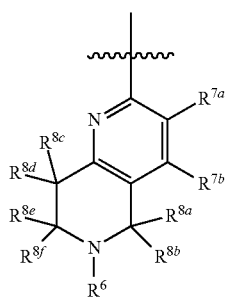

IA

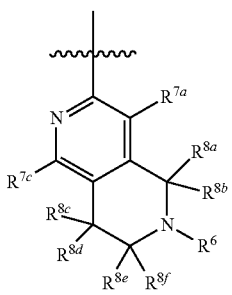

IB

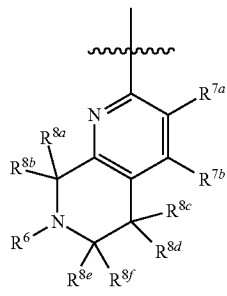

IC

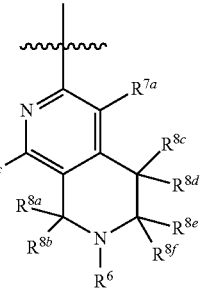

ID wherein the ⌇⌇ symbol indicates the point of attachment of the group of Formula IA, IB, IC, or ID to the rest of the molecule;

$R^2$ is a $C_5$-$C_7$ cycloalkyl group, is a 5 to 7-membered heterocyclyl group that has 1, 2, or 3 heteroatoms selected from N, O, and S, or is a $C_7$-$C_{10}$ bicyclic group; wherein the $C_5$-$C_7$ cycloalkyl group, the 5 to 7 membered heterocyclyl group, or the $C_7$-$C_{10}$ bicyclic group is unsubstituted or is substituted with 1-3 substituents independently selected from unsubstituted —($C_1$-$C_6$ alkyl), —OH, halo, —O—($C_1$-$C_6$ alkyl), —CO$_2$H, —C(=O)—O—($C_1$-$C_6$ alkyl), —C(=O)—NR'R", —NR'R", or a substituted —($C_1$-$C_4$ alkyl), wherein the substituted —($C_1$-$C_4$ alkyl) is substituted with 1-3 substituents independently selected from halo, —OH, —OCH$_3$, —S(=O)$_2$—CH$_3$, or —C(=O)—CH$_3$;

$R^{3a}$ is selected from —H, —F, or —Cl, —($C_1$-$C_3$ alkyl), or —O—($C_1$-$C_3$ alkyl);

$R^{3b}$ is —H, halo, —OH, —O—($C_1$-$C_6$ alkyl), unsubstituted —($C_1$-$C_6$ alkyl), —NR'R", —C(=O)—($C_1$-$C_6$ alkyl), —C(=O)—O—($C_1$-$C_6$ alkyl), —C(=O)—NR'R", or a substituted —($C_1$-$C_6$ alkyl), wherein the substituted —($C_1$-$C_6$ alkyl) is substituted with 1-3 substituents independently selected from halo, —OH, —OCH$_3$, —CN, or —NO$_2$;

$R^{3c}$ is —H, —($C_1$-$C_3$ alkyl), or halo;

$R^4$ is —H;

$R^5$ is —H;

$R^6$ is selected from —H, —($C_1$-$C_6$ alkyl), —C(=O)—($C_1$-$C_6$ alkyl), —C(=O)—O—($C_1$-$C_6$ alkyl), —C(=O)—C(=O)—OH, —C(=O)—NR'R", or —S(=O)—NR'R", wherein the alkyl group of the —($C_1$-$C_6$ alkyl), —C(=O)—($C_1$-$C_6$ alkyl), and —C(=O)—O—($C_1$-$C_6$ alkyl) groups is unsubstituted or is substituted with 1-3 substituents independently selected from —OH, F, —S(=O)$_2$—($C_1$-$C_6$ alkyl), —O—($C_1$-$C_6$ alkyl), —NR'R", or —CN;

$R^{7a}$ is —H, —CH$_3$, or halo;

$R^{7b}$ is —H, —($C_1$-$C_6$ alkyl), or halo; or $R^{7b}$ is absent if $R^1$ is a group of Formula IB or Formula ID;

$R^{7c}$ is —H, unsubstituted —($C_1$-$C_6$ alkyl), halo, —O—($C_1$-$C_6$ alkyl), —NO$_2$, —CN, —NR'R", —CO$_2$H, —C(=O)—O—($C_1$-$C_6$ alkyl), —C(=O)—NR'R", or a substituted —($C_1$-$C_6$ alkyl), wherein the substituted —($C_1$-$C_6$ alkyl) is substituted with 1-3 substituents independently selected from —OH, halo, —O—($C_1$-$C_6$ alkyl), —CN, —NR'R", or —S(=O)$_2$—CH$_3$; or $R^{7c}$ is absent if $R^1$ is a group of Formula IA or Formula IC;

$R^{8a}$ is —H, unsubstituted —($C_1$-$C_6$ alkyl), or a substituted —($C_1$-$C_6$ alkyl), wherein the substituted —($C_1$-$C_6$ alkyl) is substituted with 1-3 substituents independently selected from —OH, halo, or —O—($C_1$-$C_6$ alkyl);

$R^{8b}$ is —H, unsubstituted —($C_1$-$C_6$ alkyl), or a substituted —($C_1$-$C_6$ alkyl), wherein the substituted —($C_1$-$C_6$ alkyl) is substituted with 1-3 substituents independently selected from —OH, halo, or —O—($C_1$-$C_6$ alkyl); or $R^{8a}$ and $R^{8b}$, when taken together, can represent =O;

$R^{8c}$ is selected from —H, —OH, unsubstituted —($C_1$-$C_6$ alkyl), or a substituted —($C_1$-$C_6$ alkyl), wherein the substituted —($C_1$-$C_6$ alkyl) is substituted with 1-3 substituents independently selected from —OH, halo, or —O—($C_1$-$C_6$ alkyl);

$R^{8d}$ is —H, unsubstituted —($C_1$-$C_6$ alkyl), or a substituted —($C_1$-$C_6$ alkyl), wherein the substituted —($C_1$-$C_6$ alkyl) is substituted with 1-3 substituents independently selected from —OH, halo, or —O—($C_1$-$C_6$ alkyl);

$R^{8e}$ is —H, unsubstituted —($C_1$-$C_6$ alkyl), or a substituted —($C_1$-$C_6$ alkyl), wherein the substituted —($C_1$-$C_6$ alkyl) is substituted with 1-3 substituents independently selected from —OH, halo, or —O—($C_1$-$C_6$ alkyl);

$R^{8f}$ is —H, unsubstituted —($C_1$-$C_6$ alkyl), or a substituted —($C_1$-$C_6$ alkyl), wherein the substituted —($C_1$-$C_6$ alkyl) is substituted with 1-3 substituents independently selected from —OH, halo, or —O—($C_1$-$C_6$ alkyl); or $R^{8e}$ and $R^{8f}$, when taken together, can represent =O; and R' and R" are independently selected from —H, unsubstituted —($C_1$-$C_4$ alkyl), or —($C_1$-$C_4$ alkyl) substituted with 1 to 3 substituents independently selected from —OH or —F.

In some embodiments of the compound of Formula I or the pharmaceutically acceptable salt thereof, the hydrate thereof, or the mixture thereof, $R^2$ is a $C_5$-$C_7$ cycloalkyl group that is unsubstituted or is substituted with 1-3 substituents independently selected from unsubstituted —($C_1$-$C_6$ alkyl), —OH, halo, —O—($C_1$-$C_6$ alkyl), —$CO_2$H, —C(=O)—O—($C_1$-$C_6$ alkyl), —C(=O)—NR'R", —NR'R", or a substituted —($C_1$-$C_4$ alkyl), wherein the substituted —($C_1$-$C_4$ alkyl) is substituted with 1-3 substituents independently selected from halo, —OH, —$OCH_3$, —S(=O)$_2$—$CH_3$, or —C(=O)—$CH_3$.

In some embodiments of the compound of Formula I or the pharmaceutically acceptable salt thereof, the hydrate thereof, or the mixture thereof, $R^2$ is an unsubstituted or substituted cyclohexyl ring. In some such embodiments, $R^2$ is a cyclohexyl group substituted with a —($C_1$-$C_2$ alkyl) group. In still further such embodiments, $R^2$ is a cyclohexyl group substituted with a methyl group. In some such embodiments, $R^2$ is a group of formula

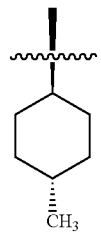

where the ⁓ symbol indicates the point of attachment to the rest of the molecule. In some embodiments, $R^2$ is an unsubstituted cyclohexyl group.

In some embodiments of the compound of Formula I or the pharmaceutically acceptable salt thereof, the hydrate thereof, or the mixture thereof, R' and R" are independently selected from —H or unsubstituted —($C_1$-$C_4$ alkyl).

In some embodiments of the compound of Formula I or the pharmaceutically acceptable salt thereof, the hydrate thereof, or the mixture thereof, $R^2$ is an unsubstituted or substituted cyclopentyl ring. In some such embodiments, $R^2$ is a cyclopentyl group substituted with a —($C_1$-$C_2$ alkyl) group. In still further such embodiments, $R^2$ is a cyclopentyl group substituted with a methyl group. In some such embodiments, $R^2$ is an unsubstituted cyclopentyl group.

In some embodiments of the compound of Formula I or the pharmaceutically acceptable salt thereof, the hydrate thereof, or the mixture thereof, $R^1$ is a group of Formula IA or IB. In some such embodiments, $R^1$ is a group of Formula IA. In other such embodiments, $R^1$ is a group of Formula IB.

In some embodiments of the compound of Formula I or the pharmaceutically acceptable salt thereof, the hydrate thereof, or the mixture thereof, $R^1$ is a group of Formula IC or ID. In some such embodiments, $R^1$ is a group of Formula IC. In other such embodiments, $R^1$ is a group of Formula ID.

In some embodiments of the compound of Formula I or the pharmaceutically acceptable salt thereof, the hydrate thereof, or the mixture thereof, $R^2$ is a $C_5$-$C_7$ cycloalkyl group that is unsubstituted or is substituted with 1-3-($C_1$-$C_6$ alkyl) groups;

$R^{3a}$ is selected from —H, —($C_1$-$C_3$ alkyl), or —O—($C_1$-$C_3$ alkyl);

$R^{3b}$ is —H;

$R^{3c}$ is —H;

$R^4$ is —H;

$R^5$ is —H;

$R^6$ is selected from —H, —($C_1$-$C_6$ alkyl), —C(=O)—($C_1$-$C_6$ alkyl), or —C(=O)—C(=O)—OH, wherein the alkyl group of the —($C_1$-$C_6$ alkyl) and —C(=O)—($C_1$-$C_6$ alkyl) groups is unsubstituted or is substituted with 1-3 substituents independently selected from —OH, F, —S(=O)$_2$—($C_1$-$C_6$ alkyl), or —O—($C_1$-$C_6$ alkyl);

$R^{7a}$ is —H;

$R^{7b}$ is —H; or is absent if $R^1$ is a group of Formula IB or Formula ID;

$R^{7c}$ is —H; or is absent if $R^1$ is a group of Formula IA or Formula IC;

$R^{8a}$ is —H;

$R^{8b}$ is —H;

$R^{8c}$ is selected from —H, —OH, or unsubstituted —($C_1$-$C_6$ alkyl);

$R^{8d}$ is —H;

$R^{8e}$ is —H; and $R^{8f}$ is —H.

In some such embodiments, $R^1$ is a group of Formula IA. In other embodiments, $R^1$ is a group of Formula IB. In other embodiments, $R^1$ is a group of Formula IC. In other embodiments, $R^1$ is a group of Formula ID.

In some embodiments of the compound of Formula I or the pharmaceutically acceptable salt thereof, the hydrate thereof, or the mixture thereof, $R^6$ is selected from —H, —($C_1$-$C_6$ alkyl), —C(=O)—($C_1$-$C_6$ alkyl), —C(=O)—C(=O)—OH, —C(=O)—NR'R", or —S(=O)—NR'R", wherein the alkyl group of the —($C_1$-$C_6$ alkyl) and —C(=O)—($C_1$-$C_6$ alkyl) groups is unsubstituted or is substituted with 1-3 substituents independently selected from —OH, F, —S(=O)$_2$—($C_1$-$C_6$ alkyl), —O—($C_1$-$C_6$ alkyl), —NR'R", or —CN. In some embodiments of the compound of Formula I or the pharmaceutically acceptable salt thereof, the hydrate thereof, or the mixture thereof, $R^6$ is —C(=O)—($C_1$-$C_6$ alkyl) and the alkyl is substituted with a —NR'R". In some such embodiments, $R^6$ is selected from —C(=O)—$CH_2$—N($CH_3$)$_2$ or —C(=O)—$CH_2$—N($CH_2CH_3$)$_2$.

In some embodiments of the compound of Formula I or the pharmaceutically acceptable salt thereof, the hydrate thereof, or the mixture thereof, the compound is the glucuronide adduct.

In some embodiments of the compound of Formula I or the pharmaceutically acceptable salt thereof, the hydrate thereof, or the mixture thereof, the compound has the Formula IIA

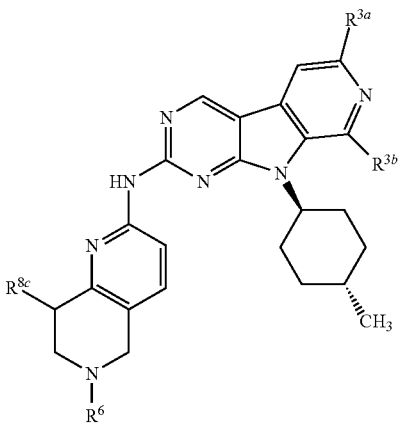

$R^{3a}$ is selected from —H, —F, or —Cl, —($C_1$-$C_3$ alkyl), or —O—($C_1$-$C_3$ alkyl);

$R^{3b}$ is —H, halo, —OH, —O—($C_1$-$C_6$ alkyl), unsubstituted —($C_1$-$C_6$ alkyl), —NR'R", —C(=O)—($C_1$-$C_6$ alkyl), —C(=O)—O—($C_1$-$C_6$ alkyl), —C(=O)—NR'R", or a substituted —($C_1$-$C_6$ alkyl), wherein the substituted —($C_1$-$C_6$ alkyl) is substituted with 1-3 substituents independently selected from halo, —OH, —OCH$_3$, —CN, or —NO$_2$;

$R^6$ is selected from —H, —($C_1$-$C_6$ alkyl), —C(=O)—($C_1$-$C_6$ alkyl), —C(=O)—C(=O)—OH, —C(=O)—NR'R", or —S(=O)—NR'R", wherein the alkyl group of the —($C_1$-$C_6$ alkyl) and —C(=O)—($C_1$-$C_6$ alkyl) groups is unsubstituted or is substituted with 1-3 substituents independently selected from —OH, F, —S(=O)$_2$—($C_1$-$C_6$ alkyl), —O—($C_1$-$C_6$ alkyl), —NR'R", or —CN; and $R^{8c}$ is selected from —H, —OH, unsubstituted —($C_1$-$C_6$ alkyl), or a substituted —($C_1$-$C_6$ alkyl), wherein the substituted —($C_1$-$C_6$ alkyl) is substituted with 1-3 substituents independently selected from —OH, halo, or —O—($C_1$-$C_6$ alkyl).

In some embodiments of the compound of Formula IIA or the pharmaceutically acceptable salt thereof, stereoisomer thereof, pharmaceutically acceptable salt of the stereoisomer, or the mixture thereof, $R^{3a}$ is selected from —H, —($C_1$-$C_3$ alkyl), or —O—($C_1$-$C_3$ alkyl);

$R^{3b}$ is —H;

$R^6$ is selected from —H, —($C_1$-$C_6$ alkyl), —C(=O)—($C_1$-$C_6$ alkyl), or —C(=O)—C(=O)—OH, wherein the alkyl group of the —($C_1$-$C_6$ alkyl) and —C(=O)—($C_1$-$C_6$ alkyl) groups is unsubstituted or is substituted with 1-3 substituents independently selected from —OH, F, —S(=O)$_2$—($C_1$-$C_6$ alkyl), or —O—($C_1$-$C_6$ alkyl); and $R^{8c}$ is selected from —H, unsubstituted —($C_1$-$C_6$ alkyl), or —OH.

In some embodiments of the compound of Formula IIA or the pharmaceutically acceptable salt thereof, the hydrate thereof, or the mixture thereof, $R^{8c}$ is selected from —H, —CH$_3$, or —OH. In some such embodiments, $R^{8c}$ is —H.

In some embodiments of the compound of Formula IIA or the pharmaceutically acceptable salt thereof, the hydrate thereof, or the mixture thereof, $R^{3b}$ is —H.

In some embodiments of the compound of Formula IIA or the pharmaceutically acceptable salt thereof, the hydrate thereof, or the mixture thereof, $R^{3a}$ is —H or —OCH$_3$. In some such embodiments, $R^{3a}$ is —H.

In some embodiments of the compound of Formula IIA or the pharmaceutically acceptable salt thereof, the hydrate thereof, or the mixture thereof, $R^6$ is selected from —H, —C(=O)—CH$_3$, —CH$_2$CH$_2$OH, —CH$_2$CH$_2$CH$_2$OH, —C(=O)—CH$_2$OH, —C(=O)—C(=O)—OH, —CH$_2$CH$_2$CF$_3$, —CH$_2$CH$_2$F, —CH$_2$CH$_2$S(=O)$_2$—CH$_3$, or —CH$_2$CH$_2$OCH$_3$. In some embodiments, $R^6$ is —H. In other embodiments, $R^6$ is selected from —C(=O)—CH$_3$ or —C(=O)—CH$_2$OH. In still other embodiments, $R^6$ is selected from —CH$_2$CH$_2$OH, —CH$_2$CH$_2$CH$_2$OH, or —CH$_2$CH$_2$OCH$_3$. In still other embodiments, $R^6$ is selected from —CH$_2$CH$_2$CF$_3$, —CH$_2$CH$_2$F, or —CH$_2$CH$_2$S(=O)$_2$—CH$_3$. In some embodiments of any of these embodiments, $R^{3a}$ is —H and $R^{3b}$ is —H. In still other such embodiments, $R^{8c}$ is —H.

In some embodiments of the compound of Formula I or the pharmaceutically acceptable salt thereof, the hydrate thereof, or the mixture thereof, the compound has the Formula IIIA

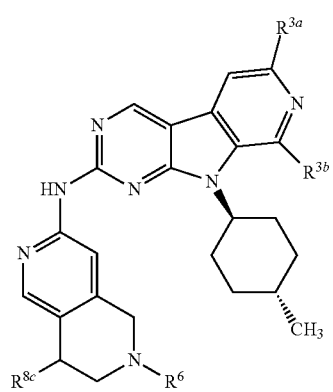

$R^{3a}$ is selected from —H, —F, or —Cl, —($C_1$-$C_3$ alkyl), or —O—($C_1$-$C_3$ alkyl);

$R^{3b}$ is —H, halo, —OH, —O—($C_1$-$C_6$ alkyl), unsubstituted —($C_1$-$C_6$ alkyl), —NR'R", —C(=O)—($C_1$-$C_6$ alkyl), —C(=O)—O—($C_1$-$C_6$ alkyl), —C(=O)—NR'R", or a substituted —($C_1$-$C_6$ alkyl), wherein the substituted —($C_1$-$C_6$ alkyl) is substituted with 1-3 substituents independently selected from halo, —OH, —OCH$_3$, —CN, or —NO$_2$;

$R^6$ is selected from —H, —($C_1$-$C_6$ alkyl), —C(=O)—($C_1$-$C_6$ alkyl), —C(=O)—C(=O)—OH, —C(=O)—NR'R", or —S(=O)—NR'R", wherein the alkyl group of the —($C_1$-$C_6$ alkyl) and —C(=O)—($C_1$-$C_6$ alkyl) groups is unsubstituted or is substituted with 1-3 substituents independently selected from —OH, F, —S(=O)$_2$—($C_1$-$C_6$ alkyl), —O—($C_1$-$C_6$ alkyl), —NR'R", or —CN; and $R^{8c}$ is selected from —H, —OH, unsubstituted —($C_1$-$C_6$ alkyl), or a substituted —($C_1$-$C_6$ alkyl), wherein the substituted —($C_1$-$C_6$ alkyl) is substituted with 1-3 substituents independently selected from —OH, halo, or —O—($C_1$-$C_6$ alkyl).

In some embodiments of the compound of Formula IIIA or the pharmaceutically acceptable salt thereof, the hydrate thereof, or the mixture thereof, $R^{3a}$ is selected from —H, —($C_1$-$C_3$ alkyl), or —O—($C_1$-$C_3$ alkyl);

$R^{3b}$ is —H;

$R^6$ is selected from —H, —($C_1$-$C_6$ alkyl), —C(=O)—($C_1$-$C_6$ alkyl), or —C(=O)—C(=O)—OH, wherein the alkyl group of the —($C_1$-$C_6$ alkyl) and —C(=O)—($C_1$-$C_6$ alkyl) groups is unsubstituted or is substituted with 1-3 substituents independently selected from —OH, F, —S(=O)$_2$—(C$_1$-C$_6$ alkyl), or —O—(C$_1$-C$_6$ alkyl); and R$^{8c}$ is selected from —H, unsubstituted —(C$_1$-C$_6$ alkyl), or —OH.

In some embodiments of the compound of Formula IIIA or the pharmaceutically acceptable salt thereof, the hydrate thereof, or the mixture thereof, R$^{8c}$ is —H.

In some embodiments of the compound of Formula IIIA or the pharmaceutically acceptable salt thereof, the hydrate thereof, or the mixture thereof, R$^{3b}$ is —H.

In some embodiments of the compound of Formula IIIA or the pharmaceutically acceptable salt thereof, the hydrate thereof, or the mixture thereof, R$^{3a}$ is —H or —OCH$_3$. In some such embodiments, R$^{3a}$ is —H In some embodiments of the compound of Formula IIIA or the pharmaceutically acceptable salt thereof, the hydrate thereof, or the mixture thereof, R$^6$ is selected from —H, —C(=O)—CH$_3$, —CH$_2$CH$_2$OH, —CH$_2$CH$_2$CH$_2$OH, —C(=O)—CH$_2$OH, —C(=O)—C(=O)—OH, —CH$_2$CH$_2$CF$_3$, —CH$_2$CH$_2$F, —CH$_2$CH$_2$S(=O)$_2$—CH$_3$, or —CH$_2$CH$_2$OCH$_3$. In other embodiments, R$^6$ is —H. In still other embodiments, R$^6$ is selected from —C(=O)—CH$_3$ or —C(=O)—CH$_2$OH. In still other embodiments, R$^6$ is selected from —CH$_2$CH$_2$OH, —CH$_2$CH$_2$CH$_2$OH, or —CH$_2$CH$_2$OCH$_3$. In still further embodiments, R$^6$ is selected from —CH$_2$CH$_2$CF$_3$, —CH$_2$CH$_2$F, or —CH$_2$CH$_2$S(=O)$_2$—CH$_3$. In some embodiments of any of these embodiments, R$^{3a}$ is —H and R$^{3b}$ is —H. In still other such embodiments, R$^{8c}$ is —H.

In some embodiments of the compound of Formula, the compound is selected from

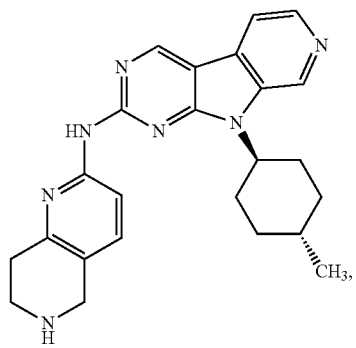

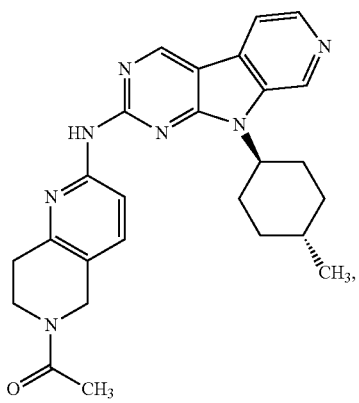

-continued

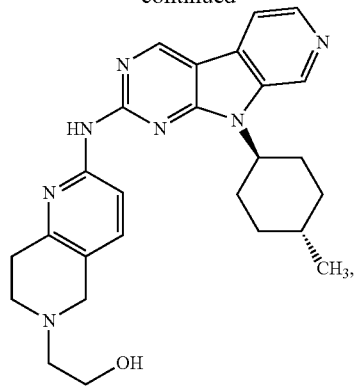

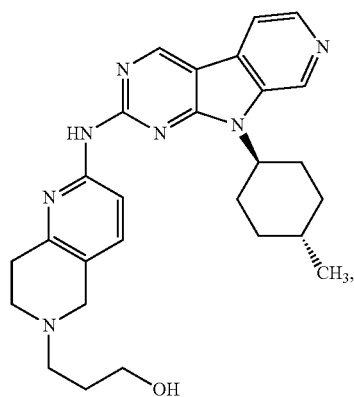

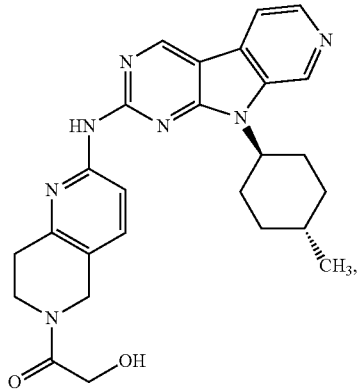

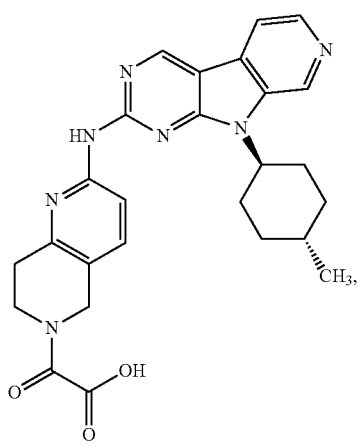

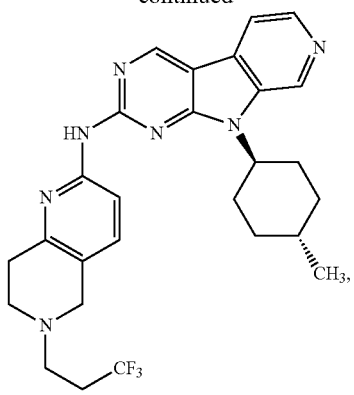
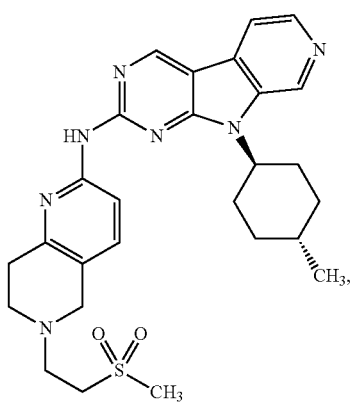
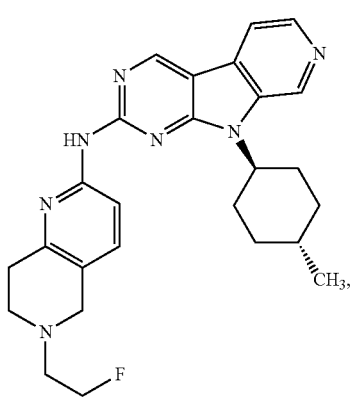
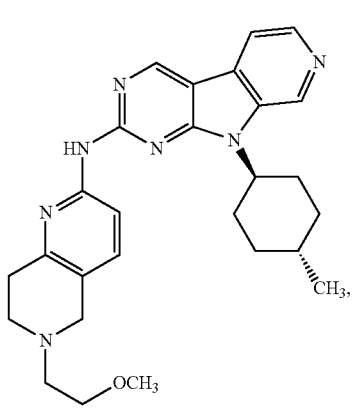
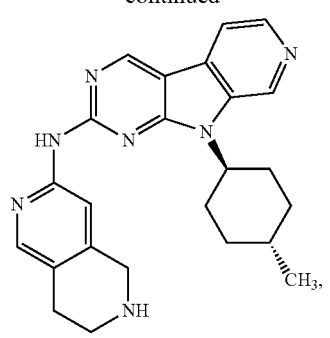
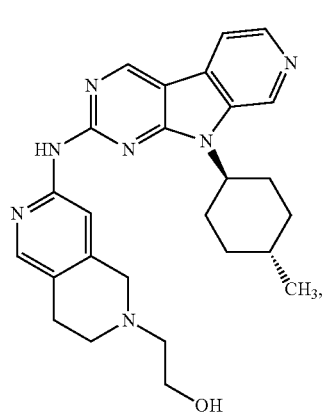
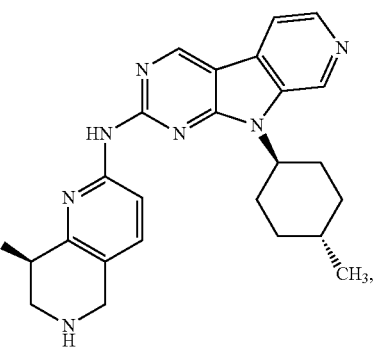
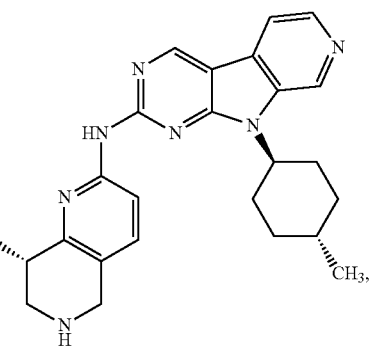

-continued
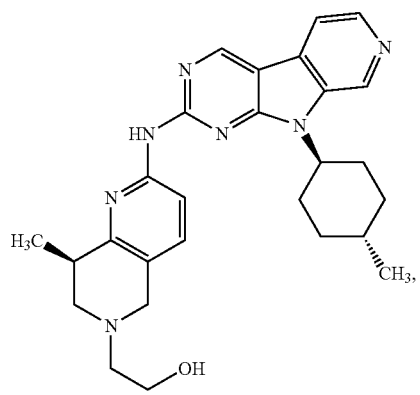
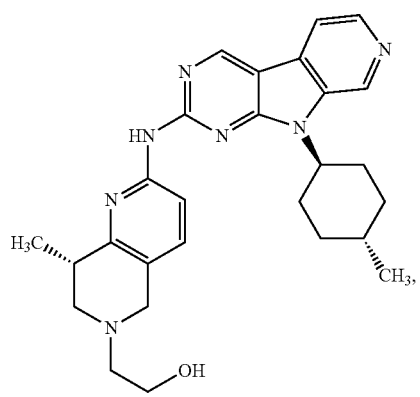
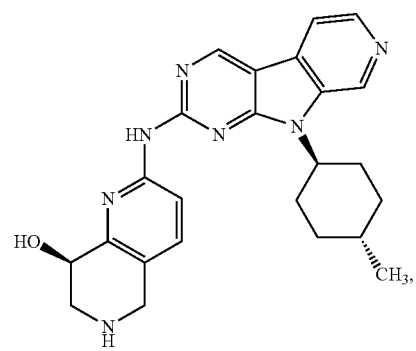
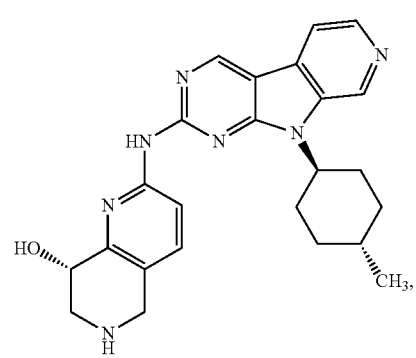
-continued
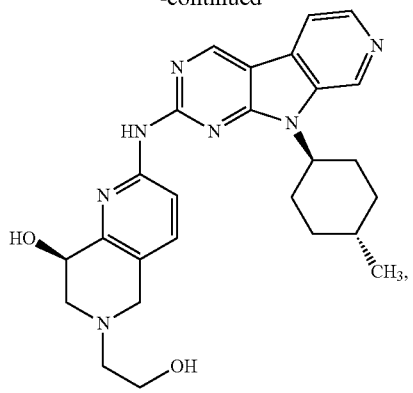
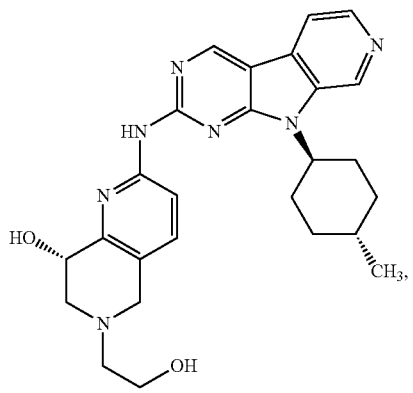
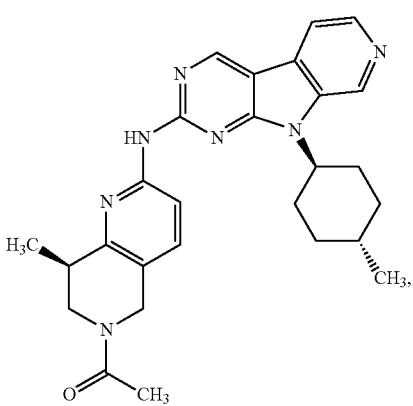
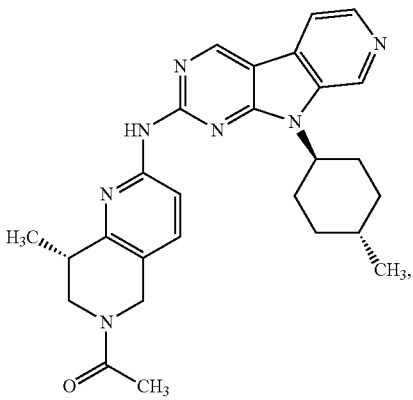

-continued

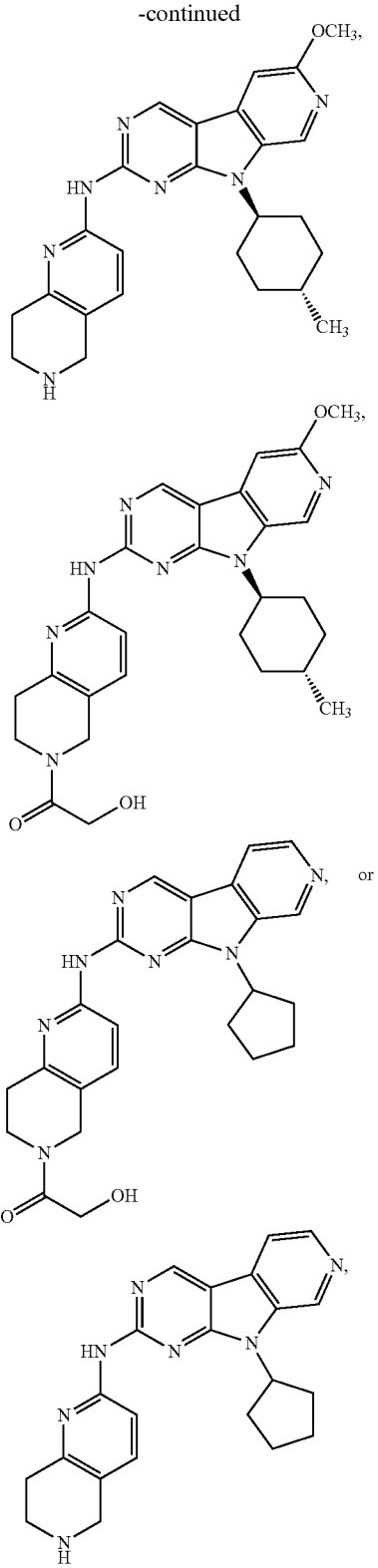

or is a pharmaceutical salt or hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt. For example, in some embodiments, the compound may be a chloride salt that is a monohydrate, a dihydrate, or a trihydrate.

In some embodiments of the compound of Formula I, the compound is

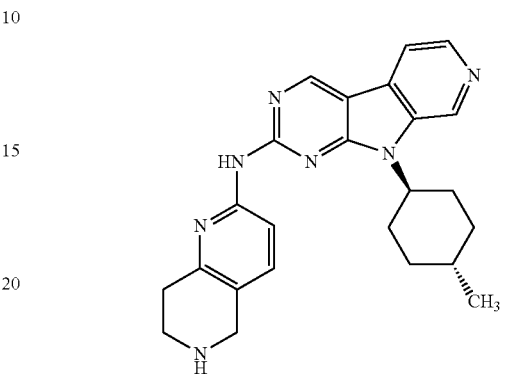

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

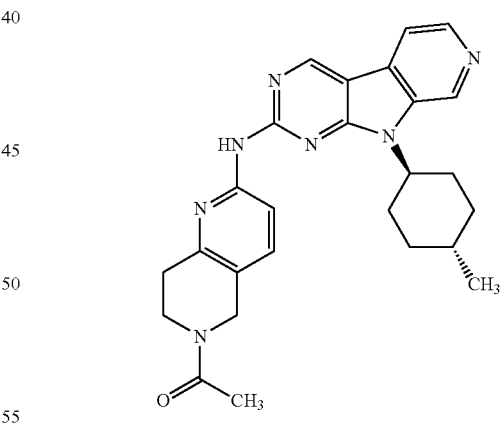

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

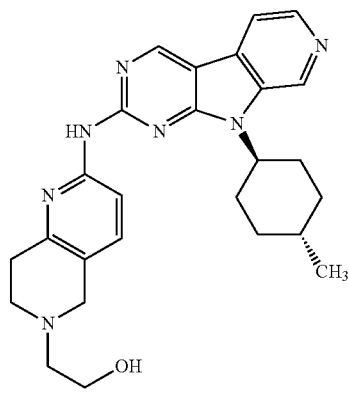 [SMILES: C[C@H]1CC[C@H](n2c3cnccc3c3cnc(Nc4ccc5c(n4)CCN(CCO)C5)nc32)CC1]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

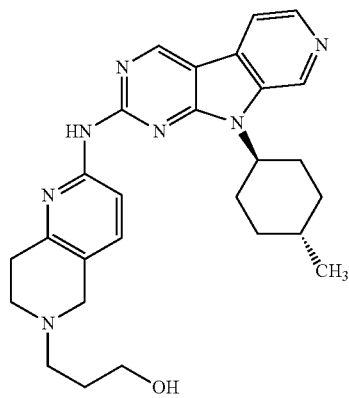 [SMILES: C[C@H]1CC[C@H](n2c3cnccc3c3cnc(Nc4ccc5c(n4)CCN(CCCO)C5)nc32)CC1]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

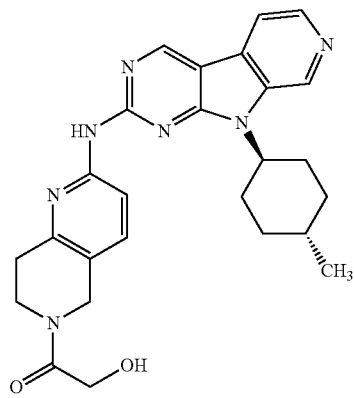 [SMILES: C[C@H]1CC[C@H](n2c3cnccc3c3cnc(Nc4ccc5c(n4)CCN(C(=O)CO)C5)nc32)CC1]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate. In some such embodiments, the salt is a chloride salt. In still other embodiments, the compound is the glucuronide adduct where the glucuronide is bonded to the terminal O atom of the —C(=O)—CH$_2$—OH group.

In some embodiments of the compound of Formula I, the compound is

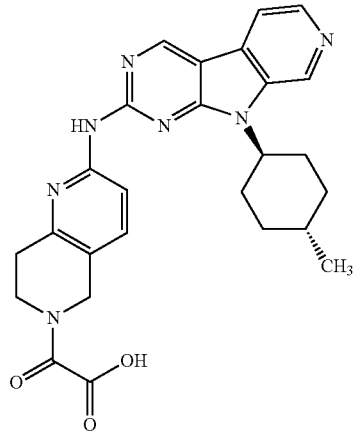 [SMILES: C[C@H]1CC[C@H](n2c3cnccc3c3cnc(Nc4ccc5c(n4)CCN(C(=O)C(=O)O)C5)nc32)CC1]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

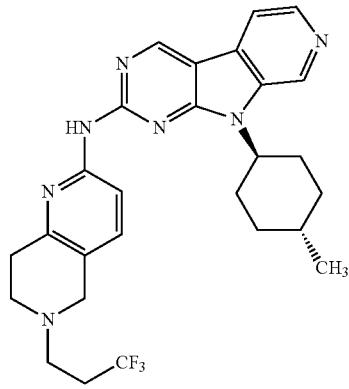 [SMILES: C[C@H]1CC[C@H](n2c3cnccc3c3cnc(Nc4ccc5c(n4)CCN(CCC(F)(F)F)C5)nc32)CC1]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

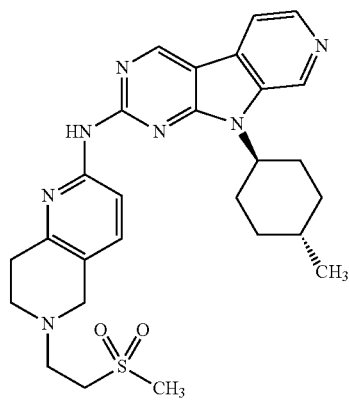 [SMILES: CS(=O)(=O)CCN1CCc2nc(Nc3ncc4c5ccncc5n([C@H]5CC[C@H](C)CC5)c4n3)ccc2C1]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

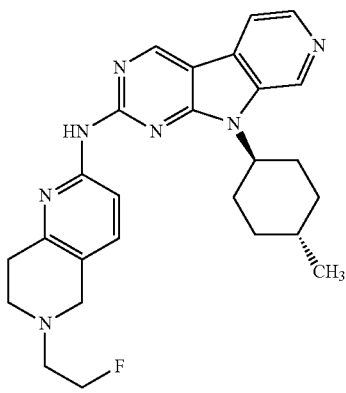 [SMILES: C[C@H]1CC[C@H](n2c3cnccc3c3cnc(Nc4ccc5c(n4)CCN(CCF)C5)nc32)CC1]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

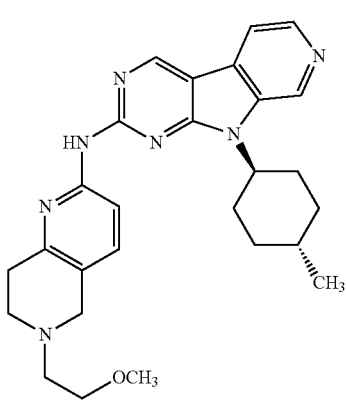 [SMILES: COCCN1CCc2nc(Nc3ncc4c5ccncc5n([C@H]5CC[C@H](C)CC5)c4n3)ccc2C1]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

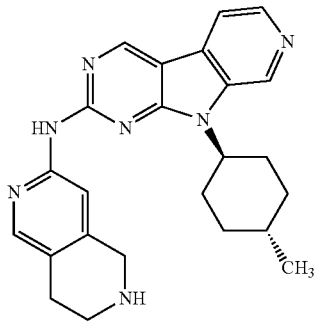 [SMILES: C[C@H]1CC[C@H](n2c3cnccc3c3cnc(Nc4cc5c(cn4)CCNC5)nc32)CC1]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

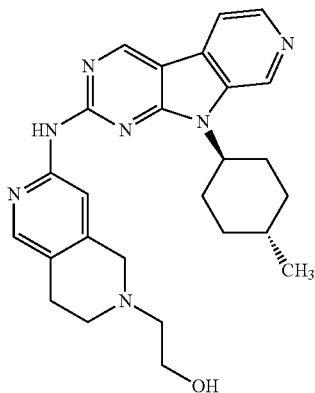 [SMILES: C[C@H]1CC[C@H](n2c3cnccc3c3cnc(Nc4cc5c(cn4)CCN(CCO)C5)nc32)CC1]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

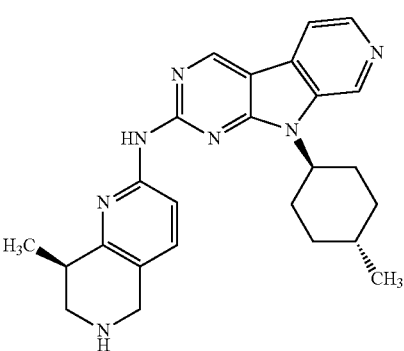

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

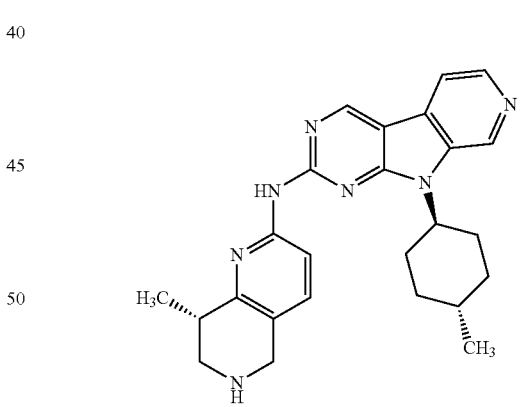

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

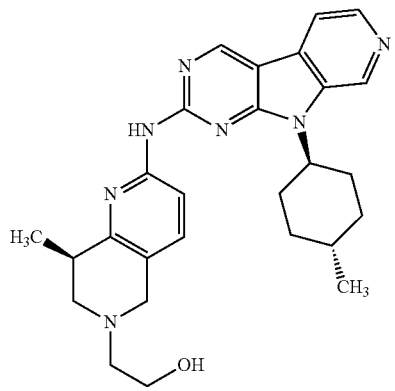 [SMILES: C[C@@H]1CN(CCO)Cc2ccc(Nc3ncc4c5ccncc5n([C@H]5CC[C@H](C)CC5)c4n3)nc21]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

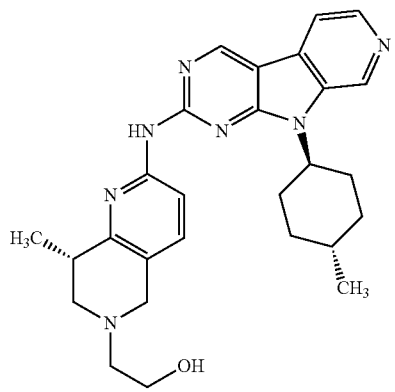 [SMILES: C[C@H]1CN(CCO)Cc2ccc(Nc3ncc4c5ccncc5n([C@H]5CC[C@H](C)CC5)c4n3)nc21]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

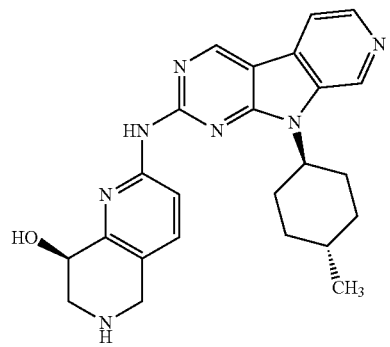 [SMILES: C[C@H]1CC[C@H](n2c3cnccc3c3cnc(Nc4ccc5c(n4)[C@H](O)CNC5)nc32)CC1]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

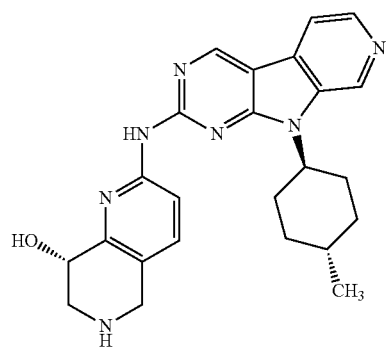 [SMILES: C[C@H]1CC[C@H](n2c3cnccc3c3cnc(Nc4ccc5c(n4)[C@@H](O)CNC5)nc32)CC1]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

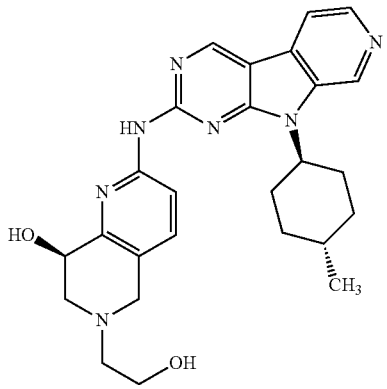 [SMILES: C[C@H]1CC[C@H](n2c3cnccc3c3cnc(Nc4ccc5c(n4)[C@H](O)CN(CCO)C5)nc32)CC1]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

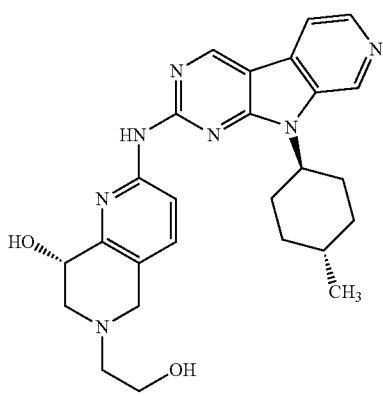 [SMILES: C[C@H]1CC[C@H](n2c3cnccc3c3cnc(Nc4ccc5c(n4)[C@@H](O)CN(CCO)C5)nc32)CC1]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

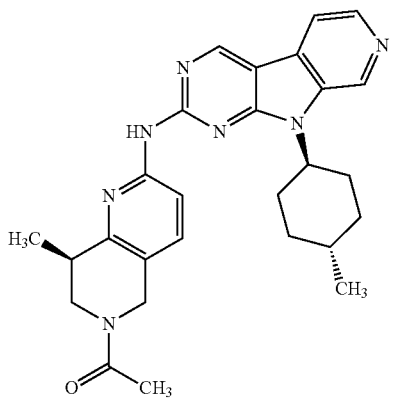 [SMILES: CC(=O)N1Cc2ccc(Nc3ncc4c5ccncc5n([C@H]5CC[C@H](C)CC5)c4n3)nc2[C@H](C)C1]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

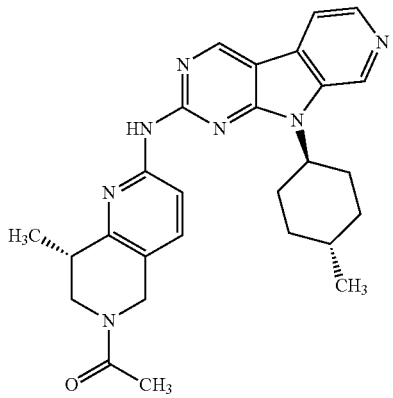

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

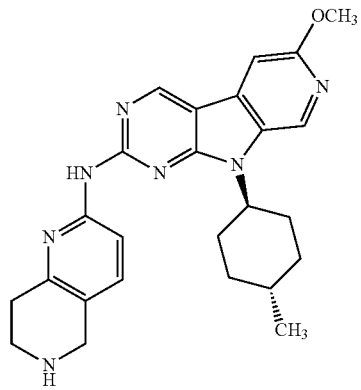 [SMILES: COc1cc2c3cnc(Nc4ccc5c(n4)CCNC5)nc3n([C@H]3CC[C@H](C)CC3)c2cn1]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

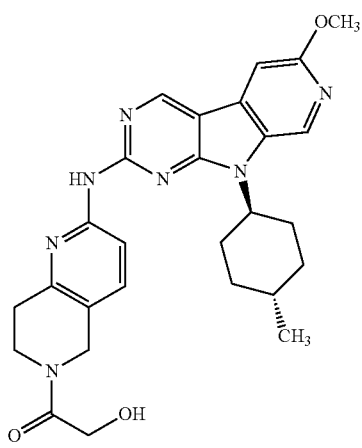 [SMILES: COc1cc2c3cnc(Nc4ccc5c(n4)CCN(C(=O)CO)C5)nc3n([C@H]3CC[C@H](C)CC3)c2cn1]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

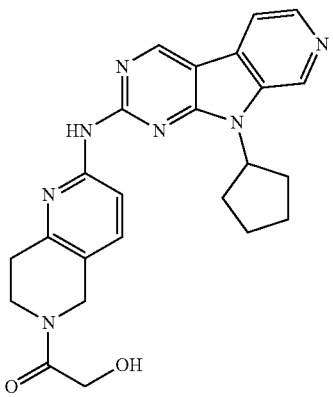 [SMILES: O=C(CO)N1CCc2nc(Nc3ncc4c5ccncc5n(C5CCCC5)c4n3)ccc2C1]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

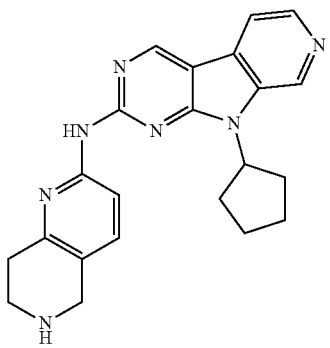 [SMILES: c1cc2c3cnc(Nc4ccc5c(n4)CCNC5)nc3n(C3CCCC3)c2cn1]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

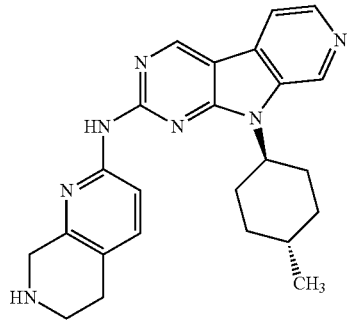 [SMILES: C[C@H]1CC[C@H](n2c3cnccc3c3cnc(Nc4ccc5c(n4)CNCC5)nc32)CC1]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

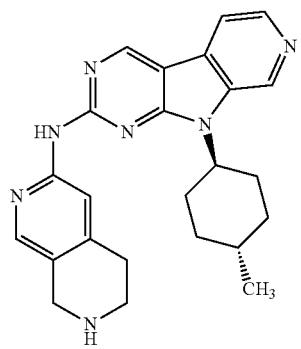 [SMILES: C[C@H]1CC[C@H](n2c3cnccc3c3cnc(Nc4cc5c(cn4)CNCC5)nc32)CC1]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

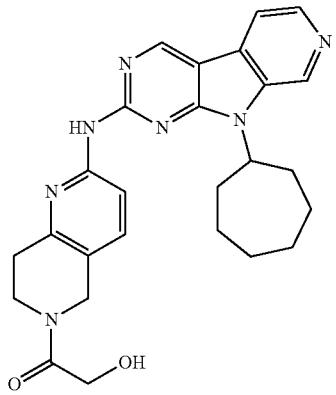 [SMILES: O=C(CO)N1CCc2nc(Nc3ncc4c5ccncc5n(C5CCCCCC5)c4n3)ccc2C1]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I, the compound is

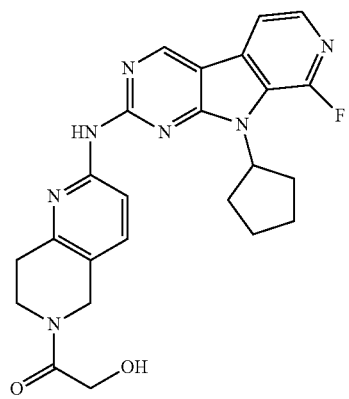 [SMILES: O=C(CO)N1CCc2nc(Nc3ncc4c5ccnc(F)c5n(C5CCCC5)c4n3)ccc2C1]

or is a pharmaceutically acceptable salt or a hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula, the compound is selected from
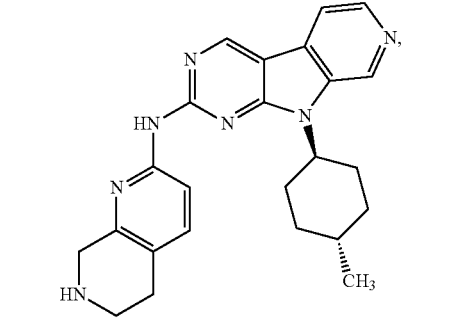
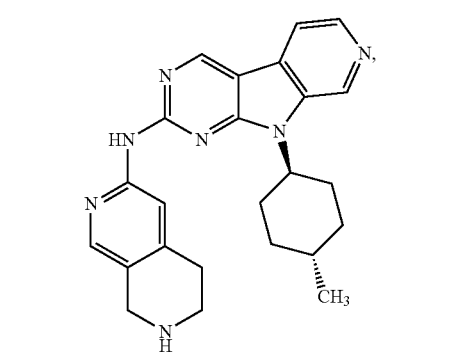
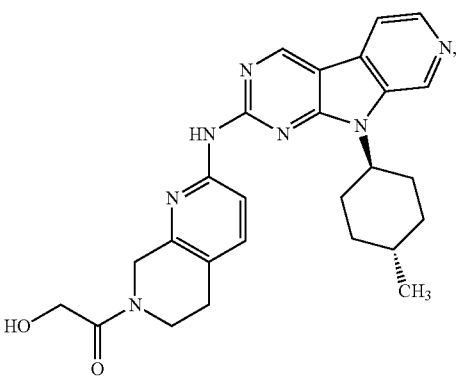
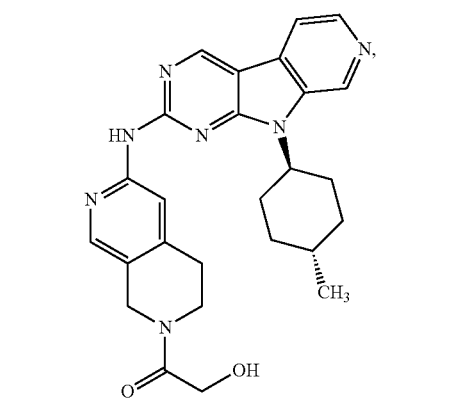
-continued
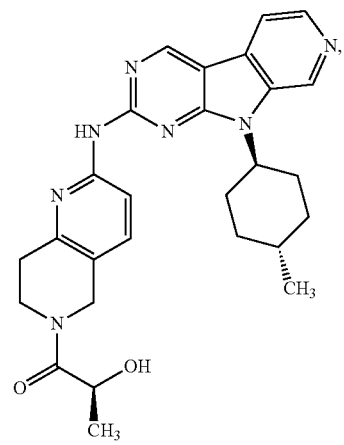
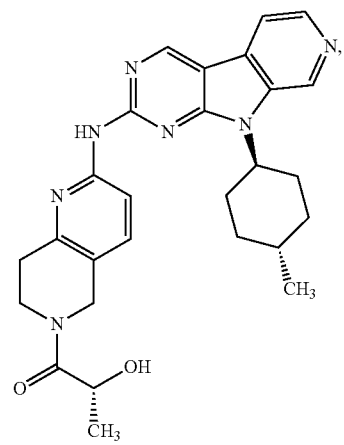
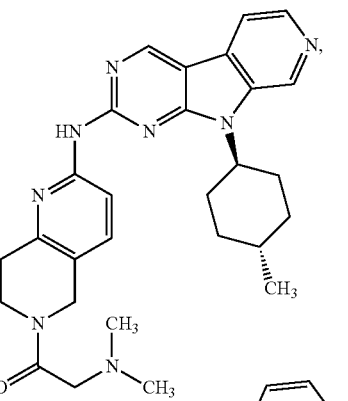
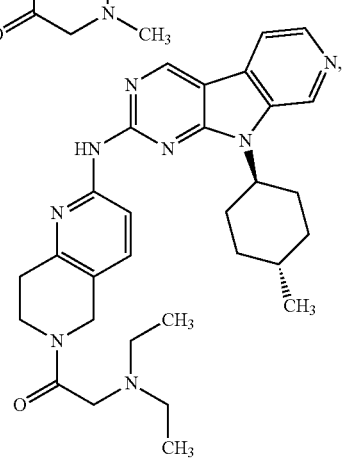

or is a pharmaceutical salt or hydrate thereof. In some embodiments, the compound is in a neutral form whereas in others it is a pharmaceutically acceptable salt. In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In other embodiments, the compound is a hydrate of the neutral compound or of the salt such as a monohydrate, a dihydrate, or a trihydrate.

In some embodiments of the compound of Formula I or the pharmaceutically acceptable salt thereof, the hydrate thereof, or the mixture thereof, the compound is in a neutral form. In some such embodiments, the compound is in a hydrate form such as a monohydrate, a dihydrate, or a trihydrate.

In some embodiments of the compound of Formula I or the pharmaceutically acceptable salt thereof, the hydrate thereof, or the mixture thereof, the compound is a pharmaceutically acceptable salt or a hydrate thereof. In some embodiments, the salt is selected from a chloride, citrate, tartrate, salicylate, ethanesulfonate, methanesulfonate, benzenesulfonate (besylate), tosylate, phosphate, sulfate, or ethane disulfonate salt. In some such embodiments, the salt is selected from a chloride salt, a methanesulfonate salt, or a benzenesulfonate salt. In some embodiments, the salt is selected from a chloride, citrate, tartrate, salicylate, ethanesulfonate, benzenesulfonate, tosylate, phosphate, sulfate (½ equivalent), sulfate (1 equivalent), ethane disulfonate, (½ equivalent), or an ethane disulfonate (1 equivalent). In some such embodiments, the salt is selected from a chloride salt, a methanesulfonate salt, or a benzenesulfonate salt. In some such embodiments, the salt is a chloride salt. In other embodiments, the salt is a methanesulfonate salt. In still other embodiments, the compound is a benzenesulfonate salt. In any of these embodiments, the salt may be a hydrate such as a monohydrate, a dihydrate, or a trihydrate. In some embodiments, the salt is not a hydrate.

Also provided are pharmaceutical compositions that include at least one pharmaceutically acceptable carrier, excipient or diluent and a therapeutically effective amount of the compound, the pharmaceutically acceptable salt, the hydrate thereof, or the mixture thereof according to any of the embodiments described herein. In some such embodiments, the compound is present in an amount effective for the treatment of cancer. In some embodiments, the pharmaceutical composition includes at least one pharmaceutically acceptable carrier, excipient or diluent and a therapeutically effective amount of the compound in a neutral form such as in an anhydrous form or as a hydrate. In other embodiments, the pharmaceutical composition includes at least one pharmaceutically acceptable carrier, excipient or diluent and a therapeutically effective amount of the pharmaceutically acceptable salt or a hydrate thereof. In some such embodiments, the salt is a chloride salt. In other embodiments the salt is a methanesulfonate salt. In still other embodiments, the salt is a benzenesulfonate salt. In some of any of these embodiments, the pharmaceutical composition further includes at least one second therapeutic agent. In some such embodiments, the second therapeutic agent is one that is used in treating cancer. In some such embodiments, the second therapeutic agent is used in treating acute myeloid leukemia or any of the other cancers described below. In some embodiments, the second therapeutic agent is selected from cytosine arabinoside, daunorubicin, idarubicin, doxorubicin, cyclophosphamide, etoposide, carboplatin, fludarabine, mitoxantrone, dexamethasone, rituximab, midostaurin, a granulocyte colony-stimulating factor, filgrastim, PEG-filgrastim, lenograstim, decitabine, azacitidine, paclitaxel, gemcitibine, motesanib disphosphate, panitumumab, an antibody directed against CD33, or a CD33 bispecific T-cell engager antibody. In other embodiments, the second therapeutic agent is selected from cytosine arabinoside, daunorubicin, idarubicin, doxorubicin, cyclophosphamide, etoposide, carboplatin, fludarabine, mitoxantrone, dexamethasone, rituximab, midostaurin, a granulocyte colony-stimulating factor, filgrastim, PEG-filgrastim, lenograstim, decitabine, azacitidine, paclitaxel, gemcitibine, motesanib disphosphate, panitumumab. In still other such embodiments, the second therapeutic agent is selected from cytosine arabinoside, daunorubicin, idarubicin, doxorubicin, cyclophosphamide, etoposide, carboplatin, fludarabine, mitoxantrone, dexamethasone, rituximab, midostaurin, decitabine, azacitidine, paclitaxel, gemcitibine, or motesanib disphosphate. In some such embodiments, the second therapeutic agent is cytosine arabinoside. In other embodiments, the second therapeutic agent is daunorubicin, idarubicin, or doxorubicin. In still other embodiments, the second therapeutic agent is azacitidine or decitabine. In some embodiments, the second therapeutic agent is an anthracycline. In some embodiments, the second therapeutic agent is an aurora kinase inhibitor such as N-(4-((3-(2-amino-4-pyrimidinyl)-2-pyridinyl)oxy)phenyl)-4-(4-methyl-2-thienyl)-1-phthalazinamine or another compound disclosed in WO 2007/087276.

Further provided are pharmaceutical compositions that include at least one pharmaceutically acceptable carrier, and a therapeutically effective amount of the composition of matter of any of the embodiments described herein in combination with at least one additional compound such as a cytotoxic agent or a compound that inhibits another kinase.

In other embodiments, the invention provides a method of treating cancer. In some such embodiments, the cancer is resistant to other agents such as to an anthracycline therapeutic agent. Such methods typically include administering to a subject an effective amount of the compound, the pharmaceutically acceptable salt thereof, the hydrate thereof, or the mixture thereof of any of the embodiments or a pharmaceutical composition of any of the embodiments. In some such embodiments, the cancer is selected from acute myeloid leukemia, acute lymphoblastic leukemia myelodysplastic syndrome, multiple myeloma, chronic myeloid leukemia, acute lymphocytic leukemia, chronic lymphocytic leukemia, non-Hodgkin lymphoma, another lymphoma, another myeloma, or another leukemia. Examples of other cancers that may be treated with the compounds of the present invention include Burkitt's lymphoma and mantle cell lymphoma. In some such embodiments, the cancer is acute myeloid leukemia. In some such embodiments, the subject is a patient with acute myeloid leukemia that is 60 years of age or older. In some such embodiments, the subject is a patient with acute myeloid leukemia that is 70 years of age or older. In some embodiments, the subject is a human patient with mutant FLT3 such as a patient with FLT3-ITD positive acute myeloid leukemia. In some such embodiments, the method may also include determining whether the patient has FLT3-ITD positive acute myeloid leukemia. For example, such a method might include obtaining a sample from a patient and analyzing whether the sample is FLT3-ITD positive. In other such embodiments, the subject is a human patient with wild type FLT3 acute myeloid leukemia. In another embodiment, the cancer is acute lymphoblastic leukemia. In other embodiments, the cancer is selected from breast cancer, colorectal cancer, small cell lung carcinoma, head and neck, glioblastoma, pancreatic, gastrointestinal, liver, prostate, ovarian, testicular, endometrial, bladder, melanoma, osteosarcoma, or another sarcoma. In some embodiments, the cancer is Rb-positive whereas in other embodiments, the cancer is not Rb-positive. In some embodiments, the subject is a mammal, and in some embodiments, is a human cancer patient. In some such embodiments, the cancer is a hematological cancer. In other embodiments, the cancer is a solid tumor. In some embodiments, the method includes administering to a subject an effective amount of the compound, the pharmaceutically acceptable salt thereof, the hydrate thereof, or the mixture thereof of any of the embodiments or a pharmaceutical composition of any of the embodiments where the patient is a human cancer patient with mutant FLT3 and in some such embodiments is a human cancer patient with FLT3-ITD. In some embodiments, the method includes administering to a subject an effective amount of the compound, the pharmaceutically acceptable salt thereof, the hydrate thereof, or the mixture thereof of any of the embodiments or a pharmaceutical composition of any of the embodiments where the patient is a human cancer patient with elevated levels of FLT3 ligand, for example a human patient with acute myeloid leukemia that has elevated FLT3 ligand.

As noted above, the compounds of the invention have been found to be active in cancer cells, for example acute myeloid leukemia cells, that are both wild type and mutant with respect to FLT3. Therefore, in some embodiments, the invention provides methods for treating cancer in patients with wild type FLT3 whereas in other embodiments, the invention provides methods for treating cancer in patients with mutant FLT3. Such methods typically include administering to a subject such as a human cancer patient an effective amount of the compound, the pharmaceutically acceptable salt thereof, the hydrate thereof, or the mixture thereof of any of the embodiments or a pharmaceutical composition of any of the embodiments. In some such embodiments, the cancer is acute myeloid leukemia. In some such embodiments, the subject is a human patient with mutant FLT3 such as a patient that tests positive for a mutant FLT3 acute myeloid leukemia. Examples of FLT3 mutants include, but are not limited to, FLT3-ITD, FLT3 with activation loop point mutations such as FLT3-D835Y, FLT3-D835H, and FLT3-D835V, FLT3-K663Q, and FLT3-N841I. Therefore, in some embodiments, the FLT3 mutant is FLT3-ITD. In other embodiments, the FLT3 mutant is FLT3-D835Y. In still other embodiments, the FLT3 mutant is FLT3-D835H. In other embodiments, the FLT3 mutant is FLT3-D835V. In still other embodiments, the FLT3 mutant is FLT3-K663Q. In still further such embodiments, the FLT3 mutant is FLT3-N841I. In some such embodiments, the method may include determining whether the patient has mutant FLT3 acute myeloid leukemia. For example, such a method might include obtaining a sample from a patient and analyzing whether the sample tests positive for one or more FLT3 mutant. In some embodiments, the method includes administering to a subject an effective amount of the compound, the pharmaceutically acceptable salt thereof, the hydrate thereof, or the mixture thereof of any of the embodiments or a pharmaceutical composition of any of the embodiments where the patient is a human cancer patient with mutant FLT3 and in some such embodiments is a human cancer patient with acute myeloid leukemia.

In some methods of treating cancer, the patient is a human cancer patient with a solid or hematological tumor in which the tumor exhibits low $p15^{INK4B}$ and/or low $p16^{INK4A}$ expression and in some such embodiments is a human patient with acute myeloid leukemia where the tumor exhibits low $p15^{INK4B}$ and/or low $p16^{INK4A}$ expression. In some embodiments, a tumor that exhibits low $p15^{INK4B}$ and/or low $p16^{INK4A}$ expression is determined using an assay that measures the levels of these proteins or mRNA or both and compares them to the levels in a normal myeloid tumor. This method could also be used for other tumor types. A tumor that contains less of the $p15^{INK4B}$ and/or $p16^{INK4A}$ proteins or mRNA or both than is found in a normal cell would be one that exhibits low $p15^{INK4B}$ and/or $p16^{INK4A}$ expression. In some embodiments, the tumor includes less than 90%, less than 80%, less than 70%, less than 60%, or less than 50% of $p15^{INK4B}$ and/or $p16^{INK4A}$ than occurs in a normal cell such as a C34+ cell taken from healthy bone marrow.

Various assays may be used to evaluate whether a particular patient has wild type or mutant FLT3. For example, LabPMM (San Diego, Calif.), a subsidiary of Invivoscribe Technologies, Inc. (San Diego, Calif.) is a commercial source providing assay services such as FLT3-ITD and D835 mutation assays. Such assays may be used in accordance with the invention to screen patients or determine whether a patient, such as a patient with acute myeloid leukemia, acute lymphocytic leukemia, or myelodysplastic syndrome has or tests positive for FLT3 mutations such as FLT3-ITD or for mutations in the codon for the aspartic acid residue at position 835 (D835) in the FLT3 kinase domain such as in the FLT3-D835Y and FLT3-D-835H mutations. See also U.S. Pat. No. 6,846,630 which is hereby incorporated by reference in its entirety and for all purposes as if specifically set forth herein.

Assays for determining p15 mRNA expression are described by Matsuno et al. and may be used in accordance with the invention to screen or access patients or tumors for $p15^{INK4B}$ expression. Matsuno et al. "p15 mRNA expression detected by real-time quantitative reverse transcriptase-polymerase chain reaction correlates with the methylation density of the gene in adult acute leukemia," Leukemia Res., 29(5), pp. 557-564 (2005) which is hereby incorporated by reference in its entirety and for all purposes as if specifically set forth herein. The assay described in this publication is a quantitative assay of p15 mRNA expression in the bone marrow cells using real-time quantitative reverse transcriptase-polymerase chain reaction. Furthermore, this references describes the quantification of p15 mRNA expression in normal controls.

Assays for determining p16 mRNA expression are described by de Jonge et al. and may be used in accordance with the invention to screen or access patients or tumors for $p16^{INK4A}$ expression. De Jonge et al. "AML at older age: age related gene expression profiles reveal a paradoxical down-regulation of $P16^{INK4A}$ mRNA with prognostic significance," Blood, 114(14), pp. 2869-2877 (2012) which is hereby incorporated by reference in its entirety and for all purposes as if specifically set forth herein. The assay described in this publication uses quantitative reverse transcriptase polymerase chain reaction (RT-PCR). To verify the gene expression profiles, quantitative RT-PCR studies were performed using CD34+ cells derived from healthy bone marrow and AML samples of persons of various ages. The levels of $p16^{INK4B}$ expression was determined on the isolated CD34+ cells derived from healthy bone marrow and derived from AML samples.

Wild type FLT3 means the protein encoded by the nucleic acid sequence of Gen Bank accession number BC144040.1. Mutant FLT3 is any FLT3 sequence that differs from wild type FLT3 amino acid sequence (UniProtKB/Swiss-Prot Accession number P36888). Examples of FLT3 mutants include, but are not limited to FLT3-ITD, FLT3-D835Y, FLT3-D835H, FLT3-D835V, FLT3-K663Q, and FLT3-N841I.

Any of the methods described herein may include the use of a second therapeutic agent such as those described above. For example, in one embodiment, the invention provides a method of treating cancer which includes administering to a subject (a) an effective amount of the compound, the pharmaceutically acceptable salt thereof, the hydrate thereof, or the mixture thereof of any of the embodiments or the pharmaceutical composition of any of the embodiments; and (b) at least one second therapeutic agent used in the treatment of cancer. In some such embodiments, the second therapeutic agent is used in treating acute myeloid leukemia or any of the other cancers described herein. In some embodiments, the second therapeutic agent is selected from cytosine arabinoside, daunorubicin, idarubicin, doxorubicin, cyclophosphamide, etoposide, carboplatin, fludarabine, mitoxantrone, dexamethasone, rituximab, midostaurin, a granulocyte colony-stimulating factor, filgrastim, PEG-filgrastim, lenograstim, decitabine, azacitidine, paclitaxel, gemcitibine, motesanib disphosphate, panitumumab, an antibody directed against CD33, or a CD33 bispecific T-cell engager antibody. In other embodiments, the second therapeutic agent is selected from cytosine arabinoside, daunorubicin, idarubicin, doxorubicin, cyclophosphamide, etoposide, carboplatin, fludarabine, mitoxantrone, dexamethasone, rituximab, midostaurin, a granulocyte colony-stimulating factor, filgrastim, PEG-filgrastim, lenograstim, decitabine, azacitidine, paclitaxel, gemcitibine, motesanib disphosphate, panitumumab. In still other such embodiments, the second therapeutic agent is selected from cytosine arabinoside, daunorubicin, idarubicin, doxorubicin, cyclophosphamide, etoposide, carboplatin, fludarabine, mitoxantrone, dexamethasone, rituximab, midostaurin, decitabine, azacitidine, paclitaxel, gemcitibine, or motesanib disphosphate. In some such embodiments, the second therapeutic agent is cytosine arabinoside. In other embodiments, the second therapeutic agent is daunorubicin, idarubicin, or doxorubicin. In still other embodiments, the second therapeutic agent is azacitidine or decitabine. In some embodiments, the second therapeutic agent is an anthracycline. In some embodiments, the second therapeutic agent is an aurora kinase inhibitor such as N-(4-((3-(2-amino-4-pyrimidinyl)-2-pyridinyl)oxy)phenyl)-4-(4-methyl-2-thienyl)-1-phthalazinamine or another compound disclosed in WO 2007/087276. In some embodiments, the compound, the pharmaceutically acceptable salt thereof, the hydrate thereof, or the mixture thereof of any of the embodiments or the pharmaceutical composition of any of the embodiments is administered to the subject after the at least one second therapeutic agent is administered to the subject. In other embodiments, the compound, the pharmaceutically acceptable salt thereof, the hydrate thereof, or the mixture thereof of any of the embodiments or the pharmaceutical composition of any of the embodiments is administered to the subject before the at least one second therapeutic agent is administered to the subject. In still other embodiments, the compound, the pharmaceutically acceptable salt thereof, the hydrate thereof, or the mixture thereof of any of the embodiments or the pharmaceutical composition of any of the embodiments is administered to the subject at the same time that the at least one second therapeutic agent is administered to the subject.

The invention further provides a compound for use in the preparation of a medicament. Any of the compounds, salts, hydrates, or mixtures of any of the embodiments described herein can be used to prepare the medicament. In some embodiments, the cancer is selected from acute myeloid leukemia, acute lymphoblastic leukemia, myelodysplastic syndrome, multiple myeloma, chronic myeloid leukemia, acute lymphocytic leukemia, chronic lymphocytic leukemia, non-Hodgkin lymphoma, another lymphoma, another myeloma, or another leukemia. In some such embodiments, the cancer is acute myeloid leukemia. In other embodiments, the cancer is selected from breast cancer, colorectal cancer, small cell lung carcinoma, head and neck, glioblastoma, pancreatic, gastrointestinal, liver, prostate, ovarian, testicular, endometrial, bladder, melanoma, osteosarcoma, or another sarcoma. In some embodiments, the cancer is Rb-positive whereas in other embodiments, the cancer is not Rb-positive. In some embodiments, the subject is a human cancer patient and, in some such embodiments, the cancer is a hematological cancer.

In another embodiment, the invention provides a method of treating a proliferation-related disorder in a mammal in need thereof. Such methods include administering to the mammal a therapeutically effective amount of a compound, a salt, a hydrate, or a mixture of any of the embodiments described herein or a pharmaceutical composition comprising the compound, salt, hydrate, or mixture. Another embodiment of the invention comprises treating abnormal cell growth by administering a therapeutically effective amount of a compound, salt, hydrate, or mixture of the invention or a pharmaceutical composition of the invention to a subject in need thereof. In some embodiments, the invention provides the use of a compound, salt, hydrate, or mixture of any of the embodiments or a pharmaceutical composition of the invention for treating abnormal cell growth. The abnormal cell growth can be a benign growth or a malignant growth. In particular, the abnormal cell growth can be a carcinoma, sarcoma, lymphoma, or leukemia. In one embodiment of this method, the abnormal cell growth is a cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. The method of the invention also comprises treating a patient having cancer where the cancer is selected from small cell lung carcinoma, non-small cell lung carcinoma, esophageal cancer, kidney cancer, pancreatic cancer, melanoma, bladder cancer, breast cancer, colon cancer, liver cancer, lung cancer, sarcoma, stomach cancer, cholangiocarcinoma, mesothelioma, or prostate cancer. In another embodiment, the abnormal cell growth is a benign proliferative disease, including, but not limited to, psoriasis, benign prostatic hypertrophy or restenosis.

ADDITIONAL EMBODIMENTS

The embodiments listed below are presented in numbered form for convenience and are in addition to the embodiments described above.

1. A compound of Formula I:

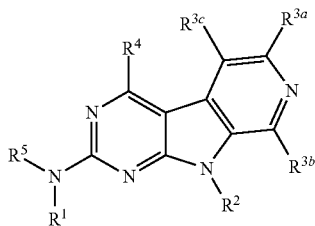

I or a pharmaceutically acceptable salt thereof, a hydrate thereof, or a mixture thereof, wherein:

$R^1$ is a group of Formula IA, Formula IB, Formula IC, or Formula ID

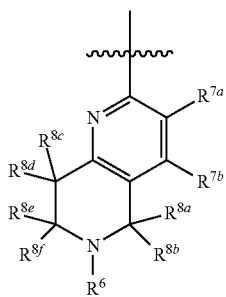

IA

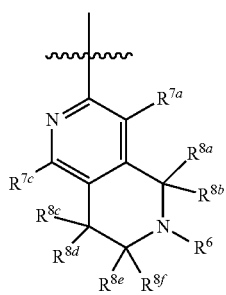

IB

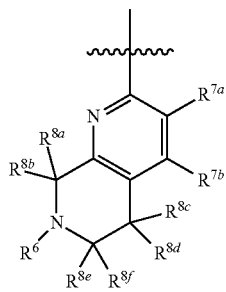

IC

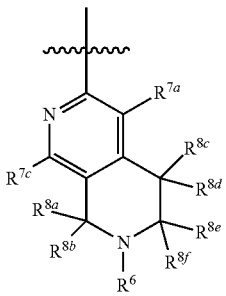

ID wherein the 〰 symbol indicates the point of attachment of the group of Formula IA, IB, IC, or ID to the rest of the molecule;

$R^2$ is a $C_5$-$C_7$ cycloalkyl group, is a 5 to 7-membered heterocyclyl group that includes 1, 2, or 3 heteroatoms selected from N, O, and S, or is a $C_7$-$C_{10}$ bicyclic group; wherein the $C_5$-$C_7$ cycloalkyl group, the 5 to 7 membered heterocyclyl group, or the $C_7$-$C_{10}$ bicyclic group is unsubstituted or is substituted with 1-3 substituents independently selected from unsubstituted —($C_1$-$C_6$ alkyl), —OH, halo, —O—($C_1$-$C_6$ alkyl), —CO$_2$H, —C(=O)—O—($C_1$-$C_6$ alkyl), —C(=O)—NR'R", —NR'R", or a substituted —($C_1$-$C_4$ alkyl), wherein the substituted —($C_1$-$C_4$ alkyl) is substituted with 1-3 substituents independently selected from halo, —OH, —OCH$_3$, —S(=O)$_2$—CH$_3$, or —C(=O)—CH$_3$;

$R^{3a}$ is selected from —H, —F, or —Cl, —($C_1$-$C_3$ alkyl), or —O—($C_1$-$C_3$ alkyl);

$R^{3b}$ is —H, halo, —OH, —O—($C_1$-$C_6$ alkyl), unsubstituted —($C_1$-$C_6$ alkyl), —NR'R", —C(=O)—($C_1$-$C_6$ alkyl), —C(=O)—O—($C_1$-$C_6$ alkyl), —C(=O)—NR'R", or a substituted —($C_1$-$C_6$ alkyl), wherein the substituted —($C_1$-$C_6$ alkyl) is substituted with 1-3 substituents independently selected from halo, —OH, —OCH$_3$, —CN, or —NO$_2$;

$R^{3c}$ is —H, —($C_1$-$C_3$ alkyl), or halo;

$R^4$ is —H;

$R^5$ is —H;

$R^6$ is selected from —H, —($C_1$-$C_6$ alkyl), —C(=O)—($C_1$-$C_6$ alkyl), —C(=O)—O—($C_1$-$C_6$ alkyl), —C(=O)—C(=O)—OH, —C(=O)—NR'R", or —S(=O)—NR'R", wherein the alkyl group of the —($C_1$-$C_6$ alkyl), —C(=O)—($C_1$-$C_6$ alkyl), and —C(=O)—O—($C_1$-$C_6$ alkyl) groups is unsubstituted or is substituted with 1-3 substituents independently selected from —OH, F, —S(=O)$_2$—($C_1$-$C_6$ alkyl), —O—($C_1$-$C_6$ alkyl), —NR'R", or —CN;

$R^{7a}$ is —H, —CH$_3$, or halo;

$R^{7b}$ is —H, —($C_1$-$C_6$ alkyl), or halo; or $R^{7b}$ is absent if $R^1$ is a group of Formula IB or Formula ID;

$R^{7c}$ is —H, unsubstituted —($C_1$-$C_6$ alkyl), halo, —O—($C_1$-$C_6$ alkyl), —NO$_2$, —CN, —NR'R", —CO$_2$H, —C(=O)—O—($C_1$-$C_6$ alkyl), —C(=O)—NR'R", or a substituted —($C_1$-$C_6$ alkyl), wherein the substituted —($C_1$-$C_6$ alkyl) is substituted with 1-3 substituents independently selected from —OH, halo, —O—($C_1$-$C_6$ alkyl), —CN, —NR'R", or —S(=O)$_2$—CH$_3$; or $R^{7e}$ is absent if $R^1$ is a group of Formula IA or Formula IC;

$R^{8a}$ is —H, unsubstituted —($C_1$-$C_6$ alkyl), or a substituted —($C_1$-$C_6$ alkyl), wherein the substituted —($C_1$-$C_6$ alkyl) is substituted with 1-3 substituents independently selected from —OH, halo, or —O—($C_1$-$C_6$ alkyl);

$R^{8b}$ is —H, unsubstituted —($C_1$-$C_6$ alkyl), or a substituted —($C_1$-$C_6$ alkyl), wherein the substituted —($C_1$-$C_6$ alkyl) is substituted with 1-3 substituents independently selected from —OH, halo, or —O—(C$_1$-C$_6$ alkyl); or R$^{8a}$ and R$^{8b}$, when taken together, can represent =O;

R$^{8c}$ is selected from —H, —OH, unsubstituted —(C$_1$-C$_6$ alkyl), or a substituted —(C$_1$-C$_6$ alkyl), wherein the substituted —(C$_1$-C$_6$ alkyl) is substituted with 1-3 substituents independently selected from —OH, halo, or —O—(C$_1$-C$_6$ alkyl);

R$^{8d}$ is —H, unsubstituted —(C$_1$-C$_6$ alkyl), or a substituted —(C$_1$-C$_6$ alkyl), wherein the substituted —(C$_1$-C$_6$ alkyl) is substituted with 1-3 substituents independently selected from —OH, halo, or —O—(C$_1$-C$_6$ alkyl);

R$^{8e}$ is —H, unsubstituted —(C$_1$-C$_6$ alkyl), or a substituted —(C$_1$-C$_6$ alkyl), wherein the substituted —(C$_1$-C$_6$ alkyl) is substituted with 1-3 substituents independently selected from —OH, halo, or —O—(C$_1$-C$_6$ alkyl);

R$^{8f}$ is —H, unsubstituted —(C$_1$-C$_6$ alkyl), or a substituted —(C$_1$-C$_6$ alkyl), wherein the substituted —(C$_1$-C$_6$ alkyl) is substituted with 1-3 substituents independently selected from —OH, halo, or —O—(C$_1$-C$_6$ alkyl); or R$^{8e}$ and R$^{8f}$, when taken together, can represent =O; and R' and R" are independently selected from —H, unsubstituted —(C$_1$-C$_4$ alkyl), or —(C$_1$-C$_4$ alkyl) substituted with 1 to 3 substituents independently selected from —OH or —F.

2. The compound of embodiment 1 or the pharmaceutically acceptable salt thereof, the hydrate thereof, or the mixture thereof, wherein R$^2$ is a C$_5$-C$_7$ cycloalkyl group that is unsubstituted or is substituted with 1-3 substituents independently selected from unsubstituted —(C$_1$-C$_6$ alkyl), —OH, halo, —O—(C$_1$-C$_6$ alkyl), —CO$_2$H, —C(=O)—O—(C$_1$-C$_6$ alkyl), —C(=O)—NR'R", —NR'R", or a substituted —(C$_1$-C$_4$ alkyl), wherein the substituted —(C$_1$-C$_4$ alkyl) is substituted with 1-3 substituents independently selected from halo, —OH, —OCH$_3$, —S(=O)$_2$—CH$_3$, or —C(=O)—CH$_3$.

3. The compound of embodiment 1 or the pharmaceutically acceptable salt thereof, the hydrate thereof, or the mixture thereof, wherein R$^2$ is an unsubstituted or substituted cyclohexyl ring.

4. The compound of embodiment 3 or the pharmaceutically acceptable salt thereof, the hydrate thereof, or the mixture thereof, wherein R$^2$ is a cyclohexyl group substituted with a —(C$_1$-C$_2$ alkyl) group.

5. The compound of embodiment 4 or the pharmaceutically acceptable salt thereof, the hydrate thereof, or the mixture thereof, wherein R$^2$ is a group of formula

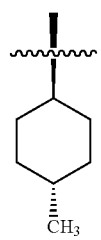

wherein the ⌇ symbol indicates the point of attachment to the rest of the molecule.

6. The compound of embodiment 1 or the pharmaceutically acceptable salt thereof, the hydrate thereof, or the mixture thereof, wherein R$^2$ is an unsubstituted or substituted cyclopentyl ring.

7. The compound of any one of embodiments 1-6 or the pharmaceutically acceptable salt thereof, the hydrate thereof, or the mixture thereof, wherein R$^1$ is a group of Formula IA or IB.

8. The compound of embodiment 7 or the pharmaceutically acceptable salt thereof, the hydrate thereof, or the mixture thereof, wherein R$^1$ is a group of Formula IA.

9. The compound of embodiment 7 or the pharmaceutically acceptable salt thereof, the hydrate thereof, or the mixture thereof, wherein R$^1$ is a group of Formula IB.

10. The compound of any one of embodiments 1-6 or the pharmaceutically acceptable salt thereof, the hydrate thereof, or the mixture thereof, wherein R$^1$ is a group of Formula IC or ID.

11. The compound of embodiment 10 or the pharmaceutically acceptable salt thereof, the hydrate thereof, or the mixture thereof, wherein R$^1$ is a group of Formula IC.

12. The compound of embodiment 10 or the pharmaceutically acceptable salt thereof, the hydrate thereof, or the mixture thereof, wherein R$^1$ is a group of Formula ID.

13. The compound of embodiment 1, wherein:

R$^2$ is a C$_5$-C$_7$ cycloalkyl group that is unsubstituted or is substituted with 1-3-(C$_1$-C$_6$ alkyl) groups;

R$^{3a}$ is selected from —H, —(C$_1$-C$_3$ alkyl), or —O—(C$_1$-C$_3$ alkyl);

R$^{3b}$ is —H;

R$^{3c}$ is —H;

R$^4$ is —H;

R$^5$ is —H;

R$^6$ is selected from —H, —(C$_1$-C$_6$ alkyl), —C(=O)—(C$_1$-C$_6$ alkyl), or —C(=O)—C(=O)—OH, wherein the alkyl group of the —(C$_1$-C$_6$ alkyl) and —C(=O)—(C$_1$-C$_6$ alkyl) groups is unsubstituted or is substituted with 1-3 substituents independently selected from —OH, F, —S(=O)$_2$—(C$_1$-C$_6$ alkyl), or —O—(C$_1$-C$_6$ alkyl);

R$^{7a}$ is —H;

R$^{7b}$ is —H; or is absent if R$^1$ is a group of Formula IB or Formula ID;

R$^{7c}$ is —H; or is absent if R$^1$ is a group of Formula IA or Formula IC;

R$^{8a}$ is —H;

R$^{8b}$ is —H;

R$^{8c}$ is selected from —H, —OH, or unsubstituted —(C$_1$-C$_6$ alkyl);

R$^{8d}$ is —H;

R$^{8e}$ is —H; and

R$^{8f}$ is —H, or the pharmaceutically acceptable salt thereof, the hydrate thereof, or the mixture thereof 14. The compound of embodiment 1, wherein the compound has the Formula IIA

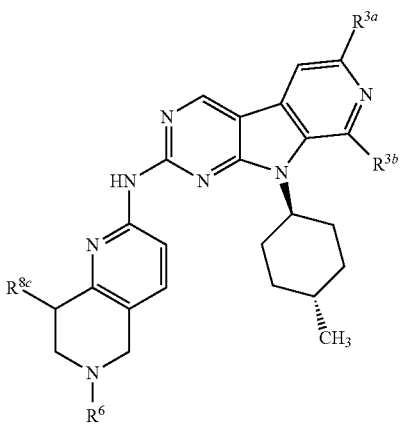

or the pharmaceutically acceptable salt thereof, the hydrate thereof, or the mixture thereof, wherein:

$R^{3a}$ is selected from —H, —F, or —Cl, —($C_1$-$C_3$ alkyl), or —O—($C_1$-$C_3$ alkyl);

$R^{3b}$ is —H, halo, —OH, —O—($C_1$-$C_6$ alkyl), unsubstituted —($C_1$-$C_6$ alkyl), —NR'R", —C(=O)—($C_1$-$C_6$ alkyl), —C(=O)—O—($C_1$-$C_6$ alkyl), —C(=O)—NR'R", or a substituted —($C_1$-$C_6$ alkyl), wherein the substituted —($C_1$-$C_6$ alkyl) is substituted with 1-3 substituents independently selected from halo, —OH, —OCH$_3$, —CN, or —NO$_2$;

$R^6$ is selected from —H, —($C_1$-$C_6$ alkyl), —C(=O)—($C_1$-$C_6$ alkyl), —C(=O)—C(=O)—OH, —C(=O)—NR'R", or —S(=O)—NR'R", wherein the alkyl group of the —($C_1$-$C_6$ alkyl) and —C(=O)—($C_1$-$C_6$ alkyl) groups is unsubstituted or is substituted with 1-3 substituents independently selected from —OH, F, —S(=O)$_2$—($C_1$-$C_6$ alkyl), —O—($C_1$-$C_6$ alkyl), —NR'R", or —CN; and $R^{8c}$ is selected from —H, —OH, unsubstituted —($C_1$-$C_6$ alkyl), or a substituted —($C_1$-$C_6$ alkyl), wherein the substituted —($C_1$-$C_6$ alkyl) is substituted with 1-3 substituents independently selected from —OH, halo, or —O—($C_1$-$C_6$ alkyl).

15. The compound of embodiment 14, wherein:

$R^{3a}$ is selected from —H, —($C_1$-$C_3$ alkyl), or —O—($C_1$-$C_3$ alkyl);

$R^{3b}$ is —H;

$R^6$ is selected from —H, —($C_1$-$C_6$ alkyl), —C(=O)—($C_1$-$C_6$ alkyl), or —C(=O)—C(=O)—OH, wherein the alkyl group of the —($C_1$-$C_6$ alkyl) and —C(=O)—($C_1$-$C_6$ alkyl) groups is unsubstituted or is substituted with 1-3 substituents independently selected from —OH, F, —S(=O)$_2$—($C_1$-$C_6$ alkyl), or —O—($C_1$-$C_6$ alkyl); and $R^{8c}$ is selected from —H, unsubstituted —($C_1$-$C_6$ alkyl), or —OH, or the pharmaceutically acceptable salt thereof, the hydrate thereof, or the mixture thereof 16. The compound of embodiment 14 or embodiment 15 or the pharmaceutically acceptable salt thereof, the hydrate thereof, or the mixture thereof, wherein $R^{8c}$ is selected from —H, —CH$_3$, or —OH.

17. The compound of embodiment 16 or the pharmaceutically acceptable salt thereof, the hydrate thereof, or the mixture thereof, wherein $R^{8c}$ is —H.

18. The compound of any one of embodiments 14-17 or the pharmaceutically acceptable salt thereof, the hydrate thereof, or the mixture thereof, wherein $R^{3a}$ is —H or —OCH$_3$.

19. The compound of embodiment 18 or the pharmaceutically acceptable salt thereof, the hydrate thereof, or the mixture thereof, wherein $R^{3a}$ is —H.

20. The compound of any one of embodiments 14-19 or the pharmaceutically acceptable salt thereof, the hydrate thereof, or the mixture thereof, wherein $R^6$ is selected from —H, —C(=O)—CH$_3$, —CH$_2$CH$_2$OH, —CH$_2$CH$_2$CH$_2$OH, —C(=O)—CH$_2$OH, —C(=O)—C(=O)—OH, —CH$_2$CH$_2$CF$_3$, —CH$_2$CH$_2$F, —CH$_2$CH$_2$S(=O)$_2$—CH$_3$, or —CH$_2$CH$_2$OCH$_3$.

21. The compound of any one of embodiments 14-19 or the pharmaceutically acceptable salt thereof, the hydrate thereof, or the mixture thereof, wherein $R^6$ is —H.

22. The compound of any one of embodiments 14-19 or the pharmaceutically acceptable salt thereof, the hydrate thereof, or the mixture thereof, wherein $R^6$ is selected from —C(=O)—CH$_3$ or —C(=O)—CH$_2$OH.

23. The compound of any one of embodiments 14-19 or the pharmaceutically acceptable salt thereof, the hydrate thereof, or the mixture thereof, wherein $R^6$ is selected from —CH$_2$CH$_2$OH, —CH$_2$CH$_2$CH$_2$OH, or —CH$_2$CH$_2$OCH$_3$.

24. The compound of any one of embodiments 14-19 or the pharmaceutically acceptable salt thereof, the hydrate thereof, or the mixture thereof, wherein $R^6$ is selected from —CH$_2$CH$_2$CF$_3$, —CH$_2$CH$_2$F, or —CH$_2$CH$_2$S(=O)$_2$—CH$_3$.

25. The compound of any one of embodiments 14-19 or the pharmaceutically acceptable salt thereof, the hydrate thereof, or the mixture thereof, wherein $R^6$ is —C(=O)—($C_1$-$C_6$ alkyl) and the alkyl is substituted with a —NR'R".

26. The compound of embodiment 25 or the pharmaceutically acceptable salt thereof, the hydrate thereof, or the mixture thereof, wherein $R^6$ is —C(=O)—CH$_2$—N(CH$_3$)$_2$ or —C(=O)—CH$_2$—N(CH$_2$CH$_3$)$_2$.

27. The compound of embodiment 1, wherein the compound has the Formula IIIA

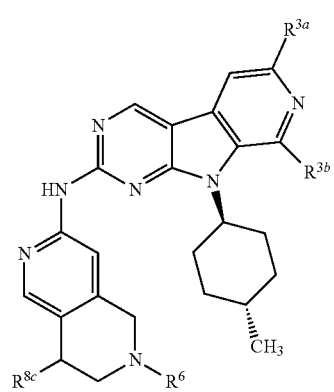

or the pharmaceutically acceptable salt thereof, the hydrate thereof, or the mixture thereof, wherein:

$R^{3a}$ is selected from —H, —F, or —Cl, —($C_1$-$C_3$ alkyl), or —O—($C_1$-$C_3$ alkyl);

$R^{3b}$ is —H, halo, —OH, —O—($C_1$-$C_6$ alkyl), unsubstituted —($C_1$-$C_6$ alkyl), —NR'R", —C(=O)—($C_1$-$C_6$ alkyl), —C(=O)—O—($C_1$-$C_6$ alkyl), —C(=O)—NR'R", or a substituted —($C_1$-$C_6$ alkyl), wherein the substituted —($C_1$-$C_6$ alkyl) is substituted with 1-3 substituents independently selected from halo, —OH, —OCH$_3$, —CN, or —NO$_2$;

$R^6$ is selected from —H, —($C_1$-$C_6$ alkyl), —C(=O)—($C_1$-$C_6$ alkyl), —C(=O)—C(=O)—OH, —C(=O)—NR'R", or —S(=O)—NR'R", wherein the alkyl group of the —(C₁-C₆ alkyl) and —C(=O)—(C₁-C₆ alkyl) groups is unsubstituted or is substituted with 1-3 substituents independently selected from —OH, F, —S(=O)₂—(C₁-C₆ alkyl), —O—(C₁-C₆ alkyl), —NR'R", or —CN; and R$^{8c}$ is selected from —H, —OH, unsubstituted —(C₁-C₆ alkyl), or a substituted —(C₁-C₆ alkyl), wherein the substituted —(C₁-C₆ alkyl) is substituted with 1-3 substituents independently selected from —OH, halo, or —O—(C₁-C₆ alkyl).

28. The compound of embodiment 27, wherein:

R$^{3a}$ is selected from —H, —(C₁-C₃ alkyl), or —O—(C₁-C₃ alkyl);

R$^{3b}$ is —H;

R$^6$ is selected from —H, —(C₁-C₆ alkyl), —C(=O)—(C₁-C₆ alkyl), or —C(=O)—C(=O)—OH, wherein the alkyl group of the —(C₁-C₆ alkyl) and —C(=O)—(C₁-C₆ alkyl) groups is unsubstituted or is substituted with 1-3 substituents independently selected from —OH, F, —S(=O)₂—(C₁-C₆ alkyl), or —O—(C₁-C₆ alkyl); and R$^{8c}$ is selected from —H, unsubstituted —(C₁-C₆ alkyl), or —OH, or the pharmaceutically acceptable salt thereof, the hydrate thereof, or the mixture thereof.

29. The compound of embodiment 27 or embodiment 28 or the pharmaceutically acceptable salt thereof, the hydrate thereof, or the mixture thereof, wherein R$^{8c}$ is —H.

30. The compound of any one of embodiments 27-29 or the pharmaceutically acceptable salt thereof, the hydrate thereof, or the mixture thereof, wherein R$^{3a}$ is —H or —OCH₃.

31. The compound of embodiment 30 or the pharmaceutically acceptable salt thereof, the hydrate thereof, or the mixture thereof, wherein R$^{3a}$ is —H.

32. The compound of any one of embodiments 27-31 or the pharmaceutically acceptable salt thereof, the hydrate thereof, or the mixture thereof, wherein R$^6$ is selected from —H, —C(=O)—CH₃, —CH₂CH₂OH, —CH₂CH₂CH₂OH, —C(=O)—CH₂OH, —C(=O)—C(=O)—OH, —CH₂CH₂CF₃, —CH₂CH₂F, —CH₂CH₂S(=O)₂—CH₃, or —CH₂CH₂OCH₃.

33. The compound of any one of embodiments 27-31 or the pharmaceutically acceptable salt thereof, the hydrate thereof, or the mixture thereof, wherein R$^6$ is —H.

34. The compound of any one of embodiments 27-31 or the pharmaceutically acceptable salt thereof, the hydrate thereof, or the mixture thereof, wherein R$^6$ is selected from —C(=O)—CH₃ or —C(=O)—CH₂OH.

35. The compound of any one of embodiments 27-31 or the pharmaceutically acceptable salt thereof, the hydrate thereof, or the mixture thereof, wherein R$^6$ is selected from —CH₂CH₂OH, —CH₂CH₂CH₂OH, or —CH₂CH₂OCH₃.

36. The compound of any one of embodiments 27-31 or the pharmaceutically acceptable salt thereof, the hydrate thereof, or the mixture thereof, wherein R$^6$ is selected from —CH₂CH₂CF₃, —CH₂CH₂F, or —CH₂CH₂S(=O)₂—CH₃.

37. The compound of embodiment 1, wherein the compound is selected from

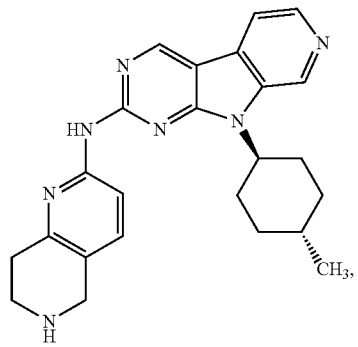

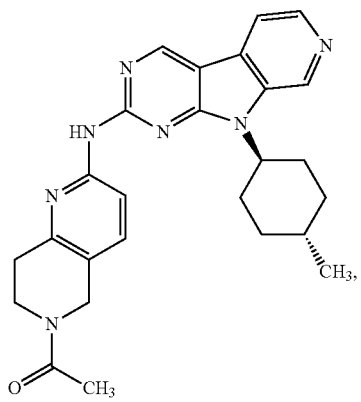

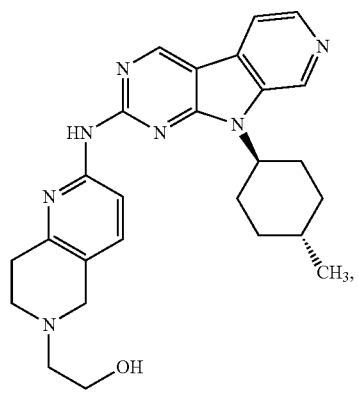

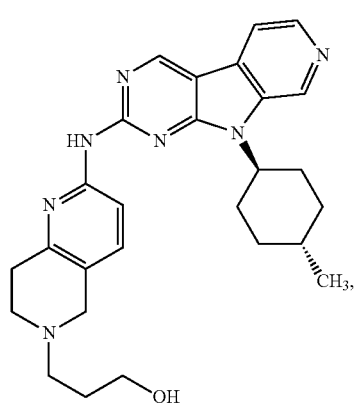

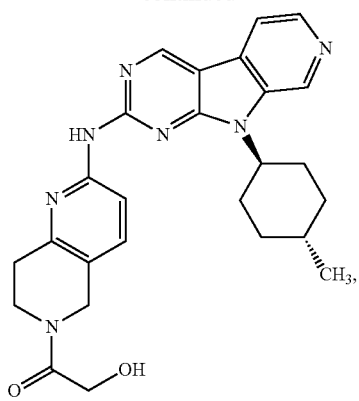
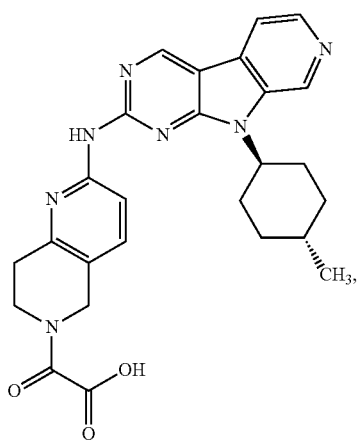
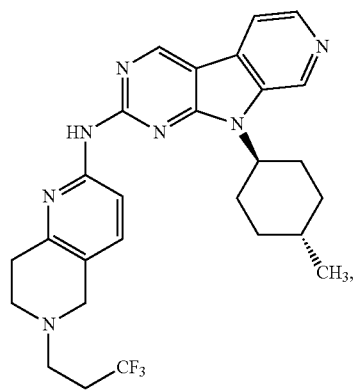
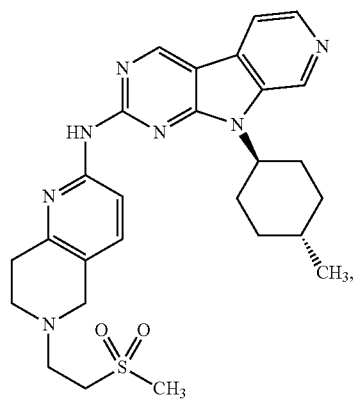
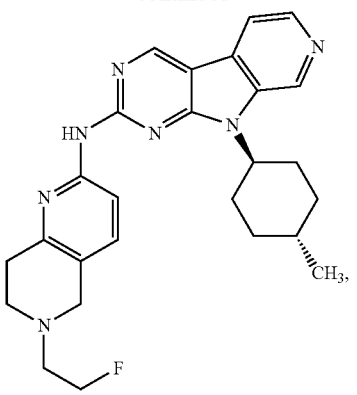
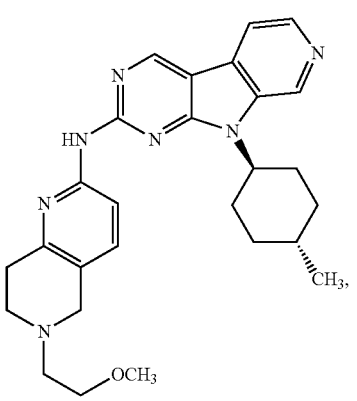
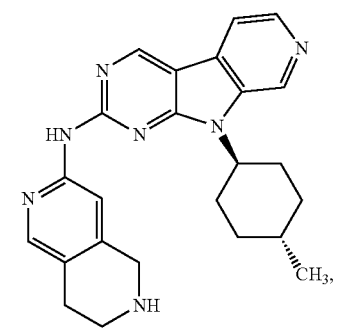
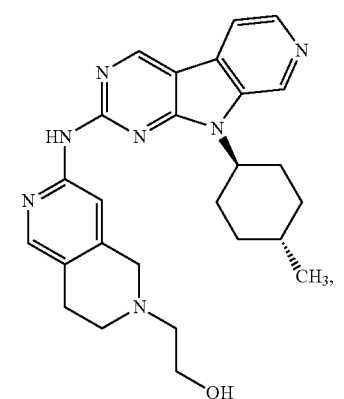

75
-continued
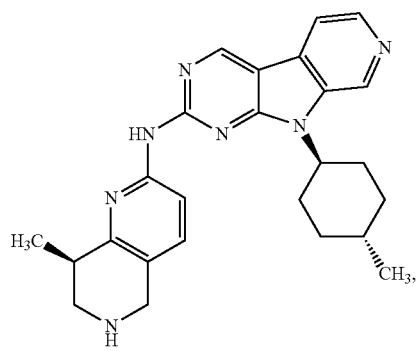
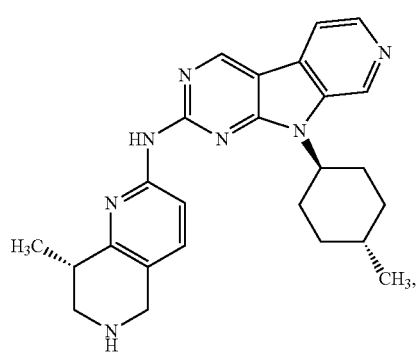
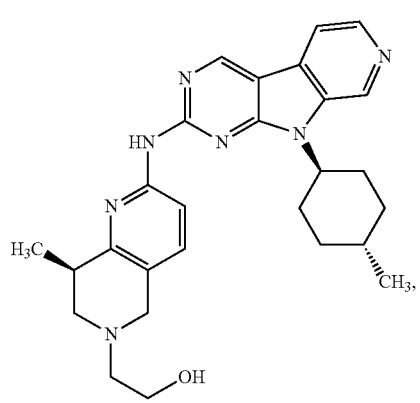
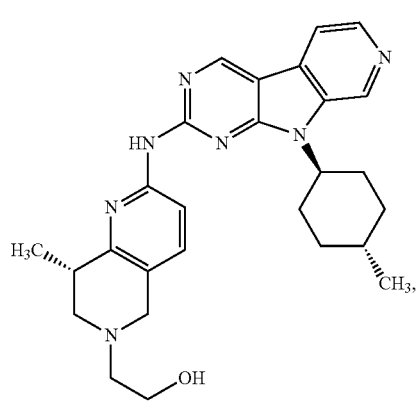
76
-continued
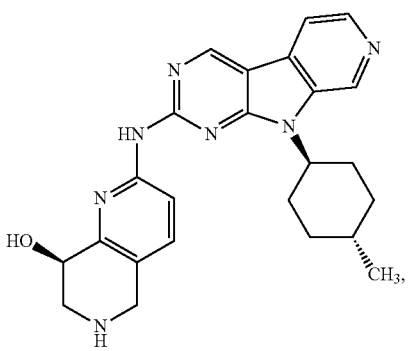
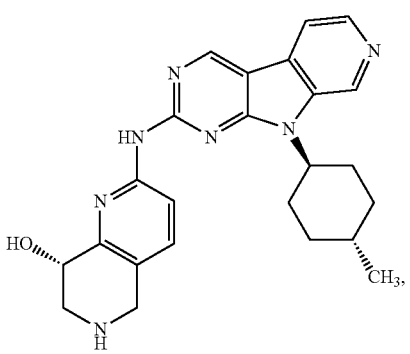
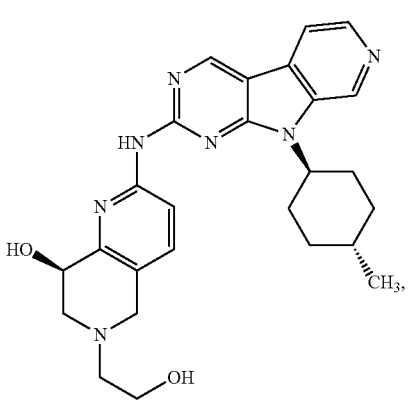
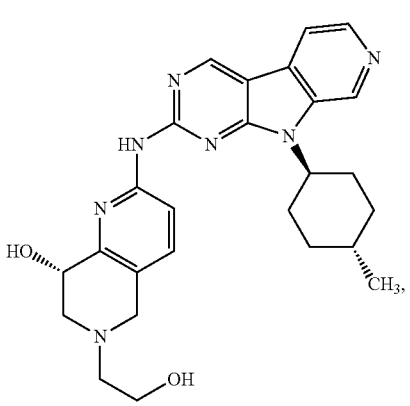

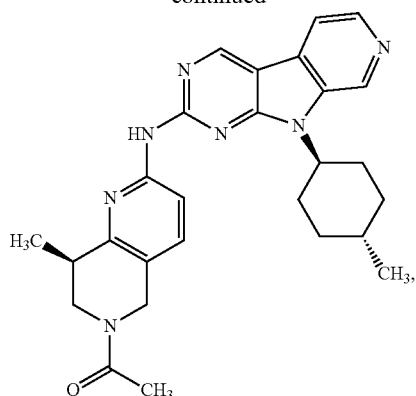
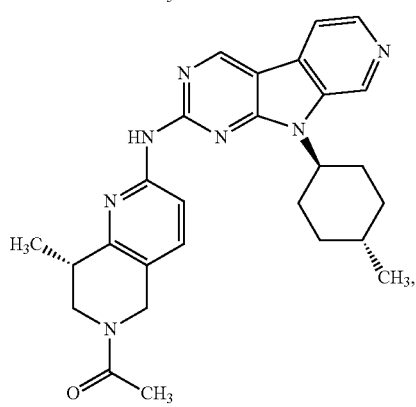
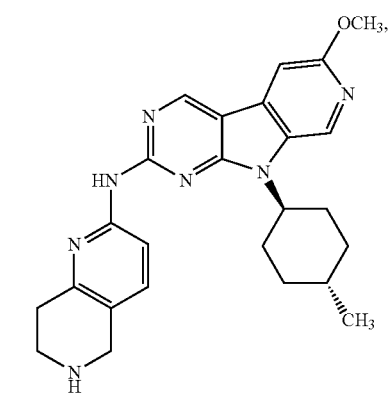
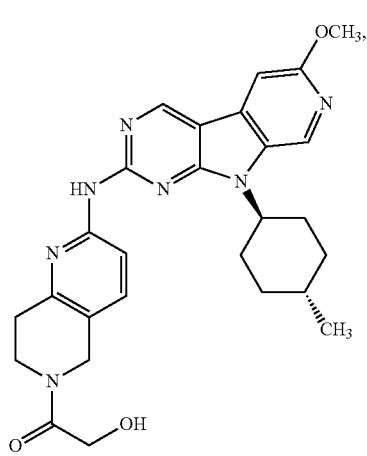
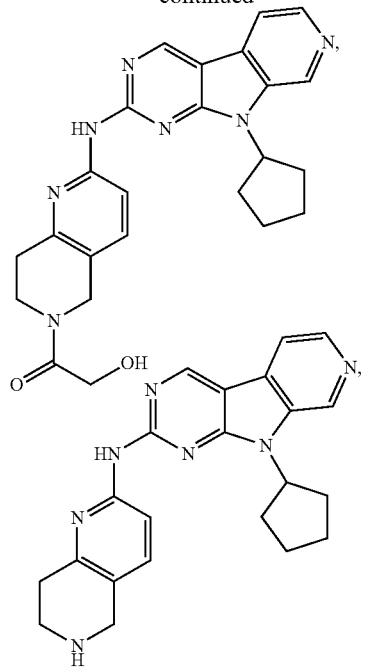
or the pharmaceutically acceptable salt or the hydrate thereof
38. The compound of embodiment 1, wherein the compound is
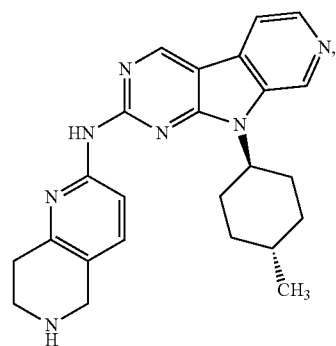 [SMILES: C[C@H]1CC[C@H](n2c3cnccc3c3cnc(Nc4ccc5c(n4)CCNC5)nc32)CC1]
or the pharmaceutically acceptable salt or the hydrate thereof.
39. The compound of embodiment 1, wherein the compound is
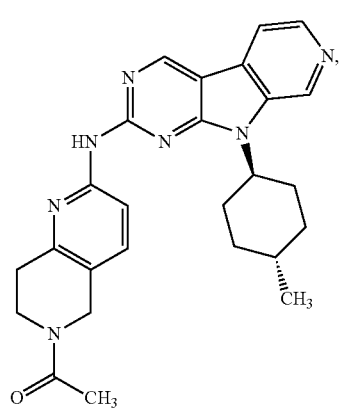 [SMILES: CC(=O)N1CCc2nc(Nc3ncc4c5ccncc5n([C@H]5CC[C@H](C)CC5)c4n3)ccc2C1]
or the pharmaceutically acceptable salt or the hydrate thereof 40. The compound of embodiment 1, wherein the compound is

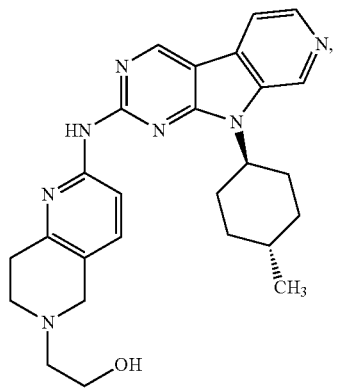 [SMILES: C[C@H]1CC[C@H](n2c3cnccc3c3cnc(Nc4ccc5c(n4)CCN(CCO)C5)nc32)CC1]

or the pharmaceutically acceptable salt or the hydrate thereof

41. The compound of embodiment 1, wherein the compound is

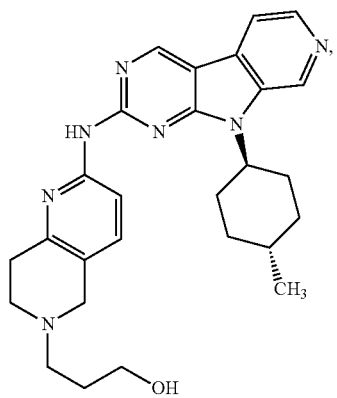 [SMILES: C[C@H]1CC[C@H](n2c3cnccc3c3cnc(Nc4ccc5c(n4)CCN(CCCO)C5)nc32)CC1]

or the pharmaceutically acceptable salt or the hydrate thereof.

42. The compound of embodiment 1, wherein the compound is

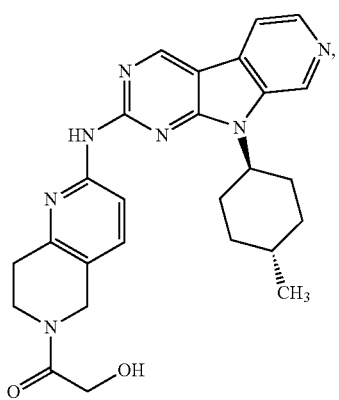 [SMILES: C[C@H]1CC[C@H](n2c3cnccc3c3cnc(Nc4ccc5c(n4)CCN(C(=O)CO)C5)nc32)CC1]

or the pharmaceutically acceptable salt or the hydrate thereof

43. The compound of embodiment 1, wherein the compound is

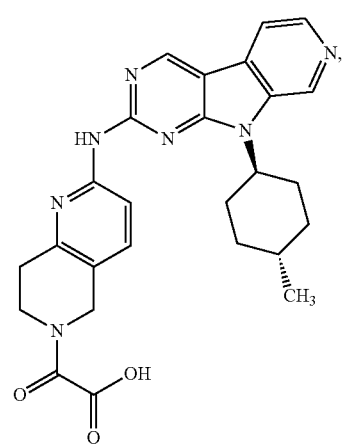 [SMILES: C[C@H]1CC[C@H](n2c3cnccc3c3cnc(Nc4ccc5c(n4)CCN(C(=O)C(=O)O)C5)nc32)CC1]

or the pharmaceutically acceptable salt or the hydrate thereof

44. The compound of embodiment 1, wherein the compound is

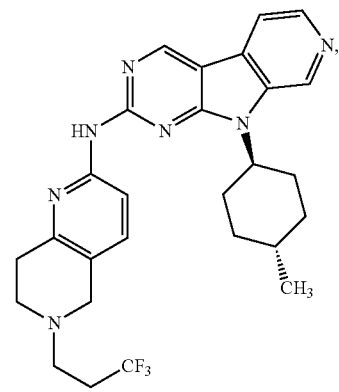 [SMILES: C[C@H]1CC[C@H](n2c3cnccc3c3cnc(Nc4ccc5c(n4)CCN(CCC(F)(F)F)C5)nc32)CC1]

or the pharmaceutically acceptable salt or the hydrate thereof.

45. The compound of embodiment 1, wherein the compound is

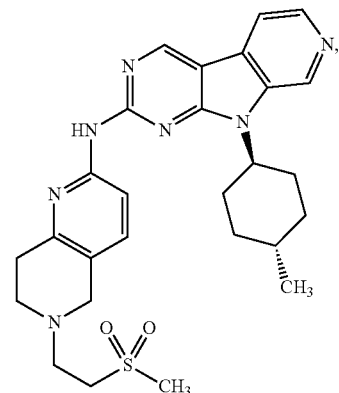

or the pharmaceutically acceptable salt or the hydrate thereof

46. The compound of embodiment 1, wherein the compound is

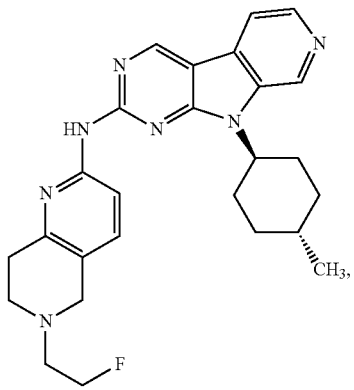 [SMILES: C[C@H]1CC[C@H](n2c3cnccc3c3cnc(Nc4ccc5c(n4)CCN(CCF)C5)nc32)CC1]

or the pharmaceutically acceptable salt or the hydrate thereof

47. The compound of embodiment 1, wherein the compound is

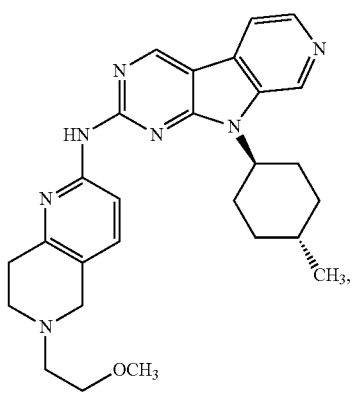 [SMILES: COCCN1CCc2nc(Nc3ncc4c5ccncc5n([C@H]5CC[C@H](C)CC5)c4n3)ccc2C1]

or the pharmaceutically acceptable salt or the hydrate thereof.

48. The compound of embodiment 1, wherein the compound is

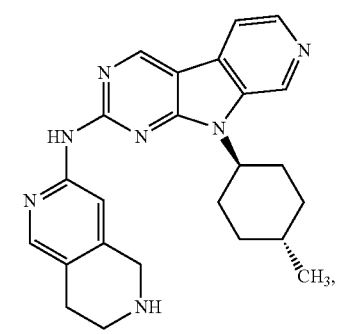 [SMILES: C[C@H]1CC[C@H](n2c3cnccc3c3cnc(Nc4cc5c(cn4)CCNC5)nc32)CC1]

or the pharmaceutically acceptable salt or the hydrate thereof

49. The compound of embodiment 1, wherein the compound is

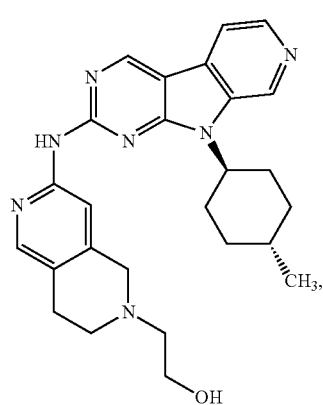

or the pharmaceutically acceptable salt or the hydrate thereof

50. The compound of embodiment 1, wherein the compound is

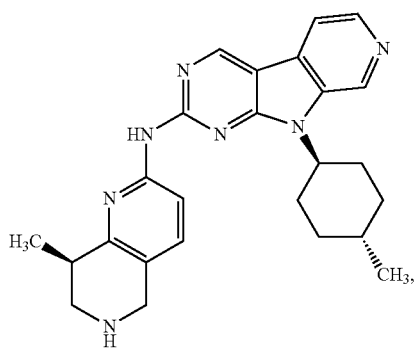

or the pharmaceutically acceptable salt or the hydrate thereof.

51. The compound of embodiment 1, wherein the compound is

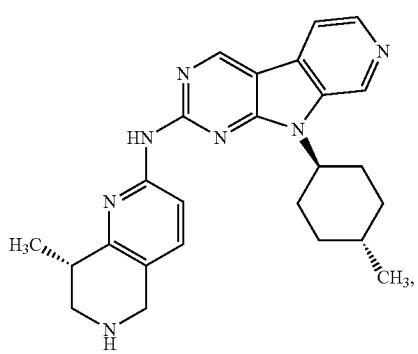

or the pharmaceutically acceptable salt or the hydrate thereof

52. The compound of embodiment 1, wherein the compound is

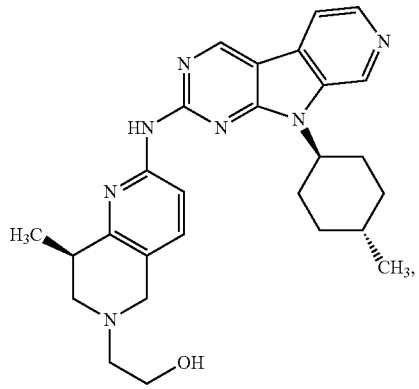 [SMILES: C[C@@H]1CN(CCO)Cc2ccc(Nc3ncc4c5ccncc5n([C@H]5CC[C@H](C)CC5)c4n3)nc21]

or the pharmaceutically acceptable salt or the hydrate thereof

53. The compound of embodiment 1, wherein the compound is

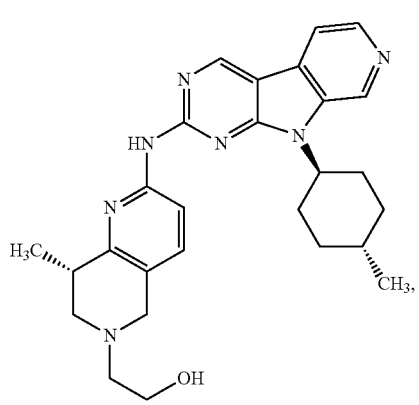 [SMILES: C[C@H]1CN(CCO)Cc2ccc(Nc3ncc4c5ccncc5n([C@H]5CC[C@H](C)CC5)c4n3)nc21]

or the pharmaceutically acceptable salt or the hydrate thereof.

54. The compound of embodiment 1, wherein the compound is

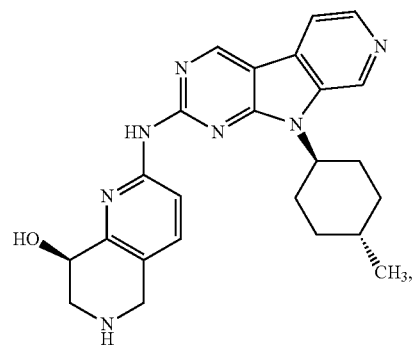 [SMILES: C[C@H]1CC[C@H](n2c3cnccc3c3cnc(Nc4ccc5c(n4)[C@H](O)CNC5)nc32)CC1]

or the pharmaceutically acceptable salt or the hydrate thereof

55. The compound of embodiment 1, wherein the compound is

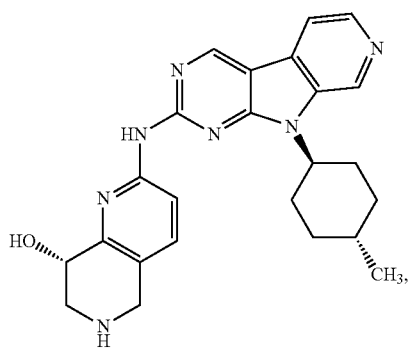 [SMILES: C[C@H]1CC[C@H](n2c3cnccc3c3cnc(Nc4ccc5c(n4)[C@@H](O)CNC5)nc32)CC1]

or the pharmaceutically acceptable salt or the hydrate thereof

56. The compound of embodiment 1, wherein the compound is

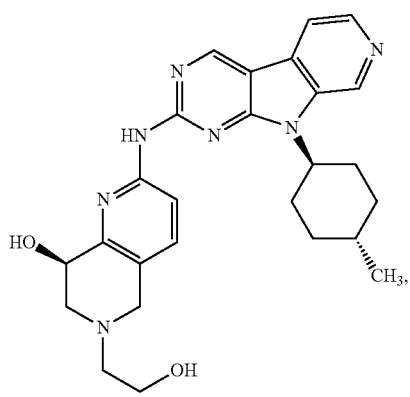 [SMILES: C[C@H]1CC[C@H](n2c3cnccc3c3cnc(Nc4ccc5c(n4)[C@H](O)CN(CCO)C5)nc32)CC1]

or the pharmaceutically acceptable salt or the hydrate thereof.

57. The compound of embodiment 1, wherein the compound is

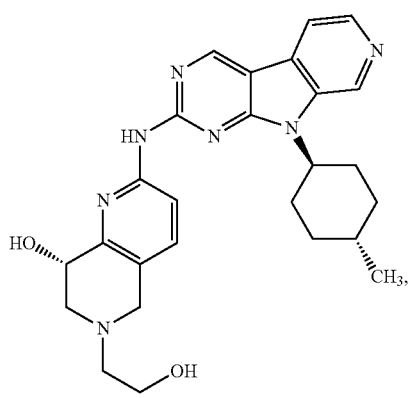 [SMILES: C[C@H]1CC[C@H](n2c3cnccc3c3cnc(Nc4ccc5c(n4)[C@@H](O)CN(CCO)C5)nc32)CC1]

or the pharmaceutically acceptable salt or the hydrate thereof

58. The compound of embodiment 1, wherein the compound is

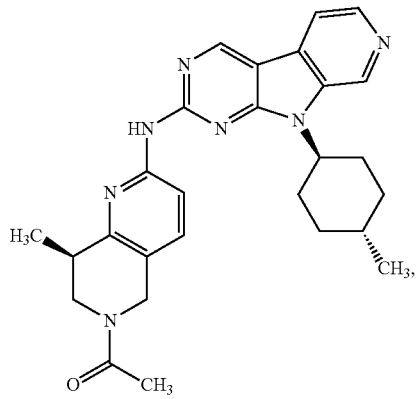 [SMILES: CC(=O)N1Cc2ccc(Nc3ncc4c5ccncc5n([C@H]5CC[C@H](C)CC5)c4n3)nc2[C@H](C)C1]

or the pharmaceutically acceptable salt or the hydrate thereof

59. The compound of embodiment 1, wherein the compound is

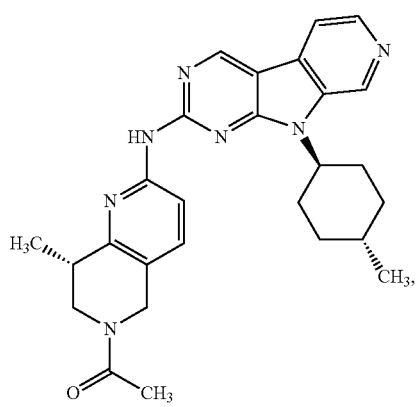 [SMILES: CC(=O)N1Cc2ccc(Nc3ncc4c5ccncc5n([C@H]5CC[C@H](C)CC5)c4n3)nc2[C@@H](C)C1]

or the pharmaceutically acceptable salt or the hydrate thereof.

60. The compound of embodiment 1, wherein the compound is

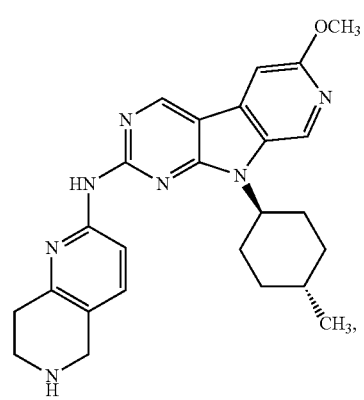 [SMILES: COc1cc2c3cnc(Nc4ccc5c(n4)CCNC5)nc3n([C@H]3CC[C@H](C)CC3)c2cn1]

or the pharmaceutically acceptable salt or the hydrate thereof

61. The compound of embodiment 1, wherein the compound is

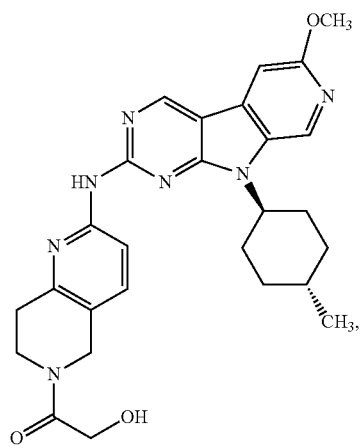 [SMILES: COc1cc2c3cnc(Nc4ccc5c(n4)CCN(C(=O)CO)C5)nc3n([C@H]3CC[C@H](C)CC3)c2cn1]

or the pharmaceutically acceptable salt or the hydrate thereof

62. The compound of embodiment 1, wherein the compound is

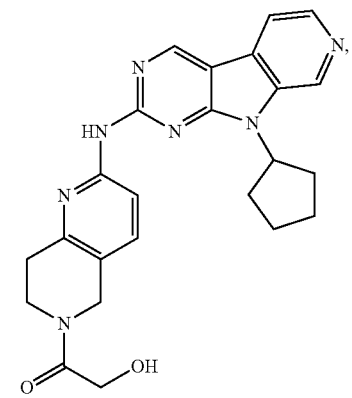 [SMILES: O=C(CO)N1CCc2nc(Nc3ncc4c5ccncc5n(C5CCCC5)c4n3)ccc2C1]

or the pharmaceutically acceptable salt or the hydrate thereof

63. The compound of embodiment 1, wherein the compound is

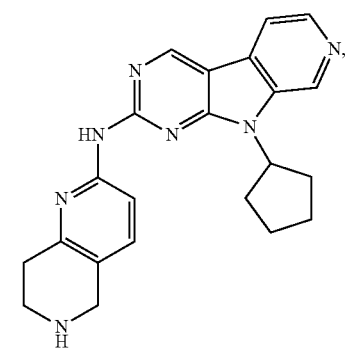 [SMILES: c1cc2c3cnc(Nc4ccc5c(n4)CCNC5)nc3n(C3CCCC3)c2cn1]

or the pharmaceutically acceptable salt or the hydrate thereof

64. The compound of embodiment 1, wherein the compound is

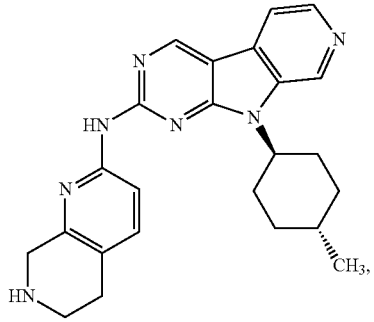 [SMILES: C[C@H]1CC[C@H](n2c3cnccc3c3cnc(Nc4ccc5c(n4)CNCC5)nc32)CC1]

or the pharmaceutically acceptable salt or the hydrate thereof

65. The compound of embodiment 1, wherein the compound is

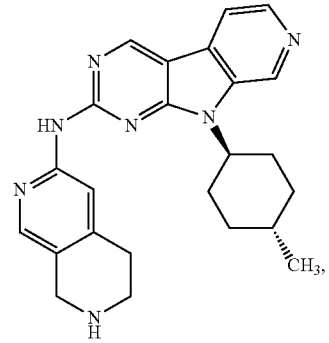 [SMILES: C[C@H]1CC[C@H](n2c3cnccc3c3cnc(Nc4cc5c(cn4)CNCC5)nc32)CC1]

or the pharmaceutically acceptable salt or the hydrate thereof

66. The compound of embodiment 1, wherein the compound is

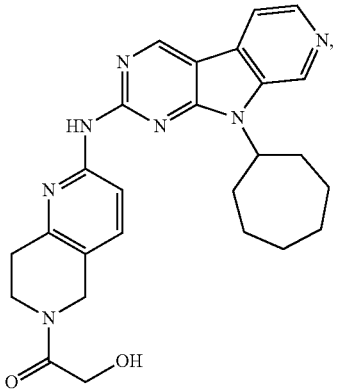 [SMILES: O=C(CO)N1CCc2nc(Nc3ncc4c5ccncc5n(C5CCCCCC5)c4n3)ccc2C1]

or the pharmaceutically acceptable salt or the hydrate thereof

67. The compound of embodiment 1, wherein the compound is

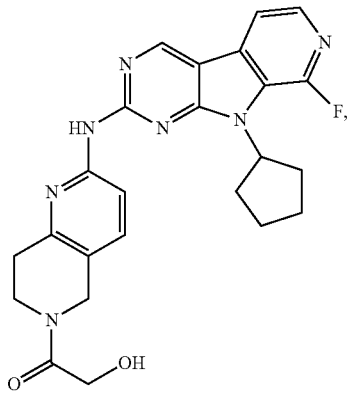 [SMILES: O=C(CO)N1CCc2nc(Nc3ncc4c5ccnc(F)c5n(C5CCCC5)c4n3)ccc2C1]

or the pharmaceutically acceptable salt or the hydrate thereof

68. The compound of embodiment 1, wherein the compound is selected from

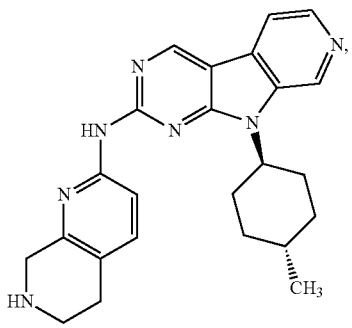

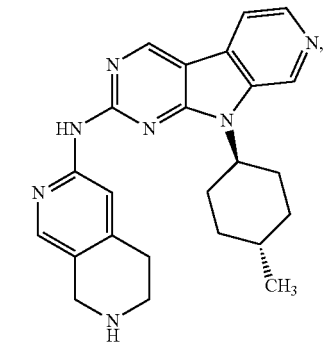

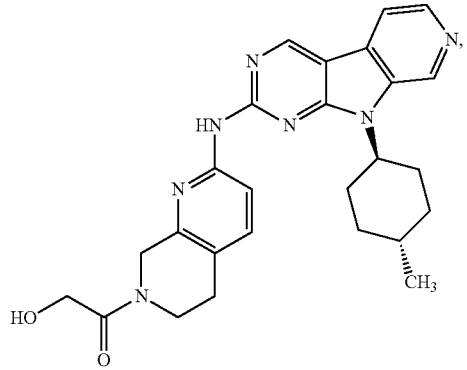

89
-continued
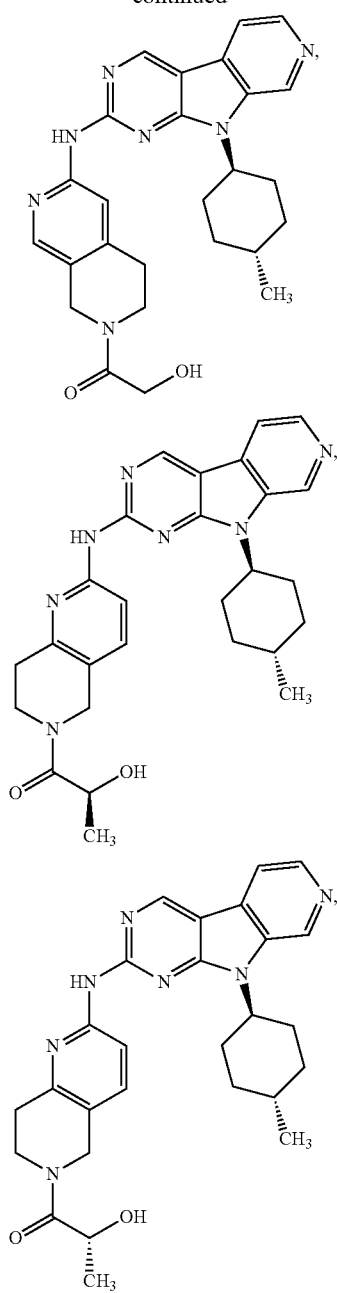
or
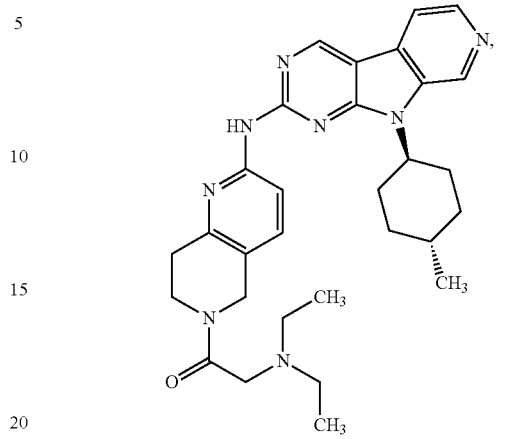
or the pharmaceutically acceptable salt or the hydrate thereof
69. The compound of embodiment 1, wherein the compound is
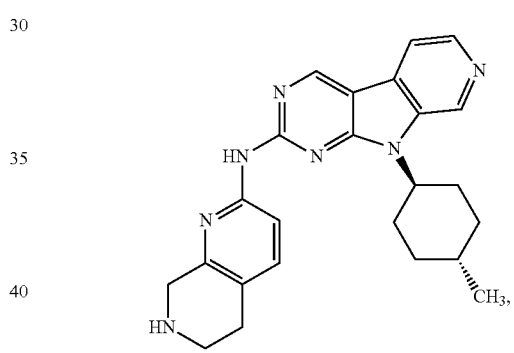
or the pharmaceutically acceptable salt or the hydrate thereof
70. The compound of embodiment 1, wherein the compound is
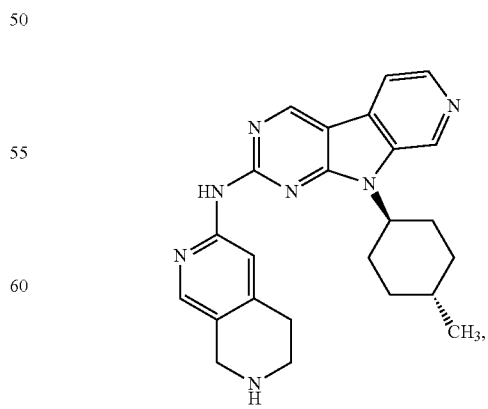
or the pharmaceutically acceptable salt or the hydrate thereof.

71. The compound of embodiment 1, wherein the compound is

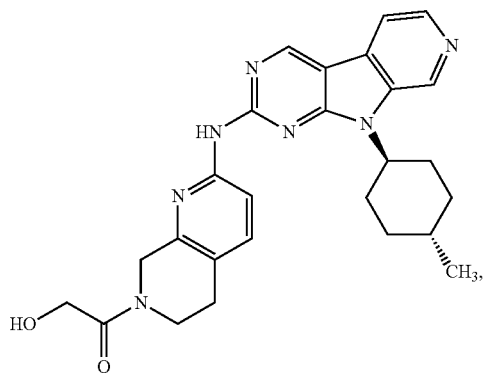 [SMILES: C[C@H]1CC[C@H](n2c3cnccc3c3cnc(Nc4ccc5c(n4)CN(C(=O)CO)CC5)nc32)CC1]

or the pharmaceutically acceptable salt or the hydrate thereof

72. The compound of embodiment 1, wherein the compound is

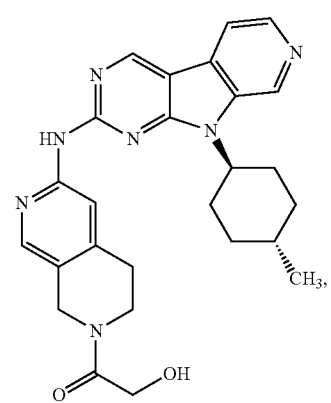 [SMILES: C[C@H]1CC[C@H](n2c3cnccc3c3cnc(Nc4cc5c(cn4)CN(C(=O)CO)CC5)nc32)CC1]

or the pharmaceutically acceptable salt or the hydrate thereof

73. The compound of embodiment 1, wherein the compound is

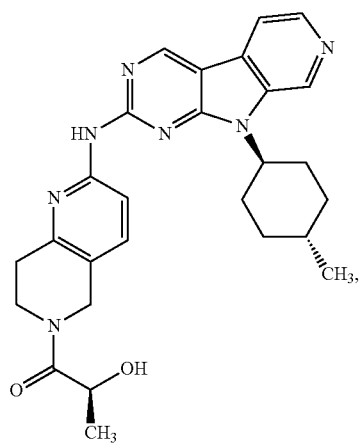 [SMILES: C[C@H](O)C(=O)N1CCc2nc(Nc3ncc4c5ccncc5n([C@H]5CC[C@H](C)CC5)c4n3)ccc2C1]

or the pharmaceutically acceptable salt or the hydrate thereof

74. The compound of embodiment 1, wherein the compound is

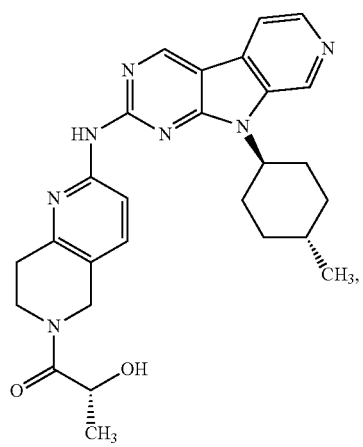 [SMILES: C[C@@H](O)C(=O)N1CCc2nc(Nc3ncc4c5ccncc5n([C@H]5CC[C@H](C)CC5)c4n3)ccc2C1]

or the pharmaceutically acceptable salt or the hydrate thereof

75. The compound of embodiment 1, wherein the compound is

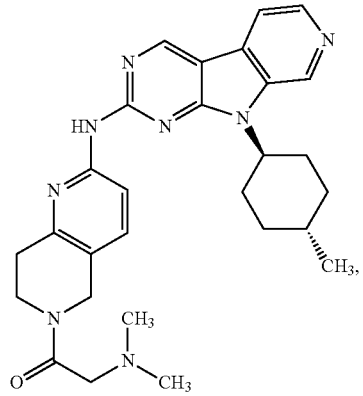 [SMILES: CN(C)CC(=O)N1CCc2nc(Nc3ncc4c5ccncc5n([C@H]5CC[C@H](C)CC5)c4n3)ccc2C1]

or the pharmaceutically acceptable salt or the hydrate thereof

76. The compound of embodiment 1, wherein the compound is

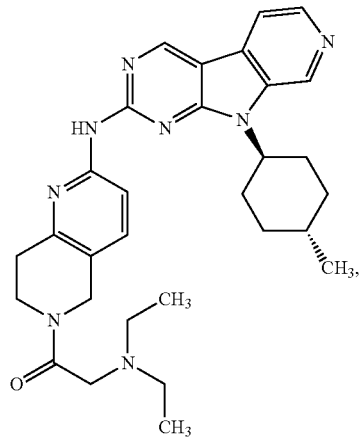 [SMILES: CCN(CC)CC(=O)N1CCc2nc(Nc3ncc4c5ccncc5n([C@H]5CC[C@H](C)CC5)c4n3)ccc2C1]

or the pharmaceutically acceptable salt or the hydrate thereof

77. The compound of any one of embodiments 1-76 in a neutral form.

78. The pharmaceutically acceptable salt of any one of embodiments 1-76.

79. The pharmaceutically acceptable salt of embodiment 78, wherein the pharmaceutically acceptable salt is selected from a chloride salt, a methanesulfonate salt, or a benzenesulfonate salt.

80. The pharmaceutically acceptable salt of embodiment 78, wherein the pharmaceutically acceptable salt is a chloride salt.

81. The pharmaceutically acceptable salt of embodiment 78, wherein the pharmaceutically acceptable salt is a methanesulfonate salt.

82. The pharmaceutically acceptable salt of embodiment 78, wherein the pharmaceutically acceptable salt is a benzenesulfonate salt.

83. A pharmaceutical composition, the pharmaceutical composition comprising a therapeutically effective amount of the compound, the pharmaceutically acceptable salt, the hydrate thereof, or the mixture thereof according to any one of embodiments 1-82 and at least one pharmaceutically acceptable excipient, carrier, or diluent.

84. A method of treating cancer, the method comprising: administering to a subject an effective amount of the compound, the pharmaceutically acceptable salt thereof, the hydrate thereof, or the mixture thereof of any one of embodiments 1-82 or the pharmaceutical composition of embodiment 83.

85. The method of embodiment 84, wherein the cancer is selected from acute myeloid leukemia, acute lymphoblastic leukemia, myelodysplastic syndrome, multiple myeloma, chronic myeloid leukemia, acute lymphocytic leukemia, chronic lymphocytic leukemia, non-Hodgkin lymphoma, another lymphoma, another myeloma, or another leukemia.

86. The method of embodiment 85, wherein the cancer is acute myeloid leukemia.

87. The method of embodiment 84, wherein the cancer is selected from breast cancer, colorectal cancer, small cell lung carcinoma, head and neck, glioblastoma, pancreatic, gastrointestinal, liver, prostate, ovarian, testicular, endometrial, bladder, melanoma, osteosarcoma, or another sarcoma.

88. The method of any one of embodiments 84-88, wherein the cancer is Rb-positive.

89. The method of embodiment 84, wherein the subject is a human patient, and the cancer is a hematological cancer.

90. A method of treating cancer, the method comprising: administering to a subject
(a) an effective amount of the compound, the pharmaceutically acceptable salt thereof, the hydrate thereof, or the mixture thereof of any one of embodiments 1-82 or the pharmaceutical composition of embodiment 83; and
(b) at least one second therapeutic agent used in the treatment of cancer.

91. The method of embodiment 90, wherein the second therapeutic agent is cytosine arabinoside, daunorubicin, idarubicin, doxorubicin, cyclophosphamide, etoposide, carboplatin, fludarabine, mitoxantrone, dexamethasone, rituximab, midostaurin, a granulocyte colony-stimulating factor, filgrastim, PEG-filgrastim, lenograstim, decitabine, azacitidine, paclitaxel, gemcitibine, motesanib disphosphate, panitumumab, an antibody directed against CD33, or a CD33 bispecific T-cell engager antibody.

92. The method of embodiment 90, wherein the second therapeutic agent is cytosine arabinoside.

93. The method of embodiment 90, wherein the second therapeutic agent is an agent used in the treatment of acute myeloid leukemia.

94. The method of any one of embodiments 90-93, wherein the effective amount of the compound, the pharmaceutically acceptable salt thereof, the hydrate thereof, or the mixture thereof of any one of embodiments 1-82 or the pharmaceutical composition of embodiment 83 is administered to the subject after the at least one second therapeutic agent is administered to the subject.

95. The method of any one of embodiments 90-93, wherein the effective amount of the compound, the pharmaceutically acceptable salt thereof, the hydrate thereof, or the mixture thereof of any one of embodiments 1-82 or the pharmaceutical composition of embodiment 83 is administered to the subject before the at least one second therapeutic agent is administered to the subject.

96. The method of any one of embodiments 90-93, wherein the effective amount of the compound, the pharmaceutically acceptable salt thereof, the hydrate thereof, or the mixture thereof of any one of embodiments 1-82 or the pharmaceutical composition of embodiment 83 is administered to the subject at the same time that the at least one second therapeutic agent is administered to the subject.

97. The compound of any one of embodiments 1-82 in the preparation of a medicament.

98. The compound of any one of embodiments 1-82 or the pharmaceutically acceptable salt, or the hydrate thereof, or the mixture thereof or the pharmaceutical composition of embodiment 83 for treating cancer.

99. The compound of embodiment 98 or the pharmaceutically acceptable salt, or the hydrate thereof, or the mixture thereof, wherein the cancer is selected from acute myeloid leukemia, acute lymphoblastic leukemia, myelodysplastic syndrome, multiple myeloma, chronic myeloid leukemia, acute lymphocytic leukemia, chronic lymphocytic leukemia, non-Hodgkin lymphoma, another lymphoma, another myeloma, or another leukemia.

100. The compound of embodiment 98 or the pharmaceutically acceptable salt, or the hydrate thereof, or the mixture thereof, wherein the cancer is acute myeloid leukemia.

101. The compound of embodiment 98 or the pharmaceutically acceptable salt, or the hydrate thereof, or the mixture thereof, wherein the cancer is selected from breast cancer, colorectal cancer, small cell lung carcinoma, head and neck, glioblastoma, pancreatic, gastrointestinal, liver, prostate, ovarian, testicular, endometrial, bladder, melanoma, osteosarcoma, or another sarcoma.

102. The compound of embodiment 98 or the pharmaceutically acceptable salt, or the hydrate thereof, or the mixture thereof, wherein the cancer is Rb-positive.

103. The compound of embodiment 98 or the pharmaceutically acceptable salt, or the hydrate thereof, or the mixture thereof, wherein the compound is for use in treating a human cancer patient, and the cancer is a hematological cancer.

104. The compound, the pharmaceutically acceptable salt thereof, the hydrate thereof, or the mixture thereof of any one of embodiments 1-82 or the pharmaceutical composition of embodiment 83 for treating cancer, the treatment of cancer comprising: administering to a subject
(a) an effective amount of the compound, the pharmaceutically acceptable salt thereof, the hydrate thereof, or the mixture thereof of any one of embodiments 1-82 or the pharmaceutical composition of embodiment 83; and
(b) at least one second therapeutic agent used in the treatment of cancer.

105. The compound of embodiment 104 or the pharmaceutically acceptable salt, or the hydrate thereof, or the mixture thereof, wherein the second therapeutic agent is cytosine arabinoside, daunorubicin, idarubicin, doxorubicin, cyclophosphamide, etoposide, carboplatin, fludarabine, mitoxantrone, dexamethasone, rituximab, midostaurin, a granulocyte colony-stimulating factor, filgrastim, PEG-filgrastim, lenograstim, decitabine, azacitidine, paclitaxel, gemcitibine, motesanib disphosphate, panitumumab, an antibody directed against CD33, or a CD33 bispecific T-cell engager antibody.

106. The compound of embodiment 104 or the pharmaceutically acceptable salt, or the hydrate thereof, or the mixture thereof, wherein the second therapeutic agent is cytosine arabinoside.

107. The compound of embodiment 104 or the pharmaceutically acceptable salt, or the hydrate thereof, or the mixture thereof, wherein the second therapeutic agent is an agent used in the treatment of acute myeloid leukemia.

108. The compound of any one of embodiments 104-107 or the pharmaceutically acceptable salt, or the hydrate thereof, or the mixture thereof, wherein the effective amount of the compound, the pharmaceutically acceptable salt thereof, or the mixture thereof of any one of embodiments 1-82 or the pharmaceutical composition of embodiment 83 is administered to the subject after the at least one second therapeutic agent is administered to the subject.

109. The compound of any one of embodiments 104-107 or the pharmaceutically acceptable salt, or the hydrate thereof, or the mixture thereof, wherein the effective amount of the compound, the pharmaceutically acceptable salt thereof, or the mixture thereof of any one of embodiments 1-82 or the pharmaceutical composition of embodiment 83 is administered to the subject before the at least one second therapeutic agent is administered to the subject.

110. The compound of any one of embodiments 104-107 or the pharmaceutically acceptable salt, or the hydrate thereof, or the mixture thereof, wherein the effective amount of the compound, the pharmaceutically acceptable salt thereof, or the mixture thereof of any one of embodiments 1-74 or the pharmaceutical composition of embodiment 75 is administered to the subject at the same time that the at least one second therapeutic agent is administered to the subject.

The pharmaceutical compositions or compositions for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Compositions for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such compositions may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The compounds of the invention may be used to treat or prevent various kinase-related disorders. Thus, the present invention provides methods for treating or preventing such disorders. In some embodiments, the invention provides a method for treating a kinase-mediated disorder in a subject that includes administering a therapeutically effective amount of a compound of any of the embodiments of the invention or a pharmaceutical composition to the subject. In some embodiments, the subject is a mammal, and in some such embodiments is a human. In some embodiments the disorder is mediated by CDK4, CDK6, and/or FLT3 complex. In some such embodiments, the disorder is mediated by CDK4 and/or CDK6. In other embodiments, the disease is mediated by FLT3. In some embodiments, administration of the compound, salt, or pharmaceutical composition produces inhibition of CDK4 and FLT3. In some embodiments, the disorder is cancer. The present invention thus provides methods for treating or preventing CDK4 and FLT3-mediated disease states, such as cancer. In some embodiments, the cancer is a tumor such as a solid tumor. However, in other embodiments, the cancer is a hematological cancer. In some embodiments, the cancer is acute myeloid leukemia. In some embodiments, the disorder is mediated by p16 and p15 expression and in some such embodiments is correlated with low expression levels of p15$^{INK4B}$ and/or p16$^{INK4A}$.

As described above, the compounds of the invention may also be used to treat proliferation-related disorders. Thus, the invention further provides methods for treating such proliferation-related disorders in a subject. Such methods include administering to a subject in need thereof a therapeutically effective amount of the compound or pharmaceutical composition of any of the embodiments. In some embodiments, the subject is a mammal. In some such embodiments, the mammal is a human. In some embodiments, the proliferation-related disorder is abnormal cell growth. In other embodiments, the disorder is inflammation or an inflammation-related disorder. In still other embodiments, the disorder is a metabolic disease such as diabetes. In still other embodiments, the disorder is cancer. In some such embodiments, the cancer is a solid tumor. In other such embodiments, the cancer is a hematological cancer, and, in some such embodiments, is acute myeloid leukemia.

The magnitude of a prophylactic or therapeutic dose of a compound of any of the embodiments or a pharmaceutically acceptable salt, solvate, hydrate, or stereoisomer thereof in the acute or chronic treatment or prevention of a cancer or other disease or condition will vary with the nature and aggressiveness of the condition, and the route by which the active ingredient is administered. The dose, and in some cases the dose frequency, will also vary according to the condition to be treated, the age, body weight, and response of the individual patient. Suitable dosing regimens can be readily selected by those skilled in the art with due consideration of such factors. In one embodiment, the dose administered depends upon the specific compound to be used, and the weight and condition of the patient. In general, the dose per day is in the range of from about 0.001 to 100 mg/kg, preferably about 1 to 25 mg/kg, more preferably about 1 to about 5 mg/kg. For treatment of humans having a cancer, about 0.1 mg to about 15 g per day is administered in about one to four divisions a day, preferably 10 mg to 12 g per day, more preferably from 40 mg to 500 mg per day. In one embodiment the compounds of the invention are administered from 40 mg to 500 mg per day in about one to four divisions a day. Additionally, the recommended daily dose can be administered in cycles as single agents or in combination with other therapeutic agents. In one embodiment, the daily dose is administered in a single dose or in equally divided doses. In a related embodiment, the recommended daily dose can be administered one time per week, two times per week, three times per week, four times per week or five times per week. In some embodiments, a compound or pharmaceutical composition of the invention is dosed QD whereas in other embodiments, it is dosed BID.

The compounds of the invention can be administered to provide systemic distribution of the compound within the patient. Therefore, in some embodiments, the compounds of the invention are administered to produce a systemic effect in the body.

The compounds of the invention may also be administered directly to a site affected by a condition, as, for example, an in the treatment of an accessible area of skin or an esophageal cancer.

As indicated above, the compounds of the invention may be administered via oral, mucosal (including sublingual, buccal, rectal, nasal, or vaginal), parenteral (including subcutaneous, intramuscular, bolus injection, intra-arterial, or intravenous), transdermal, or topical administration. In some embodiments, the compounds of the invention are administered via mucosal (including sublingual, buccal, rectal, nasal, or vaginal), parenteral (including subcutaneous, intramuscular, bolus injection, intra-arterial, or intravenous), transdermal, or topical administration. In other embodiments, the compounds of the invention are administered via oral administration. In still other embodiments, the compounds of the invention are not administered via oral administration.

Different therapeutically effective amounts may be applicable for different conditions, as will be readily known by those of ordinary skill in the art. Similarly, amounts sufficient to treat or prevent such conditions, but insufficient to cause, or sufficient to reduce, adverse effects associated with conventional therapies are also encompassed by the above described dosage amounts and dose frequency schedules.

Some methods of the invention comprise the administration of a compound of the invention and an additional therapeutic agent (i.e., a therapeutic agent other than a compound of the invention). Thus, the compounds of the invention can be used in combination with at least one other therapeutic agent, for example with a second therapeutic agent. Examples of additional therapeutic agents include, but are not limited to, antibiotics, anti-emetic agents, antidepressants, antifungal agents, anti-inflammatory agents, antineoplastic agents, antiviral agents, cytotoxic agents, and other anticancer agents, immunomodulatory agents, alpha-interferons, β-interferons, alkylating agents, hormones, and cytokines. In one embodiment, the invention encompasses administration of an additional therapeutic agent that demonstrates anti-cancer activity. In another embodiment, an additional therapeutic agent that demonstrates cytotoxic activity is administered to a subject such as a cancer patient. In some embodiments, the second therapeutic agent is selected from cytosine arabinoside, daunorubicin, idarubicin, doxorubicin, cyclophosphamide, etoposide, carboplatin, fludarabine, mitoxantrone, dexamethasone, rituximab, midostaurin, a granulocyte colony-stimulating factor, filgrastim, PEG-filgrastim, lenograstim, decitabine, azacitidine, paclitaxel, gemcitibine, motesanib disphosphate, panitumumab, an antibody directed against CD33, or a CD33 bispecific T-cell engager antibody. In other embodiments, the second therapeutic agent is selected from cytosine arabinoside, daunorubicin, idarubicin, doxorubicin, cyclophosphamide, etoposide, carboplatin, fludarabine, mitoxantrone, dexamethasone, rituximab, midostaurin, a granulocyte colony-stimulating factor, filgrastim, PEG-filgrastim, lenograstim, decitabine, azacitidine, paclitaxel, gemcitibine, motesanib disphosphate, panitumumab. In still other such embodiments, the second therapeutic agent is selected from cytosine arabinoside, daunorubicin, idarubicin, doxorubicin, cyclophosphamide, etoposide, carboplatin, fludarabine, mitoxantrone, dexamethasone, rituximab, midostaurin, decitabine, azacitidine, paclitaxel, gemcitibine, or motesanib disphosphate. In some such embodiments, the second therapeutic agent is cytosine arabinoside. In other embodiments, the second therapeutic agent is daunorubicin, idarubicin, or doxorubicin. In still other embodiments, the second therapeutic agent is azacitidine or decitabine.

The compounds of the invention and the other therapeutics agent can act additively or, preferably, synergistically. In some embodiments, a composition comprising a compound of the invention is administered concurrently with the administration of another therapeutic agent, which can be part of the same composition or can be in a different composition from the one that comprises the compound of the invention. In other embodiments, a compound of the invention is administered prior to, or subsequent to, administration of another therapeutic agent. In still other embodiments, a compound of the invention is administered to a patient who has not previously undergone or is not currently undergoing treatment with another therapeutic agent. A compound of the invention may be administered to a subject that has had, is currently undergoing, or is scheduled to receive radiation therapy. In some such embodiments, the subject is a cancer patient.

When administered as a combination, the therapeutic agents can be formulated as separate compositions that are administered at the same time or sequentially at different times, or the therapeutic agents can be given as a single composition. The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent. Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of any of the embodiments described herein may also be administered sequentially with known anticancer or cytotoxic agents when a combination formulation is inappropriate. The invention is not limited in the sequence of administration as compounds of the invention may be administered either prior to, simultaneous with, or after administration of a known anticancer or cytotoxic agent.

There are large numbers of antineoplastic agents available in commercial use, in clinical evaluation and in pre-clinical development, which may be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from, but are not limited to, the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT, and uricytin.

A second family of antineoplastic agents which may be used in combination with compounds of the present invention consists of alkylating-type antineoplastic agents. Suitable alkylating-type antineoplastic agents may be selected from, but are not limited to, the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin, and trimelamol.

A third family of antineoplastic agents which may be used in combination with compounds of the present invention consists of antibiotic-type antineoplastic agents. Suitable antibiotic-type antineoplastic agents may be selected from, but are not limited to, the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibringen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko) UCN-10028A, Fujisawa WF-3405, Yoshitomi Y-25024, and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from, but not limited to, the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemex CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCl (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

The compounds of the invention may further be used with VEGFR inhibitors. Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. Nos. 6,630,500, 6,515,004, 6,713,485, 5,521,184, 5,770,599, 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089, and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAPT™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., U.S. Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., U.S. Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-lalfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Alternatively, the present compounds may also be used in co-therapies with other anti-neoplastic agents, such as VEGF antagonists, other kinase inhibitors including p38 inhibitors, aurora kinase inhibitors, c-met inhibitors, KDR inhibitors, EGF inhibitors and CDK inhibitors, TNF inhibitors, matrix metalloproteinases (MMP) inhibitors, COX-2 inhibitors including celecoxib, NSAID's, or $\alpha_v\beta_3$ inhibitors.

The compounds of the invention can be prepared using the general synthetic routes shown in the following schemes and described more fully in the Examples.

Scheme 1

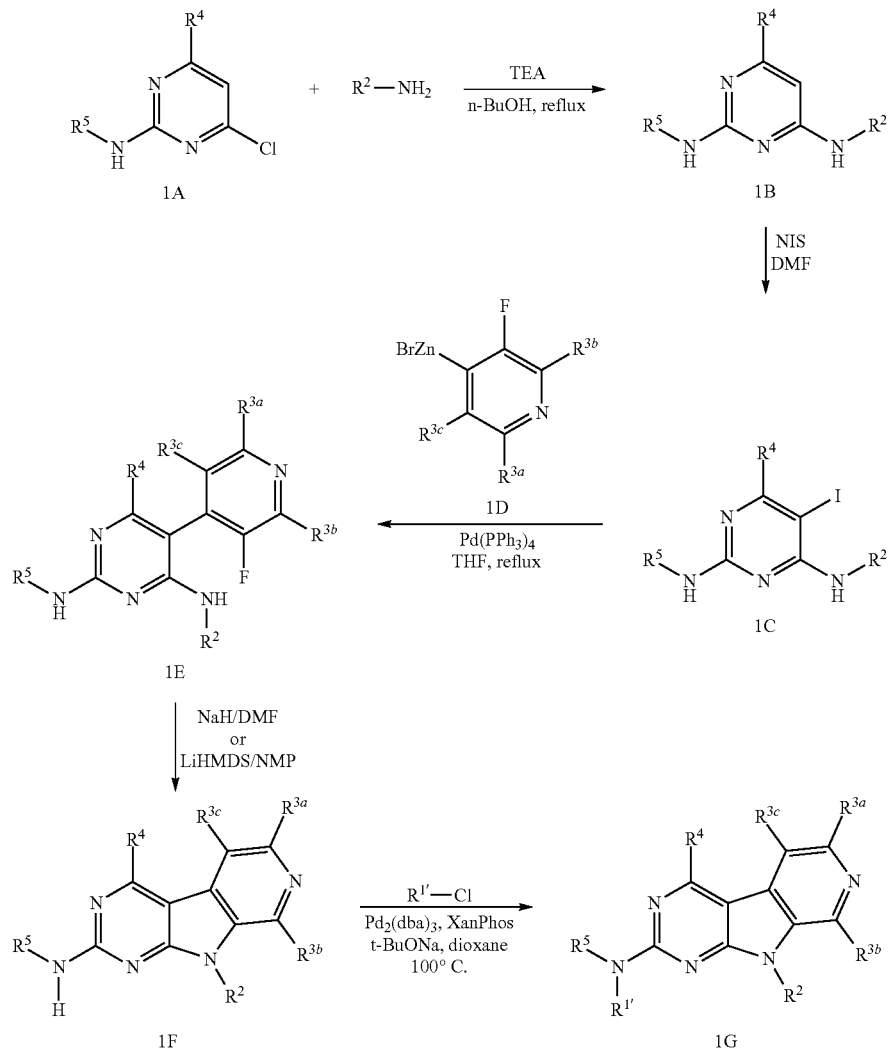

Scheme 1 illustrates how compounds of the invention can be prepared starting from chloropyrimidine 1A. Reaction of chloropyrimidine 1A with an appropriate amine provides diaminopyridimine 1B which can be iodinated to form 1C with N-iodosuccinimide. Iodopyrimidine 1C can be reacted with the appropriate zinc reagent 1D to form the unfused bicyclic intermediate 1E which can then be cyclized to form the useful reagent 1F. Reaction of 1F with suitable chloro substituted and protected $R^1$ groups or precursors (See Scheme 3) may be used to convert 1F to 1G which may then be converted into various compounds of the invention as shown in Scheme 4.

Scheme 2

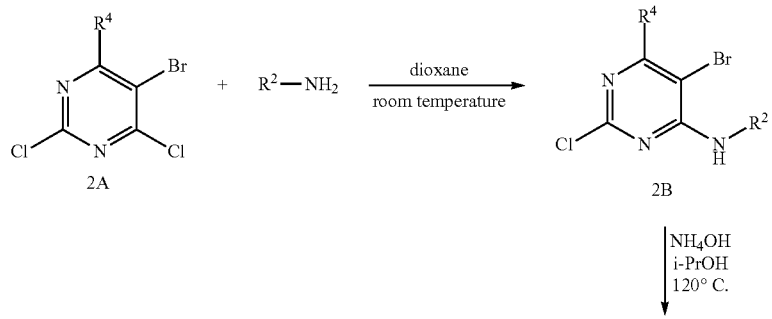

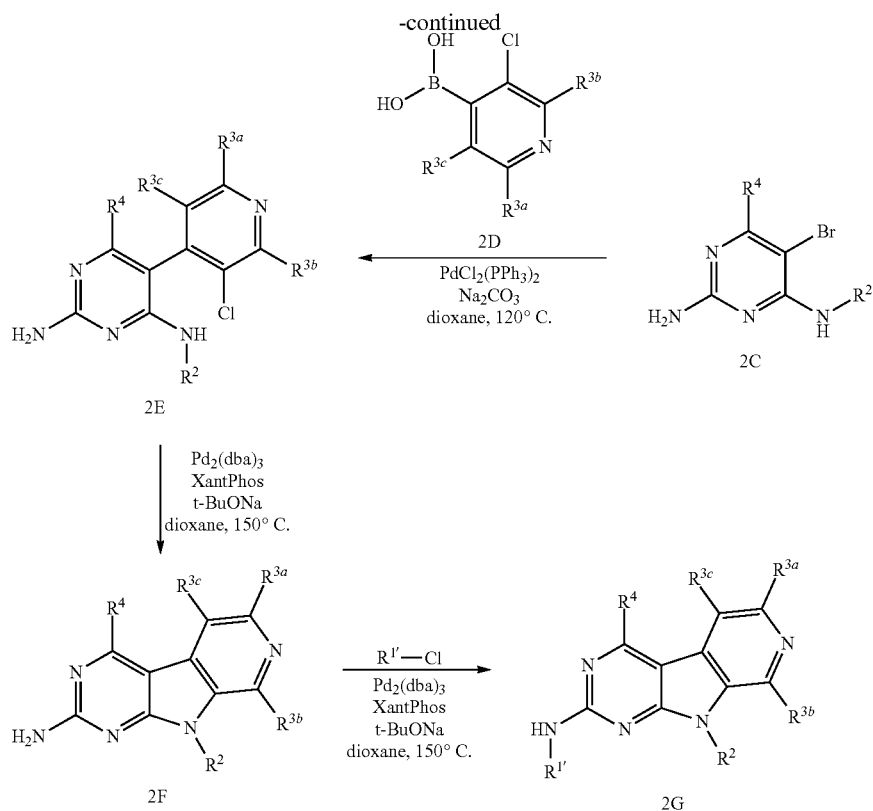

Scheme 2 provides an alternative route showing how compounds of the invention can be prepared starting from bromodichloropyrimidine 2A. Reaction of bromodichloropyrimidine 2A with an appropriate amine provides aminobromochloropyridimine 2B which can be converted to diaminobromopyrimidine 2C by reaction with ammonium hydroxide in isopropanol. Diaminobromopyrimidine 2C can be reacted with the boronic acid reagent 2D to form the unfused bicyclic intermediate 2E which can then be cyclized to form the useful reagent 2F. Reaction of 2F with suitable chloro substituted and protected $R^1$ groups or precursors (See Scheme 3) may be used to convert 2F to 2G which may then be converted into various compounds of the invention as shown in Scheme 4.

Scheme 3

$R^{1'}$—Cl

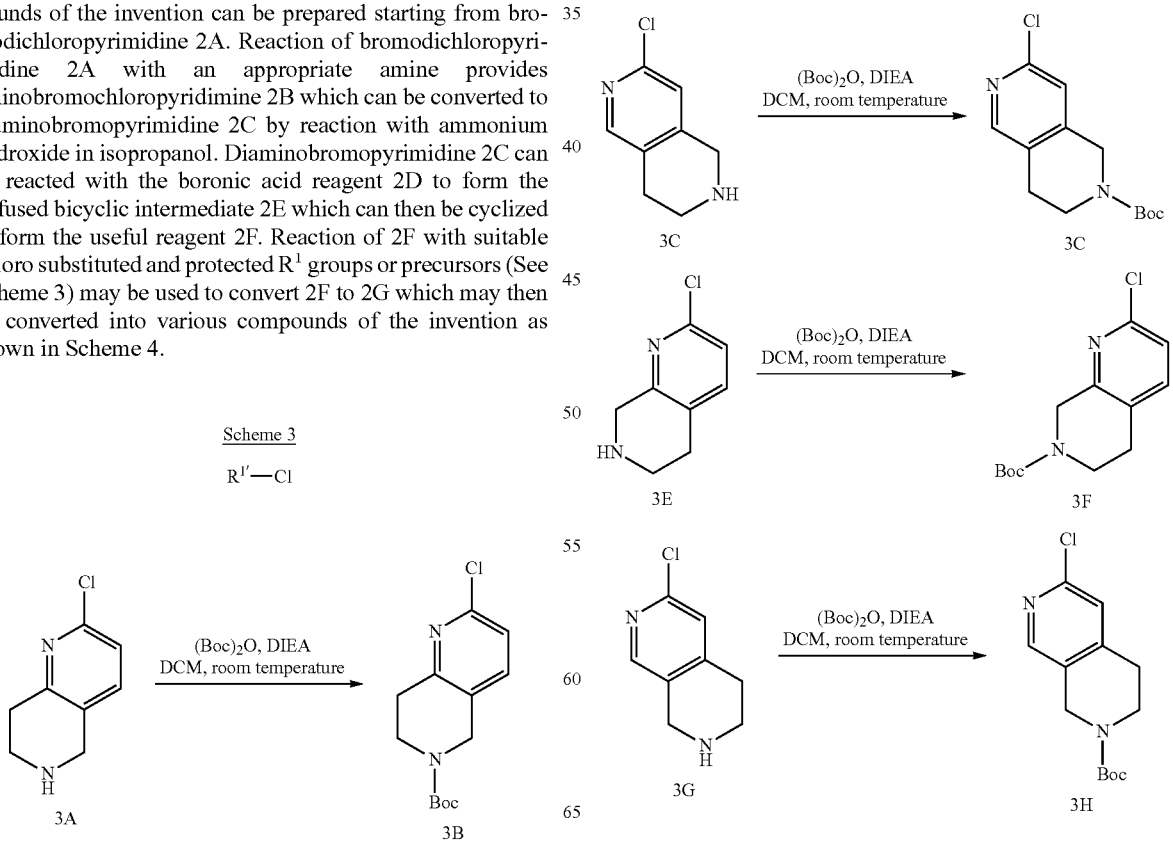

Scheme 3 shows how various R[1']—Cl Boc protected compounds may be prepared from the starting amine. The Boc-protected chloro-substituted compounds 3B, 3D, 3F, and 3H are useful reagents for preparing compounds of the invention as shown in Schemes 1 and 2.
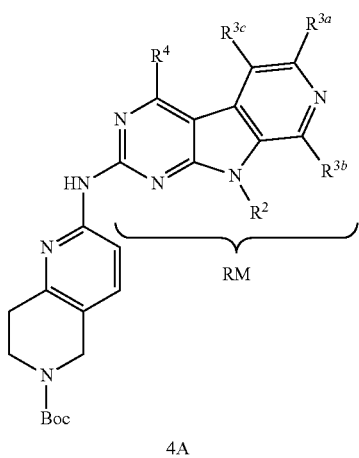
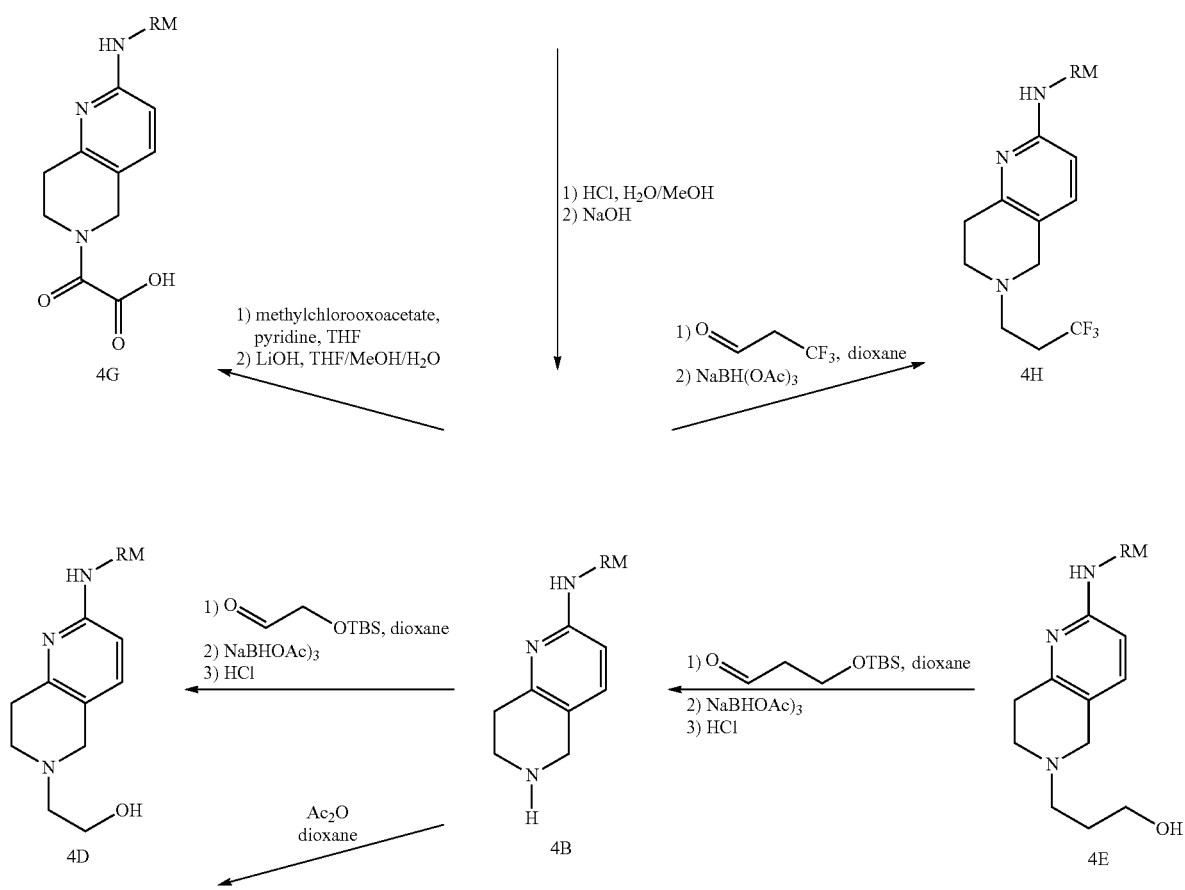

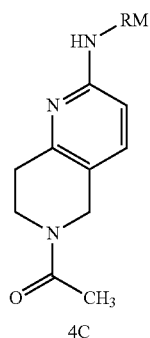

4C

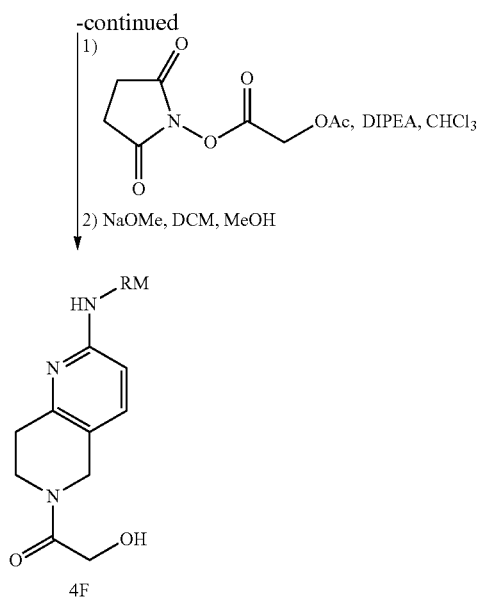

2) NaOMe, DCM, MeOH

4F

Scheme 4 shows how Boc-protected compound 4A prepared from Boc-protected chloro compound 3B and 1F (see Scheme 1) can be deprotected to form 4B. The deprotected 4B may be used to prepare a wide variety of derivatives as shown in Scheme 4. For example, reaction of 4B with acetic anhydride can be used to prepare 4C. Similarly 4B can be reacted with commercially available (t-butyldimethylsilyloxy)acetaldehyde and (t-butyldimethylsilyloxy)propanal and then be reduced to respectively form 4D and 4E. As described in Example 5, compounds such as 4B may be reacted with 2,5-dioxopyrrolidin-1-yl 2-acetoxyacetate to form 4F after treatment with sodium methoxide. 4B may also be used to form compounds such as 4G by treatment with methylchlorooxoacetate followed by reaction with LiOH in a mixture of tetrahydrofuran, methanol, and water. As a final, but non-exhaustive example, compounds such as 4B may be treated with reagents such as commercially available 3,3,3-trifluoropropanal and then reduced to form trifluoromethyl compounds such as 4H. Various other compounds can be prepared from compound 4B. For example, a reagent such as an alkyl chloroformate, for example ethyl chloroformate, may be reacted with the deprotected compound 4B to produce compounds in which $R^6$ is —C(=O)—O—($C_1$-$C_6$ alkyl).

The invention is further described by reference to the following examples, which are intended to exemplify the claimed invention but not to limit it in any way.

EXAMPLES

Unless otherwise stated, all starting materials were obtained from commercial sources such as Sigma-Aldrich, St. Louis, Mo., or were obtained using literature procedures.

$^1$H-NMR spectra were typically acquired on a Bruker Avance III 500 spectrometer system (Bruker, Bilerica, Mass.) operating at a $^1$H frequency of 500.13 MHz, equipped with a Bruker 5 mm PABBI probe with a z-axis gradient; or on a Bruker Avance II 400 spectrometer operating at a $^1$H frequency of 400.23 MHz, equipped with a Bruker 5 mm PABBO probe with a z-axis gradient. Samples were typically dissolved in 500 μL DMSO-$d_6$, $CD_3OD$, $CDCl_3$, or another deuterated NMR solvent for NMR analysis. $^1$H chemical shifts are referenced to the residual solvent signals from DMSO-$d_6$ at δ 2.50, $CD_3OD$ at δ 3.30, or other reference solvents, or may be referenced to tetramethylsilane. Significant peaks were tabulated and typically include: number of protons, multiplicity (s, singlet; d, doublet; dd, doublet of doublets; t, triplet; q, quartet; m, multiplet; br s, broad singlet) and coupling constant(s) in Hertz.

Electron Ionization (EI) mass spectra were typically recorded on an Agilent Technologies 6140 Quadrupole LC/MS mass spectrometer. Mass spectrometry results are reported as the ratio of mass over charge, sometimes followed by the relative abundance of each ion (in parentheses).

The following Abbreviations are used to refer to various reagents and solvents:
$Ac_2O$ Acetic anhydride
AcOH Acetic acid
ATP Adenosine Triphosphate
BSA Bovine Serum Albumin
n-BuLi n-butyllithium
DCM Dichloromethane
DMEM Dulbecco's Modified Eagle Medium
DMF N,N-Dimethylformamide
DMSO Dimethylsulfoxide
DTT Dithiothreitol
EDC N-(3-dimethylaminopropyl)-N'-ethylcarbodiimide hydrochloride
EDTA Ethyelenediaminetetraacetic acid
EGTA Ethyleneglycol bis(2-aminoethyl ether)-N,N,N',N' tetraacetic acid
EtOAc Ethyl Acetate
EtOH Ethanol
HPLC-MS High Performance Liquid Chromatography Mass Spectrometry
HTS High Throughput Screen
HTRF Homogeneous Time-Resolved Fluorescence
LCMS Liquid Chromatography Mass Spectrometry
LiHMDS Lithium bis(trimethylsilyl)amide
MeOH Methanol
NIS N-Iodosuccinimide
RPMI-1640 A cell growth medium developed at Roswell Park Memorial Institute
TBS t-Butyldimethylsilyl TEA Triethylamine
TFA Trifluoroacetic acid
THF Tetrahydrofuran Preparation Of Examples Example 1

9-((1r,4r)-4-Methylcyclohexyl)-N-(5,6,7,8-tetrahydro-1,6-naphthyridin-2-yl)-9H-pyrido[4',':4,5]pyrrolo[2,3-d]pyrimidin-2-amine

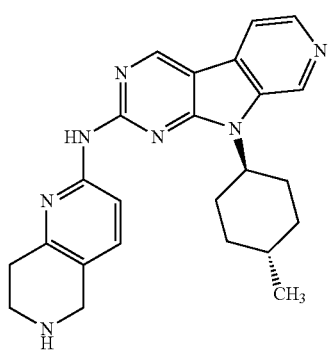

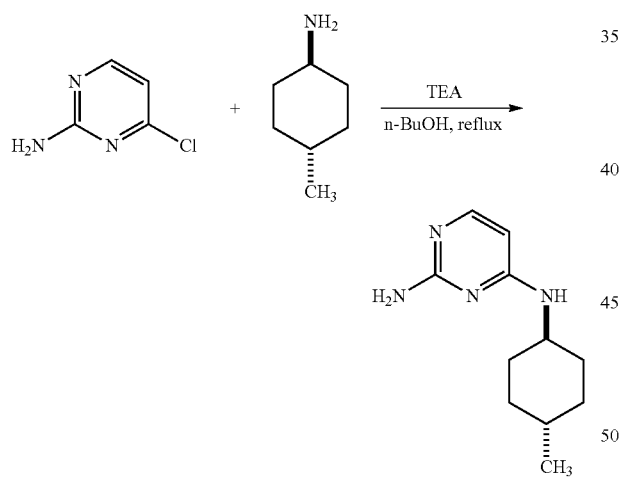

Synthesis of $N^4$-((1r,4r)-4-methylcyclohexyl)pyridine-2,4-diamine. 4-Chloropyrimidine-2-amine (commercially available from Sigma-Aldrich, St. Louis, Mo.) (1000 g, 7.72 mol, 1.0 eq), trans-4-methylcyclohexylamine hydrochloride (commercially available from TCI America, M1780) (1500 g, 10.03 mol, 1.3 eq) and TEA (3.23 L, 23.2 mol, 3.0 eq) were mixed together in n-butanol (8 L). The reaction mixture was heated at reflux for 36 hours and monitored using LCMS. Upon completion, the reaction mixture was cooled to room temperature, diluted with water (8 L) and extracted with EtOAc (2×10 L). The organic layers were combined, dried over $Na_2SO_4$, and concentrated under reduced pressure to give the title compound (1770 g) which was used in the next step without further purification.

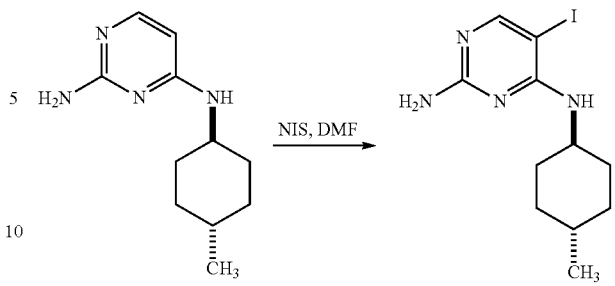

Synthesis of 5-iodo-$N^4$-((1r,4r)-4-methylcyclohexyl)pyridine-2,4-diamine. $N^4$-((1r,4r)-4-Methylcyclohexyl)pyridine-2,4-diamine (1770 g, 8.58 mol, 1.0 eq) was dissolved in anhydrous DMF (8 L). To this solution under $N_2$ atmosphere at 10° C. was added NIS (1.93 kg, 8.58 mol, 1.0 eq) in portions over 10 minutes. Upon completion of the addition, the reaction mixture was stirred at room temperature for 2 hours. The reaction was monitored using LCMS. Upon completion, the reaction mixture was cooled using an ice bath, quenched with saturated aqueous sodium carbonate (5 L) and extracted with EtOAc (2×15 L). The combined organic extracts were washed with saturated aqueous sodium carbonate (2×5 L), water (3×2 L), dried over $Na_2SO_4$, and concentrated under reduced pressure. The residue was purified using column chromatography eluting with 25% to 40% EtOAc in hexanes to provide the title compound (1.47 kg, 57% over two steps). $^1$H-NMR (300 MHz, DMSO-$d_6$) δ ppm 0.85 (3H, d, J=7.2 Hz), 0.98 (1H, dd, J=12.9, 2.7 Hz), 1.41-1.27 (3H, m), 1.66 (2H, d, J=12.3 Hz), 1.78 (2H, d, J=12.3 Hz), 3.85 (1H, m), 5.48 (1H, d, J=8.1 Hz), 6.16 (2H, br s), 7.86 (1H, s) ppm; MS m/z: 333 (M+1).

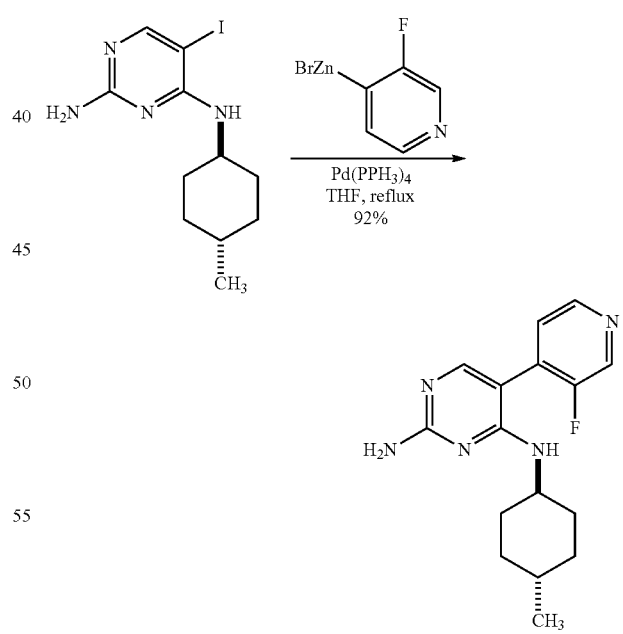

Synthesis of 5-(3-fluoropyridin-4-yl)-$N^4$-((1r,4r)-4-methylcyclohexyl)pyrimidine-2,4-diamine. To a solution of 2,2,6,6-tetramethylpiperidine (commercially available from Sigma-Aldrich, St. Louis, Mo.) (997 mL, 5.87 mol, 3 eq) in anhydrous THF (6 L) under $N_2$ atmosphere at 0° C., was added n-BuLi (2.5 M in hexanes, 2.35 L, 5.87 mol, 3 eq) via an addition funnel over 30 minutes. Upon completion of the addition, the reaction mixture was stirred at 0° C. for 1 hour. The reaction mixture was cooled to −74° C. (acetone/dry ice bath) and a solution of 3-fluoropyridine (commercially available from Sigma-Aldrich, St. Louis, Mo.) (561 g, 5.773 mol, 2.95 eq) in anhydrous THF (500 mL) was added over 15 minutes keeping the temperature below −63° C. Upon completion of the addition, the reaction mixture was stirred at −74° C. for an additional 2 hours. A solution of $ZnBr_2$ (1422 g, 6.32 mol, 3.22 eq) in anhydrous THF (3 L) was then added dropwise over 35 minutes keeping the temperature below −60° C. Upon completion of the addition, the cold bath was removed and the reaction mixture was allowed to warm to room temperature. Then 5-iodo-$N^4$-((1r,4r)-4-methylcyclohexyl)pyridine-2,4-diamine (650 g, 1.95 mol, 1.0 eq) was added in one portion followed by $Pd(PPh_3)_4$ (113 g, 97.8 mmol, 0.05 eq). The reaction mixture was heated at reflux overnight and monitored using LCMS. Upon completion, the reaction mixture was cooled to room temperature, quenched with saturated aqueous $NaHCO_3$ (6 L) and extracted with EtOAc (10 L×2). The organic extracts were washed with saturated $NaHCO_3$ (2.5 L×2) and brine (2.5 L), and were then concentrated under vacuum. The residue was dissolved in 2N HCl (2.5 L) and washed with DCM (1.25 L×3). The aqueous phase was adjusted to pH 10-12 by addition of aqueous 4N NaOH and extracted with DCM (1.5 L×3). The organic extracts were washed with water (1.25 L×2), dried and concentrated to give the title compound (540 g, 92%). $^1$H-NMR (300 MHz, DMSO-$d_6$) δ ppm 0.85 (3H, d, J=7.2 Hz), 0.98 (1H, dd, J=12.9, 2.7 Hz), 1.30-1.18 (3H, m), 1.64 (2H, d, J=12.3 Hz), 1.74 (2H, d, J=11.7 Hz), 3.96 (1H, m), 5.00 (1H, d, J=8.4 Hz), 6.24 (2H, br s), 7.35 (1H, dd, J=6.6, 4.4 Hz), 7.58 (1H, s), 8.37 (1H, d, J=4.8 Hz), 8.50 (1H, d, J=6.6 Hz) ppm.

Synthesis of 9-((1r,4r)-4-methylcyclohexyl)-9H-pyrido[4',:4,5]pyrrolo[2,3-d]pyrimidin-2-amine. To a solution of 5-(3-fluoropyridin-4-yl)-$N^4$-((1r,4r)-4-methylcyclohexyl)pyrimidine-2,4-diamine (854 g, 2.84 mol, 1.0 eq) in anhydrous 1-methyl-2-pyrrolidinone (8 L) under $N_2$ atmosphere at room temperature, was added LiHMDS (1.0 M in toluene, 8.5 L, 8.5 mol, 3.0 eq) over 30 minutes. Upon completion of the addition, the reaction mixture was heated at 90° C. overnight and monitored using LCMS. Upon completion, the reaction mixture was cooled to room temperature, quenched with ice cold water (10 L) and extracted with EtOAc (12 L). The organic phase was washed with saturated aqueous $NaHCO_3$ (4 L×2), and water (2 L×3). The aqueous layers were combined and back extracted with EtOAc (15 L×2). The organic layers were combined, dried over $Na_2SO_4$, and concentrated under reduced pressure. The solid thus obtained was suspended in DCM (2.5 L) and agitated using a rotary evaporator for 30 minutes. The solid was collected by filtration, washed with DCM and dried to afford the title compound (400 g). The mother liquor was purified by column chromatography (eluting with DCM/MeOH=50:1) to afford, after triturating with DCM (750 mL), additional title compound (277 g, total: 677 g, yield: 84%). $^1$H NMR (300 MHz, CD$_3$OD) δ ppm 1.02 (d, J=6.3 Hz, 3H), 1.33-1.20 (m, 2H), 1.67-1.60 (m, 2H), 1.95-1.84 (m, 4H), 1.58-1.45 (m, 2H), 4.87-4.77 (m, 1H), 7.94 (d, J=5.1 Hz, 1H), 8.31 (d, J=5.1 Hz, 1H), 8.87 (s, 1H), 8.96 (s, 1H) ppm; MS m/z: 282.0 (M+1).

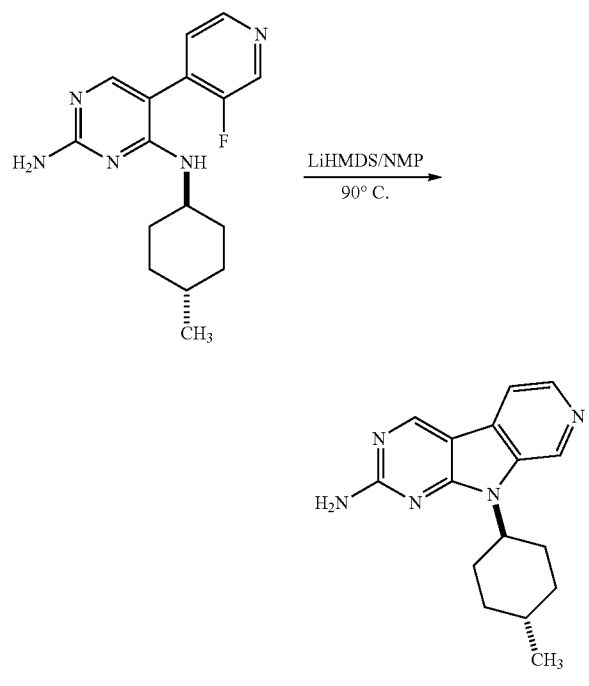

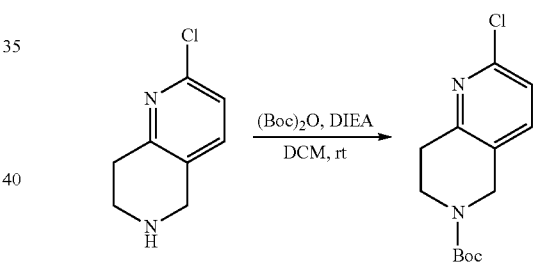

Synthesis of tert-butyl 2-chloro-7,8-dihydro-1,6-naphthyridine-6(5H)-carboxylate. To a slurry of 2-chloro-5,6,7,8-tetrahydro-1,6-naphthyridine hydrochloride (106.1 g, 517 mmol, commercially available from D-L Chiral Chemicals, ST-0143) and N,N-diisopropylethylamine (80 g, 108 mL, 621 mmol, 1.2 eq) in DCM (1 L) was added a solution of di-tert-butyl dicarbonate (119 g, 543 mmol, 1.05 eq) in DCM (100 mL) via an addition funnel within 1 hr. The reaction mixture became a clean solution and the solution thus obtained was stirred at room temperature for an additional hour and monitored using LCMS. Upon completion, the reaction mixture was concentrated. The residue was dissolved in EtOAc (1 L) and washed with water (3×300 mL), washed with brine (300 mL) and dried over $MgSO_4$. The solvent was evaporated under vacuum to give the title compound as an off-white solid (139 g, yield: 100%). $^1$H NMR (400 MHz, CDCl$_3$) δ ppm 1.49 (9H, s), 2.97 (2H, t, J=5.9 Hz), 3.73 (2H, t, J=6.0 Hz), 4.57 (2H, s), 7.17 (1H, d, J=8.0 Hz), 7.38 (1H, d, J=8.0 Hz) ppm; LCMS m/z: 269 (M+1).

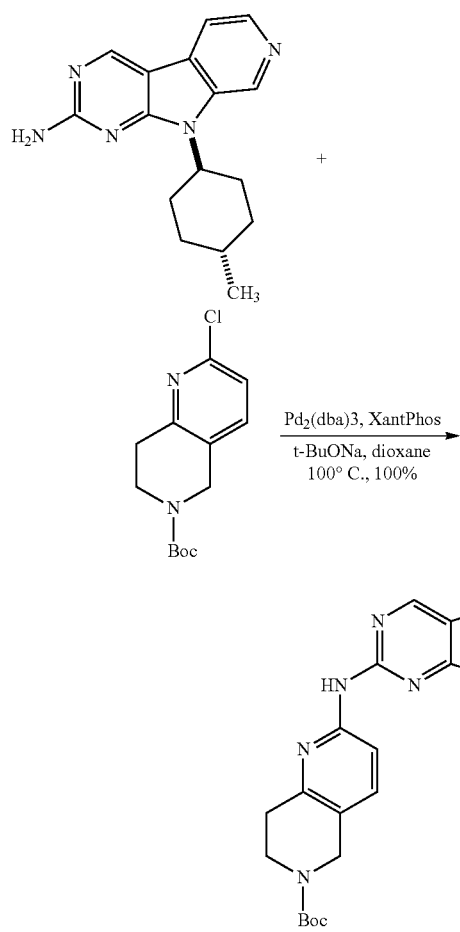

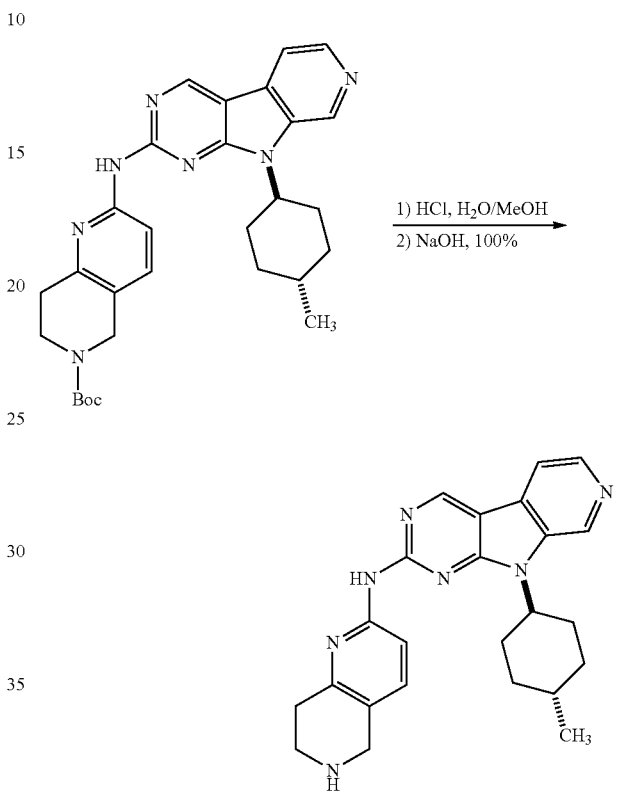

Synthesis of tert-butyl 2-((9-((1r,4r)-4-methylcyclohexyl)-9H-pyrido[4',3':4,5]pyrrolo[2,3-d]pyrimidin-2-yl)amino)-7,8-dihydro-1,6-naphthyridine-6(5H)-carboxylate. To a solution of 9-((1r,4r)-4-methylcyclohexyl)-9H-pyrido[4',3':4,5]pyrrolo[2,3-d]pyrimidin-2-amine (2.81 g, 10 mmol) in 1,4-dioxane (45 mL) were added tert-butyl 2-chloro-7,8-dihydro-1,6-naphthyridine-6(5H)-carboxylate (2.57 g, 9.55 mmol), 4,5-bis(diphenylphosphino)-9,9-dimethylxanene (231 mg, 0.40 mmol), and sodium t-butoxide (1.44 g, 15 mmol). Argon was bubbled through the mixture for 10 minutes. Tris(dibenzylideneacetone)dipalladium (0)(183 mg, 0.20 mmol) was added, and argon was again bubbled through the mixture for 5 minutes. The reaction mixture thus obtained was stirred at 100° C. for 3 hours whereupon HPLC-MS analysis indicated that the reaction was complete. The reaction mixture was cooled to 40° C. and diluted with DCM (90 mL) and treated with Si-triamine (functionalized silica gel, from Silicycle, FR31017TR130B) (2.8 g) overnight at room temperature. Celite® brand filter aid 545 (6 g) was added, and the mixture was filtered with a sintered glass funnel and the solid phase was rinsed with DCM (100 mL). The filtrate was concentrated to 25 mL on a rotary evaporator and diluted with a mixture of EtOAc and hexane (20 mL, 4:1). The resulting slurry was stirred at room temperature for 5 hours. The solid was collected by filtration, washed with a mixture of EtOAc and hexane (20 mL, 1:1) and air dried for a few hours to provide the title compound as an off-white solid (4.90 g, 100% yield).

$^1$H NMR (500 MHz, CD$_2$Cl$_2$) δ ppm 1.06 (3H, d, J=6.4 Hz), 1.34-1.22 (2H, m), 1.48 (9H, s), 1.67 (1H, br. s), 2.02-1.93 (4H, m), 2.63 (2H, dq, J=3.1, 12.8 Hz), 2.88 (2H, t, J=5.7 Hz), 3.74 (2H, t, J=6.0 Hz), 4.57 (2H, s), 7.51 (1H, d, J=8.6 Hz), 7.85 (1H, d, J=5.1 Hz), 8.10 (1H, br. s), 8.42 (1H, d, J=8.3 Hz), 8.46 (1H, d, J=4.9 Hz), 8.97 (1H, s), 9.10 (1H, s) ppm; LCMS m/z: 514(M+1).

Synthesis of 9-((1r,4r)-4-methylcyclohexyl)-N-(5,6,7,8-tetrahydro-1,6-naphthyridin-2-yl)-9H-pyrido[4',3':4,5]pyrrolo[2,3-d]pyrimidin-2-amine (1). To a suspension of tert-butyl 2-((9-((1r,4r)-4- methylcyclohexyl)-9H-pyrido[4',3':4,5]pyrrolo[2,3-d]pyrimidin-2-yl)amino)-7,8-dihydro-1,6-naphthyridine-6(5H)-carboxylate: 9-((1r,4r)-4-methylcyclohexyl)-9H-pyrido[4',3':4,5]pyrrolo[2,3-d]pyrimidin-2-amine (4.65 g, 9.05 mmol) in MeOH (30 mL) were added concentrated HCl (6.74 mL) and water (14 mL). The mixture thus obtained was stirred at room temperature overnight. 50% NaOH in water (4.8 mL) was added at 0° C. to the reaction mixture to adjust the pH value to 9. The precipitated yellow solid was collected by filtration, rinsed with water (25 mL) and air dried for 3 days to give the title compound (3.75 g, 100%). $^1$H NMR (400 MHz, CDCl$_3$) δ ppm 1.07 (3H, d, J=6.5 Hz), 1.29-1.25 (3H, m), 2.00-1.95 (3H, m), 2.02 (2H, s), 2.69-2.53 (2H, m), 2.89 (2H, t, J=6.0 Hz), 3.26 (2H, t, J=6.0 Hz), 4.04 (2H, s), 4.71 (1H, m, J=12.8, 12.8 Hz), 7.41 (1H, d, J=8.4 Hz), 7.84 (1H, d, J=6.1 Hz), 7.84 (1H, d, J=6.1 Hz), 8.03 (1H, s), 8.34 (1H, d, J=8.4 Hz), 8.50 (1H, d, J=5.3 Hz), 8.96 (1H, s), 9.08 (1H, s) ppm; LCMS m/z: 414 (M+1).

Example 2

1-(2-((9-((1r,4r)-4-Methylcyclohexyl)-9H-pyrido[4', 3':4,5]pyrrolo[2,3-d]pyrimidin-2-yl)amino)-7,8-dihydro-1,6-naphthyridin-6(5H)-yl)ethanone

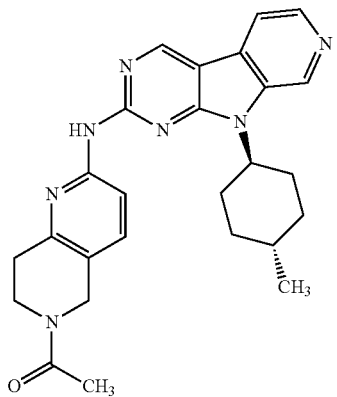 [SMILES: CC(=O)N1CCc2nc(Nc3ncc4c5ccncc5n([C@H]5CC[C@H](C)CC5)c4n3)ccc2C1]

6,7,8-tetrahydro-1,6-naphthyridin-2-yl)-9H-pyrido[4',3':4,5]pyrrolo[2,3-d]pyrimidin-2-amine (1) (90 mg, 0.22 mmol) in 3 mL of 1,4-dioxane was added acetic anhydride (33.3 mg, 0.33 mmol). After stirring for 10 minutes, 20 mL of DCM and 10 mL of water were added. The resulting solution was washed sequentially with saturated aqueous NaHCO$_3$ solution, water and brine, dried over anhydrous MgSO$_4$, and evaporated under vacuum. The residue was purified by preparatory LC to give the title compound (50 mg, 50%). $^1$H NMR (400 MHz, CD3OD) δ ppm 1.10 (3H, d, J=6.46 Hz) 1.31-1.43 (2H, m) 1.70-1.80 (1H, br. s.) 2.00-2.09 (4H, m) 2.27 (3H, d, J=7.24 Hz) 2.67-2.79 (2H, m) 3.10 (1H, t, J=6.16 Hz) 3.15-3.22 (1H, m) 3.98 (2H, dt, J=13.16, 6.04 Hz) 4.79-4.84 (2H, m) 4.91-5.00 (1H, m) 7.90-7.98 (2H, m) 8.61-8.65 (2H, m) 9.40-9.41 (1H, m) 9.62 (1H, d, J=2.74 Hz) ppm; LCMS m/z: 456 (M+1).

Example 3

2-(2-((9-((1r,4r)-4-Methylcyclohexyl)-9H-pyrido[4', 3':4,5]pyrrolo[2,3-d]pyrimidin-2-yl)amino)-7,8-dihydro-1,6-naphthyridin-6(5H)-yl)ethanol

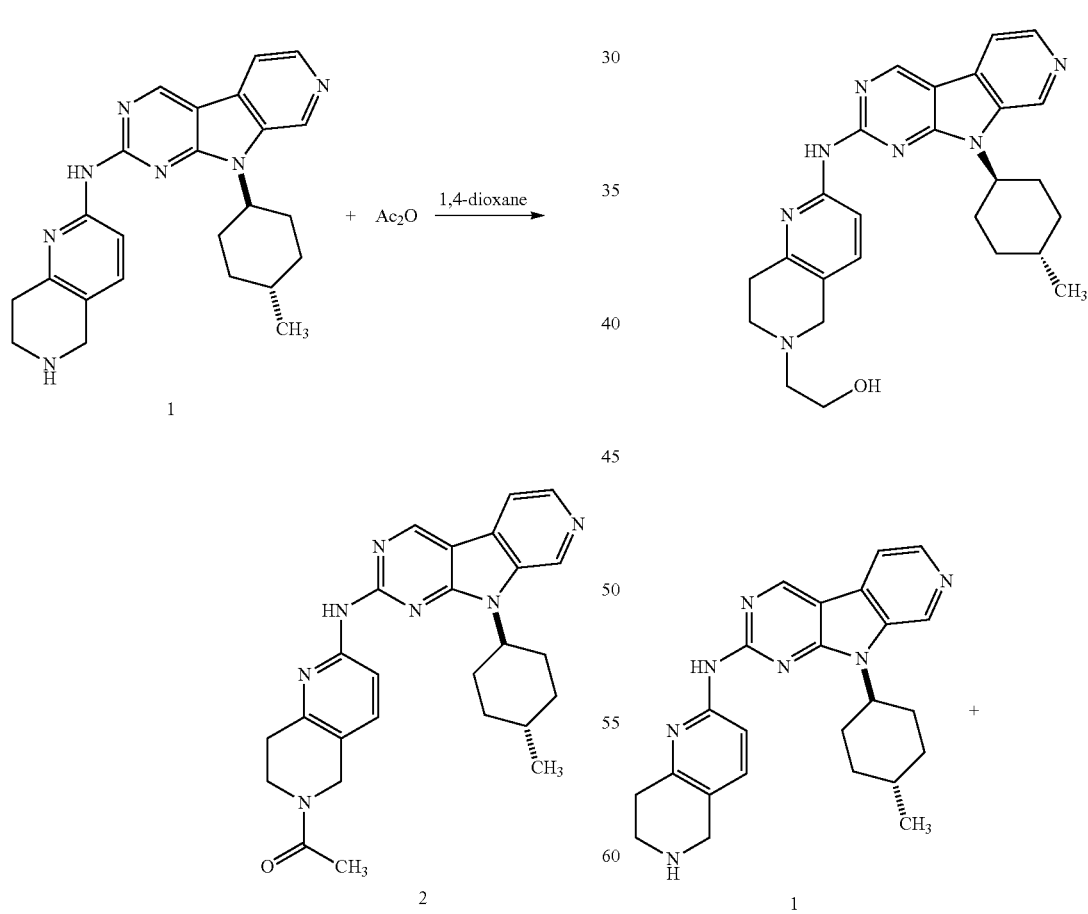

Synthesis of 1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone (2). To a stirred ice-cooled solution of 9-((1r,4r)-4-methylcyclohexyl)-N-(5,

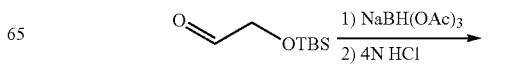

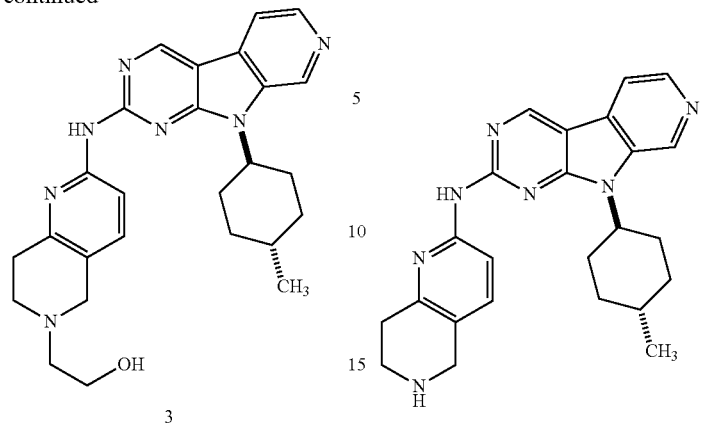

3

Synthesis of 2-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanol (3). A slurry of 9-((1r,4r)-4-methylcyclohexyl)-N-(5,6,7,8-tetrahydro-1,6-naphthyridin-2-yl)-9H-pyrido[4',3':4,5]pyrrolo[2,3-d]pyrimidin-2-amine (1) (50 mg, 0.12 mmol) and (tert-butyldimethylsilyloxy)acetaldehyde (commercially available from Sigma-Aldrich, St. Louis, Mo.) (31.6 mg, 0.18 mmol) in 3 mL 1,4-dioxane was stirred for 5 minutes and then sodium triacetoxyborohydride (commercially available from Sigma-Aldrich, St. Louis, Mo.) (77 mg, 0.363 mmol) was added. After stirring for 10 minutes, DCM (30 in L) was added to the reaction mixture. The resulting solution was washed sequentially with saturated aqueous NaHCO₃ solution, water and brine, dried over anhydrous MgSO₄, and evaporated under vacuum to give the intermediate TBS protected alcohol (LCMS m/z: 572 (M+1)). The TBS protected alcohol was treated with 3 mL of 4 N HCl/dioxane to remove the TBS group. After 30 minutes, the reaction was concentrated and purified by flash chromatography on silica gel eluting with 0 to 20% 2N NH₃ MeOH solution in DCM to give the title compound (38 mg, 68% yield). ¹H NMR (400 MHz, CDCl₃) δ ppm 1.09 (3H, d, J=6.65 Hz) 1.24-1.36 (2H, m) 1.56-1.73 (3H, m) 1.96-2.06 (4H, m) 2.63 (2H, qd, J=12.88, 3.81 Hz) 2.81 (2H, t, J=5.38 Hz) 2.94-3.04 (4H, m) 3.73-3.80 (4H, m) 4.70-4.79 (1H, m) 7.44 (1H, m, J=8.61 Hz) 7.86 (1H, dd, J=5.18, 1.08 Hz) 8.08 (1H, s) 8.37 (1H, m, J=8.41 Hz) 8.53 (1H, d, J=5.28 Hz) 8.97-9.00 (1H, m) 9.10-9.12 (1H, m) ppm; LC/MS m/z: 458 (M+1).

Example 4

3-(2-((9-((1r,4r)-4-Methylcyclohexyl)-9H-pyrido[4',3':4,5]pyrrolo[2,3-d]pyrimidin-2-yl)amino)-7,8-dihydro-1,6-naphthyridin-6(5H)-yl)propan-1-ol

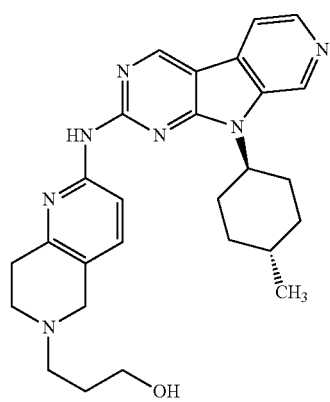 [SMILES: C[C@H]1CC[C@H](n2c3cnccc3c3cnc(Nc4ccc5c(n4)CCN(CCCO)C5)nc32)CC1]

4

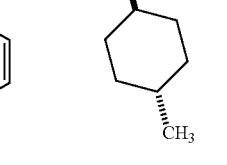

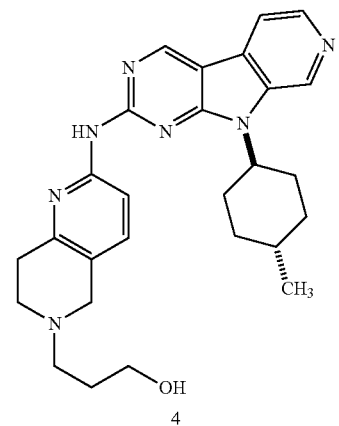

4

Synthesis of 3-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)propan-1-ol (4). The title compound (4) was prepared from 9-((1r,4r)-4-methylcyclohexyl)-N-(5,6,7,8-tetrahydro-1,6-naphthyridin-2-yl)-9H-pyrido[4',3':4,5]pyrrolo[2,3-d]pyrimidin-2-amine (1) using chemistry similar to that described in Example 3 using (tert-butyldimethylsilyloxy)propanal (commercially available from ChemPacific, Baltimore, Md.) in place of (tert-butyldimethylsilyloxy)acetaldehyde. ¹H NMR (400 MHz, CD₃OD) δ ppm 1.10 (3H, d, J=6.65 Hz), 1.32-1.44 (2H, m), 1.75 (1H, m), 1.98-2.16 (6H, m), 2.37-2.45 (2H, m), 2.67-2.80 (2H, m), 3.30-3.40 (2H, m), 3.46-3.57 (2H, m), 3.66-3.90 (2H, m), 4.55-4.64 (2H, m), 4.95 (1H, m), 7.81 (1H, dd, J=8.51, 1.27 Hz), 8.36 (1H, d, J=8.80 Hz), 8.62 (2H, q, J=6.26 Hz), 9.42 (1H, s), 9.59 (1H, m) ppm; LC/MS m/z: 472 (M+1).

Example 5

2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone

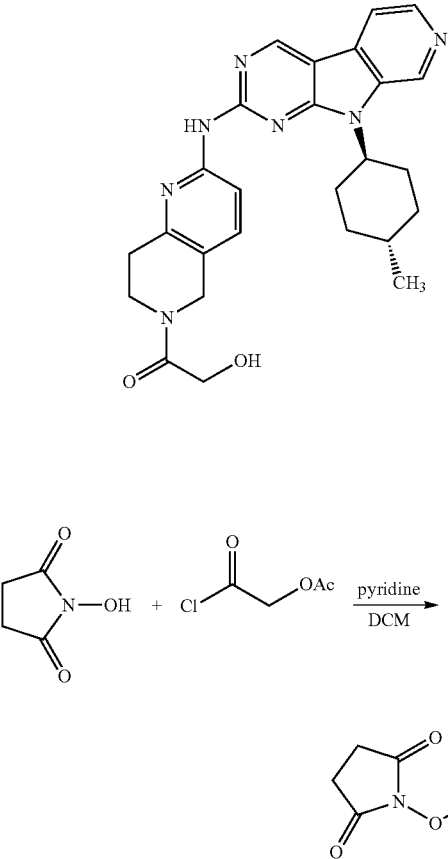

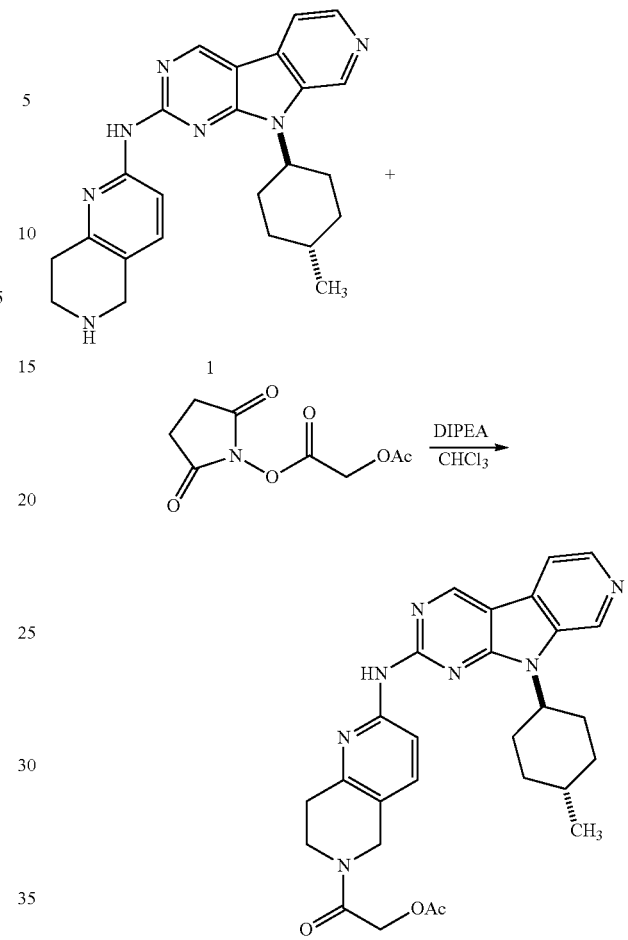

Synthesis of 2,5-dioxopyrrolidin-1-yl 2-acetoxyacetate. A 3-neck round-bottom flask equipped with a mechanical stirrer, thermocouple and addition funnel with nitrogen inlet was charged with N-hydroxysuccinimide (commercially available from Sigma-Aldrich, St. Louis, Mo.) (211 g, 1.83 mol) and DCM (2.25 L) at room temperature, resulting in a suspension. Pyridine (178 mL, 2.2 mol) was added in one portion with no change in the internal temperature. A solution of acetoxyacetyl chloride (commercially available from Sigma-Aldrich, St. Louis, Mo.) (197 mL, 1.83 mol) in DCM (225 mL) was added dropwise over 60 minutes and the temperature rose to 35° C. Stirring was continued at room temperature for 2.5 hours. The reaction mixture was washed with water (1×1 L), 1N HCl (2×1 L) and brine (1×1 L). The organic layer was concentrated under vacuum and azeotroped with toluene (1×1 L) to obtain the product as a white solid (367 g, 93%). $^1$H NMR (400 MHz, CDCl$_3$) δ 4.96 (2H, s), 2.86 (4H, s), 2.19 (3H, s) ppm; LCMS m/z: 238 (M+Na).

Synthesis of 2-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)-2-oxoethyl acetate. To a suspension of 9-((1r,4r)-4-methylcyclohexyl)-N-(5,6,7,8-tetrahydro-1,6-naphthyridin-2-yl)-9H-pyrido[4',3':4,5]pyrrolo[2,3-d]pyrimidin-2-amine (1) (827 mg, 2.0 mmol) in chloroform (10 mL) were added diisopropylethylamine (258 mg, 348 uL, 2.0 mmol) and 2,5-dioxopyrrolidin-1-yl 2-acetoxyacetate (560 mg, 2.6 mmol). The reaction mixture thus obtained was stirred at room temperature for 30 minutes whereupon the mixture became a yellow solution. HPLC-MS analysis indicated that the reaction was complete. The reaction mixture was concentrated. MeOH (5 mL) and water (6 mL) were added to form a slurry which was stirred at room temperature for 1 hour. The solid was collected by filtration to give the title compound as a light yellow solid (1.04 g, 98% yield). $^1$H NMR (400 MHz, CDCl$_3$, rotamers) δ ppm 1.08 (3H, d, J=6.5 Hz), 1.37-1.20 (2H, m), 2.03-1.97 (4H, m), 2.22 (3H, s), 2.69-2.52 (2H, m, J=2.9, 12.8, 12.8, 12.8 Hz), 3.08-2.93 (2H, m), 3.75 (1H, t, J=5.9 Hz), 3.97 (1H, t, J=5.6 Hz), 4.59 (1H, s),), 4.80-4.65 (2H, m),), 4.90-4.82 (2H, m), 7.57-7.45 (1H, m), 7.86 (1H, d, J=5.7 Hz), 8.21-8.10 (1H, m), 8.49-8.40 (1H, m), 8.52 (1H, d, J=5.3 Hz), 8.98 (1H, s), 9.11 (1H, s) ppm; LCMS m/z: 514 (M+1).

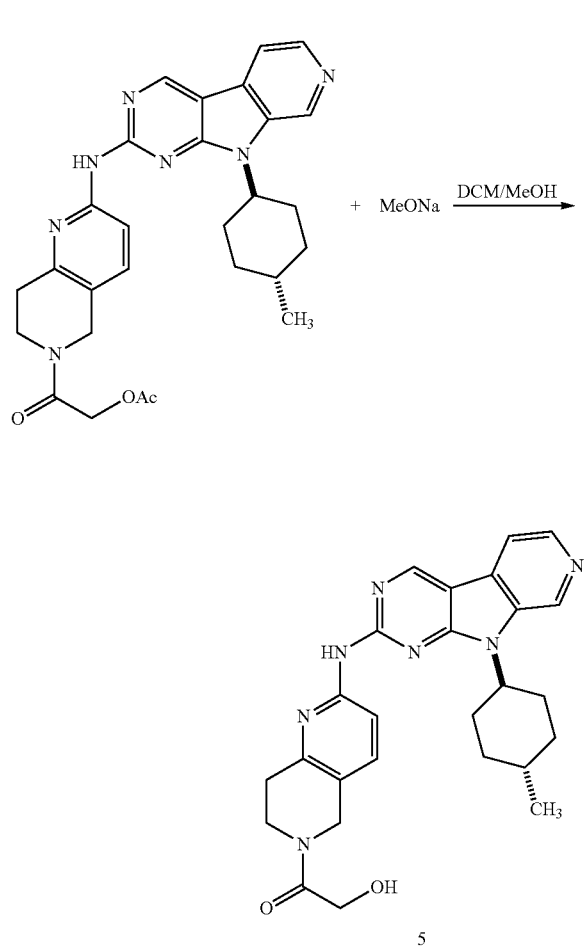

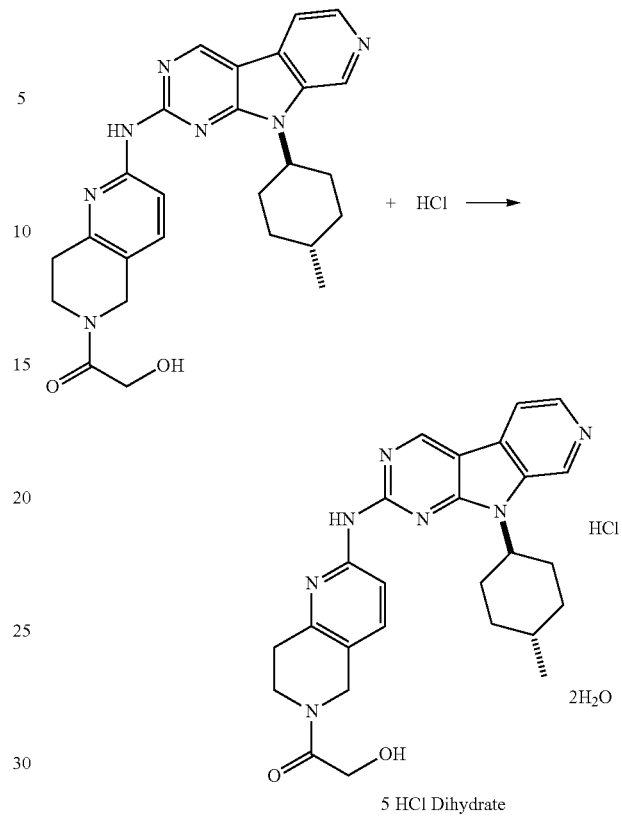

5 HCl Dihydrate

Synthesis of 2-hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone (5). To a solution of 2-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)-2-oxoethyl acetate (514 mg, 1.0 mmol) in DCM (7.5 mL) and MeOH (2.5 mL) was added 0.5 M sodium methoxide solution in MeOH (0.30 mL, 0.15 mmol), and the reaction mixture was stirred at room temperature for 1 hour and monitored using LCMS. Upon completion, the reaction mixture was concentrated. The residue was treated with EtOH (5 mL) and water (10 mL) to provide a solid which was collected by filtration, washed with water, and dried in a vacuum oven at 55° C. overnight to give the title compound (5) as a white solid (468 mg, 99% yield). $^1$H NMR (500 MHz, acetic acid-$d_4$, 373 K) δ ppm 1.09 (3H, d, J=6.5 Hz), 1.31-1.43 (2H, m), 1.70-1.80 (1H, m), 1.99-2.03 (2H, m), 2.06-2.13 (2H, m), 2.68 (2H, dq, J=3.3, 12.7 Hz), 3.10 (2H, t, J=5.4 Hz), 3.88 (2H, br. s.), 4.46 (2H, br. s.), 4.77 (2H, br. s), 4.90 (1H, tt, J=3.9, 12.4 Hz), 7.76 (1H, d, J=8.5 Hz), 8.33 (1H, d, J=8.5 Hz), 8.40 (1H, d, J=6.0 Hz), 8.63 (1H, d, J=6.0 Hz), 9.35 (1H, s), 9.43 (1H, s) ppm; LCMS m/z: 472 (M+1).

Synthesis of 2-hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone monohydrochloride dehydrate. To a suspension of 2-hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone (472 mg, 1.0 mmol) in water (2 mL) was added 2 N HCl (2 mL). The mixture became a clear solution. The pH value of the solution was adjusted to 4 by addition of 2 N NaOH at 0° C. and the precipitated light yellow solid was collected by filtration. The collected solid was washed with cold water three times. The solid was dried under vacuum to give the title compound as a light yellow solid (469 mg, 92% yield). $^1$H NMR (500 MHz, DMSO-$d_6$) δ 1.02 (3H, d, J=5.0 Hz), 1.20-1.30 (2H, m), 1.64 (1H, m), 1.88-1.90 (4H, m), 2.59-2.66 (2H, m), 2.85-2.95 (2H, m), 3.71 (1H, m), 3.83 (1H, m), 4.19-4.22 (2H, m), 4.60-4.67 (2H, m), 4.85 (1H, m), 7.75 (1H, d, J=8.5 Hz), 8.19 (1H, d, J=8.5 Hz), 8.55 (1H, d, J=5.0 Hz), 8.63 (1H, d, J=5.0 Hz), 9.47 (1H, s), 9.58 (1H, s), 10.59 (1H, br.s) ppm; LCMS m/z: 472 (M+1). Anal. ($C_{26}H_{29}N_7O_2$—HCl.2$H_2O$) Calc: C=57.40, H=6.30, N=18.02. Found: C=57.06, H=6.31, N=17.92.

Alternative Synthesis of Hydrochloride Salt of 2-Hydroxy-1-(2-((9-((1r,4r)-4-methylcyclohexyl)-9H-pyrido[4',3':4,5]pyrrolo[2,3-d]pyrimidin-2-yl) amino)-7,8-dihydro-1,6-naphthyridin-6(5H)-yl)ethanone. To a suspension of 2-hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone (2.385 g, 5.0 mmol) in water (10 mL) was added 2N HCl (10 mL) at 20° C. The mixture became a clear light yellow solution. The pH value of the solution was adjusted to 4 by addition of 2N NaOH through addition funnel at 0° C., and the precipitated yellow solid was collected by filtration. The resulting solid was washed with cold water three times. The solid was dried under vacuum at 50° C. for two days to provide 2.49 g of the hydrochloride salt of 2-hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone as a solid. This salt was also obtained as a hydrate.

Preparation of Other Salts of Example 5

The following salts were prepared as described below. Whether or not these were obtained as the hydrates or as anhydrous forms has not yet been determined Synthesis of Phosphate Salt of 2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone. 2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone (100 mg) was added to a 20 mL vial. Approximately 15 mL of a mixture of 70% DCM and 30% EtOH (v/v) was added to the vial, and the mixture was vortexed for approximately 30 seconds to dissolve most of the neutral compound. Aqueous 0.1 M phosphoric acid (1 equivalent) was added to the vial, and the mixture was sonicated for approximately 30 seconds. The solvents were then allowed to evaporate slowly to provide the phosphate salt of 2-hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone. The salt was characterized using XRPD and differential scanning calorimetry thermograms.

Synthesis of Citrate Salt of 2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone. 2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone (100 mg) was added to a 20 mL vial. Approximately 15 mL of a mixture of 70% DCM and 30% EtOH (v/v) was added to the vial, and the mixture was vortexed for approximately 30 seconds to dissolve most of the neutral compound. Aqueous 0.1 M citric acid (1 equivalent) was added to the vial, and the mixture was sonicated for approximately 30 seconds. The solvents were then allowed to evaporate slowly to provide the citrate salt of 2-hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone. The salt was characterized using XRPD and differential scanning calorimetry thermograms.

Synthesis of Tartrate Salt of 2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone. 2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone (100 mg) was added to a 20 mL vial. Approximately 15 mL of a mixture of 70% DCM and 30% EtOH (v/v) was added to the vial, and the mixture was vortexed for approximately 30 seconds to dissolve most of the neutral compound. Aqueous 0.1 M tartaric acid (1 equivalent) was added to the vial, and the mixture was sonicated for approximately 30 seconds. The solvents were then allowed to evaporate slowly to provide the tartrate salt of 2-hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone. The salt was characterized using XRPD and differential scanning calorimetry thermograms.

Synthesis of Salicylate Salt of 2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone. 2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone (100 mg) was added to a 20 mL vial. Approximately 15 mL of a mixture of 70% DCM and 30% EtOH (v/v) was added to the vial, and the mixture was vortexed for approximately 30 seconds to dissolve most of the neutral compound. Aqueous 0.1 M salicylic acid (1 equivalent) was added to the vial, and the mixture was sonicated for approximately 30 seconds. The solvents were then allowed to evaporate slowly to provide the salicylate salt of 2-hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone. The salt was characterized using XRPD and differential scanning calorimetry thermograms.

Synthesis of Benzenesulfonate (Besylate) Salt of 2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone. 2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone (100 mg) was added to a 20 mL vial. Approximately 15 mL of a mixture of 70% DCM and 30% EtOH (v/v) was added to the vial, and the mixture was vortexed for approximately 30 seconds to dissolve most of the neutral compound. Aqueous 0.1 M benzenesulfonic acid (1 equivalent) was added to the vial, and the mixture was sonicated for approximately 30 seconds. The solvents were then allowed to evaporate slowly to provide the benzenesulfonate salt of 2-hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone. The salt was characterized using XRPD and differential scanning calorimetry thermograms.

Synthesis of p-Toluenesulfonate (Tosylate) Salt of 2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone 2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone (100 mg) was added to a 20 mL vial. Approximately 15 mL of a mixture of 70% DCM and 30% EtOH (v/v) was added to the vial, and the mixture was vortexed for approximately 30 seconds to dissolve most of the neutral compound. Aqueous 0.1 M p-toluenesulfonic acid (1 equivalent) was added to the vial, and the mixture was sonicated for approximately 30 seconds. The solvents were then allowed to evaporate slowly to provide the tosylate salt of 2-hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone. The salt was characterized using XRPD and differential scanning calorimetry thermograms.

Synthesis of ethanesulfonate Salt of 2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone. 2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone (100 mg) was added to a 20 mL vial. Approximately 15 mL of a mixture of 70% DCM and 30% EtOH (v/v) was added to the vial, and the mixture was vortexed for approximately 30 seconds to dissolve most of the neutral compound. Aqueous 0.1 M ethanesulfonic acid (1 equivalent) was added to the vial, and the mixture was sonicated for approximately 30 seconds. The solvents were then allowed to evaporate slowly to provide the ethanesulfonate salt of 2-hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone. The salt was characterized using XRPD and differential scanning calorimetry thermograms.

Synthesis of Sulfate Salt (1 Equivalent) of 2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone. 2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone (100 mg) was added to a 20 mL vial. Approximately 15 mL of a mixture of 70% DCM and 30% EtOH (v/v) was added to the vial, and the mixture was vortexed for approximately 30 seconds to dissolve most of the neutral compound. Aqueous 0.1 M sulfuric acid (1 equivalent) was added to the vial, and the mixture was sonicated for approximately 30 seconds. The solvents were then allowed to evaporate slowly to provide the sulfate salt (1 equivalent) of 2-hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone. The salt was characterized using XRPD and differential scanning calorimetry thermograms.

Synthesis of Sulfate Salt (½ Equivalent) of 2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone. 2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone (100 mg) was added to a 20 mL vial. Approximately 15 mL of a mixture of 70% DCM and 30% EtOH (v/v) was added to the vial, and the mixture was vortexed for approximately 30 seconds to dissolve most of the neutral compound. Aqueous 0.1 M sulfuric acid (½ equivalent) was added to the vial, and the mixture was sonicated for approximately 30 seconds. The solvents were then allowed to evaporate slowly to provide the sulfate salt (½ equivalent) of 2-hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone. The salt was characterized using XRPD and differential scanning calorimetry thermograms.

Synthesis of Ethanedisulfonate (1 Equivalent) Salt of 2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone. 2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone (100 mg) was added to a 20 mL vial. Approximately 15 mL of a mixture of 70% DCM and 30% EtOH (v/v) was added to the vial, and the mixture was vortexed for approximately 30 seconds to dissolve most of the neutral compound. Aqueous 0.1 M ethanedisulfonic acid (1 equivalent) was added to the vial, and the mixture was sonicated for approximately 30 seconds. The solvents were then allowed to evaporate slowly to provide the ethanedisulfonate (1 equivalent) salt of 2-hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone. The salt was characterized using XRPD and differential scanning calorimetry thermograms.

Synthesis of Ethanedisulfonate (½ Equivalent) Salt of 2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone. 2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone (100 mg) was added to a 20 mL vial. Approximately 15 mL of a mixture of 70% DCM and 30% EtOH (v/v) was added to the vial, and the mixture was vortexed for approximately 30 seconds to dissolve most of the neutral compound. Aqueous 0.1 M ethanedisulfonic acid (½ equivalent) was added to the vial, and the mixture was sonicated for approximately 30 seconds. The solvents were then allowed to evaporate slowly to provide the ethanedisulfonate (½ equivalent) salt of 2-hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone. The salt was characterized using XRPD and differential scanning calorimetry thermograms.

Example 6

2-(2-((9-((1r,4r)-4-Methylcyclohexyl)-9H-pyrido[4',3':4,5]pyrrolo[2,3-d]pyrimidin-2-yl)amino)-7,8-dihydro-1,6-naphthyridin-6(5H)-yl)-2-oxoacetic acid

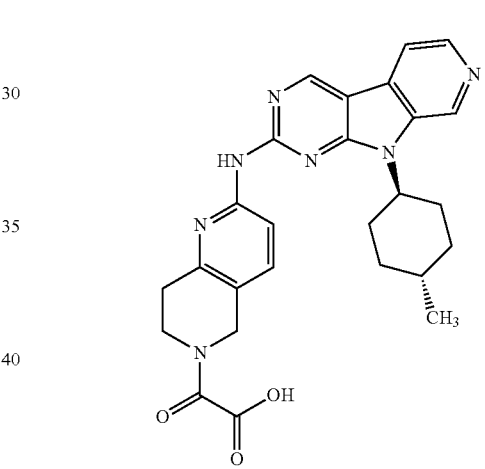

6

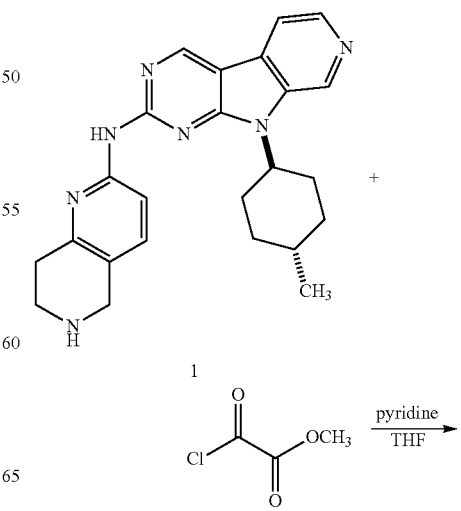

1

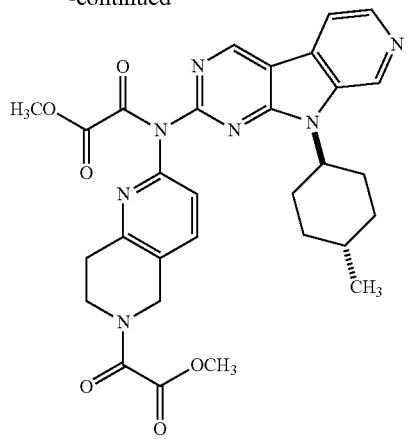

Synthesis of methyl 2-((6-(2-methoxy-2-oxoacetyl)-5,6,7,8-tetrahydro-1,6-naphthyridin-2-yl)(9-((1r,4r)-4-methylcyclohexyl)-9H-pyrido[4',3':4,5]pyrrolo[2,3-d]pyrimidin-2-yl)amino)-2-oxoacetate. To a solution at room temperature of 9-((1r,4r)-4-methylcyclohexyl)-N-(5,6,7,8-tetrahydro-1,6-naphthyridin-2-yl)-9H-pyrido[4',3':4,5]pyrrolo[2,3-d]pyrimidin-2-amine (1) (83 mg, 0.2 mmol) in THF (10 mL), were added pyridine (129 uL, 1.6 mmol) and methyl chlorooxoacetate (commercially available from Sigma-Aldrich, St. Louis, Mo.) (74 uL, 0.8 mmol). The mixture thus obtained was stirred at room temperature overnight. The reaction mixture was concentrated to give the title compound which was used in the next step without purification. LCMS m/z: 586 (M+1).

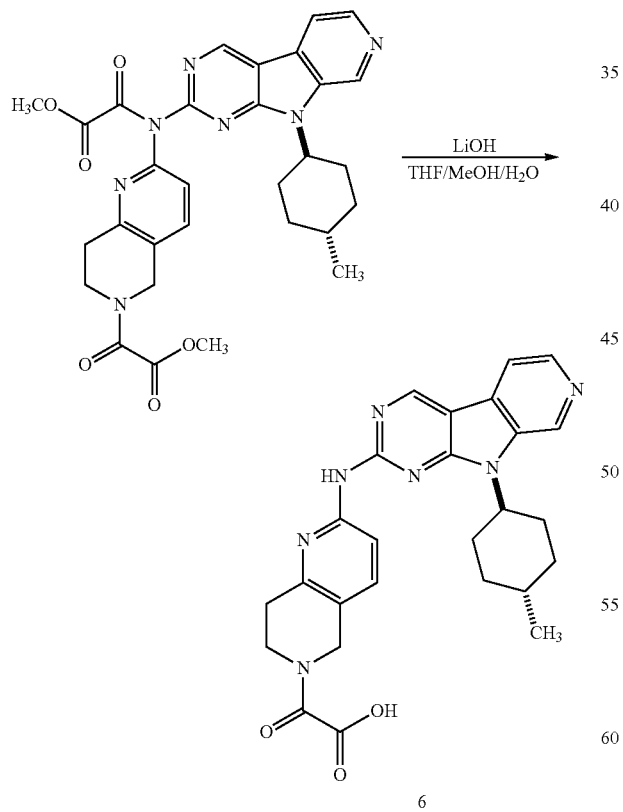

Synthesis of 2-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)-2-oxoacetic acid (6). To a solution of unpurified methyl 2-((6-(2-methoxy-2-oxoacetyl)-5,6,7,8-tetrahydro-1,6-naphthyridin-2-yl)(9-((1r,4r)-4-methylcyclohexyl)-9H-pyrido[4',3':4,5]pyrrolo[2,3-d]pyrimidin-2-yl)amino)-2-oxoacetate in THF/MeOH/H$_2$O (3/1/1, 5 mL) was added lithium hydroxide (19 mg, 0.80 mmol). The mixture thus obtained was stirred at room temperature for 2 hours. The reaction mixture was concentrated, and the residue was dissolved in acidic water and purified by reverse phase prep-HPLC. The fractions containing the desired product were collected and lyophilized to give the title compound (6) as a light yellow solid (32 mg, 33% over two steps). $^1$H NMR (500 MHz, DMSO-d$_6$) δ ppm 1.02 (3H, d, J=5.0 Hz), 1.28 (2H, m), 1.65 (1H, m), 1.85-1.95 (4H, m), 2.60-2.70 (2H, m), 2.91 (1H, m), 2.95 (2H, m), 3.77 (2H, m), 4.70 (1H, s), 4.84 (1H, m), 7.79 (1H, d, J=10 Hz), 8.21 (1H, dd, J$_1$=10 Hz, J$_2$=5.0 Hz), 8.59 (1H, m), 8.66 (1H, d, J=5.0 Hz), 9.47 (1H, br. s), 9.59 (1H, s), 10.65 (1H, br. s) ppm; LCMS m/z: 486 (M+1).

Example 7

9-((1r,4r)-4-Methylcyclohexyl)-N-(6-(3,3,3-trifluoropropyl)-5,6,7,8-tetrahydro-1,6-naphthyridin-2-yl)-9H-pyrido[4',3':4,5]pyrrolo[2,3-d]pyrimidin-2-amine

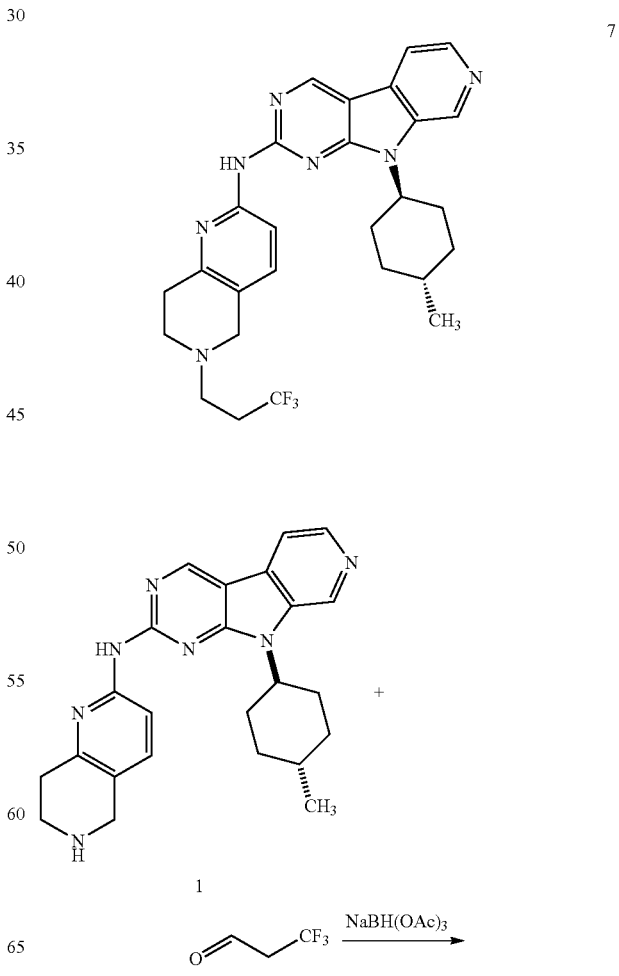

-continued

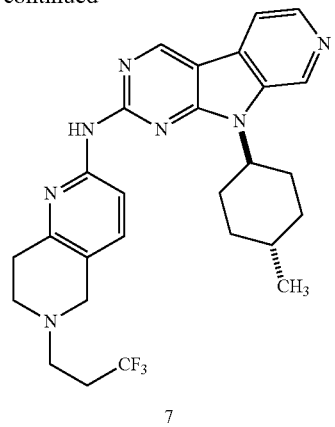

7

Synthesis of 9-((1r,4r)-4-methylcyclohexyl)-N-(6-(3,3,3-trifluoropropyl)-5,6,7,8-tetrahydro-1,6-naphthyridin-2-yl)-9H-pyrido[4',3':4,5]pyrrolo[2,3-d]pyrimidin-2-amine (7). A slurry of 9-((1r,4r)-4-methylcyclohexyl)-N-(5,6,7,8-tetrahydro-1,6-naphthyridin-2-yl)-9H-pyrido[4',3':4,5]pyrrolo[2,3-d]pyrimidin-2-amine (1) (40 mg, 0.10 mmol) and 3,3,3-trifluoropropanal (commercially available from ChemPacific, Baltimore, Md.) (10.8 mg, 0.10 mmol) in 1,4-dioxane (2 mL) was stirred for 5 minutes, and then sodium triacetoxyborohydride (61.5 mg, 0.29 mmol) was added. After 10 minutes, the reaction mixture was diluted with DCM (30 mL). The resulting solution was washed sequentially with saturated aqueous $NaHCO_3$ solution, water and brine, dried over anhydrous $MgSO_4$, and concentrated under vacuum. The residue was purified by preparative LC to give the title compound (7) (32 mg, 65%). $^1$H NMR (400 MHz, $CD_3OD$) δ ppm 1.10 (3H, d, J=6.46 Hz), 1.31-1.45 (2H, m), 1.69-1.81 (1H, m), 1.98-2.09 (4H, m), 2.67-2.79 (2H, m), 2.90-3.03 (2H, m), 3.62-3.70 (2H, m), 3.80 (2H, t, J=6.36 Hz), 4.58 (2H, s), 4.92-5.00 (3H, m), 7.80 (1H, d, J=8.61 Hz), 8.36 (1H, d, J=8.80 Hz), 8.62 (2H, q, J=6.13 Hz), 9.41 (1H, s), 9.58 (1H, s) ppm; LC/MS m/z: 510 (M+1).

Example 8

9-((1r,4r)-4-Methylcyclohexyl)-N-(6-(2-(methylsulfonyl)ethyl)-5,6,7,8-tetrahydro-1,6-naphthyridin-2-yl)-9H-pyrido[4',3':4,5]pyrrolo[2,3-d]pyrimidin-2-amine

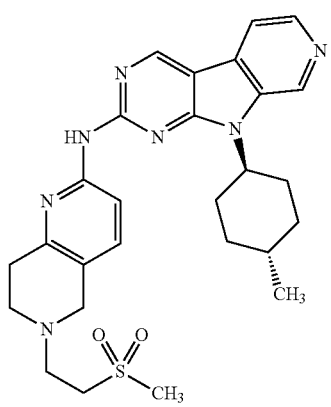 [SMILES: CS(=O)(=O)CCN1CCc2nc(Nc3ncc4c5ccncc5n([C@H]5CC[C@H](C)CC5)c4n3)ccc2C1]

8

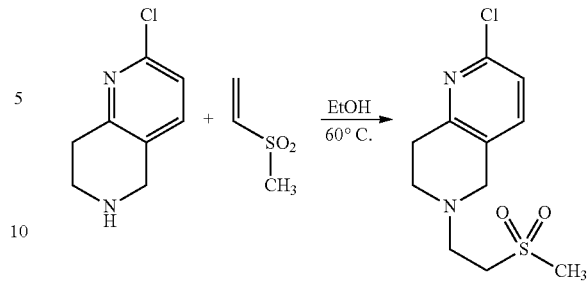

Synthesis of 2-chloro-6-(2-(methylsulfonyl)ethyl)-5,6,7,8-tetrahydro-1,6-naphthyridine. Methylsulfonylethene (commercially available from Sigma-Aldrich, St. Louis, Mo.) (142 mg, 1.33 mmol) was added dropwise to a solution of 2-chloro-5,6,7,8-tetrahydro-1,6-naphthyridine (150 mg, 0.89 mmol, commercially available from D-L Chiral Chemicals, ST-0143) in EtOH (10 mL). The reaction mixture was stirred at 60° C. for 2 hours, and then concentrated and purified by flash chromatography on silica gel eluting with 0% to 5% MeOH in DCM to give 2-chloro-6-(2-(methylsulfonyl)ethyl)-5,6,7,8-tetrahydro-1,6-naphthyridine (220 mg, 90% yield). $^1$H NMR (400 MHz, $CD_3OD$) δ ppm 2.91-3.11 (9H, m) 3.43 (2H, t, J=6.65 Hz) 3.73-3.77 (2H, m) 7.26 (1H, d, J=8.22 Hz) 7.56 (1H, d, J=8.02 Hz) ppm; LC/MS m/z: 275 (M+1).

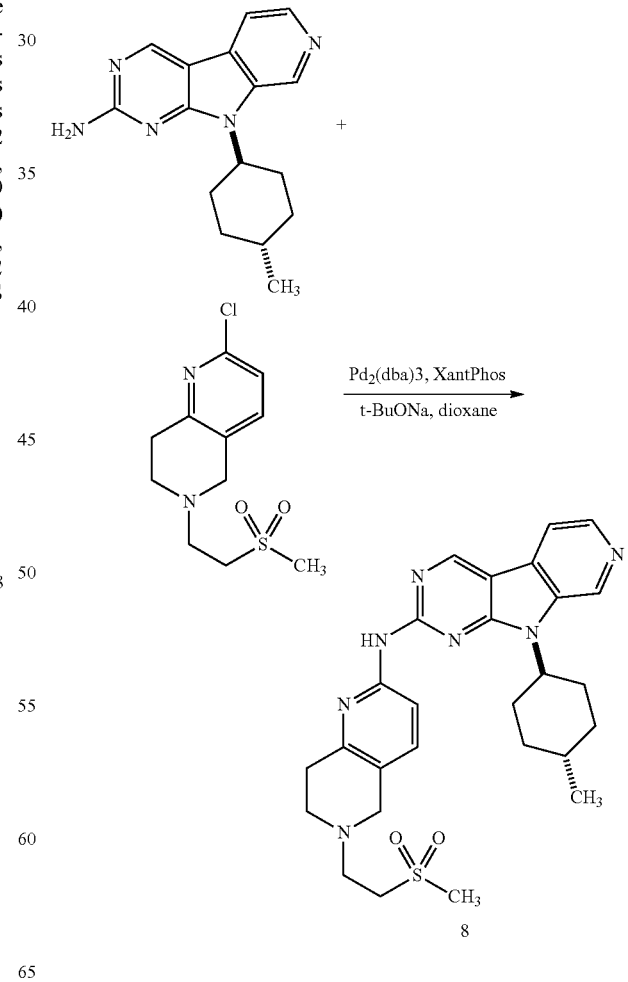

8

Synthesis of 9-((1r,4r)-4-methylcyclohexyl)-N-(6-(2-(methylsulfonyl)ethyl)-5,6,7,8-tetrahydro-1,6-naphthyridin-2- yl)-9H-pyrido[4',3':4,5]pyrrolo[2,3-d]pyrimidin-2-amine (8). The title compound was prepared using chemistry similar to that described in Example 1 using 2-chloro-6-(2-(methylsulfonyl)ethyl)-5,6,7,8-tetrahydro-1,6-naphthyridine in place of tert-butyl 2-chloro-7,8-dihydro-1,6-naphthyridine-6 (5H)-carboxylate. $^1$H NMR (400 MHz, DMSO-d$_6$) δ ppm 1.09 (3H, d, J=6.60 Hz), 1.34 (1H, br. s.), 1.26-1.40 (2H, m), 1.68-1.72 (1H, br. s.), 1.98-2.04 (4H, m), 2.66-2.72 (2H, m), 2.98-3.06 (4H, m), 3.09 (3H, s), 3.13 (2H, t, J=6.60 Hz), 3.43-3.48 (2H, m), 3.80 (2H, s), 4.89 (1H, br. s.), 7.62 (1H, d, J=8.31 Hz), 8.14-8.15 (1H, m), 8.25 (1H, d, J=8.22 Hz), 8.45 (1H, d, J=5.38 Hz), 9.05 (1H, s), 9.28-9.29 (1H, m) ppm; LC/MS m/z: 520 (M+1).

Example 9

N-(6-(2-Fluoroethyl)-5,6,7,8-tetrahydro-1,6-naphthyridin-2-yl)-9-((1r,4r)-4-methylcyclohexyl)-9H-pyrido[4',3':4,5]pyrrolo[2,3-d]pyrimidin-2-amine

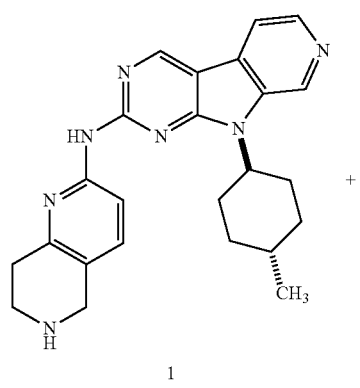

1

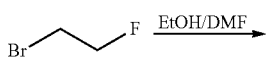

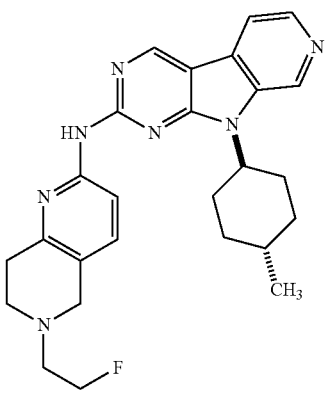

9

Synthesis of N-(6-(2-fluoroethyl)-5,6,7,8-tetrahydro-1,6-naphthyridin-2-yl)-9-((1r,4r)-4-methylcyclohexyl)-9H-pyrido[4',3':4,5]pyrrolo[2,3-d]pyrimidin-2-amine (9). To a solution of 9-((1r,4r)-4-methylcyclohexyl)-N-(5,6,7,8-tetrahydro-1,6-naphthyridin-2-yl)-9H-pyrido[4',3':4,5]pyrrolo[2,3-d]pyrimidin-2-amine (1) (149 mg, 0.36 mmol) in absolute EtOH (4 mL) and DMF (2 mL), was added 1-bromo-2-fluoroethane (commercially available from AK Scientific, Mountain View, Calif.) (50 μL, 0.67 mmol). The resulting reaction mixture was stirred while being heated at 90° C. in a pre-heated oil bath. After 70 minutes of heating, a second aliquot of 1-bromo-2-fluoroethane (50 μL, 0.67 mmol) was added. After 7.5 hours of heating, when LCMS analysis indicated that the majority of the starting material had been consumed, the mixture was allowed to cool and volatiles were removed in vacuo. The resulting solution was diluted in DCM and sequentially washed with aqueous saturated Na$_2$CO$_3$, water, and brine. The organic layers were dried over sodium sulfate, filtered, and concentrated to a residue which was purified by flash chromatography on silica gel eluting with a 10% to 45% gradient of solvent A (DCM:MeOH:NH$_4$OH, 90:9:1) in DCM. Chromatography fractions containing the desired product were combined and stripped of solvents to provide a residue which was further purified by precipitation from DCM/hexanes. The suspension so obtained was sonicated and filtered. The filter cake was dried under high vacuum overnight to give the title compound (9) as an off-white solid (35 mg, 21% yield). NMR (400 MHz, CDCl$_3$): δ ppm 1.07 (3H, d, J=6.5 Hz), 1.33-1.22 (2H, m), 1.85-1.69 (3H, br. m), 2.00-1.96 (4H, m), 2.66-2.56 (2H, m), 3.02-2.90 (6H, m), 3.78 (2H, s), 4.71 (2H, dt, J$_{F,H}$=47.6 Hz, J$_{F,H}$=4.8 Hz), 4.72 (1H, m), 7.42 (1H, d, J=8.4 Hz), 7.84 (1H, dd, J$_1$=5.1 Hz, J$_2$=0.98 Hz), 8.12 (1H, br. s), 8.35 (1H, d, J=8.4 Hz), 8.50 (1H, d, J=5.3 Hz), 8.96 (1H, s), 9.10 (1H, s) ppm; MS m/z: 460.4 (M+1), 482.2 (M+Na).

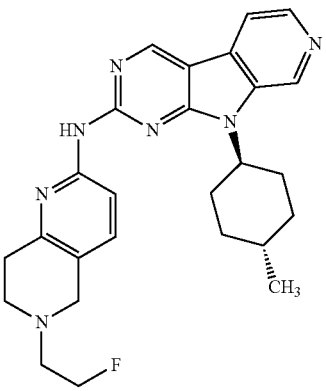 [SMILES: C[C@H]1CC[C@H](n2c3cnccc3c3cnc(Nc4ccc5c(n4)CCN(CCF)C5)nc32)CC1]

9

Example 10

N-(6-(2-Methoxyethyl)-5,6,7,8-tetrahydro-1,6-naphthyridin-2-yl)-9-((1r,4r)-4-methylcyclohexyl)-9H-pyrido[4',3':4,5]pyrrolo[2,3-d]pyrimidin-2-amine

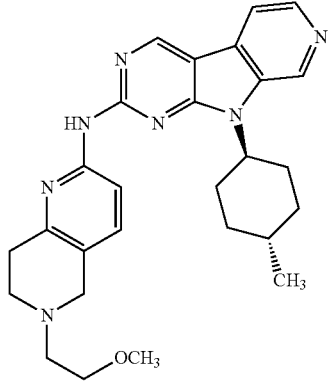 [SMILES: COCCN1CCc2nc(Nc3ncc4c5ccncc5n([C@H]5CC[C@H](C)CC5)c4n3)ccc2C1]

10

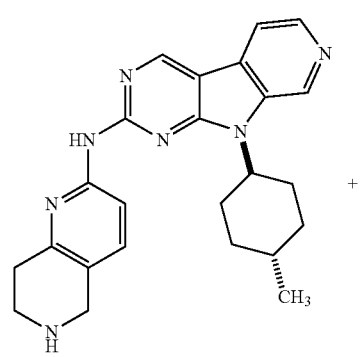

1

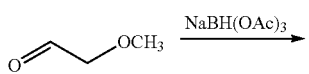

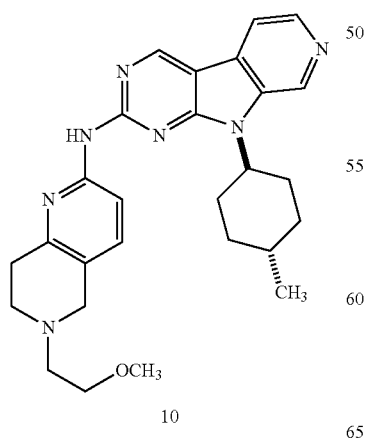

10

Synthesis of N-(6-(2-methoxyethyl)-5,6,7,8-tetrahydro-1,6-naphthyridin-2-yl)-9-((1r,4r)-4-methylcyclohexyl)-9H-pyrido[4',3':4,5]pyrrolo[2,3-d]pyrimidin-2-amine (10). An aqueous solution of methoxyacetaldehyde of indeterminate concentration was obtained by heating a solution of 1,1,2-trimethoxyethane (commercially available from Sigma-Aldrich, St. Louis, Mo.) (10 g, 83 mmol) in 0.5 M HCl (150 mL) at 50° C. for 30 minutes, followed by fractional distillation at atmospheric pressure. Sodium triacetoxyborohydride (331 mg, 1.56 mmol) was added to a solution of 9-((1r,4r)-4-methylcyclohexyl)-N-(5,6,7,8-tetrahydro-1,6-naphthyridin-2-yl)-9H-pyrido[4',3':4,5]pyrrolo[2,3-d]pyrimidin-2-amine (1) (101 mg, 0.24 mmol) in DCM (15 mL) containing glacial AcOH (100 µL, 1.7 mmol) and 400 µL of the methoxyacetaldehyde solution obtained above. The reaction mixture was stirred at ambient temperature, and additional sodium triacetoxyborohydride (474 mg, 2.24 mmol, in two successive portions) and methoxyacetaldehyde (100 µL of the aqueous solution) were added until LCMS analysis indicated that the starting material had been completely consumed. The reaction was then quenched by addition of MeOH (6 mL), and stripped of volatiles on a rotary evaporator. The resulting residue was purified by flash chromatography on silica gel eluting with a 10% to 60% gradient of solvent A (DCM:MeOH:NH$_4$OH; 90:9:1) in DCM. Chromatography fractions containing the desired product were combined and concentrated in vacuo to give a residue that was further purified by precipitation from DCM/hexanes. The suspension obtained in this way was sonicated and vacuum filtered. The filter cake was dried under high vacuum overnight to provide the titled compound (10) (32.6 mg, 28% yield). $^1$HNMR (400 MHz, CDCl$_3$): δ ppm 1.07 (3H, d, J=6.5 Hz), 1.33-1.23 (2H, m), 1.65 (3H, br. s), 2.01-1.96 (4H, m), 2.66-2.56 (2H, m), 2.86-2.83 (2H, m), 3.02-2.97 (4H, m), 3.42 (3H, s), 3.67 (2H, t, J=5.3 Hz), 3.76 (2H, br. s), 4.76-4.68 (1H, m), 7.41 (1H, d, J=8.6 Hz), 7.83 (1H, dd, J$_1$=5.3 Hz, J$_2$=0.98 Hz), 8.08 (1H, br. s), 8.34 (1H, d, J=8.4 Hz), 8.50 (1H, d, J=5.3 Hz), 8.96 (1H, s), 9.09 (1H, s) ppm; MS m/z: 472.3 (M+1), 494.2 (M+Na).

Example 11

9-((1r,4r)-4-Methylcyclohexyl)-N-(5,6,7,8-tetrahydro-2,6-naphthyridin-3-yl)-9H-pyrido[4',3':4,5]pyrrolo[2,3-d]pyrimidin-2-amine

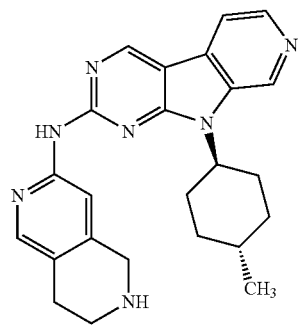 [SMILES: C[C@H]1CC[C@H](n2c3cnccc3c3cnc(Nc4cc5c(cn4)CCNC5)nc32)CC1]

11

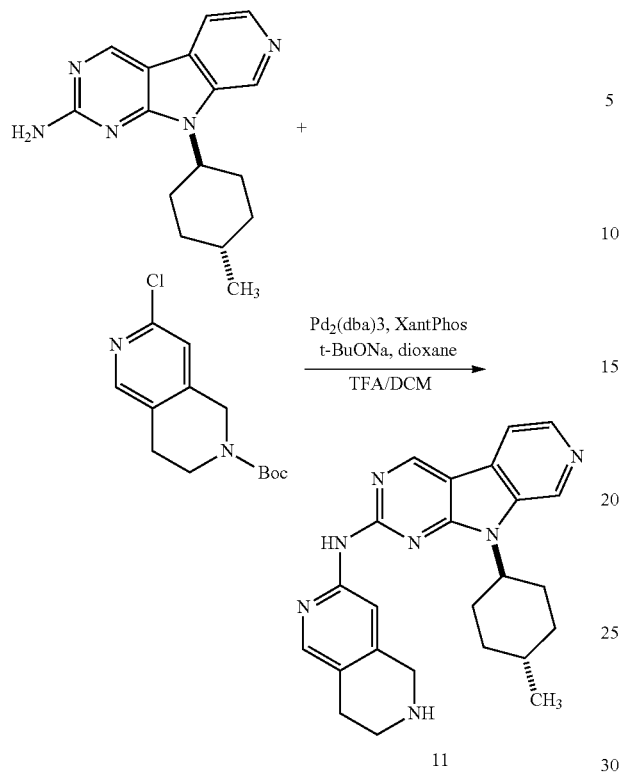

Synthesis of 9-((1r,4r)-4-methylcyclohexyl)-N-(5,6,7,8-tetrahydro-2,6-naphthyridin-3-yl)-9H-pyrrolo[2',3':4,5]pyrrolo[2,3-d]pyrimidin-2-amine (11): The title compound was prepared using chemistry similar to that described in Example 1 using 7-chloro-1,2,3,4-tetrahydro-2,6-naphthyridine hydrochloride (commercially available from Anichem, North Brunswick, N.J.) in place of 2-chloro-5,6,7,8-tetrahydro-1,6-naphthyridine hydrochloride. $^1$H NMR (400 MHz, CD$_3$OD) δ ppm 1.10 (3H, d, J=6.46 Hz), 1.33-1.45 (2H, m), 1.80-1.70 (1H, m), 2.01-2.10 (4H, m), 2.68-2.77 (2H, m), 3.22 (2H, t, J=6.36 Hz), 3.64 (2H, t, J=6.36 Hz), 4.93-5.02 (1H, m), 8.04 (1H, s), 8.39 (1H, s), 8.63-8.70 (2H, m), 9.45 (1H, s), 9.63 (1H, s) ppm; LC/MS m/z: 414 (M+1).

Example 12

2-(7-((9-((1r,4r)-4-Methylcyclohexyl)-9H-pyrido[4',3':4,5]pyrrolo[2,3-d]pyrimidin-2-yl)amino)-3,4-dihydro-2,6-naphthyridin-2(1H)-yl)ethanol

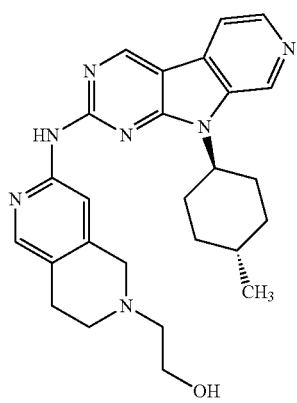 [SMILES: C[C@H]1CC[C@H](n2c3cnccc3c3cnc(Nc4cc5c(cn4)CCN(CCO)C5)nc32)CC1]

Synthesis of 2-(7-((9-((1r,4r)-4-methylcyclohexyl)-9H-pyrido[4',3':4,5]pyrrolo[2,3-d]pyrimidin-2-yl)amino)-3,4-dihydro-2,6-naphthyridin-2(1H)-yl)ethanol (12). The title compound was prepared using chemistry similar to that described in Example 3 using 9-((1r,4r)-4-methylcyclohexyl)-N-(5,6,7,8-tetrahydro-2,6-naphthyridin-3-yl)-9H-pyrido[4',3':4,5]pyrrolo[2,3-d]pyrimidin-2-amine (11) in place of 9-((1r,4r)-4-methylcyclohexyl)-N-(5,6,7,8-tetrahydro-1,6-naphthyridin-2-yl)-9H-pyrido[4',3':4,5]pyrrolo[2,3-d]pyrimidin-2-amine (1). $^1$H NMR (500 MHz, CD$_3$OD) δ ppm 1.11 (3H, d, J=6.60 Hz), 1.28-1.46 (2H, m), 1.7-1.8 (1H, m) 1.86-2.09 (4H, m), 2.61-2.76 (2H, m), 2.79 (2H, t, J=5.99 Hz), 2.86-3.01 (4H, m), 3.8-3.9 (4H, m), 4.98 (1H, m), 8.05-8.09 (1H, m), 8.11 (1H, s), 8.26-8.30 (1H, m), 8.39-8.44 (1H, m), 8.98-9.03 (1H, m), 9.21-9.25 (1H, m) ppm; LC/MS m/z: 458 (M+1).

Example 13

N-(8-Methyl-5,6,7,8-tetrahydro-1,6-naphthyridin-2-yl)-9-((1r,4r)-4-methylcyclohexyl)-9H-pyrido[4',3':4,5]pyrrolo[2,3-d]pyrimidin-2-amine

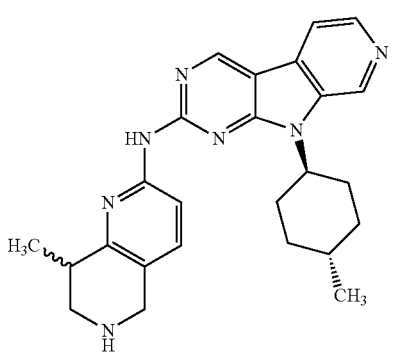 [SMILES: CC1CNCc2ccc(Nc3ncc4c5ccncc5n([C@H]5CC[C@H](C)CC5)c4n3)nc21]

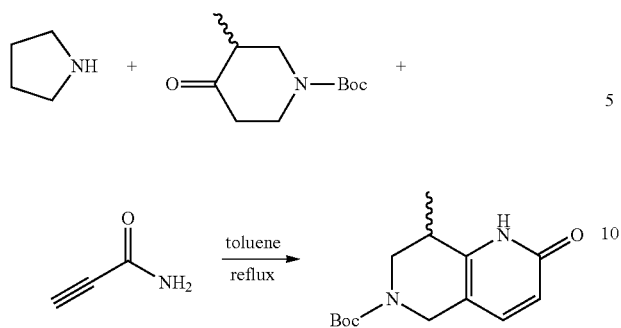

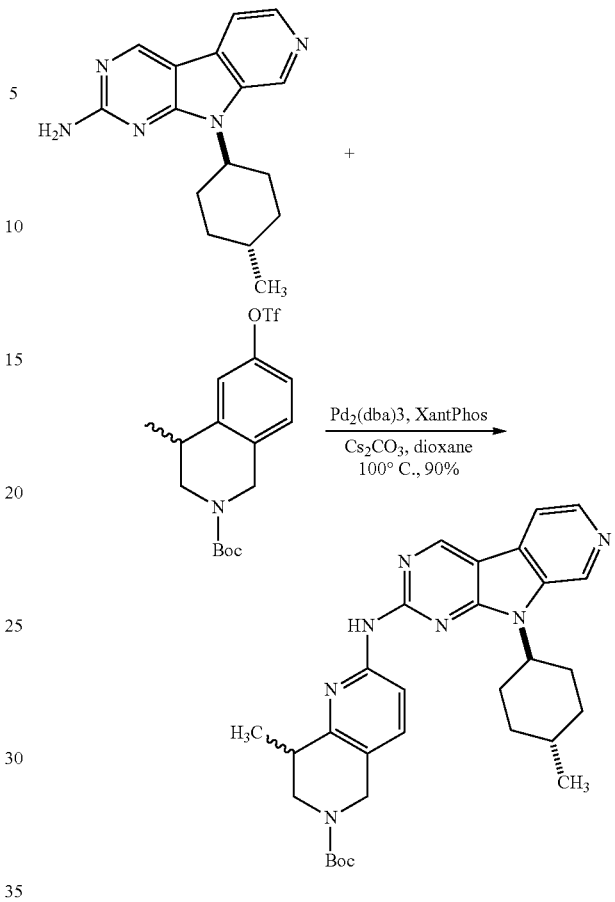

Synthesis of tert-butyl 8-methyl-2-oxo-1,2,7,8-tetrahydro-1,6-naphthyridine-6(5H)-carboxylate. tert-Butyl 3-methyl-4-oxopiperidine-1-carboxylate (commercially available from Ryan Scientific, Mt. Pleasant, S.C.)(1.7 g, 7.97 mmol) and pyrrolidine (1.3 mL, 15.94 mmol) were dissolved in toluene (9 mL), and the solution was heated under reflux, with the removal of water under Dean-Stark conditions, for 5 hours. The solution was then cooled to room temperature and propiolamide (prepared as described in EP 1813606)(1.1 g, 15.94 mmol) was added. The reaction mixture thus obtained was heated overnight under reflux. The reaction mixture was concentrated, and the residue was purified by flash chromatography on silica gel eluting with 0% to 10% MeOH in DCM to give the title compound (2.1 g, 55% yield). $^1$H NMR (400 MHz, CDCl$_3$) δ ppm 1.36 (3H, d, J=7.04 Hz), 1.52 (9H, s), 3.37-3.44 (1H, m), 3.77-3.84 (1H, m), 4.12-4.17 (1H, m), 6.48 (1H, d, J=9.39 Hz), 7.21 (1H, d, J=9.39 Hz) ppm; LC/MS m/z: 265 (M+1).

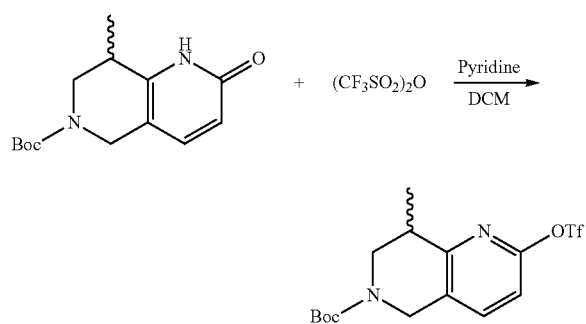

Synthesis of tert-butyl 8-methyl-2-(((trifluoromethyl)sulfonyl)oxy)-7,8-dihydro-1,6-naphthyridine-6(5H)-carboxylate. To a solution of tert-butyl 8-methyl-2-oxo-1,2,7,8-tetrahydro-1,6-naphthyridine-6(5H)-carboxylate (129 mg, 0.49 mmol) and pyridine (120 µL, 1.47 mmol) in DCM (10 mL) at 0° C. was added dropwise trifluoromethanesulfonic anhydride (commercially available from Sigma-Aldrich, St. Louis, Mo.) (99 µL, 0.59 mmol). The reaction mixture was stirred for 30 minutes and then concentrated under reduced pressure. The residue was purified by flash chromatography on silica gel eluting with 0% to 40% EtOAc in hexane to give the title compound (161 mg, 83% yield). LC/MS m/z: 397 (M+1).

Synthesis of tert-butyl 8-methyl-2-((9-((1r,4r)-4-methylcyclohexyl)-9H-pyrido[4',3':4,5]pyrrolo[2,3-d]pyrimidin-2-yl)amino)-7,8-dihydro-1,6-naphthyridine-6(5H)-carboxylate. A glass microwave reaction vessel was charged with 9-((1r,4r)-4-methylcyclohexyl)-9H-pyrido[4',3':4,5]pyrrolo[2,3-d]pyrimidin-2-amine (110 mg, 0.39 mmol) and (9,9-dimethyl-9H-xanthene-4,5-diyl)bis(diphenylphosphine) (45.2 mg, 0.078 mmol), Pd$_2$(dba)$_3$ (35.8 mg, 0.039 mmol), tert-butyl 8-methyl-2-(trifluoromethylsulfonyloxy)-7,8-dihydro-1,6-naphthyridine-6(5H)-carboxylate and 2 mL of 1,4-dioxane. The reaction mixture was heated at 100° C. for 90 minutes under microwave radiation. The reaction mixture was concentrated, and the residue was purified by flash chromatography on silica gel eluting with 0% to 70% solvent A (DCM:MeOH:NH$_4$OH, 90:9:1) in DCM to give the title compound. LCMS m/z: 528 (M+1).

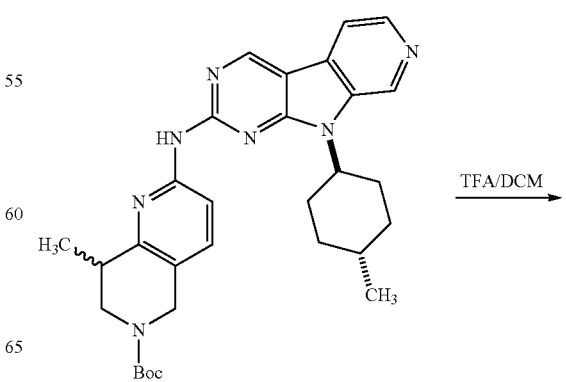

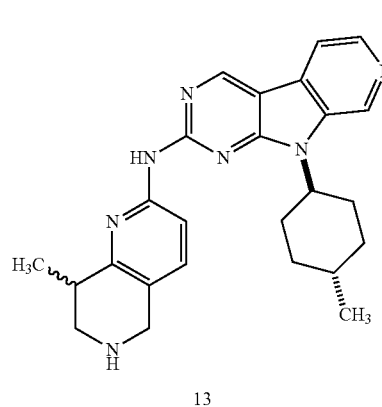

13

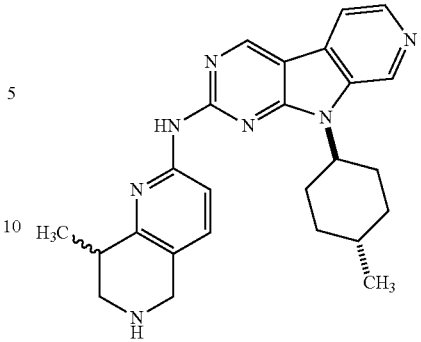

13

Synthesis of N-(8-methyl-5,6,7,8-tetrahydro-1,6-naphthyridin-2-yl)-9-((1r,4r)-4-methylcyclohexyl)-9H-pyrido[4',3':4,5]pyrrolo[2,3-d]pyrimidin-2-amine (13). A solution of tert-butyl 8-methyl-2-((9-((1r,4r)-4-methylcyclohexyl)-9H-pyrido[4',3':4,5]pyrrolo[2,3-d]pyrimidin-2-yl)amino)-7,8-dihydro-1,6-naphthyridine-6(5H)-carboxylate in 50% TFA in DCM (10 mL) was stirred at room temperature for 30 minutes and then concentrated and purified by preparatory LC to give the title compound (13) (135 mg, 81%). $^1$H NMR (400 MHz, CD$_3$OD) δ ppm 1.10 (3H, d, J=6.46 Hz), 1.36-1.41 (2H, m), 1.56 (3H, d, J=6.65 Hz), 1.70-1.80 (1H, br. s), 2.00-2.08 (4H, m), 2.65-2.71 (2H, m), 2.73 (2H, s), 3.76-3.81 (1H, m), 4.46 (2H, d, J=4.50 Hz), 4.91-4.94 (1H, m), 7.76 (1H, d, J=8.61 Hz), 8.47 (1H, d, J=8.41 Hz) 8.56-8.61 (2H, m) 9.37 (1H, s) 9.54 (1H, s) ppm; LC/MS m/z: 428 (M+1).

Example 14

1-(8-Methyl-2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone

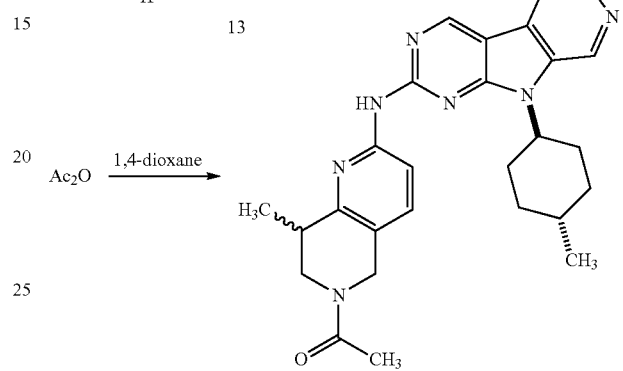

Synthesis of 1-(8-methyl-2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone (14). The title compound was prepared using chemistry similar to that described in Example 2 using N-(8-methyl-5,6,7,8-tetrahydro-1,6-naphthyridin-2-yl)-9-((1r,4r)-4-methylcyclohexyl)-9H-pyrido[4',3':4,5]pyrrolo[2,3-d]pyrimidin-2-amine (13) instead of 9-((1r,4r)-4-methylcyclohexyl)-N-(5,6,7,8-tetrahydro-1,6-naphthyridin-2-yl)-9H-pyrido[4',3':4,5]pyrrolo[2,3-d]pyrimidin-2-amine (1). $^1$H NMR (400 MHz, CD$_3$OD) δ ppm 1.10 (3H, d, J=6.46 Hz), 1.31-1.43 (2H, m), 1.48-1.57 (3H, m), 2.00-2.09 (4H, m), 2.28 (3H, s), 2.68-2.80 (2H, m), 3.70-3.89 (1H, m), 3.99 (1H, td, J=13.35, 4.79 Hz), 4.91-5.01 (1H, m), 7.92 (1H, br. s), 7.96-8.01 (1H, m), 8.64-8.69 (2H, m), 9.46 (1H, d, J=2.93 Hz), 9.70 (1H, d, J=3.52 Hz) ppm; LC/MS m/z: 470 (M+1).

Example 15

2-(8-Methyl-2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanol

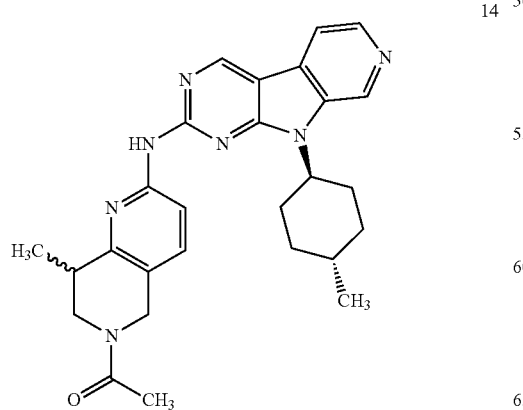

14

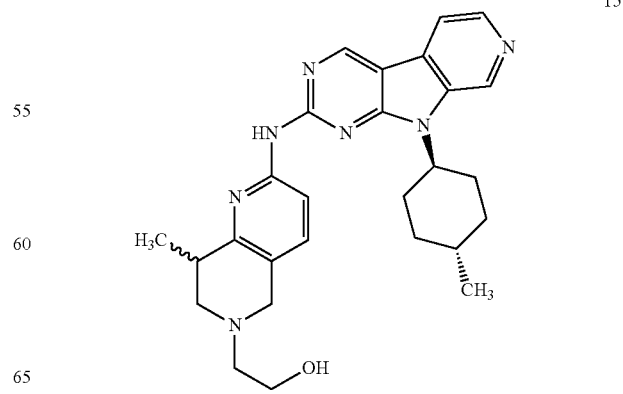

15

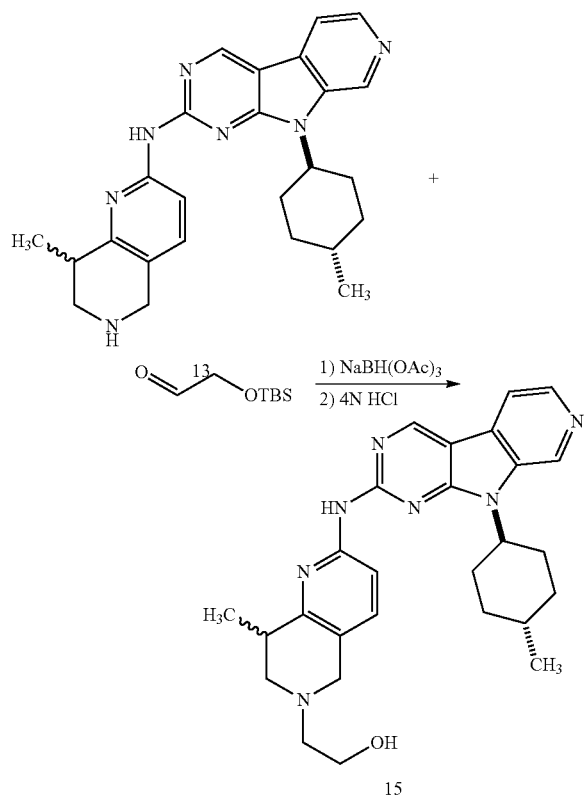

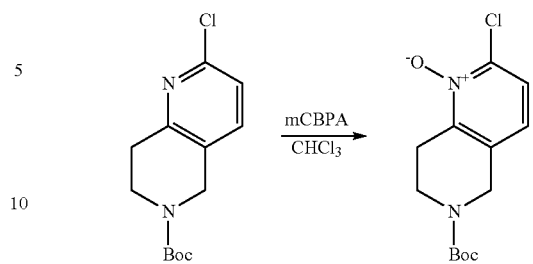

Synthesis of 6-(tert-butoxycarbonyl)-2-chloro-5,6,7,8-tetrahydro-1,6-naphthyridine 1-oxide. 3-Chlorobenzoperoxoic acid (241 mg, 1.4 mmol) was added to a solution at 0° C. of tert-butyl 2-chloro-7,8-dihydro-1,6-naphthyridine-6(5H)-carboxylate (250 mg, 0.93 mmol, see Example 1 procedure) in CHCl₃ (3 mL). The reaction mixture thus obtained was warmed to room temperature and stirred overnight. After concentration, the residue was purified by flash chromatography on silica gel eluting with 0% to 80% EtOAc in hexane to give the title compound (150 mg, 56.6% yield). $^1$H NMR (400 MHz, CDCl₃) δ ppm 1.51 (9H, s), 3.11 (2H, m), 3.77 (2H, t, J=6.16 Hz), 4.60 (2H, s), 6.99 (1H, d, J=8.41 Hz), 7.40 (1H, d, J=8.41 Hz) ppm; LC/MS m/z: 285 (M+1).

Synthesis of 2-(8-methyl-2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanol (15). The title compound was prepared using chemistry similar to that described in Example 3 using N-(8-methyl-5,6,7,8-tetrahydro-1,6-naphthyridin-2-yl)-9-((1r,4r)-4-methylcyclohexyl)-9H-pyrido[4',3':4,5]pyrrolo[2,3-d]pyrimidin-2-amine (13) instead of 9-((1r,4r)-4-methylcyclohexyl)-N-(5,6,7,8-tetrahydro-1,6-naphthyridin-2-yl)-9H-pyrido[4',3':4,5]pyrrolo[2,3-d]pyrimidin-2-amine (1). $^1$H NMR (400 MHz, CD₃OD) δ ppm 1.10 (3H, d, J=6.65 Hz), 1.30-1.47 (2H, m), 1.59 (3H, d, J=6.85 Hz), 1.69-1.83 (1H, m), 1.94-2.11 (4H, m), 2.67-2.81 (2H, m), 3.39-3.58 (4H, m), 3.92-4.10 (3H, m), 4.54-4.71 (2H, m), 4.94-5.05 (1H, m), 7.80 (1H, d, J=8.80 Hz), 8.38 (1H, d, J=8.61 Hz), 8.59-8.67 (2H, m), 9.42 (1H, s), 9.60 (1H, s) ppm; LC/MS m/z: 472 (M+1).

Example 16

2-((9-((1r,4r)-4-Methylcyclohexyl)-9H-pyrido[4',3':4,5]pyrrolo[2,3-d]pyrimidin-2-yl)amino)-5,6,7,8-tetrahydro-1,6-naphthyridin-8-ol

16

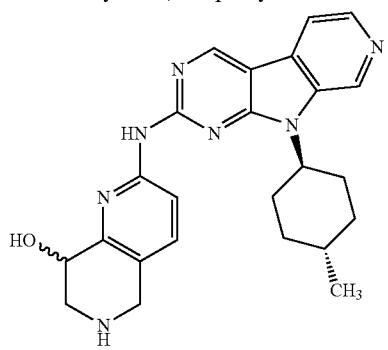

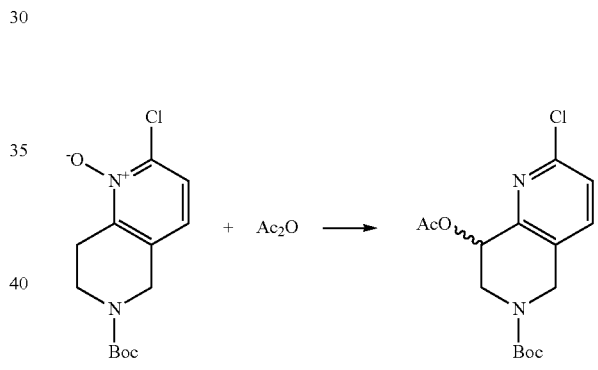

Synthesis of tert-butyl 8-acetoxy-2-chloro-7,8-dihydro-1,6-naphthyridine-6(5H)-carboxylate. A solution of 6-(tert-Butoxycarbonyl)-2-chloro-5,6,7,8-tetrahydro-1,6-naphthyridine 1-oxide (150 mg, 0.53 mmol) in acetic anhydride (2.5 mL, 26.3 mmol), was stirred and heated at 70° C. overnight under nitrogen atmosphere. DCM (20 mL) was added to the reaction mixture, and the resulting solution was washed sequentially with water, saturated aqueous NaHCO₃ solution and brine, dried over anhydrous MgSO₄, and concentrated under vacuum. The residue was purified by flash chromatography on silica gel eluting with 0% to 30% EtOAc in hexane to give the title compound (115 mg, 66.8% yield). $^1$H NMR (400 MHz, CDCl₃) δ ppm 1.51 (9H, s), 2.13 (3H, s), 3.30-3.49 (1H, d, J=12.0 Hz), 4.25-4.40 (1H, m), 4.45-4.55 (1H, d, J=12.0 Hz), 5.20-5.00 (1H, m), 5.73 (1H, br. s), 7.34 (1H, d, J=8.22 Hz), 7.51 (1H, d, J=8.41 Hz) ppm; LC/MS m/z: 327 (M+1).

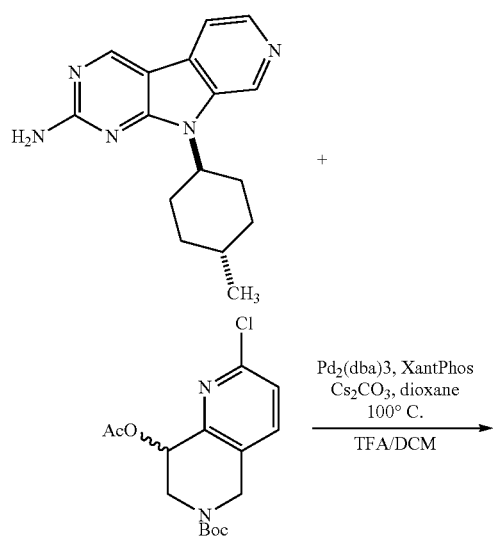

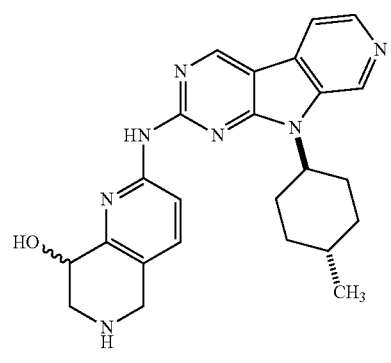 [SMILES: C[C@H]1CC[C@H](n2c3cnccc3c3cnc(Nc4ccc5c(n4)C(O)CNC5)nc32)CC1]

16

Synthesis of (2-((9-((1r,4r)-4-methylcyclohexyl)-9H-pyrido[4',3':4,5]pyrrolo[2,3-d]pyrimidin-2-yl)amino)-5,6,7,8-tetrahydro-1,6-naphthyridin-8-ol (16). Lithium hydroxide (47.6 mg, 2.0 mmol) was added to a solution of 2-((9-((1r, 4r)-4-methylcyclohexyl)-9H-pyrido[4',3':4,5]pyrrolo[2,3-d]pyrimidin-2-yl)amino)-5,6,7,8-tetrahydro-1,6-naphthyridin-8-yl acetate (106 mg, 0.226 mmol) in 10 mL of MeOH, 10 mL of THF and 5 mL of water. The reaction mixture was heated at 50° C. for 1 hour. The reaction mixture was extracted with DCM, and the organic layer was concentrated. The residue was purified by preparative LC to give the title compound (16)(87 mg, 90%). $^1$H NMR (400 MHz, CD$_3$OD) δ ppm 1.10 (3H, d, J=6.46 Hz), 1.32-1.47 (2H, m), 1.70-1.82 (1H, m), 1.99-2.11 (4H, m), 2.73 (2H, qd, J=12.91, 4.30 Hz), 3.69 (2H, d, J=3.52 Hz), 4.42-4.54 (2H, m), 4.97-5.02 (2H, m), 7.89 (1H, d, J=8.61 Hz), 8.42 (1H, d, J=8.80 Hz), 8.59-8.67 (2H, m), 9.43 (1H, s), 9.63 (1H, s) ppm; LC/MS m/z: 430 (M+1).

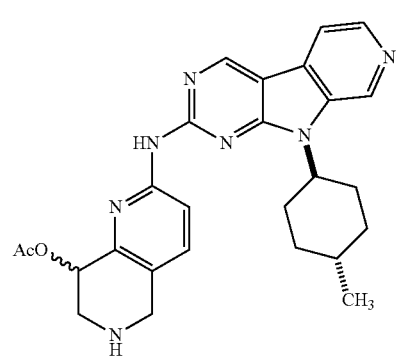

Synthesis of 2-((9-((1r,4r)-4-methylcyclohexyl)-9H-pyrido[4',3':4,5]pyrrolo[2,3-d]pyrimidin-2-yl)amino)-5,6,7,8-tetrahydro-1,6-naphthyridin-8-yl acetate. The title compound was prepared using chemistry similar to that described in Example 13 using tert-butyl 8-acetoxy-2-chloro-7,8-dihydro-1,6-naphthyridine-6(5H)-carboxylate in place of tert-butyl 8-methyl-2-(trifluoromethylsulfonyloxy)-7,8-dihydro-1,6-naphthyridine-6(5H)-carboxylate. LC/MS m/z: 472 (M+1).

Example 17

6-(2-Hydroxyethyl)-2-((9-((1r,4r)-4-methylcyclohexyl)-9H-pyrido[4',3':4,5]pyrrolo[2,3-d]pyrimidin-2-yl)amino)-5,6,7,8-tetrahydro-1,6-naphthyridin-8-ol

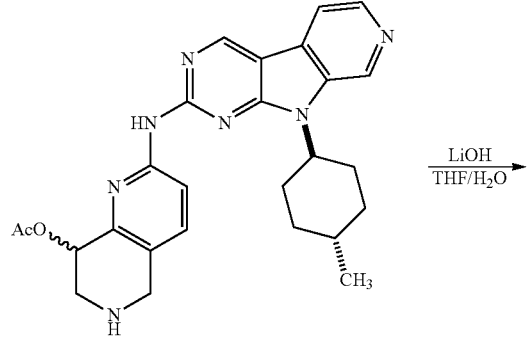

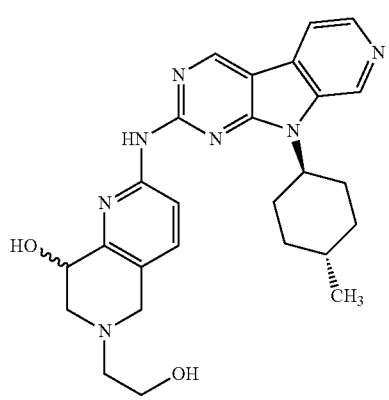

17

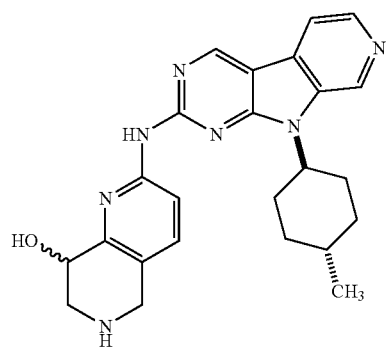

16

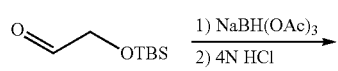

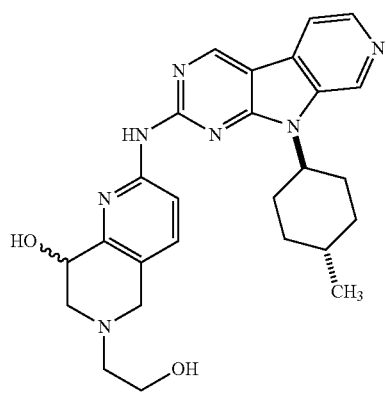 [SMILES: C[C@H]1CC[C@H](n2c3cnccc3c3cnc(Nc4ccc5c(n4)C(O)CN(CCO)C5)nc32)CC1]

17

Synthesis of 6-(2-hydroxyethyl)-2-((9-((1r,4r)-4-methyl-cyclohexyl)-9H-pyrido[4',3':4,5]pyrrolo[2,3-d]pyrimidin-2-yl)amino)-5,6,7,8-tetrahydro-1,6-naphthyridin-8-ol (17). The title compound was prepared using chemistry similar to that described in Example 3 using (2-((9-((1r,4r)-4-methyl-cyclohexyl)-9H-pyrido[4',3':4,5]pyrrolo[2,3-d]pyrimidin-2-yl)amino)-5,6,7,8-tetrahydro-1,6-naphthyridin-8-ol (16) in place of 9-((1r,4R)-4-methylcyclohexyl)-N-(5,6,7,8-tetrahydro-1,6-naphthyridin-2-yl)-9H-pyrido[4',3':4,5]pyrrolo[2,3-d]pyrimidin-2-amine (1). $^1$H NMR (400 MHz, CD$_3$OD) δ ppm 1.10 (3H, d, J=6.46 Hz), 1.32-1.46 (2H, m), 1.76 (1H, dd, J=6.75, 3.81 Hz), 1.98-2.11 (4H, m), 2.67-2.80 (2H, m), 3.49-3.62 (2H, m), 3.75-3.98 (2H, m), 3.98-4.10 (2H, m), 4.55-4.70 (2H, m), 4.92-5.06 (2H, m), 7.86 (1H, d, J=8.80 Hz), 8.50 (1H, d, J=8.61 Hz), 8.59-8.68 (2H, m), 9.42 (1H, s), 9.59-9.64 (1H, m) ppm; LC/MS m/z: 472 (M+1).

Example 18a 1-((R)-8-Methyl-2-((9-((1r,4R)-4-methylcyclo-hexyl)-9H-pyrido[4',3':4,5]pyrrolo[2,3-d]pyrimidin-2-yl)amino)-7,8-dihydro-1,6-naphthyridin-6(5H)-yl)ethanone or 1-((S)-8-methyl-2-((9-((1r,4S)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone

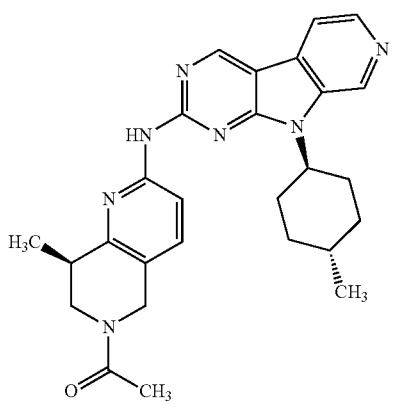

or

18a

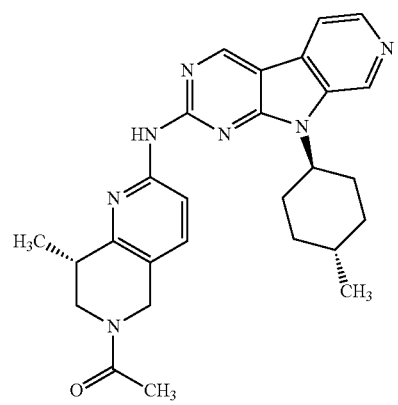 [SMILES: CC(=O)N1Cc2ccc(Nc3ncc4c5ccncc5n([C@H]5CC[C@H](C)CC5)c4n3)nc2[C@@H](C)C1]

Separation of 1-(8-methyl-2-((9-((1r,4r)-4-methylcyclo-hexyl)-9H-pyrido[4',3':4,5]pyrrolo[2,3-d]pyrimidin-2-yl)amino)-7,8-dihydro-1,6-naphthyridin-6(5H)-yl)ethanone. The racemic mixture obtained in Example 14 was separated on a Thar 350 SFC system by sequential injections (1.2 mL; 8.0 mg/mL in MeOH; 10 mL total) with a 250×30 mm IA column and with 45 mL/min IPA+(20 mM NH$_3$) and 55 g/min CO$_2$. The resulting fractions were concentrated on a rotary evaporator and analyzed. The enantiomers were each obtained with >99% ee.

The first enantiomer to elute was assigned as 18a (16 mg as an off-white solid). $^1$H NMR (500 MHz, CD$_3$OD:DCM-d$_2$ 1:1, rotamers) δ ppm 0.92-0.79 (1H, m), 1.06 (3H, d, J=6.6 Hz), 1.28-1.25 (1H, m), 1.34-1.31 (2H, m), 1.41-1.36 (2H, m), 1.75-1.62 (1H, m), 1.98 (4H, d, J=10.0 Hz), 2.22 (3H, d, J=4.2 Hz), 2.71-2.55 (2H, m), 3.12-2.97 (1H, m), 3.77-3.63 (1H, m), 3.92-3.78 (1H, m), 4.85-4.71 (1H, m), 4.91 (1H, d, J=17.1 Hz), 7.62-7.54 (1H, m), 7.98 (1H, d, J=5.4 Hz), 8.46-8.37 (2H, m), 8.92 (1H, s), 9.17-9.13 (1H, m) ppm; LCMS m/z: 470.2 (M+1); HPLC purity: 99.3% (254 nm).

Example 18b

Stereoisomer of Example 18a 1-((R)-8-Methyl-2-((9-((1r,4R)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone or 1-((S)-8-methyl-2-((9-((1r,4S)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone The second enantiomer to elute in the separation described in Example 18a was assigned as 18b (20 mg as a light tan solid). $^1$H NMR (500 MHz, CD$_3$OD:DCM-d$_2$ 1:1, rotamers) δ ppm 0.89-0.80 (m, 1H), 1.06 (3H, d, J=6.6 Hz), 1.31-1.25 (2H, m), 1.43-1.35 (3H, m), 1.74-1.62 (1H, m), 2.00 (4H, d, J=10.0 Hz), 2.22 (3H, d, J=2.2 Hz), 2.71-2.58 (2H, m), 3.17-3.12 (1H, m), 3.67 (1H, dd, J=5.7, 13.6 Hz), 3.88-3.76 (1H, m), 4.92-4.80 (2H, m), 7.67 (1H, d, J=8.3 Hz), 8.33-8.18 (2H, m), 8.47 (1H, d, J=5.6 Hz), 9.10 (1H, s), 9.35 (1H, d, J=1.7 Hz) ppm; LCMS m/z: 470.2 (M+1); HPLC purity: 98.6% (254 nm).

Example 19

6-Methoxy-9-((1r,4r)-4-methylcyclohexyl)-N-(5,6,7,8-tetrahydro-1,6-naphthyridin-2-yl)-9H-pyrido[4',3':4,5]pyrrolo[2,3-d]pyrimidin-2-amine

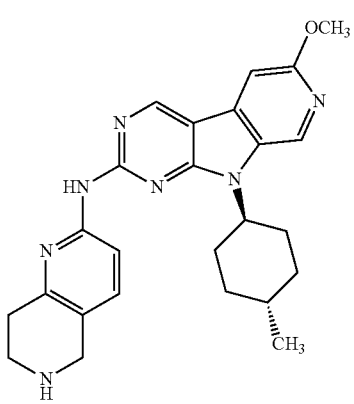

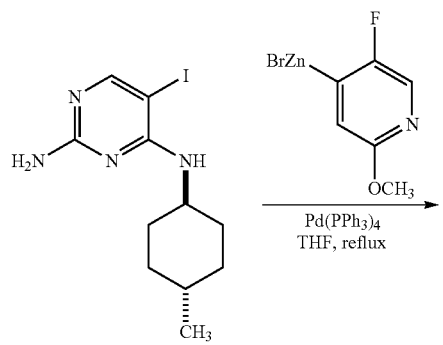

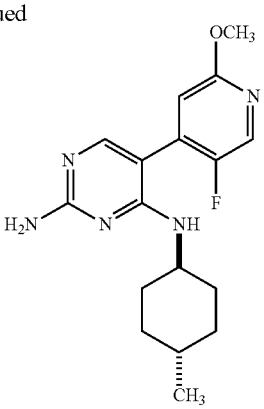

Synthesis of 5-(5-fluoro-2-methoxypyridin-4-yl)-N4-((1r,4r)-4-methylcyclohexyl)pyrimidine-2,4-diamine. A pre-cooled (−20° C.) solution of 5-fluoro-2-methoxypyridine (commercially available from Waterstone Technology, Carmel, Ind.)(3.56 g, 28.0 mmol) in THF (25 mL) was added to a 2M lithium diisopropylamide solution in THF (14.45 mL, 28.9 mmol) over 20 minutes at −78° C. The yellow-brown solution thus obtained was stirred at −78° C. for 1.5 hours, then zinc (II) chloride (58.7 mL, 29.4 mmol) was added. The cooling bath was removed, and the mixture was allowed to warm to room temperature. To the reaction mixture was added a solution of 5-iodo-N$^4$-((1r,4r)-4-methylcyclohexyl)pyrimidine-2,4-diamine (3 g, 9.03 mmol, See Example 1 procedure) and Pd[(PPh$_3$)]$_4$ (1.044 g, 0.903 mmol) in THF (20 mL). The resulting mixture was refluxed overnight. The reaction was cooled to room temperature, quenched with saturated NaHCO$_3$(50 mL) and extracted with DCM. The organic layer was concentrated, and the residue was purified by flash chromatography on silica gel eluting with 0% to 100% EtOAc in hexane to give the title compound as a yellow solid (1.5 g, 50% yield). $^1$H NMR (400 MHz, DMSO-d$_6$) δ ppm 0.86 (3H, d, J=8.0 Hz), 0.89-1.00 (2H, m), 1.16-1.32 (3H, m), 1.65 (2H, d, J=12.0 Hz), 1.76 (2H, d, J=12.0 Hz), 3.84 (3H, s), 3.92-4.02 (1H, m), 5.96 (1H, d, J=12.0 Hz), 6.20 (2H, s), 6.74 (1H, d, J=8.0 Hz), 7.57 (1H, s), 8.10 (1H, s) ppm; LCMS m/z: 332.2 (M+1).

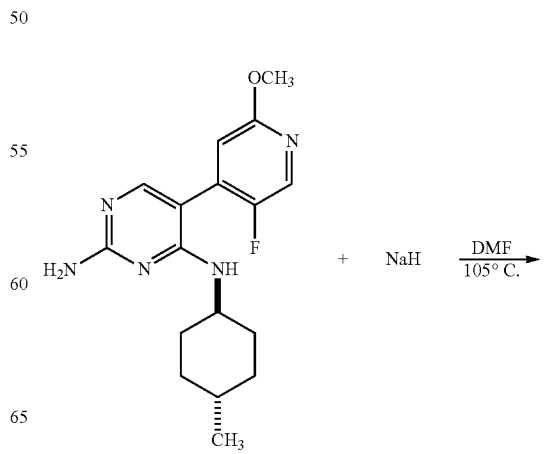

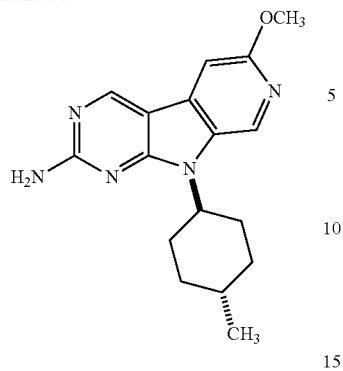

Synthesis of 6-methoxy-9-((1r,4r)-4-methylcyclohexyl)-9H-pyrido[4',3':4,5]pyrrolo[2,3-d]pyrimidin-2-amine. Sodium hydride (60% dispersion in mineral oil) (1.09 g, 27.2 mmol) was added slowly to a solution of 5-(5-fluoro-2-methoxypyridin-4-yl)-N$^4$-((1r,4r)-4-methylcyclohexyl)pyrimidine-2,4-diamine (3.0 g, 9.05 mmol) in DMF (60 mL) at 0° C. After addition, the mixture was stirred at room temperature for 20 minutes under N$_2$ atmosphere and then at 105° C. overnight. The reaction was cooled to room temperature and quenched with saturated NH$_4$Cl at 0° C. while stirring. The mixture was extracted with EtOAc and washed with water and then with brine, and dried over Na$_2$SO$_4$. The solvent was removed, and the crude product was purified by flash chromatography on silica gel eluting 0% to 50% EtOAc in hexane to give the title compound as an off-white solid (1.5 g, 50% yield). $^1$H NMR (400 MHz, DMSO-d$_6$) δ ppm 0.96 (3H, d, J=8.0 Hz), 1.05-1.24 (2H, m), 1.55-1.65 (1H, m), 1.74 (2H, d, J=8.0 Hz), 1.85 (2H, d, J=8.0 Hz), 2.30-2.45 (2H, m), 3.87 (3H, s), 4.64-4.74 (1H, m), 6.93 (2H, s), 7.31 (1H, s), 8.52 (1H, s), 8.94 (1H, s) ppm; LCMS m/z: 312.3 (M+1).

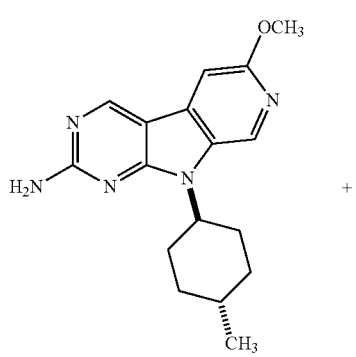

+

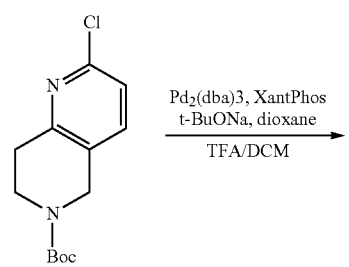

→ (Pd$_2$(dba)3, XantPhos, t-BuONa, dioxane; TFA/DCM)

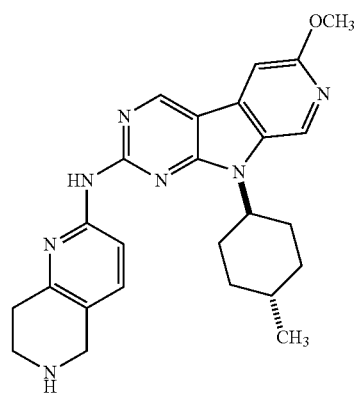 [SMILES: COc1cc2c3cnc(Nc4ccc5c(n4)CCNC5)nc3n([C@H]3CC[C@H](C)CC3)c2cn1]

Synthesis of 6-methoxy-9-((1r,4r)-4-methylcyclohexyl)-N-(5,6,7,8-tetrahydro-1,6-naphthyridin-2-yl)-9H-pyrido[4',3':4,5]pyrrolo[2,3-d]pyrimidin-2-amine (19). The title compound was prepared using chemistry similar to that described in Example 1 using 6-methoxy-9-((1r,4r)-4-methylcyclohexyl)-9H-pyrido[4',3':4,5]pyrrolo[2,3-d]pyrimidin-2-amine in place of 9-((1r,4r)-4-methylcyclohexyl)-9H-pyrido[4',3':4,5]pyrrolo[2,3-d]pyrimidin-2-amine $^1$H NMR (500 MHz, CD$_3$OD) δ ppm 1.05 (3H, d, J=6.6 Hz), 1.25-1.48 (2H, m), 1.65-1.75 (1H, m), 1.95-2.05 (4H, m), 2.51-2.74 (2H, m), 3.42 (2H, d, J=10.0 Hz), 3.70 (2H, d, J=10.0 Hz), 4.03 (3H, s), 4.45 (2H, s), 4.82-4.90 (1H, m), 7.30-7.45 (1H, m), 7.62 (1H, s), 7.84 (1H, d, J=10.0 Hz), 8.73 (1H, s), 9.35 (1H, s) ppm; LCMS m/z: 444.3 (M+1).

Example 20

2-Hydroxy-1-(2-((6-methoxy-9-((1r,4r)-4-methylcyclohexyl)-9H-pyrido[4',3':4,5]-pyrrolo[2,3-d]pyrimidin-2-yl)amino)-7,8-dihydro-1,6-naphthyridin-6(5H)-yl)ethanone

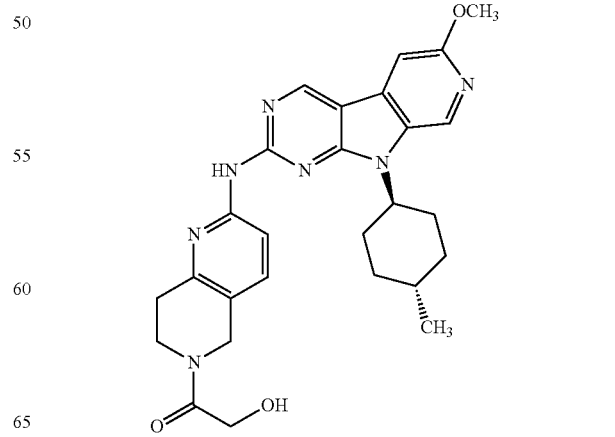

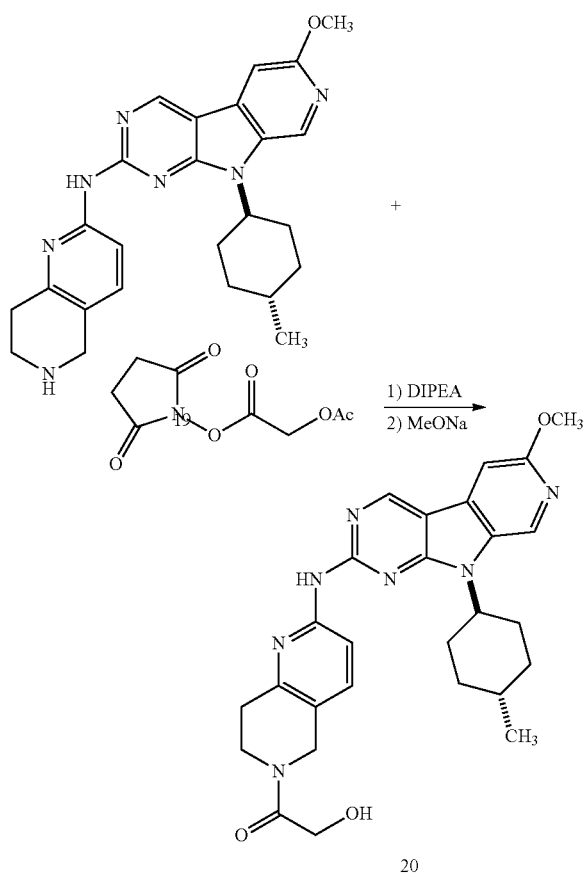

20

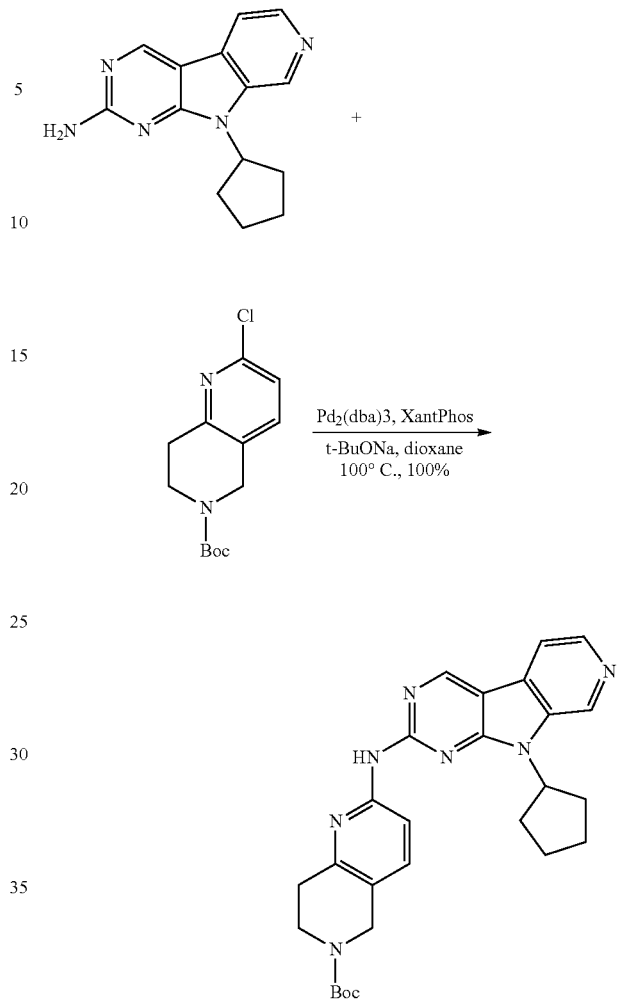

Synthesis of 2-hydroxy-1-(2-(((6-methoxy-9-((1r,4r)-4-methylcyclohexyl)-9H-pyrido[4',3':4,5]-pyrrolo[2,3-d]pyrimidin-2-yl)amino)-7,8-dihydro-1,6-naphthyridin-6(5H)-yl) ethanone (20). The title compound was prepared using chemistry similar to that described in Example 5 using 6-methoxy-9-((1r,4r)-4-methylcyclohexyl)-N-(5,6,7,8-tetrahydro-1,6-naphthyridin-2-yl)-9H-pyrido[4',3':4,5]pyrrolo[2,3-d]pyrimidin-2-amine (19) in place of 9-((1r,4r)-4-methylcyclohexyl)-N-(5,6,7,8-tetrahydro-1,6-naphthyridin-2-yl)-9H-pyrido[4',3':4,5]pyrrolo[2,3-d]pyrimidin-2-amine (1). $^1$H NMR (500 MHz, CD$_3$OD) δ ppm 1.04 (3H, d, J=6.6 Hz), 1.25-1.33 (2H, m), 1.65-1.75 (1H, m), 1.95-2.05 (4H, m), 2.51-2.62 (2H, m), 3.14-3.26 (2H, m), 3.84-3.99 (2H, m), 4.02 (3H, s), 4.37 (2H, br. s.), 4.74 (2H, br. s.), 4.82-4.91 (1H, m), 7.28 (1H, d, J=10.0 Hz), 7.59 (1H, s), 7.89-7.94 (1H, m), 8.70 (1H, s), 9.34 (1H, s) ppm; LCMS m/z: 502.2 (M+1).

Example 21

9-Cyclopentyl-N-(5,6,7,8-tetrahydro-1,6-naphthyridin-2-yl)-9H-pyrido[4',3':4,5]pyrrolo[2,3-d]pyrimidin-2-amine

21

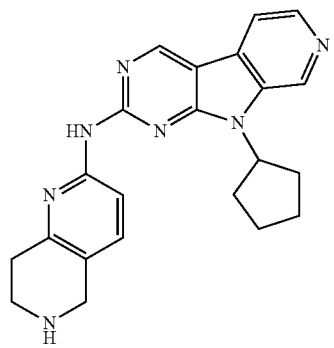

Synthesis of tert-butyl 2-((9-cyclopentyl-9H-pyrido[4',3':4,5]pyrrolo[2,3-d]pyrimidin-2-yl)amino)-7,8-dihydro-1,6-naphthyridine-6(5H)-carboxylate. To a solution of 9-cyclopentyl-9H-yrido[4',3':4,5]pyrrolo[2,3-d]pyrimidin-2-amine (prepared as described in WO 2009/085185) (152 mg, 0.6 mmol) in dioxane (6 mL) were added tert-butyl 2-chloro-7,8-dihydro-1,6-naphthyridine-6(5H)-carboxylate (177 mg, 0.66 mmol), tris(dibenzylideneacetone)dipalladium (0) (28 mg, 0.030 mmol), 4,5-bis(diphenylphosphino)-9,9-dimethylxanthene (52 mg, 0.090 mmol), and sodium t-butoxide (86 mg, 0.9 mmol). The reaction mixture thus obtained was heated at 150° C. under microwave irradiation for 1 hour. The reaction mixture was diluted with DCM, washed with brine, and then dried. The solvent was evaporated and the residue was purified by flash chromatography on silica gel eluting with 10% to 50% solvent A (DCM/MeOH/NH$_4$OH, 100:10:1) in DCM to give the title compound as a light yellow solid (211 mg, 72% yield). $^1$H NMR (500 MHz, CDCl$_3$) δ 1.52 (9H, s), 1.88-1.90 (2H, m), 2.14-2.21 (4H, m), 2.45-2.47 (2H, m), 2.92-2.94 (2H, m), 3.76-3.79 (2H, m), 4.59 (2H, m), 5.37 (1H, m), 7.49 (1H, d, J=10.0 Hz), 7.85 (1H, d, J=5.0 Hz), 8.14 (1H, br. s), 8.37 (1H, d, J=10.0 Hz), 8.52 (1H, d, J=5.0 Hz), 8.92 (1H, s), 9.11 (1H, s) ppm; LCMS m/z: 486 (M+1).

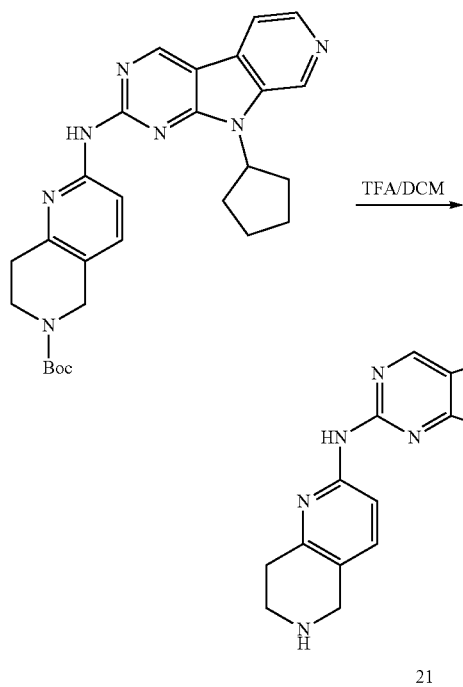

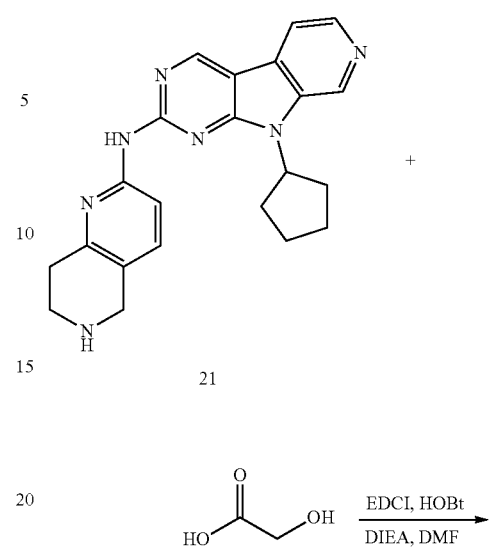

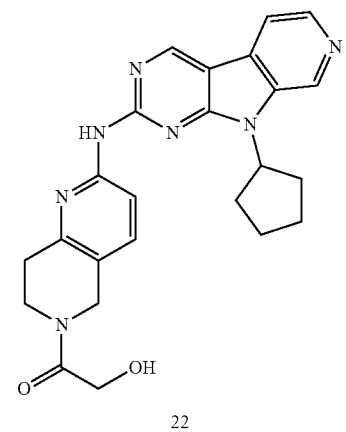

Synthesis of 9-cyclopentyl-N-(5,6,7,8-tetrahydro-1,6-naphthyridin-2-yl)-9H-pyrido[4',3':4,5]pyrrolo[2,3-d]pyrimidin-2-amine (21). A solution of tert-butyl 2((9-cyclopentyl-9H-pyrido[4',3':4,5]pyrrolo[2,3-d]pyrimidin-2-yl)amino)-7,8-dihydro-1,6-naphthyridine-6(5H)-carboxylate (217 mg, 0.477 mmol) in TFA/DCM (1:1, 2 mL) was stirred at room temperature for 30 minutes and then concentrated. The residue was purified by flash chromatography on silica gel eluting with 25% to 75% solvent A (DCM:MeOH:NH$_4$OH, 100:10:1) in DCM to give the title compound as a yellow solid (148 mg, 86% yield). $^1$H NMR (500 MHz, CDCl$_3$) δ 1.87-1.90 (2H, m), 2.14-2.21 (4H, m), 2.43-2.47 (2H, m), 2.89 (2H, t, J=5.0 Hz), 3.26 (2H, t, J=5.0 Hz), 4.02 (2H, s), 5.36 (1H, m), 7.41 (1H, d, J=10.0 Hz), 7.85 (1H, d, J=5.0 Hz), 8.19 (1H, br. s), 8.31 (1H, d, J=10.0 Hz), 8.52 (1H, d, J=5.0 Hz), 8.91 (1H, s), 9.11 (1H, s) ppm; LCMS m/z: 386 (M+1).

Example 22

1-(2-((9-Cyclopentyl-9H-pyrido[4',3':4,5]pyrrolo[2,3-d]pyrimidin-2-yl)amino)-7,8-dihydro-1,6-naphthyridin-6(5H)-yl)-2-hydroxyethanone

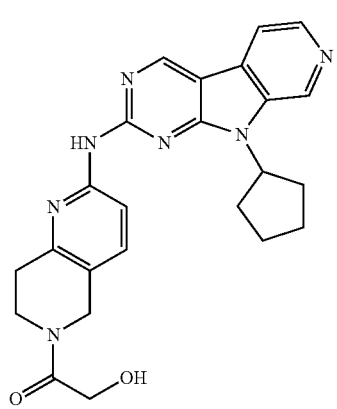

22

Synthesis of 1-(2-((9-cyclopentyl-9H-pyrido[4',3':4,5]pyrrolo[2,3-d]pyrimidin-2-yl)amino)-7,8-dihydro-1,6-naphthyridin-6(5H)-yl)-2-hydroxyethanone (22). To a solution of 9-cyclopentyl-N-(5,6,7,8-tetrahydro-1,6-naphthyridin-2-yl)-9H-pyrido[4',3':4,5]pyrrolo[2,3-d]pyrimidin-2-amine (21) (145 mg, 0.367 mmol) in DMF (10 mL) were added 2-hydroxyacetic acid (34.3 mg, 0.451 mmol), EDC (191.7 mg, 0.451 mmol), N-hydroxybenzotriazole (61 mg, 0.451 mmol), and N,N-diisopropylethylamine (157 uL, 0.903 mmol). The mixture thus obtained was stirred at room temperature for 2 hours. The reaction mixture was concentrated, and the residue was purified by flash chromatography on silica gel eluting with 20% to 75% solvent A (DCM:MeOH:NH$_4$OH, 100:10:1) to give the title compound as an off-white solid (117 mg, 70% yield). $^1$H NMR (500 MHz, DMSO-d$_6$) δ 1.77-1.80 (2H, m), 2.07-2.10 (4H, m), 2.42-2.44 (2H, m), 2.82-2.91 (2H, m), 3.66-3.82 (2H, m), 4.18-4.20 (2H, m), 4.57-4.66 (2H, m), 5.36 (1H, m), 7.68 (1H, d, J=10.0 Hz), 8.06 (1H, d, J=5.0 Hz), 8.19 (1H, d, J=10.0 Hz), 8.48 (1H, d, J=5.0 Hz), 9.03 (1H, s), 9.31 (1H, s) 9.98 (1H, br. s) ppm; LCMS m/z: 444 (M+1).

Example 23

9-((1r,4r)-4-Methylcyclohexyl)-N-(5,6,7,8-tetrahydro-1,7-naphthyridin-2-yl)-9H-pyrido[4',3':4,5]pyrrolo[2,3-d]pyrimidin-2-amine

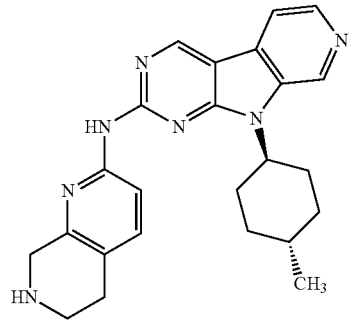 [SMILES: C[C@H]1CC[C@H](n2c3cnccc3c3cnc(Nc4ccc5c(n4)CNCC5)nc32)CC1]

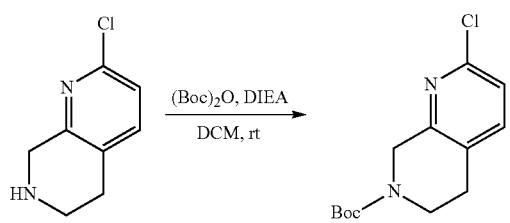

Synthesis of tert-butyl 2-chloro-5,6-dihydro-1,7-naphthyridine-7(8H)-carboxylate. The title compound was prepared using chemistry similar to that described in Example 1 using 2-chloro-5,6,7,8-tetrahydro-1,7-naphthyridine hydrochloride (commercially obtained from Anichem, North Brunswick, N.J.) in place of 2-chloro-5,6,7,8-tetrahydro-1,6-naphthyridine hydrochloride. $^1$H NMR (500 MHz, CD$_2$Cl$_2$) δ 1.47 (9H, s), 2.79 (2H, t, J=5.6 Hz), 3.64 (2H, t, J=5.6 Hz), 4.58 (2H, s), 7.13 (1H, d, J=8.0 Hz), 7.42 (1H, d, J=8.0 Hz) ppm; LCMS m/z: 269 (M+1).

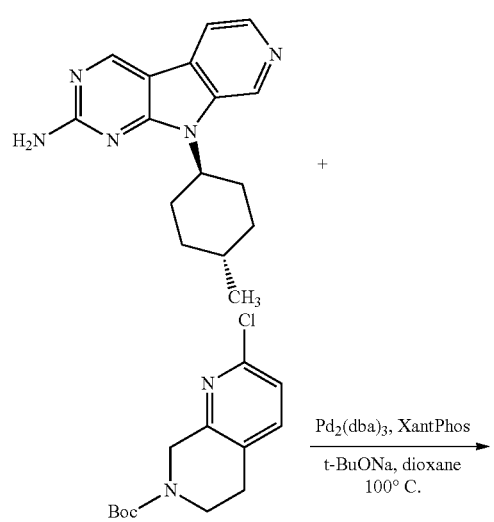

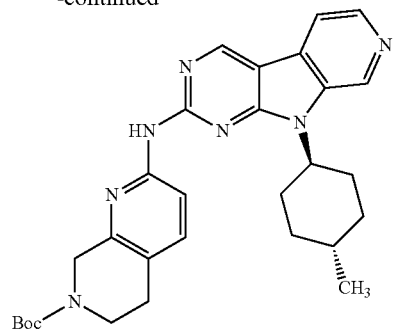

Synthesis of tert-butyl 2-((9-((1r,4r)-4-methylcyclohexyl)-9H-pyrido[4',3':4,5]pyrrolo[2,3-d]pyrimidin-2-yl)amino)-5,6-dihydro-1,7-naphthyridine-7(8H)-carboxylate. The title compound was prepared using chemistry similar to that described in Example 1 using tert-butyl 2-chloro-5,6-dihydro-1,7-naphthyridine-7(8H)-carboxylate in place of tert-butyl 2-chloro-7,8-dihydro-1,6-naphthyridine-6(5H)-carboxylate. $^1$H NMR (500 MHz, CDCl$_3$) δ 1.07 (3H, d, J=6.4 Hz), 1.23-1.33 (2H, m), 1.52 (9H, s), 1.64-1.68 (1H, m), 1.99 (4H, t, J=11.0 Hz), 2.60 (2H, dq, J=3.3, 12.3 Hz), 2.85 (2H, br. s), 3.72 (2H, br. s), 4.60 (2H, s), 4.73 (1H, t, J=12.3 Hz), 7.53 (1H, d, J=8.3 Hz), 7.87 (1H, d, J=5.4 Hz), 8.10 (1H, br. s), 8.37 (1H, d, J=8.3 Hz), 8.51 (1H, d, J=5.4 Hz), 8.97 (1H, s), 9.12 (1H, s) ppm; LCMS m/z: 514 (M+1).

Synthesis of 9-((1r,4r)-4-methylcyclohexyl)-N-(5,6,7,8-tetrahydro-1,7-naphthyridin-2-yl)-9H-pyrido[4',3':4,5]pyrrolo[2,3-d]pyrimidin-2-amine Dihydrochloride. To a solution of tert-butyl 2-((9-((1r,4r)-4-methylcyclohexyl)-9H-pyrido[4',3':4,5]pyrrolo[2,3-d]pyrimidin-2-yl)amino)-5,6-dihydro-1,7-naphthyridine-7(8H)-carboxylate (320 mg, 0.623 mmol) in DCM (5 mL) and MeOH (5 mL) was added 4.0 M HCl in dioxane (10 mL) and a slurry formed within minutes. The mixture was stirred overnight at room temperature, concentrated and then reslurried with ether. The slurry was filtered with a Buchner funnel providing 9-((1r,4r)-4-methylcyclohexyl)-N-(5,6,7,8-tetrahydro-1,7-naphthyridin-2-yl)-9H-pyrido[4',3':4,5]pyrrolo[2,3-d]pyrimidin-2-amine dihydrochloride (176 mg) as a tan solid. $^1$H NMR (500 MHz, CD$_3$OD) δ 1.09 (3H, d, J=6.4 Hz), 1.32-1.45 (2H, m), 1.77 (1H, br. s), 2.06 (4H, t, J=15.5 Hz), 2.64-2.79 (2H, m), 3.21 (2H, t, J=6.2 Hz), 3.63 (2H, t, J=6.2 Hz), 4.61 (2H, s), 4.93-5.03 (1H, m), 7.88 (1H, br. s), 7.91-7.96 (1H, m), 8.74 (1H, d, J=6.1 Hz), 8.81 (1H, d, J=6.1 Hz), 9.55 (1H, s), 9.80 (1H, s) ppm; LCMS m/z: 414 (M+1).

Example 24

9-((1r,4r)-4-Methylcyclohexyl)-N-(5,6,7,8-tetrahydro-2,7-naphthyridin-3-yl)-9H-pyrido[4',3':4,5]pyrrolo[2,3-d]pyrimidin-2-amine

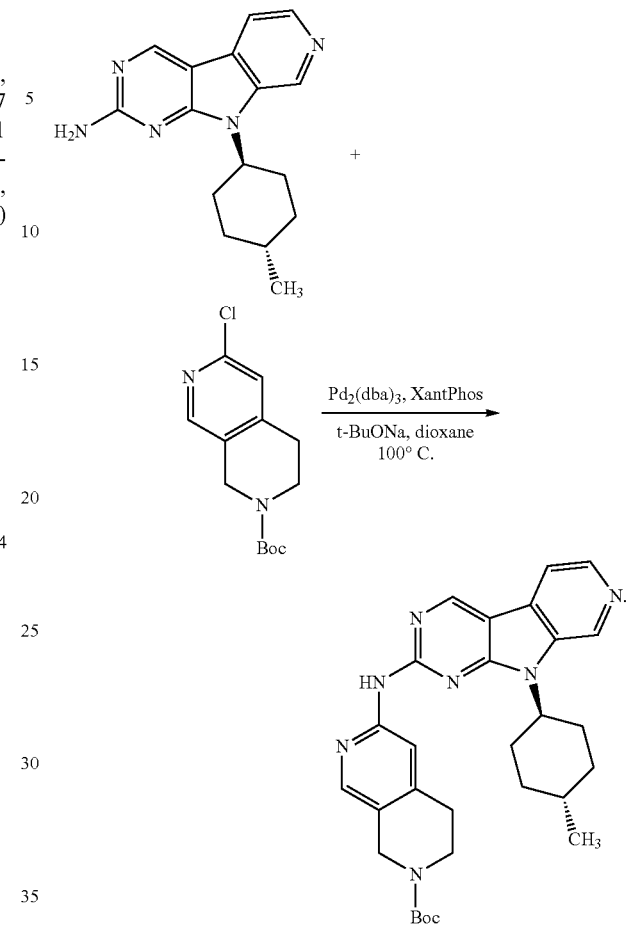

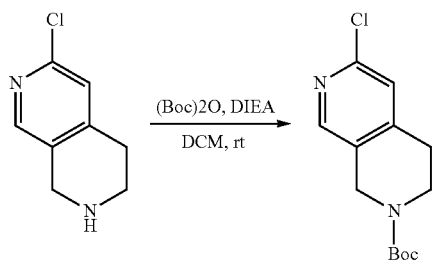

Synthesis of tert-butyl 6-chloro-3,4-dihydro-2,7-naphthyridine-2(1H)-carboxylate. 6-Chloro-1,2,3,4-tetrahydro-2,7-naphthyridine hydrochloride (commercially obtained from Anichem, North Brunswick, N.J.) (2.0 g, 9.75 mmol) and TEA (2.72 mL, 19.50 mmol) were mixed in DCM (19.50 mL). Boc$_2$O (2.34 g, 10.7 mmol) was added. The mixture was then stirred for 2 hours at room temperature. TLC indicated good consumption of the starting material and the formation of one major spot. There was also a less polar spot that was more faint. The reaction mixture was partitioned with DCM and water. The organic layer was dried with sodium sulfate, filtered, and concentrated. The residue was purified by flash column chromatography on silica gel eluting with 0% to 40% EtOAc in hexane to provide tert-butyl 6-chloro-3,4-dihydro-2,7-naphthyridine-2(1H)-carboxylate as a clear colorless oil (1.53 g). $^1$H NMR (500 MHz, CD$_2$CCl$_2$) δ 1.46 (9H, s), 2.80 (2H, t, J=6.0 Hz), 3.62 (2H, t, J=6.0 Hz), 4.55 (2H, s), 7.12 (1H, s), 8.13 (1H, s) ppm; LCMS m/z: 269 (M+1).

Synthesis of tert-butyl 6-((9-((1r,4r)-4-methylcyclohexyl)-9H-pyrido[4',3':4,5]pyrrolo[2,3-d]pyrimidin-2-yl)amino)-3,4-dihydro-2,7-naphthyridine-2(1H)-carboxylate. The title compound was prepared using chemistry similar to that described in Example 1 using tert-butyl 6-chloro-3,4-dihydro-2,7-naphthyridine-2(1H)-carboxylate in place of tert-butyl 2-chloro-7,8-dihydro-1,6-naphthyridine-6(5H)-carboxylate. $^1$H NMR (500 MHz, CDCl$_3$) δ 1.07 (3H, d, J=6.4 Hz), 1.23-1.35 (2H, m), 1.53 (9H, s), 1.62-1.73 (1H, m), 2.00 (2H, br. s), 2.48-2.67 (2H, m), 2.81-3.01 (2H, m), 3.72 (2H, br. s), 4.61 (2H, s), 4.78 (1H, t, J=12.5 Hz), 7.89 (1H, d, J=5.4 Hz), 8.10 (1H, br. s), 8.12 (1H, br. s), 8.36 (1H, br. s), 8.52 (1H, d, J=5.4 Hz), 8.98 (1H, s), 9.12 (1H, s) ppm; LCMS m/z: 514 (M+1).

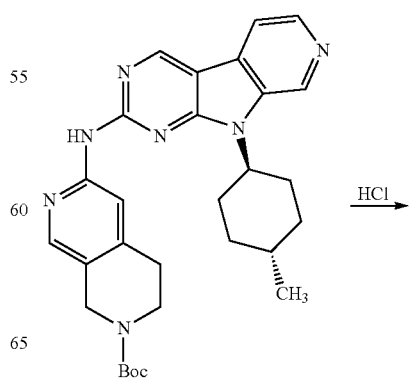

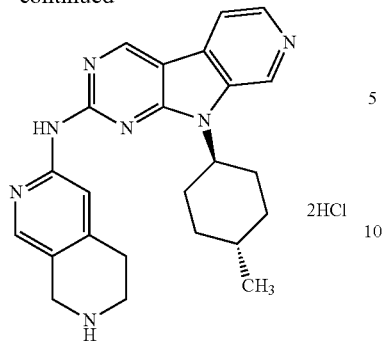

Synthesis of 9-((1r,4r)-4-methylcyclohexyl)-N-(5,6,7,8-tetrahydro-2,7-naphthyridin-3-yl)-9H-pyrido[4',3':4,5]pyrrolo[2,3-d]pyrimidin-2-amine dihydrochloride.

To a slurry of tert-butyl 6-((9-((1r,4r)-4-methylcyclohexyl)-9H-pyrido[4',3':4,5]pyrrolo[2,3-d]pyrimidin-2-yl)amino)-3,4-dihydro-2,7-naphthyridine-2(1H)-carboxylate (446 mg, 0.868 mmol) in MeOH (4.3 mL) and DCM (4.3 mL) was added 10 mL of 4.0 M HCl in dioxane. The resulting clear solution was then stirred overnight at room temperature. Solid precipitated from the reaction mixture during the course of the reaction. The mixture was concentrated, rinsed with ether and filtered to yield 9-((1r,4r)-4-methylcyclohexyl)-N-(5,6,7,8-tetrahydro-2,7-naphthyridin-3-yl)-9H-pyrido[4',3':4,5]pyrrolo[2,3-d]pyrimidin-2-amine dihydrochloride (461 mg, 0.948 mmol). $^1$H NMR (500 MHz, CD$_3$OD) δ 1.07 (3H, d, J=6.6 Hz), 1.29-1.42 (2H, m), 1.69-1.81 (1H, m), 1.98-2.09 (4H, m), 2.64-2.76 (2H, m), 3.39 (2H, t, J=6.4 Hz), 3.64 (2H, t, J=6.4 Hz), 4.54 (2H, s), 4.95-5.07 (1H, m), 7.68 (1H, br. s), 8.48 (1H, s), 8.71 (1H, d, J=6.1 Hz), 8.83 (1H, d, J=6.1 Hz), 9.55 (1H, s), 9.78 (1H, s) ppm; LCMS m/z: 414 (M+1).

Example 25

1-(2-((9-Cycloheptyl-9H-pyrido[4',3':4,5]pyrrolo[2,3-d]pyrimidin-2-yl)amino)-7,8-dihydro-1,6-naphthyridin-6(5H)-yl)-2-hydroxyethanone

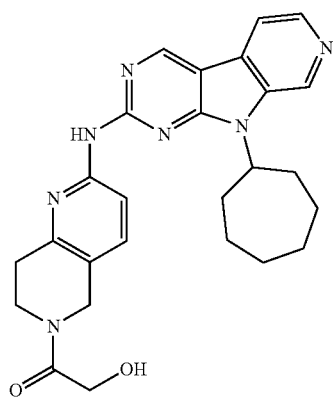

Synthesis of 1-(2-((9-cycloheptyl-9H-pyrido[4',3':4,5]pyrrolo[2,3-d]pyrimidin-2-yl)amino)-7,8-dihydro-1,6-naphthyridin-6(5H)-yl)-2-hydroxyethanone (25). The title compound can be prepared using chemistry similar to that described in Examples 1 and 5 using cycloheptylamine (commercially available from Sigma-Aldrich, St. Louis, Mo.) in place of trans-4-methylcyclohexylamine hydrochloride.

Example 26

1-(2-((9-Cyclopentyl-8-fluoro-9H-pyrido[4',3':4,5]pyrrolo[2,3-d]pyrimidin-2-yl)amino)-7,8-dihydro-1,6-naphthyridin-6(5H)-yl)-2-hydroxyethanone

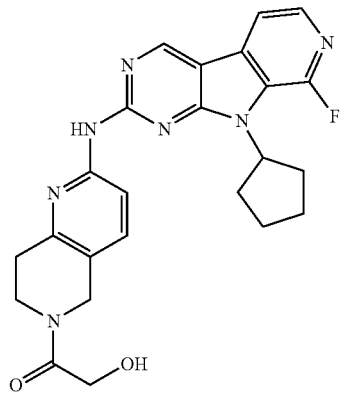

Synthesis of 1-(2-((9-cyclopentyl-8-fluoro-9H-pyrido[4',3':4,5]pyrrolo[2,3-d]pyrimidin-2-yl)amino)-7,8-dihydro-1,6-naphthyridin-6(5H)-yl)-2-hydroxyethanone (26). The title compound can be prepared using chemistry similar to that described in Examples 21 and 22 using 9-cyclopentyl-8-fluoro-9H-pyrido[4',3':4,5]pyrrolo[2,3-d]pyrimidin-2-amine (prepared as described in WO 2009/085185) in place of 9-cyclopentyl-9H-pyrido[4',3':4,5]pyrrolo[2,3-d]pyrimidin-2-amine.

Example 27

2-Hydroxy-1-(2-((9-(tetrahydro-2H-pyran-4-yl)-9H-pyrido[4',3':4,5]pyrrolo[2,3-d]pyrimidin-2-yl)amino)-7,8-dihydro-1,6-naphthyridin-6(5H)-yl)ethanone

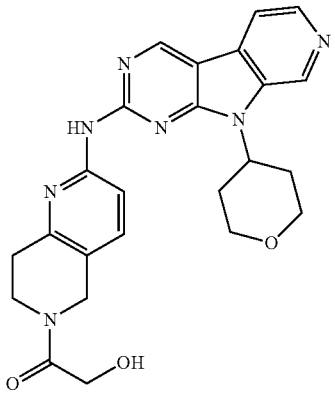

Synthesis of 2-hydroxy-1-(2-((9-(tetrahydro-2H-pyran-4-yl)-9H-pyrido[4',3':4,5]pyrrolo[2,3-d]pyrimidin-2-yl)amino)-7,8-dihydro-1,6-naphthyridin-6(5H)-yl)ethanone (27). The title compound can be prepared using chemistry similar to that described in Examples 1 and 5 using 9-(tetrahydro-2H-pyran-4-yl)-9H-pyrido[4',3':4,5]pyrrolo[2,3-d]pyrimidin-2-amine (prepared as described in WO 2009/085185) in place of 9-((1r,4r)-4-methylcyclohexyl)-9H-pyrido[4',3':4,5]pyrrolo[2,3-d]pyrimidin-2-amine.

Example 28

1-(2-((9-((1R,2R,4S)-Bicyclo[2.2.1]heptan-2-yl)-9H-pyrido[4',3':4,5]pyrrolo[2,3-d]pyrimidin-2-yl)amino)-7,8-dihydro-1,6-naphthyridin-6(5H)-yl)-2-hydroxyethanone

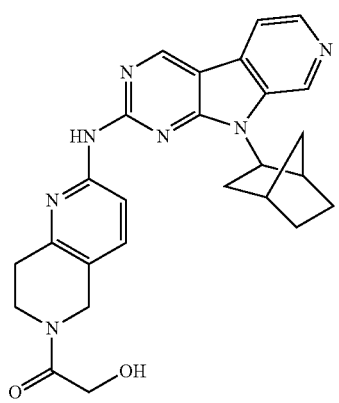

Synthesis of 1-(2-((9-((1R,2R,4S)-bicyclo[2.2.1]heptan-2-yl)-9H-pyrido[4',3':4,5]pyrrolo[2,3-d]pyrimidin-2-yl)amino)-7,8-dihydro-1,6-naphthyridin-6(5H)-yl)-2-hydroxyethanone (28). The title compound can be prepared using chemistry similar to that described in Examples 1 and 5 using 9-((1R,2R,4S)-bicyclo[2.2.1]heptan-2-yl)-9H-pyrido[4',3':4,5]pyrrolo[2,3-d]pyrimidin-2-amine (prepared as described in WO 2009/085185) in place of 9-((1r,4r)-4-methylcyclohexyl)-9H-pyrido[4',3':4,5]pyrrolo[2,3-d]pyrimidin-2-amine Example 29

1-(2-((9-((1s,3s)-Adamantan-1-yl)-9H-pyrido[4',3':4,5]pyrrolo[2,3-d]pyrimidin-2-yl)amino)-7,8-dihydro-1,6-naphthyridin-6(5H)-yl)-2-hydroxyethanone

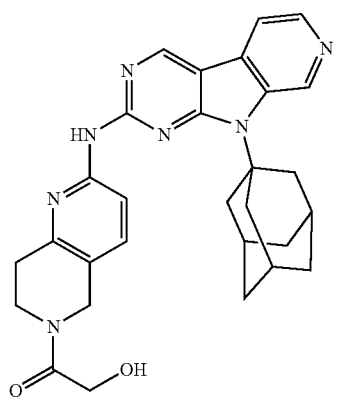

Synthesis of 1-(2-((9-((1s,3s)-adamantan-1-yl)-9H-pyrido[4',3':4,5]pyrrolo[2,3-d]pyrimidin-2-yl)amino)-7,8-dihydro-1,6-naphthyridin-6(5H)-yl)-2-hydroxyethanone (29). The title compound can be prepared using chemistry similar to that described in Examples 1 and 5 using 9-((1s,3s)-adamantan-1-yl)-9H-pyrido[4',3':4,5]pyrrolo[2,3-d]pyrimidin-2-amine (prepared as described in WO 2009/085185) in place of 9-((1r,4r)-4-methylcyclohexyl)-9H-pyrido[4',3':4,5]pyrrolo[2,3-d]pyrimidin-2-amine.

Example 30

2-Hydroxy-1-(2-((9-((1r,4r)-4-methylcyclohexyl)-9H-pyrido[4',3':4,5]pyrrolo[2,3-d]pyrimidin-2-yl)amino)-5,6-dihydro-1,7-naphthyridin-7(8H)-yl)ethanone

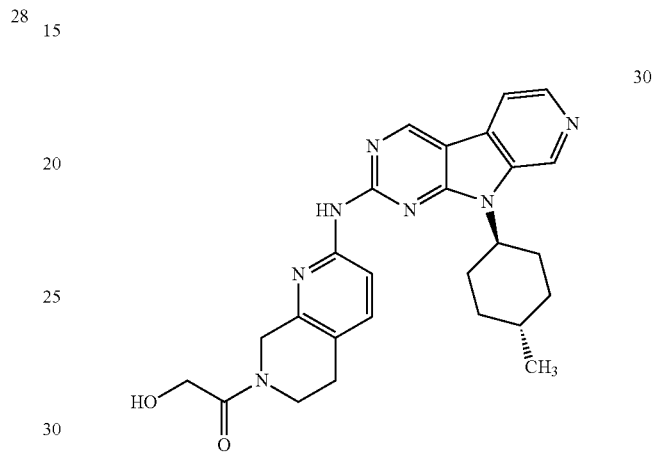

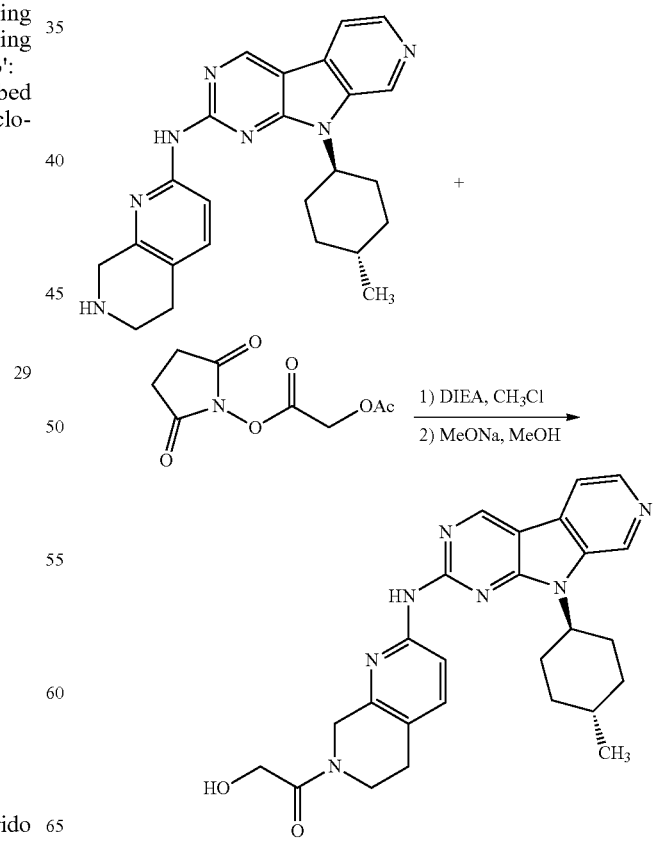

Synthesis of 2-hydroxy-1-(2-((9-((1r,4r)-4-methylcyclohexyl)-9H-pyrido[4',3':4,5]pyrrolo[2,3-d]pyrimidin-2-yl)amino)-5,6-dihydro-1,7-naphthyridin-7(8H)-yl)ethanone.

The title compound was prepared using chemistry similar to that described in Example 5 using 9-((1r,4r)-4-methylcyclohexyl)-N-(5,6,7,8-tetrahydro-1,7-naphthyridin-2-yl)-9H-pyrido[4',3':4,5]pyrrolo[2,3-d]pyrimidin-2-amine dihydrochloride (Example 23) in place of 9-((1r,4r)-4-methylcyclohexyl)-N-(5,6,7,8-tetrahydro-1,6-naphthyridin-2-yl)-9H-pyrido[4',3':4,5]pyrrolo[2,3-d]pyrimidin-2-amine.
$^1$H NMR (500 MHz, CDCl$_3$) δ 1.08 (3H, d, J=6.4 Hz), 1.21-1.35 (2H, m), 1.99 (4H, t, J=10.5 Hz), 2.60 (2H, dq, J=3.5, 12.8 Hz), 2.91 (2H, q, J=5.9 Hz), 3.58 (1H, t, J=5.9 Hz), 3.68 (1H, t, J=4.3 Hz), 3.97 (1H, t, J=5.9 Hz), 4.10 (2H, m), 4.44 (1H, s), 4.75 (1H, m), 4.82 (1H, s), 7.55 (1H, d, J=8.6 Hz), 7.88 (1H, d, J=5.4 Hz), 8.07 (1H, s), 8.43 (1H, d, J=8.6 Hz), 8.53 (1H, d, J=5.4 Hz), 8.99 (1H, s), 9.11 (1H, s) ppm; LCMS m/z: 472 (M+1).

Example 31

2-Hydroxy-1-(6-((9-((1r,4r)-4-methylcyclohexyl)-9H-pyrido[4',3':4,5]pyrrolo[2,3-d]pyrimidin-2-yl)amino)-3,4-dihydro-2,7-naphthyridin-2(1H)-yl)ethanone

31

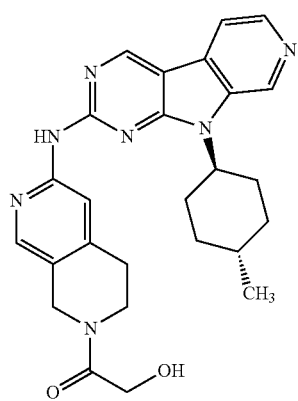

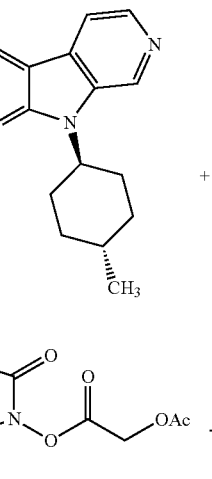

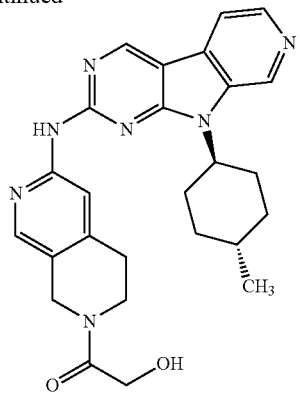

Synthesis of 2-hydroxy-1-(6-((9-((1r,4r)-4-methylcyclohexyl)-9H-pyrido[4',3':4,5]pyrrolo[2,3-d]pyrimidin-2-yl)amino)-3,4-dihydro-2,7-naphthyridin-2(1H)-yl)ethanone.

The title compound was prepared using chemistry similar to that described in Example 5 using 9-((1r,4r)-4-methylcyclohexyl)-N-(5,6,7,8-tetrahydro-2,7-naphthyridin-3-yl)-9H-pyrido[4',3':4,5]pyrrolo[2,3-d]pyrimidin-2-amine dihydrochloride (Example 24) in place of 9-((1r,4r)-4-methylcyclohexyl)-N-(5,6,7,8-tetrahydro-1,6-naphthyridin-2-yl)-9H-pyrido[4',3':4,5]pyrrolo[2,3-d]pyrimidin-2-amine.
$^1$H NMR (500 MHz, CDCl$_3$) δ 1.07 (3H, d, J=6.4 Hz), 1.25-1.36 (3H, m), 2.01 (4H, d, J=10.5 Hz), 2.51-2.64 (2H, m), 3.00 (2H, q, J=5.7 Hz), 3.59 (1H, t, J=6.0 Hz), 3.61-3.67 (1H, m), 3.97 (1H, t, J=6.0 Hz), 4.31 (2H, t, J=3.4 Hz), 4.49 (1H, s), 4.71-4.85 (2H, m), 7.09 (1H, d, J=5.1 Hz), 8.14 (1H, s), 8.16 (1H, s), 8.42 (1H, s), 8.52 (1H, d, J=5.1 Hz), 9.00 (1H, s), 9.13 (1H, s) ppm; LCMS m/z: 472 (M+1).

Example 32

(S)-2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)propan-1-one

32

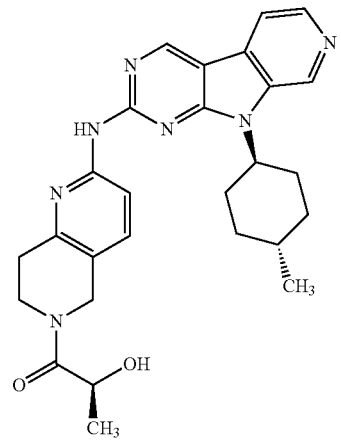

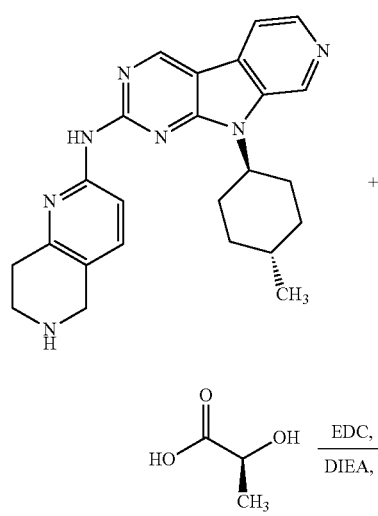

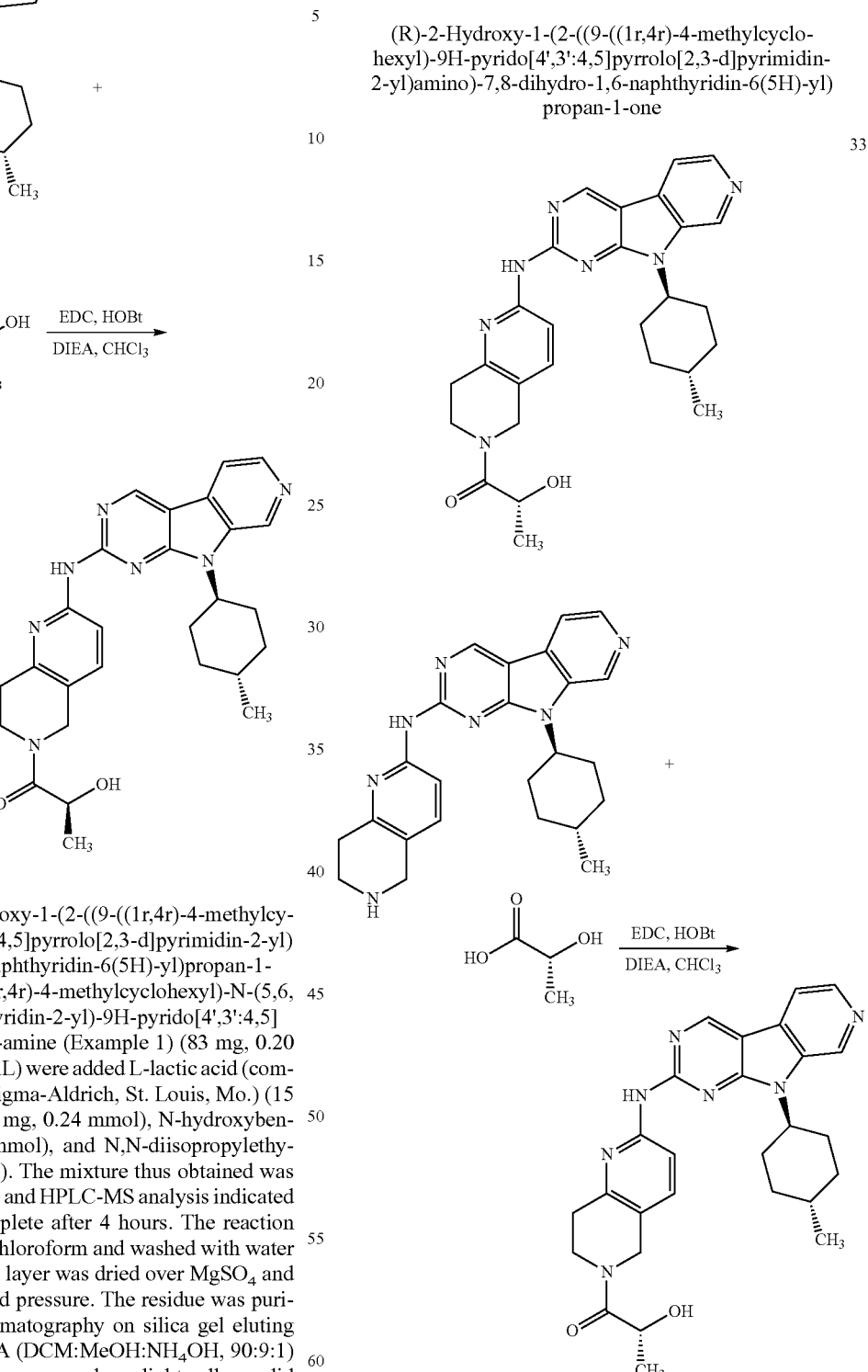

8.43 (1H, d, J=10 Hz), 8.47 (1H, d, J=10 Hz), 9.14 (1H, s), 9.16 (1H, s) ppm; LCMS m/z: 486 (M+1).

Example 33

(R)-2-Hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)propan-1-one Synthesis of (S)-2-hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)propan-1-one. To a solution of 9-((1r,4r)-4-methylcyclohexyl)-N-(5,6,7,8-tetrahydro-1,6-naphthyridin-2-yl)-9H-pyrido[4',3':4,5]pyrrolo[2,3-d]pyrimidin-2-amine (Example 1) (83 mg, 0.20 mmol) in chloroform (10 mL) were added L-lactic acid (commercially obtained from Sigma-Aldrich, St. Louis, Mo.) (15 uL, 0.20 mmol), EDC (46 mg, 0.24 mmol), N-hydroxybenzotriazole (32 mg, 0.24 mmol), and N,N-diisopropylethylamine (84 uL, 0.48 mmol). The mixture thus obtained was stirred at room temperature and HPLC-MS analysis indicated that the reaction was complete after 4 hours. The reaction mixture was diluted with chloroform and washed with water and brine, then the organic layer was dried over MgSO$_4$ and concentrated under reduced pressure. The residue was purified by flash column chromatography on silica gel eluting with 10% to 30% solvent A (DCM:MeOH:NH$_4$OH, 90:9:1) in DCM to provide the title compound as a light yellow solid (67 mg, 69% yield). $^1$H NMR (500 MHz, CDCl$_3$) δ 1.06 (3H, d, J=5.0 Hz), 1.24-1.33 (2H, m), 1.38-1.44 (3H, m), 1.63-1.68 (1H, m), 1.96-2.02 (4H, m), 2.56-2.64 (2H, m), 2.98-3.03 (2H, m), 3.78 (1H, t, J=5.0 Hz), 3.90-3.94 (1H, m), 4.12-4.15 (1H, m), 4.56-4.63 (2H, m), 4.73-4.77 (1H, m), 4.81 (1H, br. s), 7.50 (1H, d, J=10 Hz), 7.54 (1H, d, J=10 Hz), 8.30 (1H, s), Synthesis of (R)-2-hydroxy-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)propan-1-one. The title compound was prepared using chemistry similar to that described in Example 32 using D-lactic acid (commercially obtained from Sigma-Aldrich, St. Louis, Mo.) in place of L-lactic acid. $^1$H NMR (500 MHz, CDCl$_3$) δ 1.06 (3H, d, J=5.0 Hz), 1.23-1.31 (2H, m), 1.38-1.44 (3H, m), 1.63-1.67 (1H, m), 1.96-2.02 (4H, m), 2.56-2.64 (2H, m), 2.99-3.05 (2H, m), 3.78 (1H, t, J=5.0 Hz), 3.90-3.93 (1H, m), 4.12-4.15 (1H, m), 4.58-4.63 (2H, m), 4.72-4.77 (1H, m), 4.81 (1H, d, J=5.0 Hz), 7.50 (1H, d, J=10 Hz), 7.54 (1H, d, J=10 Hz), 7.84 (1H, s), 8.44 (1H, d, J=10 Hz), 8.47 (1H, d, J=10 Hz), 9.19 (1H, s), 9.23 (1H, s) ppm; LCMS m/z: 486 (M+1).

Example 34

2-(Dimethylamino)-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone

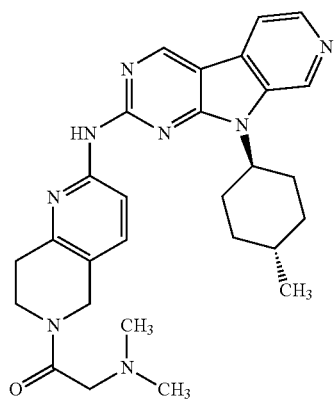

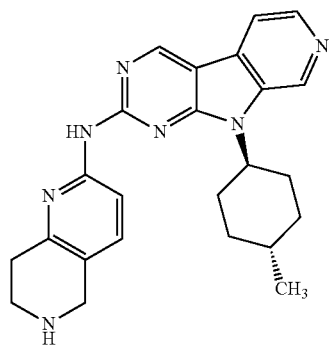

+

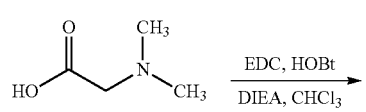

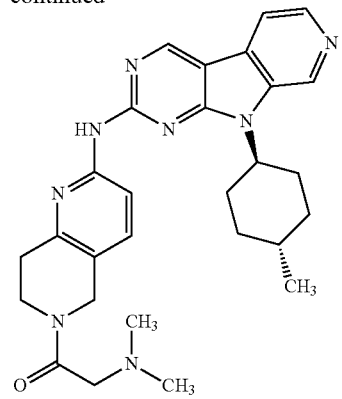

Synthesis of 2-(dimethylamino)-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone. The title compound was prepared using chemistry similar to that described in Example 32 using 2-(dimethylamino)acetic acid (commercially obtained from Sigma-Aldrich, St. Louis, Mo.) in place of L-lactic acid. $^1$H NMR (500 MHz, CDCl$_3$) δ 1.07 (3H, d, J=5.0 Hz), 1.24-1.32 (2H, m), 1.64-1.67 (1H, m), 1.96-2.02 (4H, m), 2.32 (6H, s), 2.57-2.64 (2H, m), 2.97 (1H, t, J=5.0 Hz), 3.02 (1H, t, J=5.0 Hz), 3.25 (2H, br. s), 3.93-3.98 (2H, m), 4.70-4.76 (3H, m), 7.50 (1H, d, J=10 Hz), 7.84 (1H, d, J=5.0 Hz), 8.44 (1H, d, J=10 Hz), 8.51 (1H, d, J=5.0 Hz), 8.97 (1H, s), 9.18 (1H, s) ppm; LCMS m/z: 499 (M+1).

Example 35 tert-Butyl 2-((9-((1r,4r)-4-methylcyclohexyl)-9H-pyrido[4',3':4,5]pyrrolo[2,3-d]pyrimidin-2-yl)amino)-5,6-dihydro-1,7-naphthyridine-7(8H)-carboxylate

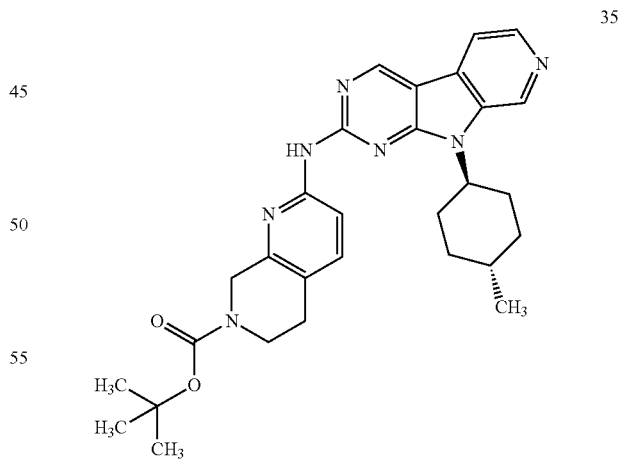

Synthesis of tert-butyl 2-((9-((1r,4r)-4-methylcyclohexyl)-9H-pyrido[4',3':4,5]pyrrolo[2,3-d]pyrimidin-2-yl)amino)-5,6-dihydro-1,7-naphthyridine-7(8H)-carboxylate. The title compound was prepared as described in Example 23. $^1$H NMR (500 MHz, CDCl$_3$) δ 1.07 (3H, d, J=6.4 Hz), 1.23-1.33 (2H, m), 1.52 (9H, s), 1.64-1.68 (1H, m), 1.99 (4H, t, J=11.0 Hz), 2.60 (2H, dq, J=3.3, 12.3 Hz), 2.85 (2H, br. s), 3.72 (2H, br. s), 4.60 (2H, s), 4.73 (1H, t, J=12.3 Hz), 7.53 (1H, d, J=8.3 Hz), 7.87 (1H, d, J=5.4 Hz), 8.10 (1H, br. s), 8.37 (1H, d, J=8.3 Hz), 8.51 (1H, d, J=5.4 Hz), 8.97 (1H, s), 9.12 (1H, s) ppm; LCMS m/z: 514 (M+1).

Example 36 tert-Butyl 6-((9-((1r,4r)-4-methylcyclohexyl)-9H-pyrido[4',3':4,5]pyrrolo[2,3-d]pyrimidin-2-yl)amino)-3,4-dihydro-2,7-naphthyridine-2(1H)-carboxylate

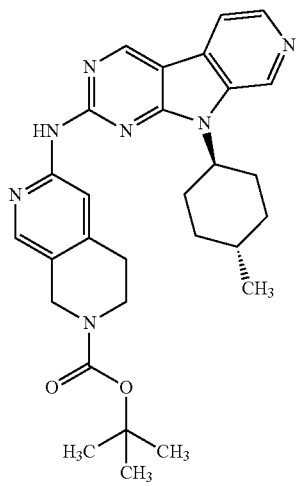

Synthesis of tert-butyl 6-((9-((1r,4r)-4-methylcyclohexyl)-9H-pyrido[4',3':4,5]pyrrolo[2,3-d]pyrimidin-2-yl)amino)-3,4-dihydro-2,7-naphthyridine-2(1H)-carboxylate. The title compound was prepared as described in Example 24. $^1$H NMR (500 MHz, CDCl$_3$) δ 1.07 (3H, d, J=6.4 Hz), 1.23-1.35 (2H, m), 1.53 (9H, s), 1.62-1.73 (1H, m), 2.00 (2H, br. s), 2.48-2.67 (2H, m), 2.81-3.01 (2H, m), 3.72 (2H, br. s), 4.61 (2H, s), 4.78 (1H, t, J=12.5 Hz), 7.89 (1H, d, J=5.4 Hz), 8.10 (1H, br. s), 8.12 (1H, br. s), 8.36 (1H, br. s), 8.52 (1H, d, J=5.4 Hz), 8.98 (1H, s), 9.12 (1H, s) ppm; LCMS m/z: 514 (M+1).

Example 37

2-(Diethylamino)-1-(2-((9-((1r,4r)-4-methylcyclohexyl)-9H-pyrido[4',3':4,5]pyrrolo[2,3-d]pyrimidin-2-yl)amino)-7,8-dihydro-1,6-naphthyridin-6(5H)-yl)ethanone

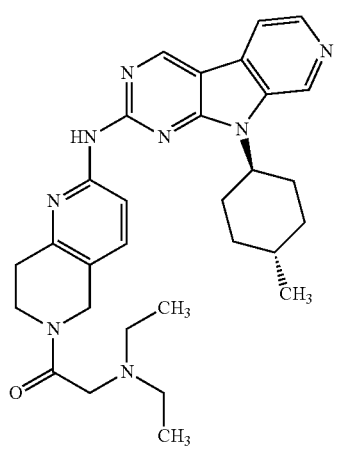

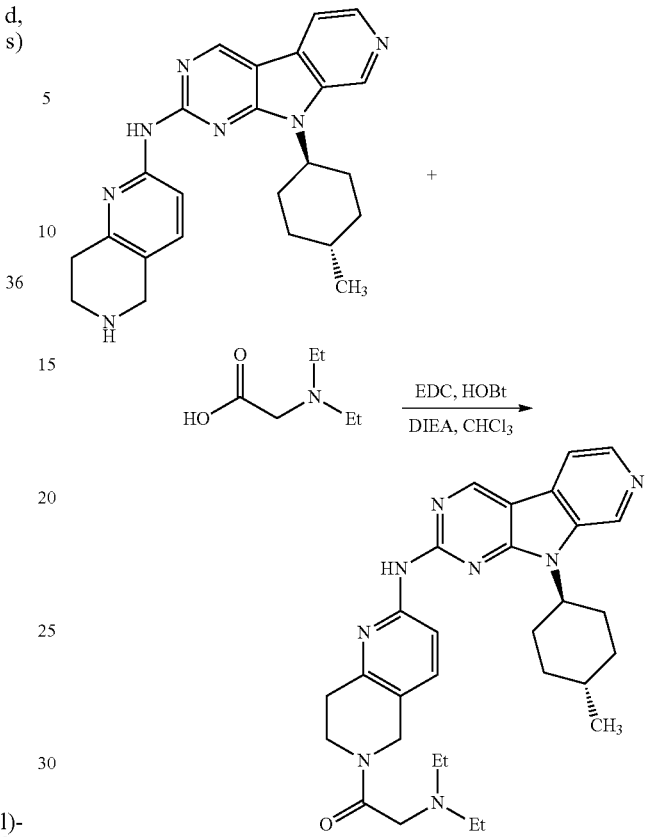

Synthesis of 2-(diethylamino)-1-(2-((9-((1r,4r)-4-methylcyclohexyD-9H-pyrido[4',3':4,5]pyrrolo[2,3-d]pyrimidin-2-yDamino)-7,8-dihydro-1,6-naphthyridin-6(5H)-yl)ethanone. The title compound was prepared using chemistry similar to that described in Example 32 using 2-(diethylamino)acetic acid (commercially obtained from Matrix Scientific, Columbia, S.C.) in place of L-lactic acid. $^1$H NMR (500 MHz, CDCl$_3$) δ ppm 1.02-1.09 (9H, m), 1.24-1.33 (2H, m), 1.63-1.69 (1H, m), 1.96-2.02 (4H, m), 2.57-2.65 (6H, m), 2.98 (2H, t, J=5.0 Hz), 3.39 (2H, br. s), 3.97 (2H, t, J=5.0 Hz), 4.71-4.77 (3H, m), 7.49 (1H, d, J=10 Hz), 7.84 (1H, d, J=5.0 Hz), 8.24 (1H, s), 8.42 (1H, d, J=10 Hz), 8.51 (1H, d, J=5.0 Hz), 8.97 (1H, s), 9.13 (1H, s); LCMS m/z: 527 (M+1).

CDK4, FLT3, and MOLM13 Assays

The CDK4 and CDK1 inhibitory activity of the CDK4/6-FLT3 inhibitors was determined with a filtration kinase assay. The compounds, kinase and substrate diluted in the kinase buffer (20 mM Tris, pH7.4, 50 mM NaCl, 1 mM DTT, 0.1% BSA) were sequentially added to a 96-well Multiscreen HTS filtration plate (Millipore). The final 100 μL reaction mixture in each well contained 0.3 μg of CDK4/Cyclin D1 or CDK1/Cyclin B (Cell Signaling Technology), 1 μg of Rb fragment (aa773-928, Millipore) for the CDK4 assay or 5 μg of histone H1 for the CDK1 assay and 1 μCi of [$^{33}$P]-ATP. The mixture was incubated at room temperature for 1 hour. The proteins in the reaction were then precipitated and washed with cold TCA solution using an aspiration/filtration vacuum system. The plates were dried at room temperature, and the retained radioactivity was measured by scintillation counting.

The FLT3 inhibitory activity of the CDK4/6-FLT3 inhibitors was determined with a HTRF kinase assay. The FLT3 enzyme (GST-FLT3 fusion) was purchased from Carna Biosciences. An ULight-labeled synthetic peptide derived from human Janus kinase 1 (aa1015-1027, ULight-JAK1, PerkinElmer) was utilized as the phosphoacceptor substrate. The assay was conducted in a 384-well white OptiPlate (PerkinElmer). The 20 μL reaction mixture contained 50 nM ULight-JAK1, 116 μM ATP, 0.0385 ng/μL FLT3 and dilutions of test compounds in the kinase buffer (50 mM Hepes, pH 7.6, 1 mM EGTA, 10 mM $MgCl_2$, 2 mM DTT, and 0.005% Tween 20). The reaction was allowed to proceed for 1 hour at room temperature and was stopped by adding 20 μL of 10 mM EDTA, 2 nM LANCE® Eu-W1024 anti-phospho-tyrosine antibody in LANCE® detection buffer (PerkinElmer). The plates were incubated at room temperature for 2 hours after addition of detection reagents and then read on an Envision multimode reader (PerkinElmer).

The cell proliferation inhibition potency of the CDK4/6-FLT3 inhibitors was determined by using a $[^{14}C]$-thymidine incorporation assay. Exponentially growing cells (MOLM-13, Colo-205, etc.) were seeded in a 96-well Cytostar T plate (GE Healthcare Biosciences) at a density of $5×10^3$ cells/well and incubated overnight. Serially diluted compounds and 0.1 μCi of $[^{14}C]$-thymidine (GE Healthcare Biosciences) were added to each well on the following day. After 72 hour incubation, isotope incorporation was determined with a β plate counter (Wallac). MOLM13 is a human AML tumor cell line expressing FLT3, $FLT3^{ITD}$ and wild type Rb.

$IC_{50}$ values of the compounds in the above assays were determined by non-linear regression analysis using Prism (GraphPad Software).

The following table includes $IC_{50}$ values obtained using the procedures set forth above for the Example compounds described herein.

| Example | Structure[a] | FLT3 $IC_{50}$ (μM)[b] | CDK4 $IC_{50}$ (μM)[b] | MOLM13 $IC_{50}$ (μM)[b] |
|---|---|---|---|---|
| 1 | | 0.0013 | 0.0021 | 0.0152 |
| 2 | | 0.0032 | 0.0045 | 0.0225 |
| 3 | | 0.0018 | 0.0026 | 0.0148 |

-continued

Table of FLT3, CDK4, and MOLM13 Data For Example Compounds

| Example | Structure[a] | FLT3 IC$_{50}$ (μM)[b] | CDK4 IC$_{50}$ (μM)[b] | MOLM13 IC$_{50}$ (μM)[b] |
|---|---|---|---|---|
| 4 | | 0.002 | 0.0046 | 0.0211 |
| 5 | | 0.0015 | 0.0024 | 0.019 |
| 6 | | 0.0033 | 0.12 | 0.046 |

-continued
Table of FLT3, CDK4, and MOLM13 Data For Example Compounds
| Example | Structure[a] | FLT3 IC$_{50}$ (μM)[b] | CDK4 IC$_{50}$ (μM)[b] | MOLM13 IC$_{50}$ (μM)[b] |
|---|---|---|---|---|
| 7 | 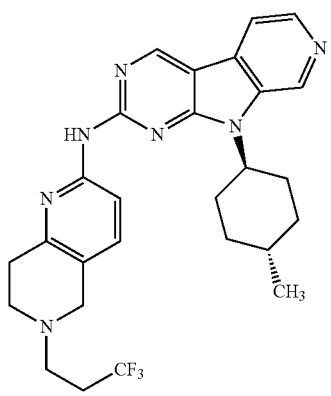 | 0.0214 | 0.0524 | 0.206 |
| 8 | 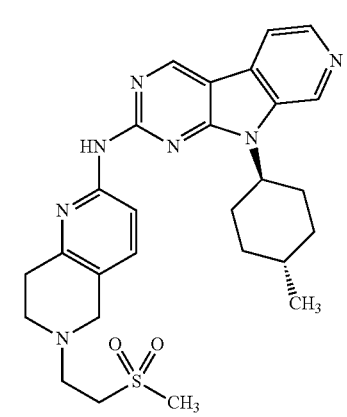 | 0.0361 | 0.0024 | 0.0091 |
| 9 | 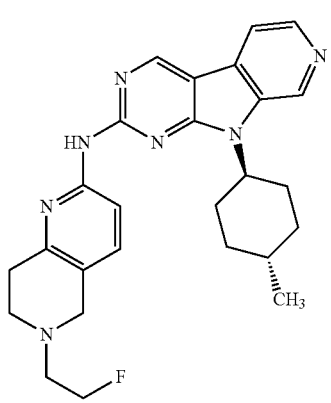 | 0.0034 | 0.0728 | 0.0649 |

-continued

Table of FLT3, CDK4, and MOLM13 Data For Example Compounds

| Example | Structure[a] | FLT3 IC$_{50}$ (μM)[b] | CDK4 IC$_{50}$ (μM)[b] | MOLM13 IC$_{50}$ (μM)[b] |
|---|---|---|---|---|
| 10 | | 0.0017 | 0.0105 | 0.0332 |
| 11 | | 0.0737 | 0.257 | >3 |
| 12 | | 0.0027 | 0.0184 | 0.0108 |
| 13 | | 0.0018 | 0.0313 | 0.0545 |

-continued

Table of FLT3, CDK4, and MOLM13 Data For Example Compounds

| Example | Structure[a] | FLT3 IC$_{50}$ (μM)[b] | CDK4 IC$_{50}$ (μM)[b] | MOLM13 IC$_{50}$ (μM)[b] |
|---|---|---|---|---|
| 14 | | 0.0032 | 0.0044 | 0.0106 |
| 15 | | 0.0031 | 0.0203 | 0.0295 |
| 16 | | 0.0014 | 0.0165 | 0.0239 |
| 17 | | 0.0029 | 0.0192 | 0.0219 |

-continued

Table of FLT3, CDK4, and MOLM13 Data For Example Compounds

| Example | Structure[a] | FLT3 IC$_{50}$ (μM)[b] | CDK4 IC$_{50}$ (μM)[b] | MOLM13 IC$_{50}$ (μM)[b] |
| --- | --- | --- | --- | --- |
| 18a | | 0.0016 | 0.0188 | 0.0242 |
| 18b | The enantiomer of 18a | 0.0023 | 0.463 | 0.02 |
| 19 | | 0.033 | 1.79 | 0.204 |

-continued

Table of FLT3, CDK4, and MOLM13 Data For Example Compounds

| Example | Structure[a] | FLT3 IC$_{50}$ (μM)[b] | CDK4 IC$_{50}$ (μM)[b] | MOLM13 IC$_{50}$ (μM)[b] |
|---|---|---|---|---|
| 20 | | 0.144 | 0.847 | 0.208 |
| 21 | | ND | ND | ND |
| 22 | | 0.00065 | 0.036 | 0.0052 |
| 23 | | ND | 0.0086 | 0.0015 |

-continued
Table of FLT3, CDK4, and MOLM13 Data For Example Compounds
| Example | Structure[a] | FLT3 IC$_{50}$ (μM)[b] | CDK4 IC$_{50}$ (μM)[b] | MOLM13 IC$_{50}$ (μM)[b] |
|---|---|---|---|---|
| 24 | 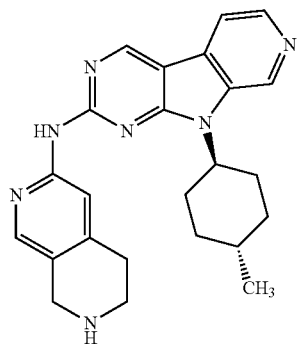 [SMILES: C[C@H]1CC[C@H](n2c3cnccc3c3cnc(Nc4cc5c(cn4)CNCC5)nc32)CC1] | ND | 0.0047 | 0.0035 |
| 25 | 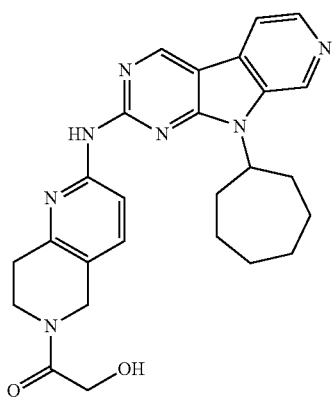 [SMILES: O=C(CO)N1CCc2nc(Nc3ncc4c5ccncc5n(C5CCCCCC5)c4n3)ccc2C1] | ND | ND | ND |
| 26 | 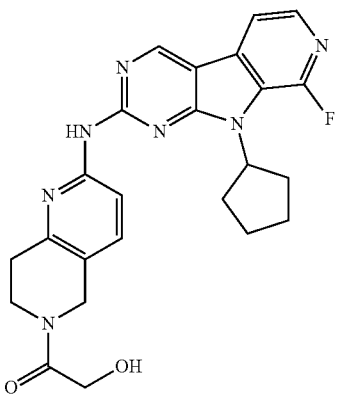 [SMILES: O=C(CO)N1CCc2nc(Nc3ncc4c5ccnc(F)c5n(C5CCCC5)c4n3)ccc2C1] | ND | ND | ND |

-continued
Table of FLT3, CDK4, and MOLM13 Data For Example Compounds
| Example | Structure[a] | FLT3 IC$_{50}$ (μM)[b] | CDK4 IC$_{50}$ (μM)[b] | MOLM13 IC$_{50}$ (μM)[b] |
|---|---|---|---|---|
| 27 | 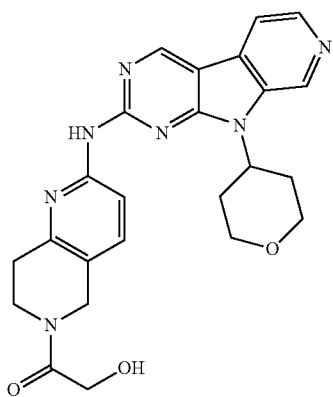 [SMILES: O=C(CO)N1CCc2nc(Nc3ncc4c5ccncc5n(C5CCOCC5)c4n3)ccc2C1] | ND | ND | ND |
| 28 | 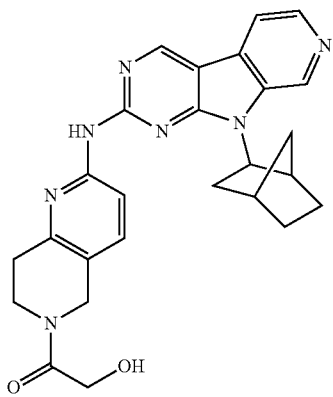 [SMILES: O=C(CO)N1CCc2nc(Nc3ncc4c5ccncc5n(C5CC6CCC5C6)c4n3)ccc2C1] | ND | ND | ND |
| 29 | 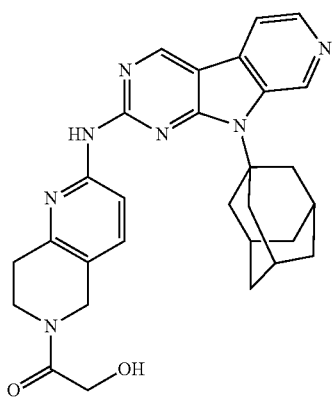 [SMILES: O=C(CO)N1CCc2nc(Nc3ncc4c5ccncc5n(C56CC7CC(CC(C7)C5)C6)c4n3)ccc2C1] | ND | ND | ND |

-continued

Table of FLT3, CDK4, and MOLM13 Data For Example Compounds

| Example | Structure[a] | FLT3 IC$_{50}$ (μM)[b] | CDK4 IC$_{50}$ (μM)[b] | MOLM13 IC$_{50}$ (μM)[b] |
|---|---|---|---|---|
| 30 | | ND | 0.0063 | 0.003 |
| 31 | | ND | 0.035 | 0.0067 |
| 32 | | ND | 0.012 | 0.0018 |

-continued

Table of FLT3, CDK4, and MOLM13 Data For Example Compounds

| Example | Structure[a] | FLT3 IC$_{50}$ (μM)[b] | CDK4 IC$_{50}$ (μM)[b] | MOLM13 IC$_{50}$ (μM)[b] |
|---|---|---|---|---|
| 33 | | ND | 0.041 | 0.0031 |
| 34 | | ND | 0.003 | 0.0003 |
| 35 | | ND | 0.026 | 0.48 |

Table of FLT3, CDK4, and MOLM13 Data For Example Compounds

| Example | Structure[a] | FLT3 IC$_{50}$ (µM)[b] | CDK4 IC$_{50}$ (µM)[b] | MOLM13 IC$_{50}$ (µM)[b] |
|---|---|---|---|---|
| 36 | | ND | 0.35 | — |
| 37 | | ND | 0.003 | 0.0014 |

[a] The ∿∿∿ symbol indicates that a mixture of the R and S isomers is present with respect to the stereocenter shown.
[b] ND means not determined Xenograft Studies Tumor Growth Inhibition in AML MOLM 13 Xenograft Tumors The anti-tumor activity of Example 5 against subcutaneous MOLM13 xenograft tumors was demonstrated after treatment with increasing doses of Example 5. The AML cell line, MOLM13, (obtained from American Type Culture Collection, Manassas, Va., USA) was cultured in RPMI-1640 cell growth medium containing 10% fetal bovine serum (commercially obtained from Invitrogen, Carlsbad, Calif. USA). This cell line expresses CDK4/6, one copy of wild type FLT3 kinase and one copy of FLT3-ITD, which results in constitutive activation of FLT3 activity. Therefore, the activity of Example 5 against both FLT3 and CDK4/6 can be tested in this tumor cell. Tumor cells (7.5 million) were injected subcutaneously onto the right flank of CrTac:NCR-Foxn1$^{nu}$ nude mice (commercially available from Taconic Farms, Inc, Hudson, N.Y. USA). Tumors were allowed to grow for 6 days. Mice were then distributed into groups of 10 mice based on ranking of initial tumor volume to achieve groups in which the average tumor size was 250 mm$^3$ Example 5 was formulated in 2% HPMC (Hypermellose; HY122-13; commercially available from Spectrum Chemical Manufacturing Gardena, CA USA)/1% Tween-80 (Crillet 4 HP; commercially available from Croda, Inc Edison, N.J. USA) and dosed daily or twice daily 6 hours apart for a total of 10 days with 6.25 mg/kg, 12.5 mg/kg, 25 mg/kg, 37.5 mg/kg, 50 mg/kg, 75 mg/kg or 150 mg/kg. Tumors were measured every other day using two-dimensional calipers and tumor volumes were estimated using the equation Width$^2$×Length×0.5. FIG. 1 shows the calculated tumor volume as a function of time after twice daily dosing with Example 5. Dose-dependent inhibition of tumor growth was observed. All doses were statistically different from the vehicle treated group. Statistical significance was evaluated using RMANOVA on log transformed tumor volume with baseline as covariate. P values are shown in FIG. 1.

Tumor Growth Inhibition in Colo205 Xenograft Tumors

Figure 2:
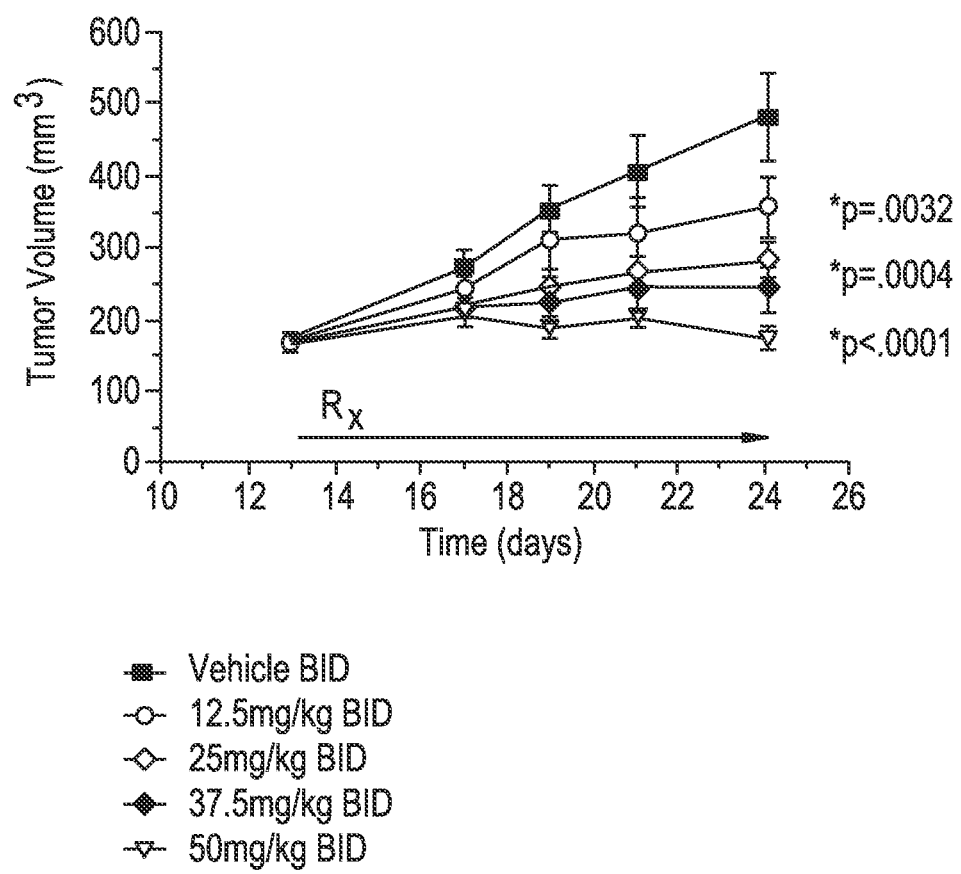
FIG. 2 is a graph showing the dose dependent anti-tumor activity observed after twice daily dosing (BID) with Example 5 in CrTac:NCR-Foxn1$^{nu}$ nude mice with Colo 205 subcutaneous xenograft tumors.

The activity of Example 5 was evaluated in the human colon carcinoma, Colo205, xenograft tumor model. This cell line expresses CDK4/6 but not FLT3. Therefore, this system will measure the activity of Example 5 against CDK4/6. Colo205 cells (obtained from American Type Culture Collection, Manassas, Va., USA) were cultured in DMEM cell growth medium containing 10% fetal bovine serum (commercially obtained from Invitrogen, Carlsbad, Calif. USA). Two million cells were innoculated on the right flank of CrTac:NCR-Foxn1$^{nu}$ nude mice (commercially available from Taconic Farms, Inc, Hudson, N.Y. USA) and allowed to grow for 13 days. Mice were then distributed into groups of 10 mice based on ranking of initial tumor volume to achieve groups in which the average tumor size was 170 mm$^3$. Example 5 was formulated in 2% HPMC (Hypermellose; HY122-13; commercially available from Spectrum Chemical Manufacturing Gardena, CA USA)/1% Tween-80 (Crillet 4 HP; commercially available from Croda, Inc Edison, N.J. USA) and dosed daily or twice daily 6 hours apart for a total of 10 days with 12.5 mg/kg, 25 mg/kg, 37.5 mg/kg, or 50 mg/kg. Tumors were measured every other day using two-dimensional calipers and tumor volumes were estimated using the equation Width$^2$×Length×0.5. FIG. 2 shows the calculated tumor volume as a function of time after twice daily dosing with Example 5. Dose-dependent inhibition of tumor growth was observed. All doses were statistically different from the vehicle treated group. Statistical significance was evaluated using RMANOVA on log transformed tumor volume with baseline as covariate. P values are shown in FIG. 2.

All publications and patent applications cited in this specification are hereby incorporated by reference herein in their entireties and for all purposes as if each individual publication or patent application were specifically and individually indicated as being incorporated by reference and as if each reference was fully set forth in its entirety. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A method of treating acute myeloid leukemia, the method comprising: administering to a subject an effective amount of a compound selected from

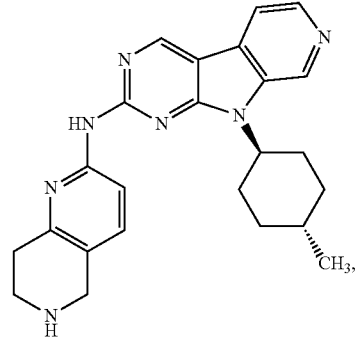

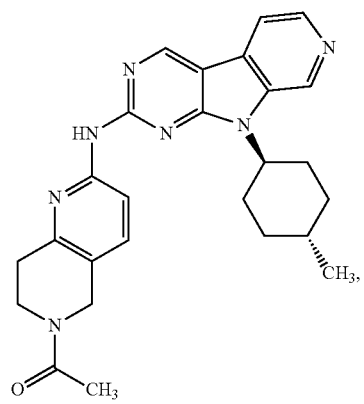

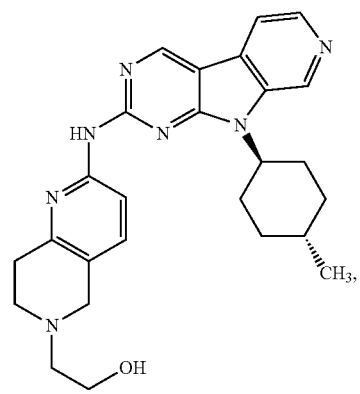

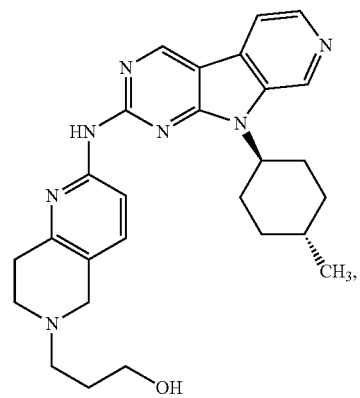

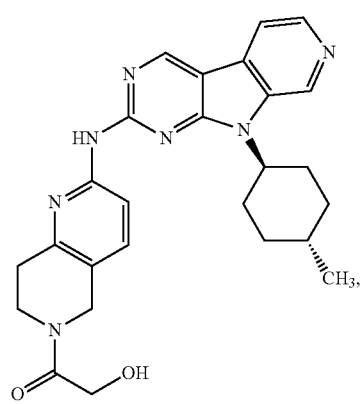

203 -continued

204 -continued

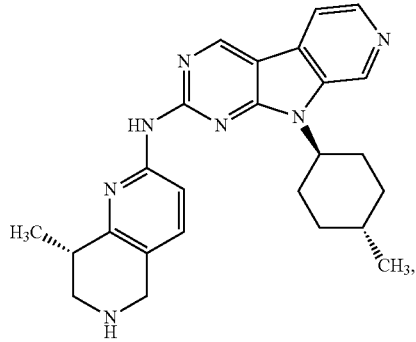
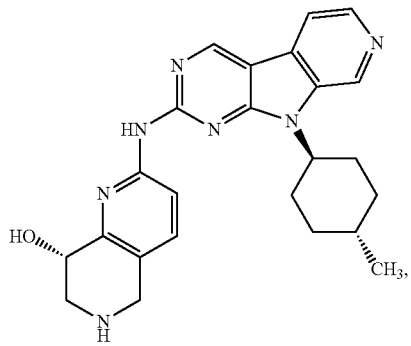
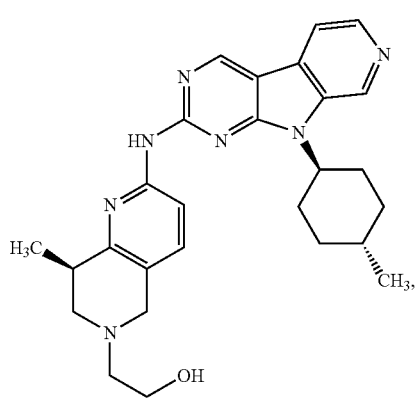
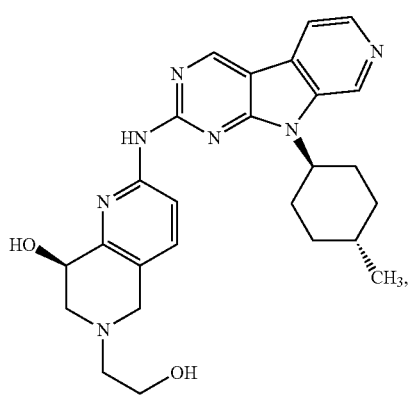
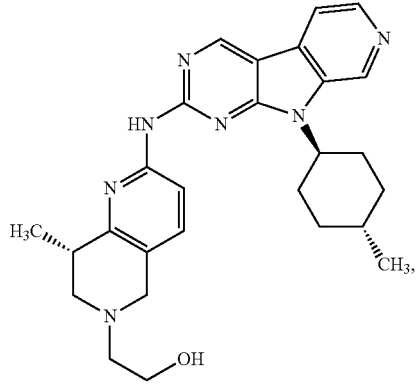
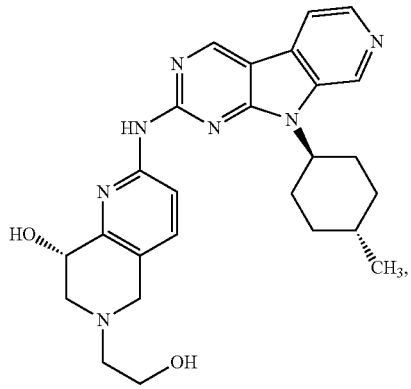
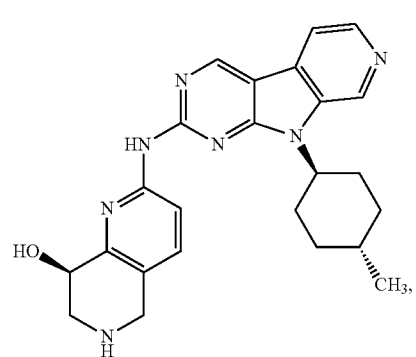
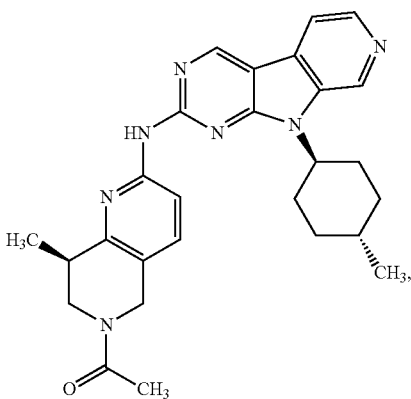

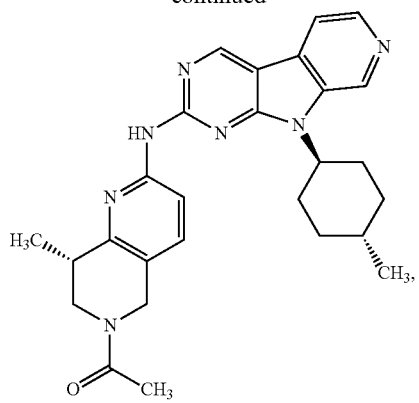

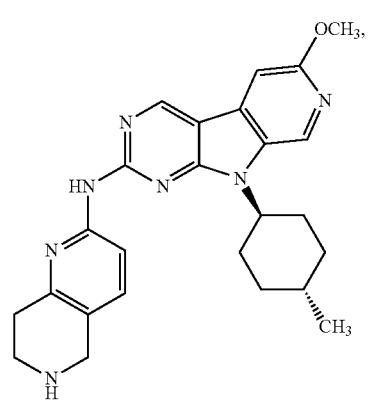

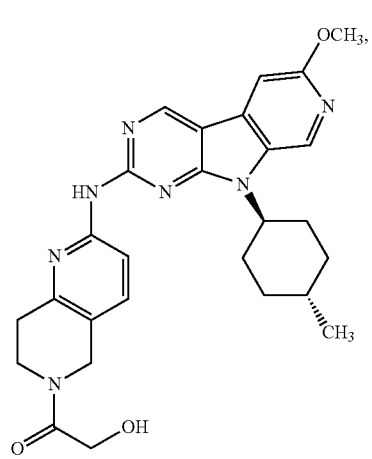

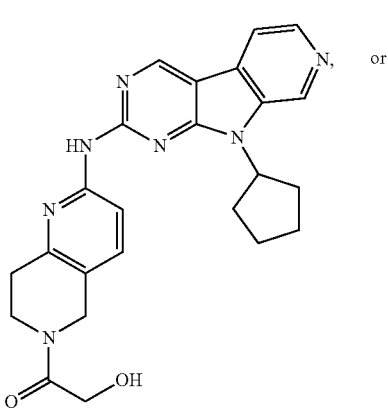

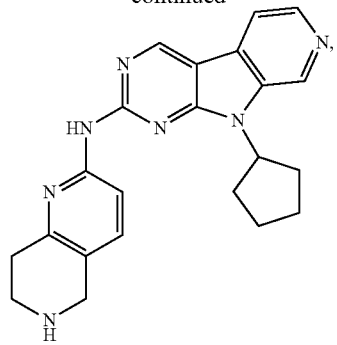

or a pharmaceutically acceptable salt or a hydrate thereof.

2. The method of claim 1, wherein the compound is

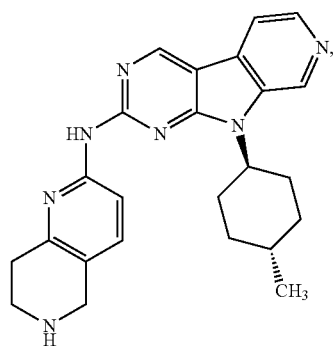 [SMILES: C[C@H]1CC[C@H](n2c3cnccc3c3cnc(Nc4ccc5c(n4)CCNC5)nc32)CC1]

or the pharmaceutically acceptable salt or the hydrate thereof.

3. The method of claim 1, wherein the compound is

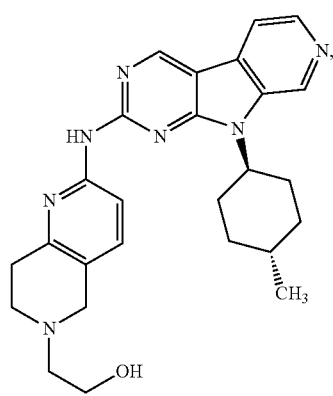

or the pharmaceutically acceptable salt or the hydrate thereof.

4. A method of treating colon carcinoma, the method comprising:
administering to a subject an effective amount of a compound having the following formula

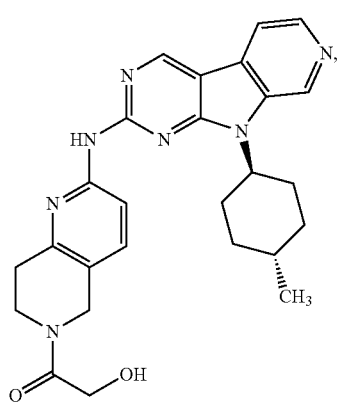 [SMILES: C[C@H]1CC[C@H](n2c3cnccc3c3cnc(Nc4ccc5c(n4)CCN(C(=O)CO)C5)nc32)CC1]
or a pharmaceutically acceptable salt or a hydrate thereof.
5. A method of treating acute myeloid leukemia, the method comprising: administering to a subject an effective amount of a compound selected from
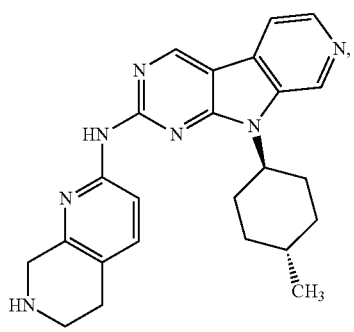
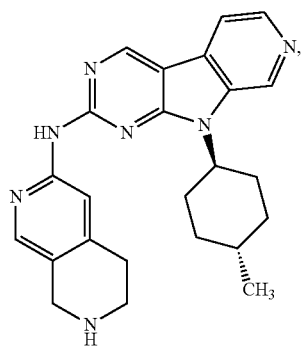
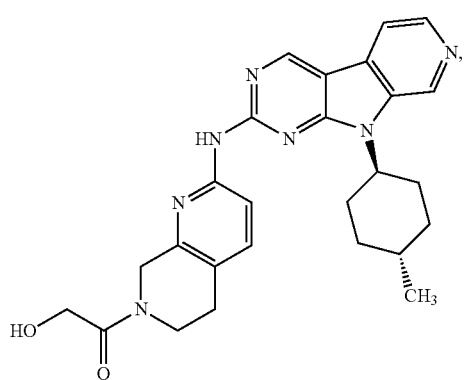
-continued
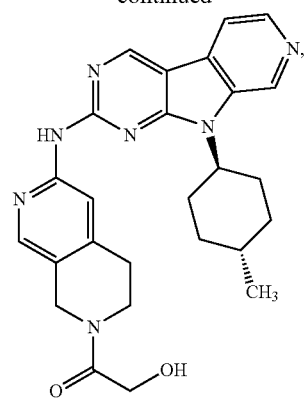
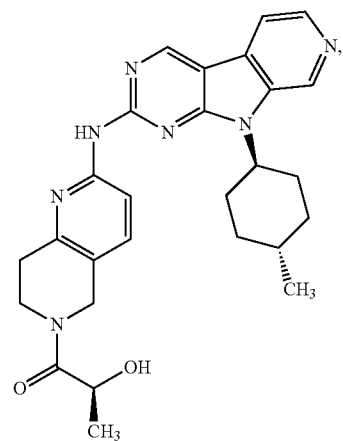
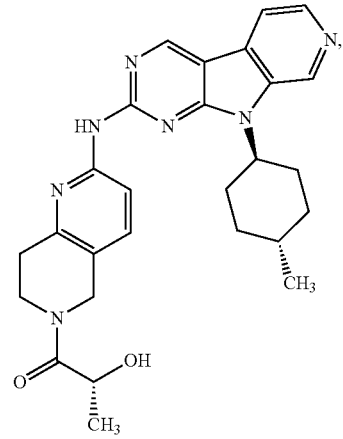
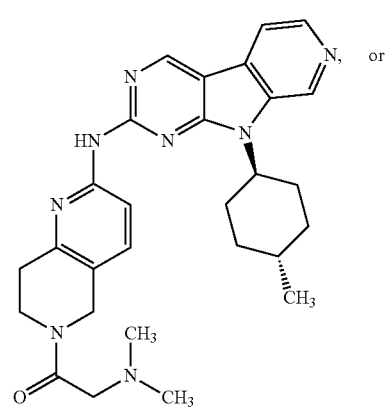
or -continued

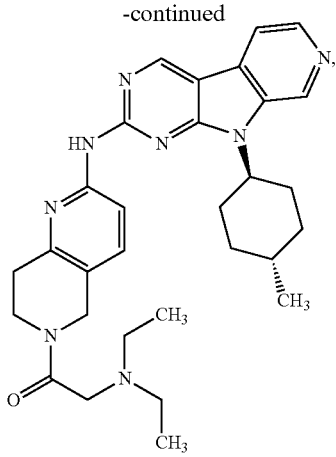

or a pharmaceutically acceptable salt or a hydrate thereof.

6. The method of claim 1, wherein the compound is in a neutral form.

7. The method of claim 1, wherein the pharmaceutically acceptable salt or the hydrate is administered to the subject.

8. The method of claim 7, wherein the pharmaceutically acceptable salt or the hydrate thereof is selected from a chloride salt, a methanesulfonate salt, or a benzenesulfonate salt.

9. The method of claim 4, wherein the compound is in a neutral form.

10. The method of claim 4, wherein the pharmaceutically acceptable salt or the hydrate is administered to the subject.

11. The method of claim 10, wherein the pharmaceutically acceptable salt or the hydrate thereof is selected from a chloride salt, a methanesulfonate salt, or a benzenesulfonate salt.

12. The method of claim 5, wherein the compound is in a neutral form.

13. The method of claim 5, wherein the pharmaceutically acceptable salt or the hydrate is administered to the subject.

14. The method of claim 13, wherein the pharmaceutically acceptable salt or the hydrate thereof is selected from a chloride salt, a methanesulfonate salt, or a benzenesulfonate salt.

* * * * *